United States Patent
Patel et al.

(10) Patent No.: US 11,834,414 B2
(45) Date of Patent: Dec. 5, 2023

(54) 1-METHYL-4-[(4-PHENYLPHENYL) SULFONYLMETHYL]CYCLOHEXYANOL AND 1-METHYL-4-[[4-(2-PYRIDYL)PHENYL] SULFONYLMETHYL]CYCLOHEXANOL COMPOUNDS AND THEIR THERAPEUTIC USE

(71) Applicant: Modern Biosciences Limited, London (GB)

(72) Inventors: Lisa Patel, London (GB); Stephen Allan Smith, Bishops Stortford (GB)

(73) Assignee: Modern Biosciences Limited, London (GB)

( * ) Notice: Subject to any disclaimer, the term of this patent is extended or adjusted under 35 U.S.C. 154(b) by 388 days.

(21) Appl. No.: 17/265,929

(22) PCT Filed: Aug. 15, 2019

(86) PCT No.: PCT/EP2019/071917
§ 371 (c)(1),
(2) Date: Feb. 4, 2021

(87) PCT Pub. No.: WO2020/035560
PCT Pub. Date: Feb. 20, 2020

(65) Prior Publication Data
US 2022/0363642 A1    Nov. 17, 2022

(30) Foreign Application Priority Data
Aug. 15, 2018 (GB) .................... 1813312

(51) Int. Cl.
*C07C 317/22* (2006.01)
*C07D 213/06* (2006.01)
*C07C 317/36* (2006.01)

(52) U.S. Cl.
CPC .......... *C07D 213/06* (2013.01); *C07C 317/22* (2013.01); *C07C 317/36* (2013.01)

(58) Field of Classification Search
None
See application file for complete search history.

(56) References Cited

FOREIGN PATENT DOCUMENTS

| WO | WO 2010/027500 A1 | 3/2010 | |
| WO | WO 2010/032009 | * 3/2010 | ........... C07C 311/20 |
| WO | WO 2010/032009 A1 | 3/2010 | |
| WO | WO 2010/032010 A1 | 3/2010 | |
| WO | WO 2014/207445 | * 12/2014 | ........... C07D 213/61 |
| WO | WO 2014/207445 A1 | 12/2014 | |
| WO | WO 2016/097001 A1 | 6/2016 | |
| WO | WO 2016/118774 A1 | 7/2016 | |
| WO | WO 2018/055551 A1 | 3/2018 | |

OTHER PUBLICATIONS

Williams et al. (in Foye's Principles of Medicinal Chemistry, 5th Ed., pp. 59-63, 2002) (Year: 2002).*
Astry et al., 2011, "A cytokine-centric view of the pathogenesis and treatment of autoimmune arthritis", J Interferon Cytokine Res., vol. 31, pp. 927-940.
Auld et al., 2009, "A basis for reduced chemical library inhibition of firefly luciferase obtained from directed evolution", J. Med. Chem., vol. 52, No. 5, pp. 1450-1458.
Baud et al., 2009, "Is NFκB a good target for cancer therapy? Hopes and pitfalls", Nat. Rev. Drug Disc., vol. 8, pp. 33-40.
Billiau, 2010, "Etanercept improves linear growth and bone mass acquisition in MTX resistant polyarticular-course juvenile idiopathic arthritis", Rheumatology (Oxford), vol. 49, pp. 1550-1558.
Brennan et al., 1992, "Enhanced expression of tumor necrosis factor receptor mRNA and protein in mononuclear cells isolated from rheumatoid arthritis synovial joints", Eur. J. Immunol., vol. 22, pp. 1907-1912.
Brennan et al., 1996, "Cytokines in autoimmunity", Curr. Opin. Immunol., vol. 8, pp. 872-877.
Bridges et al., 2014, "Effects of metformin and other biguanides on oxidative phosphorylation in mitochondria", Biochem. J., vol. 462, No. 3, pp. 475-487.
Chimenti et al., 2015, "The interplay between inflammation and metabolism in rheumatoid arthritis", Cell Death and Disease, vol. 17, No. 6, e1887, pp. 1-10.
Ellinghaus et al., 2013, "BAY 87-2243, a highly potent and selective inhibitor of hypoxia-induced gene activation has antitumor activities by inhibition of mitochondrial complex I", Cancer Med., vol. 2, No. 5, pp. 611-624.
Evans et al., 2005, "Metformin and reduced risk of cancer in diabetic patients", BMJ, vol. 330, pp. 1304-1305.
Fearon et al., 2016 "Hypoxia, mitochondrial dysfunction and synovial invasiveness in rheumatoid arthritis", Nat. Rev. Rheumatol., vol. 12, pp. 385-397.
Fiorillo et al., 2016, "Repurposing atovaquone: Targeting mitochondrial complex III and OXPHOS to eradicate cancer stem cells", Oncotarget, vol. 7, pp. 34084-34099.

(Continued)

*Primary Examiner* — Craig D Ricci
(74) *Attorney, Agent, or Firm* — McNeill Baur PLLC

(57) ABSTRACT

The present invention pertains generally to the field of therapeutic compounds. More specifically the present invention pertains to certain substituted 1-methyl-4-[(4-phenylphenyl)sulfonylmethyl]cyclohexanol and 1-methyl-4-[[4-(2-pyridyl)phenyl]sulfonylmethyl]cyclohexanol compounds (collectively referred to herein as CHMSA compounds) that are useful, for example, in the treatment of disorders (e.g., diseases) including, e.g., multiple myeloma, diffuse large B-cell lymphoma, acute myeloid leukemia, eosinophilic leukemia, glioblastoma, melanoma, ovarian cancer, chemotherapy resistant cancer, radiation resistant cancer, inflammatory arthritis, rheumatoid arthritis, psoriatic arthritis, psoriasis, ulcerative colitis, Crohn's disease, systemic lupus erythematosus (SLE), lupus nephritis, asthma, chronic obstructive pulmonary disease (COPD), non-alcoholic fatty liver disease (NAFLD), non-alcoholic steatohepatitis (NASH), autoimmune hepatitis, hidradenitis suppurativa, etc. The present invention also pertains to pharmaceutical compositions comprising such compounds, and the use of such compounds and compositions, for example, in therapy.

22 Claims, 3 Drawing Sheets

(56) References Cited

OTHER PUBLICATIONS

Firestein, 2005 "Immunologic mechanisms in the pathogenesis of rheumatoid arthritis", J. Clin. Rheumatol., vol. 11. pp. S39-S44.
Ganeshan et al., 2014, "Metabolic Regulation of Immune Responses", Ann. Rev. Immunol., vol. 32, pp. 609-634.
Garcia-Carbonnell et al., 2016, "Critical Role of Glucose Metabolism in Rheumatoid Arthritis Fibroblast-like Synoviocytes", Arthritis Rheumatol., vol. 68, No. 7, pp. 1614-1626.
Jiang et al., 2013, "Letm1, the mitochondrial Ca2+/H+ antiporter, is essential for normal glucose metabolism and alters brain function in Wolf—Hirschhorn syndrome", PNAS, E2249-E2254.
Jones et al., 2011, "Osteoimmunology at the nexus of arthritis, osteoporosis, cancer, and infection", J. Clin. Invest., vol. 121, pp. 2534-2542.
Jung et al., 2014, "Cytokine-mediated bone destruction in rheumatoid arthritis", J. Immunol. Res., vol. 2014, Article ID: 263625, pp. 1-15.
Kang et al., 2015, "Combinations of kinase inhibitors protecting myoblasts against hypoxia", PLOS, PLoS One 10(6): e0126718, pp. 1-16.
Karsenty et al., 2002, "Reaching a genetic and molecular understanding of skeletal development", Dev. Cell., vol. 2, pp. 389-406.
Klareskog et al., 2006, "Mechanisms of disease: Genetic susceptibility and environmental triggers in the development of rheumatoid arthritis," Nat. Clin. Pract. Rheumatol., vol. 2, pp. 425-433.
Kleyer et al., 2014, "Arthritis and bone loss: a hen and egg story", Curr. Opin. Rheumatol., vol. 26, No. 1, pp. 80-84.
Koppenol et al., 2011, "Otto Warburg's contributions to current concepts of cancer metabolism", Nat. Rev. Cancer, vol. 11, No. 5, pp. 325-337.
Lebleu et al., 2014, "PGC-1α mediates mitochondrial biogenesis and oxidative phosphorylation in cancer cells to promote metastasis", Nat. Cell Biol., vol. 16, pp. 992-1003.
Long, 2012, "Osteoimmunology: the expanding role of immunoreceptors in osteoclasts and bone remodeling", Bone Key Rep., vol. 1, Article No. 59, pp. 1-7.
Malemud et al., 2010, "Differential activation of JAK enzymes in rheumatoid arthritis and autoimmune disorders by proinflammatory cytokines: potential drug targets", International Journal of Interferon, Cytokine and Mediator Research, vol. 2, pp. 97-111.
Malemud et al., 2011, "Myeloid-related protein activity in Rheumatoid Arthritis", International Journal of Inflammation, Article ID: 580295, pp. 1-6.
Mantovani, 2009, "Inflaming metastasis", Nature, vol. 457, pp. 36-37.
Mcinnes et al., 2011, "The pathogenesis of rheumatoid arthritis", N. Engl. J. Med., vol. 365, No. 23, pp. 2205-2219.
Nutsch et al. 2011, "When T cells run out of breath: the HIF-1α story", Cell, vol. 146, No. 5, Sep. 2, 2011, pp. 673-674.
Ogata et al., 2012, "Safety and Efficacy of Tocilizumab for the Treatment of Rheumatoid Arthritis", Clin. Med. Insights: Arthritis and Musculoskeletal Disord., vol. 5, pp. 27-42.
Perl, 2017, "Metabolic Control of Immune System Activation in Rheumatic Diseases", Arthritis & Rheumatology, vol. 69, No. 12, pp. 2259-2270.
Philchenkov et al., 2004, "Caspases and cancer: mechanisms of inactivation and new treatment modalities", Exp. Oncol., vol. 26, pp. 82-97.
Pollak, 2014, "Repurposing biguanides to target energy metabolism for cancer treatment", Nat. Med., vol. 20, No. 6, pp. 591-593.
Procaccini et al., 2012, "Intracellular metabolic pathways control immune tolerance", Trends Immunol., vol. 33, No. 1, pp. 1-7.
Roodman, 2006, "Regulation of osteoclast differentiation", Ann. N. Y. Acad. Sci., vol. 1068, pp. 100-109.
Scott et al., 2010, "Rheumatoid Arthritis", Lancet, vol. 376, pp. 1094-1108.
Smolen et al., 2015, "Rheumatoid arthritis therapy reappraisal: strategies, opportunities and challenges", Nat. Rev. Rheumatol., vol. 11, pp. 276-289.
Spies et al., 2012, "Energy metabolism and rheumatic diseases: from cell to organism", Arthritis Research & Therapy, vol. 14, Article No. 216, pp. 1-10.
Steger et al., 2011, "Denosumab for the treatment of bone metastases in breast cancer: evidence and opinion", Ther. Adv. Med. Oncol., vol. 3, pp. 233-243.
Straub et al., 2010, "Energy regulation and neuroendocrine-immune control in chronic inflammatory diseases", J. Intern. Med., vol. 267, No. 6, pp. 543-560.
Sun, 2010, "Mechanical loading, cartilage degradation and arthritis", Annals of the New York Academy of Sciences, vol. 1211, pp. 37-50.
Takayanagi, 2009, "Osteoimmunology and the effects of the immune system on bone", Nature Reviews Rheumatology, vol. 5, pp. 667-677.
Tanaka et al., 2003, "Signal transduction pathways regulating osteoclast differentiation and function", J. Bone Miner. Metab., vol. 21, pp. 123-133.
Weaver, et al., 2003, "Cytochrome p450 inhibition using recombinant proteins and mass spectrometry/multiple reaction monitoring technology in a cassette incubation", Drug Metabolism and Disposition, vol. 31, No. 7, pp. 955-966.
Weinberg et al., 2010, "Mitochondrial metabolism and ROS generation are essential for Kras-mediated tumorigenicity", Proc. Natl. Acad. Sci., vol. 107, No. 19, pp. 8788-8793.
Weyand et al., 2017, "Immunometabolism in early and late stages of rheumatoid arthritis", Nature Reviews Rheumatology, vol. 13, pp. 291-301. Advance online publication pp. 1-11.
Weyand et al., 2017, "Metabolic Signatures of T-cells and Macrophages in Rheumatoid Arthritis", Curr. Opin. Immunol., vol. 46, pp. 112-120.
Wheaton et al., 2014, "Metformin inhibits mitochondrial complex I of cancer cells to reduce tumorigenesis", eLife, vol. 3, e02242, pp. 1-18.
Yang et al., 2013, "Phosphofructokinase deficiency impairs ATP generation, autophagy, and redox balance in rheumatoid arthritis T cells", J. Exp. Med., vol. 210, pp. 2119-2134.
Great Britain Search Report for GB1813312.4 dated Feb. 25, 2019 (unpublished), 4 pages.
International Search Report for PCT/EP2019/071917, dated Oct. 17, 2019, 3 pages.
Written Opinion of ISA for PCT/EP2019/071917, dated Feb. 16, 2021, 5 pages.
International Preliminary Report on Patentability for PCT/EP2019/071917, dated Feb. 16, 2021, 6 pages.

* cited by examiner

US 11,834,414 B2

1-METHYL-4-[(4-PHENYLPHENYL) SULFONYLMETHYL]CYCLOHEXYANOL AND 1-METHYL-4-[[4-(2-PYRIDYL)PHENYL] SULFONYLMETHYL]CYCLOHEXANOL COMPOUNDS AND THEIR THERAPEUTIC USE

RELATED APPLICATION

This application claims priority to and is a 35 U.S.C. § 371 national phase application of PCT/EP2019/071917 (W02020/035560A1), filed on Aug. 15, 2019. PCT/EP2019/ 071917 is related to, and claims priority to, Great Britain patent application number 1813312.4, filed Aug. 15, 2018, the contents of which are incorporated herein by reference in their entirety.

TECHNICAL FIELD

The present invention pertains generally to the field of therapeutic compounds. More specifically the present invention pertains to certain substituted 1-methyl-4-[(4-phenylphenyl)sulfonylmethyl]cyclohexanol and 1-methyl-4-[[4-(2-pyridyl)phenyl]sulfonylmethyl]cyclohexanol compounds (collectively referred to herein as CHMSA compounds) that are useful, for example, in the treatment of disorders (e.g., diseases) including, e.g., multiple myeloma, diffuse large B-cell lymphoma, acute myeloid leukemia, eosinophilic leukemia, glioblastoma, melanoma, ovarian cancer, chemotherapy resistant cancer, radiation resistant cancer, inflammatory arthritis, rheumatoid arthritis, psoriatic arthritis, psoriasis, ulcerative colitis, Crohn's disease, systemic lupus erythematosus (SLE), lupus nephritis, asthma, chronic obstructive pulmonary disease (COPD), non-alcoholic fatty liver disease (NAFLD), non-alcoholic steatohepatitis (NASH), autoimmune hepatitis, hidradenitis suppurativa, etc. The present invention also pertains to pharmaceutical compositions comprising such compounds, and the use of such compounds and compositions, for example, in therapy.

BACKGROUND

A number of publications are cited herein in order to more fully describe and disclose the invention and the state of the art to which the invention pertains. Each of these publications is incorporated herein by reference in its entirety into the present disclosure, to the same extent as if each individual publication was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cellular Metabolism

Cellular metabolism is a set of complex sequences of biochemical reactions which occur in the cells of living organisms to maintain life. Each sequence of reactions is known as a metabolic pathway, and these pathways act in concert to provide energy, the synthesis of new molecules and the breakdown and removal of other molecules within the cell. One key metabolic pathway is known as oxidative phosphorylation, the process by which energy, in the form of adenosine triphosphate (ATP), is formed by the transfer of electrons through carriers known as electron transport complexes. Other examples of metabolic pathways include glycolysis, the process by which glucose is broken down to release ATP and beta oxidation, the process by which fatty acids are broken down.

Glycolysis occurs in the cytoplasm. Glucose, the substrate for glycolysis, is converted to pyruvate through a series of ten-enzyme-catalyzed reactions. This pyruvate is, in turn, converted to lactic acid, the end product of glycolysis. ATP is directly formed through phosphate transfer from substrate to ATP, or substrate phosphorylation. Some of the pyruvate enters the tricarboxylic (TCA) cycle, whereas most of the end product, lactic acid, is flushed out of the cell. Oxidative phosphorylation occurs in the mitochondria of cells. Glutamine, glucose, or fatty acids are the suppliers for the electron transport chain and ATP is formed through a series of redox reactions involving oxygen as the final electron acceptor. The series of oxidative reduction reactions occur through the four complexes of the electron transport chain, which then generates an electrochemical gradient in the inner mitochondrial membrane. Protons return to the mitochondrial matrix through ATP synthase, and this process is coupled to ATP synthesis. A total of 36 mol of ATP are produced per 1 mol of glucose.

The metabolic properties of certain types of cells can vary greatly. For example, energy production in cancer cells is abnormally skewed towards aerobic glycolysis (a process known as the Warburg Effect), as well as showing increased fatty acid synthesis and increased rates of metabolism of the amino acid glutamine. In addition, changes in the metabolism of cancer cells may render them resistant to therapy and several studies have shown that chemoresistance, at least in part, is driven by mitochondrial metabolism and oxidative phosphorylation, whilst high levels of ATP in cancer cells can lead to increased efflux of chemotherapeutic agents and promote hypoxia-associated drug resistance.

Similar to cancer cells, immune cells show changes in metabolism depending on their activation status and the stimulatory signals they receive. The field of immunometabolism is the investigation of the interface between immunology and metabolism as it relates to both the governance of the function of immune cells, and their role in chronic inflammatory disease and cancer, among others.

Chronic Inflammatory Disease

Inflammation is the immune response of tissues due to bodily injury. Acute inflammation is a normal, protective response that protects and heals the body following physical injury or infection, characterised by heat, swelling, and redness at the site of the injury. However, if inflammation persists for a prolonged period, it becomes chronic. Chronic inflammation is a hallmark of, and a contributing factor to, a range of disease conditions including rheumatoid arthritis, inflammatory bowel disease, systemic lupus erythematosus, multiple sclerosis and psoriasis.

The inflammatory process is complex and involves a biological cascade of molecular and cellular signals that alter physiological responses. At the site of the injury, cells release molecular signals such as cytokines and interleukins that cause a number of changes in the affected area including dilation of blood vessels, increased blood flow, increased vascular permeability, invasion by leukocytes (white blood cells), and exudation of fluids containing proteins like immunoglobulins (antibodies). Several different types of leukocytes, including granulocytes, monocytes, and lymphocytes, are involved in the inflammatory cascade. However, chronic inflammation is primarily mediated by monocytes and long-lived macrophages; monocytes mature into macrophages once they leave the bloodstream and enter tissues. Macrophages engulf and digest microorganisms, foreign invaders, and senescent cells and macrophages release several different chemical mediators, including Tumour Necrosis Factor-alpha (TNFα), interleukins (e.g., IL-1, IL-6, IL-12 and IL-23) and prostaglandins that perpetuate the inflammatory response. At later stages, other cells, including lymphocytes, invade the affected tissues. Recent evidence has shown that many aberrant immune responses occur as a result of disruption to metabolic processes and that altering cellular metabolism may either enhance or reduce immune responses. Alterations in metabolism in monocytes, macrophages and lymphocytes (immunometabolism) are hence crucial in driving disease.

There is thus a common pathology underlying a wide variety of chronic inflammatory conditions. In addition, features of chronic inflammation are also observed in other diseases including cancer and metabolic diseases such as obesity, atherosclerosis, and diabetes.

One of the most common chronic inflammatory conditions is rheumatoid arthritis (RA), a condition which affects up to 2% of the population worldwide. Although it is a complex disease, there are a number of physiological, cellular, and biochemical factors associated with the progression of RA that are common to a range of other diseases, including those with a component of autoimmunity (e.g., multiple sclerosis), inflammation (e.g., atherosclerosis and cancer), bone loss (e.g., osteoporosis) and proliferation (e.g., haematological malignancies). This makes the understanding of RA important not only for the study of a much broader range of diseases, but also suggests that pharmaceutical agents that work via modification of these common processes may have utility beyond RA. The latter is borne out by clinical practice where RA drugs have been shown to have broad utility across a variety of other conditions.

Rheumatoid Arthritis and Related Autoimmune/Inflammatory Diseases

Rheumatoid arthritis (RA) is an autoimmune disorder characterized by chronic inflammation of the synovial lining of multiple joints coupled to progressive joint degradation. RA commonly affects the joints of the wrist and hands and may also affect the elbows, shoulders, hips, neck and knees leading to severe pain and disability (see, e.g., Scott et al., 2010). The World Health Organisation (WHO) Global Burden of Disease 2010 update estimated that 23.7 million people suffer from RA, with incidence rising due to the association between the condition and increasing age.

The exact cause of RA, as for all the autoimmune disorders, remains unclear, although possible triggers include reduced self-tolerance, an abnormal response to environmental factors, infectious agents, and hormonal stimulus (see, e.g., Klareskog et al., 2006; Firestein et al., 2005). A central feature of the condition is the dysregulation of innate and adaptive immunity, with an imbalance in pro-inflammatory and anti-inflammatory cytokines and a change in the balance between osteoclast-mediated degradation and osteoblast-mediated deposition in the bone marrow compartment (see, e.g., Kleyer et al., 2014; Jung et al., 2014).

At the cellular level, development of RA usually commences with T-cells infiltrating the synovial membrane lining the affected joint; this then leads to the activation of monocytes, macrophages and synovial fibroblasts by way of cell-cell contact and the subsequent release of various cytokines, including tumour necrosis factor-alpha (TNFα) and pro-inflammatory interleukins such as IL-1, IL-6, IL-12 and IL-23 (see, e.g., Astry et al., 2011). These pro-inflammatory cytokines are then instrumental in orchestrating several complex signal transduction cascades, including the NFκB, Interferon Regulatory Factor (IRF), Toll-like receptor (TLR), and Jak/STAT pathways (see, e.g., Malemud et al., 2010) which lead to the induction of genes coding for various products that propagate the inflammatory response and also promote tissue destruction. These products include tissue-degrading enzymes such as collagenases, matrix metalloproteinases (MMPs), cathepsins, and other pro-inflammatory factors such as selectins, integrins, leukotrienes, prostaglandins, chemokines, and other cytokines (see, e.g., McInnes et al., 2011; Chimenti et al., 2015). In addition, these cells also increase the production of MMPs, leading to the degradation of the extra cellular matrix and loss of cartilage within the joint (see, e.g., Sun, 2010), a process that also involves a specialised class of cells known as osteoclasts and a factor known as Receptor Activator of Nuclear Factor Kappa-B Ligand (RANKL) (see, e.g., Takayanagi, 2009).

RANKL is an essential factor for the generation of osteoclasts, and upregulated RANKL-production leads to increased osteoclast differentiation and ultimately bone destruction (see, e.g., Long et al., 2012). The inflammatory response in RA leads to the accumulation of lymphocytes, dendritic cells, and macrophages, all operating locally to produce cytokines and other pro-inflammatory mediators such as TNFα and IL-6 which further potentiate the effects of RANKL on bone destruction. In addition, the inflammatory cascade leads to the hyperplasia of synoviocytes (see, e.g., Takayanagi, 2009), which in turn leads to the thickening and vascularisation of the synovium into a destructive and aggressive tissue known as a pannus. The pannus contains both osteoclasts, which destroy bone, and metalloproteinases, which are involved in the destruction of cartilage. As such, the RANKL axis is critical to the progression and pathology of RA as well as to the osteoimmune system (the interplay between the immune and bone systems), which is central to the pathology of a number of different disease conditions.

The Role of Immune Metabolism in RA

All cells produce adenosine triphosphate (ATP), a high-energy molecule which acts as fuel, and synthesize macromolecules to maintain their basic cellular functions, whether they are active, replicating, or quiescent (see, e.g., Spies et al., 2012). These bioenergetic needs are met by interconnected metabolic pathways within the cell: glycolysis (the first step in the breakdown of glucose), the tricarboxylic acid cycle (a series of reactions releasing stored energy from carbohydrates, fats, and proteins), and oxidative phosphorylation (the process of forming ATP by the transfer of electrons). Changes in these pathways drive the effector functions of immune cells from lymphocytes to monocytes and macrophages and dendritic cells, and are also able to modulate cell fate.

In chronic inflammatory diseases including RA, very large amounts of energy (up to 2,000 kJ/day) are consumed by the activation of the immune system (see, e.g., Straub et al., 2010). This energy is used, at least in part, by the immune system to maintain the chronic inflammatory state in response to environmental signals (see, e.g., Procaccini et al., 2012; Nutsch et al., 2011) and the interplay between immunology and metabolism hence plays a central role in the pathophysiology of chronic inflammatory diseases (see, e.g., Perl, 2017; Ganeshan et al., 2014).

Several metabolic changes in cells that participate in inflammation are seen in immune cells in RA (see, e.g., Weyand et al., 2017a). Chronic stimulation and the synovial microenvironment alters T cell and macrophage metabolism in RA. For example, T cells from patients with RA show reduced expression of 6-phosphofructo 2-kinase/fructose-2, 6-bisphosphatase 3 (PFKFB3), an enzyme involved in ATP generation, and autophagy (see, e.g., Yang et al., 2013), whilst macrophages from patients with RA produce higher levels of ATP than cells from healthy individuals (see, e.g., Weyand et al., 2017b). In addition to direct changes in cells, the hypoxic environment in the RA synovium (see, e.g., Fearon et al., 2016) creates a chronic mitochondrial hyperpolarization, which is also seen in systemic lupus erythematosus (SLE) and in fibroblast-like synoviocytes from RA patients; there is a shift to glycolysis compared with cells from non-inflammatory settings (see, e.g., Garcia-Carbonnel et al., 2016). Thus, there is great potential for agents that modulate ATP or alter immune cell metabolism to be useful in the treatment of chronic inflammatory diseases such as RA, SLE, inflammatory bowel disease (IBD), psoriasis, and atherosclerosis.

Cellular Metabolism and Cancer

Cellular energy in the form of ATP is generated through two major pathways: mitochondrial oxidative phosphorylation and cytoplasmic glycolysis. In normal cells, glycolysis is followed by oxidation of pyruvate using the oxidative phosphorylation machinery of the mitochondria and this is the predominant pathway to generate ATP. However, in cancer cells glycolysis is upregulated and lactic acid is fermented in the cytosol of the cell in a process known as the Warburg effect. Thus, reprogrammed metabolism is a hallmark of cancer, and facilitates the growth and proliferation of cells under stressed conditions.

Mitochondrial metabolism is also important for the generation of building blocks required for cancer cell proliferation and cancer cells also require mitochondrial oxidative metabolism to maintain their redox balance. The majority of cancer cells display functional mitochondria and are able to generate ATP through mitochondrial metabolism (see, e.g., Koppenol, 2011). Depending on the cellular context, mitochondria substantially contribute to the generation of cellular reactive oxygen species (ROS) as a natural by-product of mitochondrial ATP generation. ROS formation occurs due to the incomplete reduction of molecular oxygen and in cancer cells, ROS have been shown to promote tumor development and progression by inducing oncogenic signalling, genetic instability and DNA mutations (see, e.g., Weinberg et al., 2010). However, when ROS production exceeds the capacity of intracellular ROS-detoxifying systems, cellular toxicity results. As such, cancer cells have to tightly control their metabolic machinery in order to maintain the balance between ROS generation and scavenging.

Changes in cellular and mitochondrial metabolism are thus critical for the growth and proliferation of tumours. Indeed, mitochondrial biogenesis and the associated increases in oxidative phosphorylation have been shown to promote tumour metastasis (see, e.g., LeBleu et al., 2014), whilst reducing oxidative phosphorylation has also been proposed as a means to target cancer stem cells (see, e.g., Fiorillo et al., 2016). Data also shows that targeting components of the mitochondrial electron transport chain may have anti-cancer effects. For example, complex I inhibition by the anti-diabetic metformin inhibits tumorigenesis (see, e.g., Evans et al., 2005; Pollak et al., 2014; Wheaton et al., 2014; Bridges et al., 2014) whilst novel small molecule inhibitors of electron transport also show anti-tumor activity in xenograft models of cancer (see, e.g., Ellinghaus et al., 2013). Altering cellular metabolism is thus emerging as a means by which to prevent cancer growth and progression, as well as to overcome resistance to chemotherapy and prevent metastasis.

The Osteoimmune System and Bone Disorders

The osteoimmune system is a term for the combined and related interplay between the immune system and the skeletal system.

Under normal physiological conditions, the skeletal system provides support, mobility, protection for vital organs, and a mineral reservoir for calcium and phosphate. In order to achieve and adapt to these functions, the skeleton exists in a dynamic equilibrium characterized by continuous osteoclast-mediated bone resorption and osteoblast-mediated bone deposition (see, e.g., Karsenty et al., 2002). This biological process has been termed bone "remodelling" and occurs in coupled fashion with osteoblasts producing the key osteoclast differentiation factors, including RANKL, described above, and osteoclasts promoting bone formation by producing osteoblastic mediators as they degrade bone.

Both innate and adaptive immune cells exert effects on osteoclasts and osteoblasts through a variety of cell-surface and secreted mediators (see, e.g., Takayanagi, 2009). Activation of the RANKL receptor (RANK) on osteoclast precursors starts a cascade of transcriptional changes which results in the formation of osteoclasts and the expression of the machinery needed for bone resorption including molecules needed for attachment to bone, acid secretion, and proteolysis. Many of the transcription factors important for osteoclast differentiation are key regulators of immune responses, such as NFκB and nuclear factor of activated T cells c1 (NFATc1) and this process is also potentiated by factors involved in inflammation such as TNFα and IL-6.

In addition to its critical role in the progression and pathogenesis of RA, the osteoimmune system plays a critical role in a number of other diseases including osteoporosis and other bone disorders and cancer (see, e.g., Dallas et al., 2011).

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis also arises in association with inflammatory diseases such as rheumatoid arthritis, endocrine diseases such as thyrotoxicosis, and with certain drug treatments such as treatment with glucocorticoids. Indeed, osteoporosis-related fragility fractures represent one of the most important complications that may occur in patients with rheumatic diseases such as RA, systemic lupus erythematosus, and ankylosing spondylitis.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

IL-6, TNFα, and RANKL signalling have been shown to play a major role in osteoclast over-activity and a consequent increase in bone loss (see, e.g., Tanaka et al., 2003; Roodman, 2006). The use of drugs which affect these pathways have been validated by the completion of clinical trials of the monoclonal antibody against RANKL, AMG-162 (Denosumab®, Amgen), for the treatment of osteoporosis/multiple myeloma, as well as by an increasing body of evidence that shows that the anti-TNFα and anti-IL-6 therapies also prevent bone loss in arthritic diseases (see, e.g., Ogata et al., 2012; Billiau, 2010).

The Osteoimmune System and Cancer

Many types of cancer affect bone. Cancer-associated bone disease can be manifest by the occurrence of hypercalcaemia or the development of osteolytic and/or osteosclerotic metastases. Increased osteoclastic bone resorption plays a key role in the pathogenesis of both conditions. Whilst almost any cancer can be complicated by bone metastases, the most common sources are multiple myeloma, breast carcinoma, and prostate carcinoma. The most common tumours associated with hypercalcaemia are multiple myeloma, breast carcinoma, and lung carcinoma.

As described above, RANK/RANKL signalling is essential for osteoclast formation and bone resorption that occurs during skeletal remodelling. While physiological levels of RANK/RANKL signalling stimulate the proliferation and cell survival of mammary epithelial cells, aberrant RANK/RANKL signalling in these tissues has recently been shown to influence the onset and progression of breast tumorigenesis and blocking RANKL signalling using denosumab (Xgeva®, Amgen) has been shown to be an effective in preventing the secondary complications of bone metastases, such as pathologic fracture, and hypercalcaemia in patients with breast cancer (see, e.g., Steger et al., 2011).

Therapies that block RANK/RANKL signalling may also decrease the ability of osteotropic cancers to metastasize to bone. Signalling through RANK on the surface of human epithelial tumour cells as well as melanoma cells has been shown to induce a chemotactic response in these tumour cells whilst in a murine model of melanoma metastasis, therapeutic treatment of mice with osteoprotegrin, which neutralizes the RANKL receptor, RANK, significantly reduced tumour burden within the bones but not other organs.

In addition to a role for RANKL in cancer, there is growing evidence that activation of NFκB via molecules such as TNFα can play a major role in the promotion and progression of both haematological malignancies, such as myeloma and lymphomas, and solid tumours, such as breast, prostate, and lung cancer (see, e.g., Baud et al., 2009). There is also rising awareness of the role and importance of inflammation and the osteoimmune system in cancer and in the development of resistance to radiotherapy and to chemotherapeutic agents. Furthermore, it has been suggested that inflammation is in fact one of the basic hallmarks of cancer (see, e.g., Mantovani, 2009). Improving the efficacy of anti-cancer treatments by prevention of NFκB activation is therefore a promising strategy to augment existing therapeutic regimes and is currently under investigation, most notably for the treatment of multiple myeloma.

Defects in the normal apoptotic pathways are also implicated in the development and progression of tumour cell growth as well as in inflammation. Apoptosis (programmed cell death) plays a key role in the removal of abnormal cells; defects in the signalling cascades, which would normally lead to its induction, play a key role in oncogenesis. Radiotherapy and many chemotherapeutic agents act by causing cellular damage, which would normally induce apoptosis; defects in the pathway will therefore also reduce the effectiveness of such agents. The most important effector molecules in the signalling pathway leading to apoptosis are known as the caspases, which may be triggered by a number of stimuli, including TNFα binding to its receptor. Mutations in the genes which encode for the caspases have been found in a number of tumour types, including gastric, breast, renal cell, and cervical cancers as well as commonly in T-cell lymphoblastic lymphoma and basal cell ameloblastomas (see, e.g., Philchenkov et al., 2004). Compounds which activate caspases, and thus sensitise cells to apoptosis, would be highly effective as cancer therapies either as single agents or in enhancing the effectiveness of existing cancer chemotherapy and radiotherapy.

Agents that Modulate Cellular and Immune Metabolism, Prevent Inflammation, and Modify the Osteoimmune System The inventors have identified new compounds which, for example, modulate cellular and immune metabolism, prevent inflammation, and modify the osteoimmune system, and accordingly are useful in treatment of corresponding disorders, as described herein.

Without wishing to be bound by any particular theory, the inventors believe that this action may be via a mechanism that involves modulating cellular, and immune cell metabolism by reducing cellular ATP, with consequent effects on inflammatory signalling.

Known Compounds

Greig et al., 2010a, describes certain biphenyl-4-sulfonic acid amides for the treatment of inflammation and/or joint destruction and/or bone loss; disorders mediated by excessive and/or inappropriate and/or prolonged activation of the immune system; inflammatory and autoimmune disorders, for example, rheumatoid arthritis, psoriasis, psoriatic arthritis, chronic obstructive pulmonary disease (COPD), atherosclerosis, inflammatory bowel disease, and ankylosing spondylitis; disorders associated with bone loss, such as bone loss associated with excessive osteoclast activity in rheumatoid arthritis, osteoporosis, cancer-associated bone disease, and Paget's disease; and cancer, such as a haematological malignancy and a solid tumour. Examples of compounds shown therein include the following:

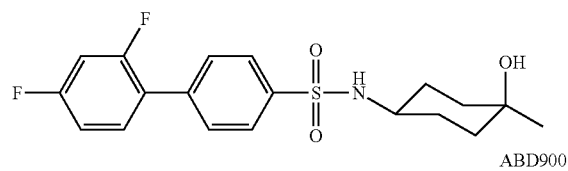

ABD899

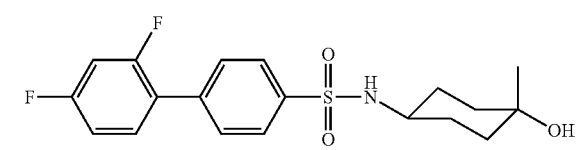

ABD900

Patel et al., 2014 and Patel et al., 2016 describe compounds of the following formulae for the treatment of inflammation and/or joint destruction and/or bone loss; disorders mediated by excessive and/or inappropriate and/or prolonged activation of the immune system; inflammatory and autoimmune disorders, for example, rheumatoid arthritis; psoriasis; psoriatic arthritis; chronic obstructive pulmonary disease (COPD); asthma; atherosclerosis; inflammatory bowel disease; ankylosing spondylitis; multiple sclerosis; systemic lupus erythematosus; Sjogren's syndrome; a disorder associated with bone loss, such as bone loss associated with excessive osteoclast activity in rheumatoid arthritis, osteoporosis, cancer-associated bone disease, or Paget's disease; cancer, such as a haematological malignancy, such as multiple myeloma, leukemia, or lymphoma, or a solid tumour cancer, such as bladder cancer, breast cancer (female and/or male), colon cancer, renal cell carcinoma, kidney cancer, lung cancer, pancreatic cancer, gastric cancer, prostate cancer, brain cancer, skin cancer, thyroid cancer, basal cell ameloblastoma, or melanoma; a disorder associated with fibrosis, such as systemic sclerosis or scleroderma; or a rare vasculitide, such as Behçet's disease.

HMC-C-01

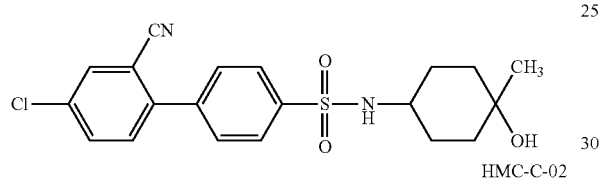

HMC-C-02

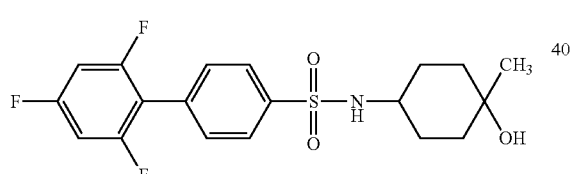

HMC-C-03

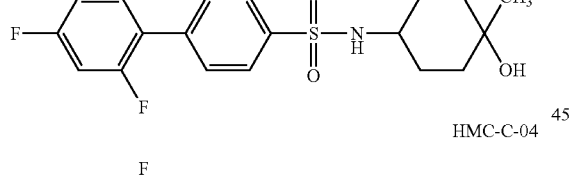

HMC-C-04

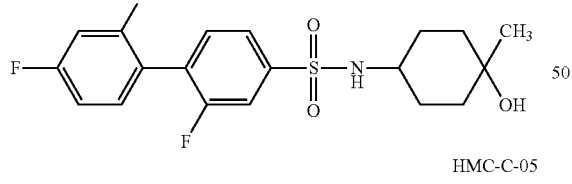

HMC-C-05

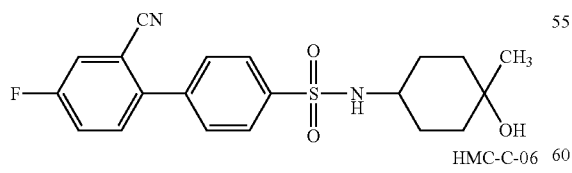

HMC-C-06

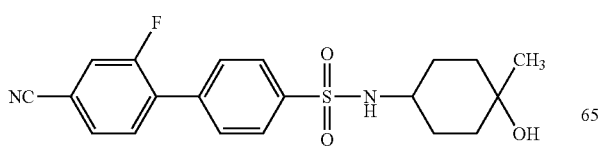

HMC-C-07

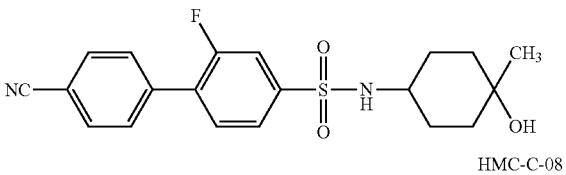

HMC-C-08

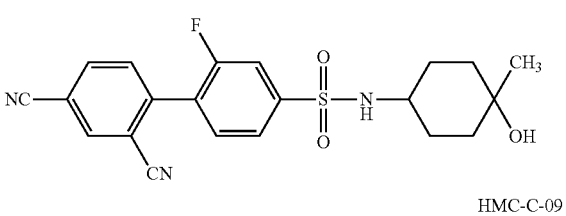

HMC-C-09

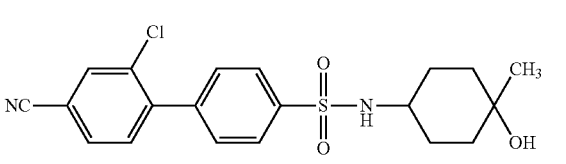

HMC-C-10

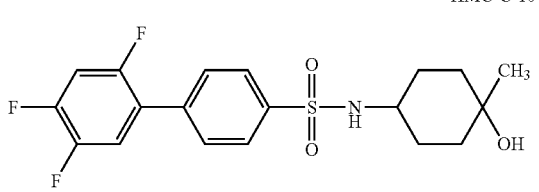

HMC-C-11

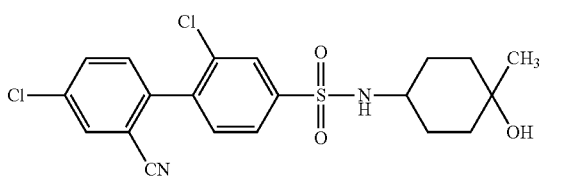

HMC-N-01

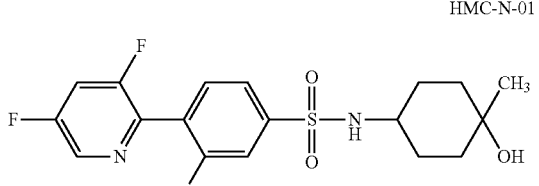

HMC-N-02

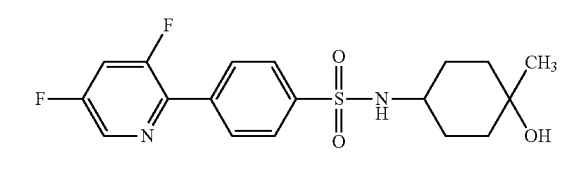

HMC-N-03

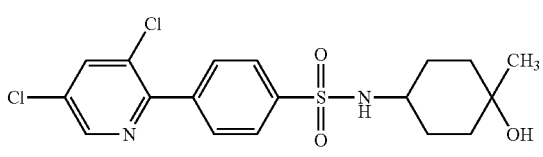

-continued

HMC-N-04

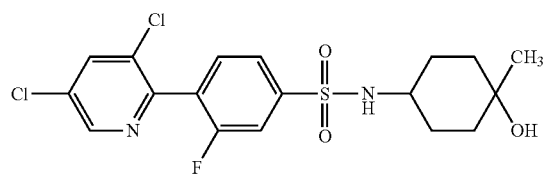

HMC-N-05

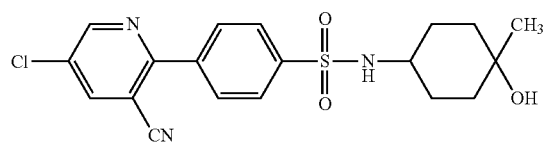

New Compounds with Improved Properties

In addition to having excellent biological properties, e.g., similar to or better than the corresponding sulfonamide compounds (for example, as described in Greig et al., 2010a, Patel et al., 2014, and Patel et al., 2016), the CHMSA compounds described herein have the additional advantage of forming little or none of an undesirable sulphonamide metabolite.

For example, as demonstrated by the data presented herein, the corresponding sulfonamide compounds (for example, reference compound HMC-C-01-A) give rise to a biaryl sulphonamide metabolite (for example, MET-001) which has a long half-life and therefore persists in the circulation. In addition, the biaryl sulphonamide metabolite acts as an inducer of metabolism in rats, which complicates the assessment of toxicity in rodents, and which in turn may impact the developability of the compounds for human use. Therefore, compounds with a lower propensity to form a biaryl sulphonamide metabolite have a greater potential developability for human use.

As demonstrated by the data presented herein, the CHMSA compounds show greatly reduced propensity to form a biaryl sulphonamide metabolite, and so have greatly increased suitability for development for human use, as compared to the known sulfonamide compounds.

In addition, the CHMSA compounds described herein have other advantageous properties, equal to and often better than the properties of the corresponding sulfonamide compounds, including, for example, improved metabolism and cardiovascular safety.

If a drug is to be used in the clinic, it must have a suitable safety and efficacy profile. It must show adequate acute safety to allow dosing to humans without the expectation of serious general side-effects. A clinically acceptable drug should also not inhibit hERG, an ion-channel which, when inhibited, can cause a fatal heart disorder known as long QT syndrome. Alongside these safety properties, the drug must have minimal interaction potential with the enzymes that metabolise the drug within the body in order to: allow robust delivery of the drug; to minimise the potential for the drug to influence the metabolism of other drugs, so-called drug-drug interaction; and to prevent serious adverse reactions that can be caused by drug-drug interactions.

The CHMSA compounds described herein are substantially protected against inhibition of the human Ether-à-go-go related gene (hERG), which represents a major cardiovascular safety liability.

The CHMSA compounds described herein also show significant advantages in minimising potential drug-drug interactions due to their in vitro metabolic profile and their reduced propensity to form the metabolism inducing sulphonamide metabolite, e.g., MET-001.

The reduction of toxicological properties (adverse effects) of a drug is a developmental barrier of equal challenge and importance as compared to the optimization of pharmacodynamics (action of the drug on the body) and pharmacokinetic (action of the body on the drug) properties. The CHMSA compounds described herein provide substantial advantages as oral therapeutic agents (as compared to the known compounds) by improving cardiovascular safety and providing an improved metabolism profile with little or no change loss of potency against the biological target.

The CHMSA compounds described herein combine the required characteristics of agents for the treatment of, for example, autoimmune/inflammatory conditions and cancer, as described herein.

SUMMARY OF THE INVENTION

One aspect of the invention pertains to certain substituted 1-methyl-4-[(4-phenylphenyl) sulfonylmethyl]cyclohexanol and 1-methyl-[[4-(2-pyridyl)phenyl]sulfonylmethyl]cyclohexanol compounds (collectively referred to herein as CHMSA compounds), as described herein.

Another aspect of the invention pertains to a composition (e.g., a pharmaceutical composition) comprising a CHMSA compound, as described herein, and a carrier, diluent, or excipient (e.g., a pharmaceutically acceptable carrier, diluent, or excipient).

Another aspect of the invention pertains to a method of preparing a composition (e.g., a pharmaceutical composition) comprising the step of mixing a CHMSA compound, as described herein, and a carrier, diluent, or excipient (e.g., a pharmaceutically acceptable carrier, diluent, or excipient).

Another aspect of the present invention pertains to a CHMSA compound, as described herein, for use in a method of treatment of the human or animal body by therapy, for example, for use a method of treatment of a disorder (e.g., a disease) as described herein.

Another aspect of the present invention pertains to use of a CHMSA compound, as described herein, in the manufacture of a medicament for treatment, for example, treatment of a disorder (e.g., a disease) as described herein.

Another aspect of the present invention pertains to a method of treatment, for example, of a disorder (e.g., a disease) as described herein, comprising administering to a patient in need of treatment a therapeutically effective amount of a CHMSA compound, as described herein, preferably in the form of a pharmaceutical composition.

Another aspect of the present invention pertains to a kit comprising (a) a CHMSA compound, as described herein, preferably provided as a pharmaceutical composition and in a suitable container and/or with suitable packaging; and (b) instructions for use, for example, written instructions on how to administer the compound.

Another aspect of the present invention pertains to a CHMSA compound obtainable by a method of synthesis as described herein, or a method comprising a method of synthesis as described herein.

Another aspect of the present invention pertains to a CHMSA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

Figure 1:
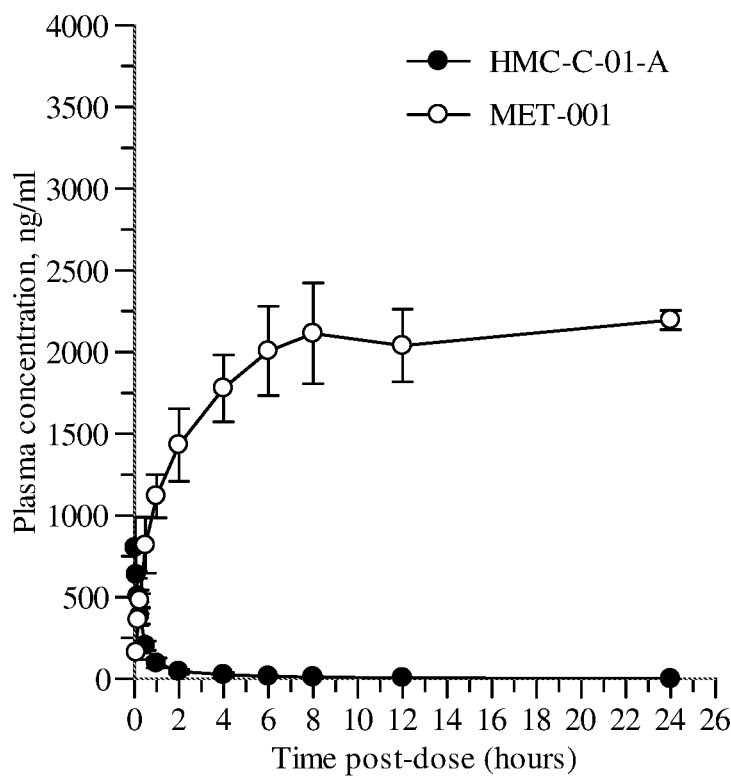
FIG. 1 is a graph of plasma concentration (ng/mL) versus time post-dose (hours) for reference compound HMC-C-01-A (filled circles) and the corresponding biaryl sulfonamide metabolite (MET-001) (open circles), as obtained using the methods described herein. The metabolite was formed in large quantities and accumulated over time.

One aspect of the present invention relates to certain cyclohexylmethylsulfonylaryl compounds.

More particularly, the compounds are certain 1-methyl-4-[arylsulfonylmethyl]cyclohexanol compounds that are related to the following biphenyl and pyridyl-phenyl compounds:

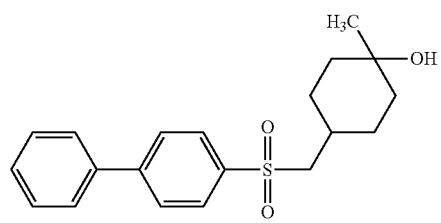

1-methyl-4-[(4-phenylphenyl)sulfonylmethyl]cyclohexanol

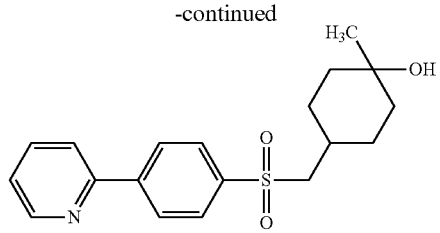

1-methyl-4-[[4-(2-pyridyl)phenyl]sulfonylmethyl]cyclohexanol

Thus, one aspect of the present invention is a compound of the following formula, or a pharmaceutically acceptable salt or solvate thereof, wherein =X—, —$R^1$, —$R^2$, —$R^3$, —$R^4$, —$R^5$, and —$R^6$ are as defined herein (for convenience, collectively referred to herein as "1-methyl-4-[arylsulfonylmethyl]cyclohexanol compounds" and "CHMSA compounds"):

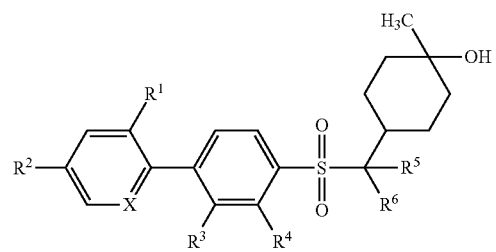

Conformation of the Cyclohexyl Ring

Note that the —OH and —$CH_3$ substituents on the cyclohexyl ring may be positioned "trans"/"cis" or "cis"/"trans", respectively, with respect to the rest of the molecule (that is, on the cyclohexyl ring to which they attached, with respect to the rest of the compound which is attached at the para position of the cyclohexyl ring).

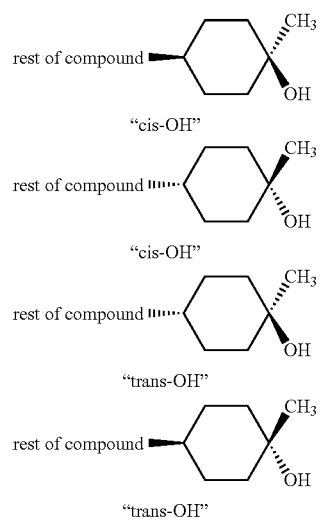

Unless otherwise indicated, it is intended that all such conformations are encompassed by a reference to a compound that does not specify a particular conformation.

Configuration of the Cyclohexyl Ring

Compounds in the "trans-OH" conformation may be indicated as follows:

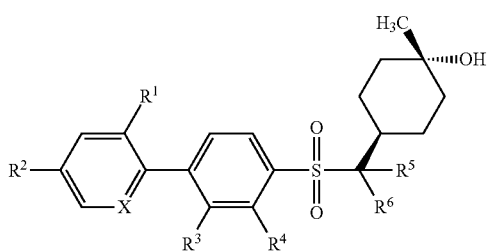

Compounds in the "cis-OH" conformation may be indicated as follows:

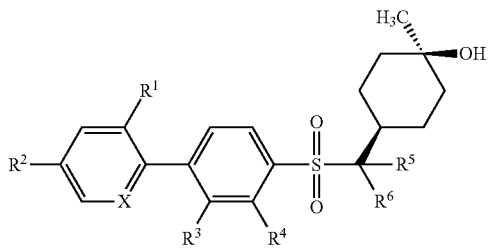

Note also that the cyclohexane ring may take a "chair", "boat", or "twist" conformation, and that interconversion between the conformations is possible. Again, unless otherwise indicated, it is intended that all such conformations (e.g., "chair", "boat", "twist", "OH is axial", "OH is equatorial", etc.) are encompassed by a reference to a compound that does not specify a particular conformation.

Configuration of Carbon to which —$R^5$ and —$R^6$ are Attached

Note that, depending upon the identity of the groups —$R^5$ and —$R^6$, the carbon atom to which they are attached may be chiral, and so may be in the (R) or (S) configuration.

Unless otherwise indicated, it is intended that all such configurations are encompassed by a reference to a compound that does not specify a particular configuration.

Compounds in one configuration may be indicated as follows:

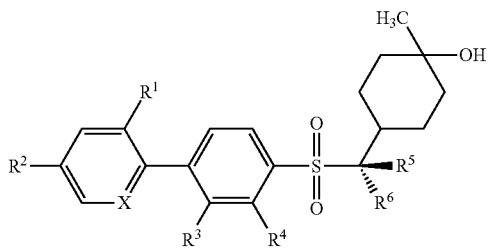

Compounds in the other configuration may be indicated as follows:

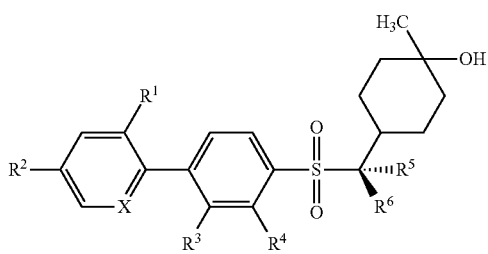

Conformation of the Biaryl Group

Note that, depending upon the identity of the groups —$R^1$, —$R^2$, —$R^3$, —$R^4$, and X, there may be free rotation about the single bond joining the two aryl groups.

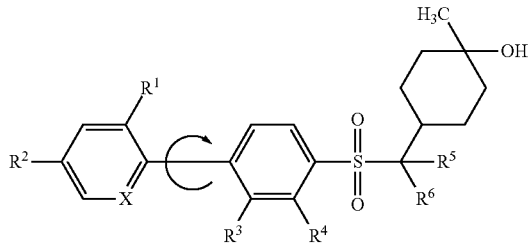

For the avoidance of doubt, it is intended that all such rotational conformations (i.e., different rotations about the single bond joining the two aryl groups) are encompassed. For example, the following formulae are intended to be equivalent and represent the same group:

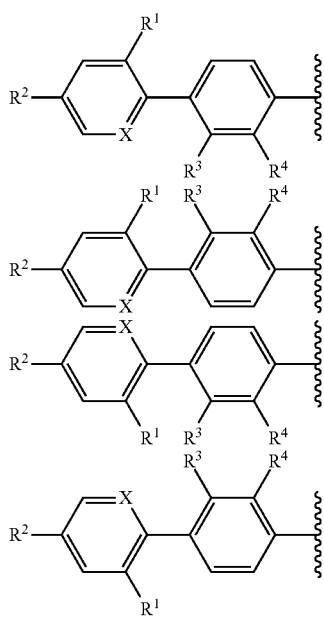

EMBODIMENTS

Some embodiments of the invention include the following:

(1) A compound of the following formula:

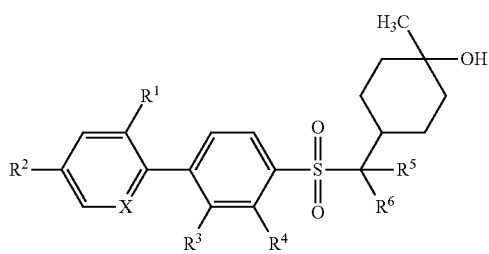

or a pharmaceutically acceptable salt or solvate thereof; wherein:
=X— is independently —CH= or —N=;
—$R^1$ is independently —H or —$R^{1X}$;
—$R^{1X}$ is independently —F, —Cl, —$R^{1C}$, —$R^{1F}$, or —CN;
—$R^{1C}$ is independently saturated linear or branched $C_{1-3}$alkyl;
—$R^{1F}$ is independently saturated linear or branched $C_{1-3}$fluoroalkyl;
—$R^2$ is independently —H or —$R^{2X}$;
—$R^{2X}$ is independently —F, —Cl, —$R^{2C}$, —$R^{2F}$, or —CN;
—$R^{2C}$ is independently saturated linear or branched $C_{1-3}$alkyl;
—$R^{2F}$ is independently saturated linear or branched $C_{1-3}$fluoroalkyl;
—$R^3$ is independently —H or —$R^{3X}$;
—$R^{3X}$ is independently —F, —Cl, —$R^{3C}$, —$R^{3F}$, or —CN;
—$R^{3C}$ is independently saturated linear or branched $C_{1-3}$alkyl;
—$R^{3F}$ is independently saturated linear or branched $C_{1-3}$fluoroalkyl;
—$R^4$ is independently —H or —$R^{4X}$;
—$R^{4X}$ is independently —F, —Cl, —$R^{4C}$, —$R^{4F}$, or —CN;
—$R^{4C}$ is independently saturated linear or branched $C_{1-3}$alkyl;
—$R^{4F}$ is independently saturated linear or branched $C_{1-3}$fluoroalkyl;
—$R^5$ is independently —H or —$R^{5X}$;
—$R^{5X}$ is independently —F, —$R^{5C}$, or —$R^{5F}$;
—$R^{5C}$ is independently saturated linear or branched $C_{1-3}$alkyl;
—$R^{5F}$ is independently saturated linear or branched $C_{1-3}$fluoroalkyl;
—$R^6$ is independently —H or —$R^{6X}$;
—$R^{6X}$ is independently —F, —$R^{6C}$, or —$R^{6F}$;
—$R^{6C}$ is independently saturated linear or branched $C_{1-3}$alkyl; and
—$R^{6F}$ is independently saturated linear or branched $C_{1-3}$fluoroalkyl;
or —$R^5$ and —$R^6$, taken together with the carbon atom to which they are attached, form saturated $C_{3-6}$cycloalkyl.

Unless otherwise indicated, where a compound is shown or described which has one or more chiral centres, and two or more stereoisomers are possible, all such stereoisomers are disclosed and encompassed, both individually (e.g., as isolated from the other stereoisomer(s)) and as mixtures (e.g., as equimolar or non-equimolar mixtures of two or more stereoisomers). For example, unless otherwise indicated, where a compound has one chiral centre, each of the (R) and (S) enantiomers are disclosed and encompassed, both individually (e.g., as isolated from the other enantiomer) and as a mixture (e.g., as equimolar or non-equimolar mixtures of the two enantiomers).

The term "saturated linear or branched $C_{1-3}$alkyl" means —$CH_3$ (methyl), —$CH_2CH_3$ (ethyl), —$CH_2CH_2CH_3$ (n-propyl), and —$CH(CH_3)_2$ (iso-propyl).

The term "saturated linear or branched $C_{1-3}$fluoroalkyl" means a saturated linear or branched $C_{1-3}$alkyl group substituted with one or more fluoro groups. Accordingly, $C_{1-3}$fluoroalkyl includes, e.g., —$CF_3$, —$CH_2F$, —$CHF_2$, —$CH_2CF_3$, —$CH_2CH_2F$, etc.

The term "saturated $C_{3-6}$ cycloalkyl" means cyclopropyl, cyclobutyl, cyclopentyl, and cyclohexyl.

The Group =X—
(2) A compound according to (1), wherein =X— is —CH=.
(3) A compound according to (1), wherein =X— is —N=.

The Group —$R^1$
(4) A compound according to any one of (1) to (3), wherein —$R^1$ is —$R^{1X}$.
(5) A compound according to any one of (1) to (3), wherein —$R^1$ is —H.

The Group —$R^{1X}$
(6) A compound according to any one of (1) to (5), wherein —$R^{1X}$, if present, is independently —F, —Cl, or —CN.
(7) A compound according to any one of (1) to (5), wherein —$R^{1X}$, if present, is —F.
(8) A compound according to any one of (1) to (5), wherein —$R^{1X}$, if present, is —Cl.
(9) A compound according to any one of (1) to (5), wherein —$R^{1X}$, if present, is —CN.
(10) A compound according to any one of (1) to (5), wherein —$R^{1X}$, if present, is —$R^{1C}$.
(11) A compound according to any one of (1) to (5), wherein —$R^{1X}$, if present, is —$R^{1F}$.

The Group —$R^{1C}$
(12) A compound according to any one of (1) to (11), wherein —$R_{1C}$, if present, is —$CH_3$.

The Group —$R^{1F}$
(13) A compound according to any one of (1) to (12), wherein —$R^{1F}$, if present, is —$CF_3$.

The Group —$R^2$
(14) A compound according to any one of (1) to (13), wherein —$R^2$ is —$R^{2X}$.
(15) A compound according to any one of (1) to (13), wherein —$R^2$ is —H.

The Group —$R^{2X}$
(16) A compound according to any one of (1) to (15), wherein —$R^{2X}$, if present, is independently —F, —Cl, or —CN.
(17) A compound according to any one of (1) to (15), wherein —$R^{2X}$, if present, is —F.
(18) A compound according to any one of (1) to (15), wherein —$R^{2X}$, if present, is —Cl.
(19) A compound according to any one of (1) to (15), wherein —$R^{2X}$, if present, is —CN.
(20) A compound according to any one of (1) to (15), wherein —$R^{2X}$, if present, is —$R^{2C}$.
(21) A compound according to any one of (1) to (15), wherein —$R^{2X}$, if present, is —$R^{2F}$.

The Group —$R^{2C}$
(22) A compound according to any one of (1) to (21), wherein —$R^{2C}$, if present, is —$CH_3$.

The Group —$R^{2F}$
(23) A compound according to any one of (1) to (22), wherein —$R^{2F}$, if present, is —$CF_3$.

The Group —$R^3$
(24) A compound according to any one of (1) to (23), wherein —$R^3$ is —$R^{3X}$.
(25) A compound according to any one of (1) to (23), wherein —$R^3$ is —H.

The Group —$R^{3X}$
(26) A compound according to any one of (1) to (25), wherein —$R^{3X}$, if present, is independently —F, —Cl, or —CN.
(27) A compound according to any one of (1) to (25), wherein —$R^{3X}$, if present, is —F.

(28) A compound according to any one of (1) to (25), wherein —$R^{3X}$, if present, is —Cl.
(29) A compound according to any one of (1) to (25), wherein —$R^{3X}$, if present, is —CN.
(30) A compound according to any one of (1) to (25), wherein —$R^{3X}$, if present, is —$R^{3C}$.
(31) A compound according to any one of (1) to (25), wherein —$R^{3X}$, if present, is —$R^{3F}$.

The Group —$R^{3C}$

(32) A compound according to any one of (1) to (31), wherein —$R^{3C}$, if present, is —$CH_3$.

The Group —$R^{3F}$

(33) A compound according to any one of (1) to (32), wherein —$R^{3F}$, if present, is —$CF_3$.

The Group —$R^4$

(34) A compound according to any one of (1) to (33), wherein —$R^4$ is —$R^{4X}$.
(35) A compound according to any one of (1) to (33), wherein —$R^4$ is —H.

The Group —$R^{4X}$

(36) A compound according to any one of (1) to (35), wherein —$R^{4X}$, if present, is independently —F, —Cl, or —CN.
(37) A compound according to any one of (1) to (35), wherein —$R^{4X}$, if present, is —F.
(38) A compound according to any one of (1) to (35), wherein —$R^{4X}$, if present, is —Cl.
(39) A compound according to any one of (1) to (35), wherein —$R^{4X}$, if present, is —CN.
(40) A compound according to any one of (1) to (35), wherein —$R^{4X}$, if present, is —$R^{4C}$.
(41) A compound according to any one of (1) to (35), wherein —$R^{4X}$, if present, is —$R^{4F}$.

The Group —$R^{4C}$

(42) A compound according to any one of (1) to (41), wherein —$R^{4C}$, if present, is —$CH_3$.

The Group —$R^{4F}$

(43) A compound according to any one of (1) to (42), wherein —$R^{4F}$, if present, is —$CF_3$.

The Group —$R^5$

(44) A compound according to any one of (1) to (43), wherein —$R^5$ is —$R^{5X}$.
(45) A compound according to any one of (1) to (43), wherein —$R^5$ is —H.

The Group —$R^{5X}$

(46) A compound according to any one of (1) to (45), wherein —$R^{5X}$ is independently —F, —$R^{5C}$ or —$R^{5F}$.
(47) A compound according to any one of (1) to (45), wherein —$R^{5X}$, if present, is —F.
(48) A compound according to any one of (1) to (45), wherein —$R^{5X}$, if present, is —$R^{5C}$.
(49) A compound according to any one of (1) to (45), wherein —$R^{5X}$, if present, is —$R^{5F}$.

The Group —$R^{5C}$

(50) A compound according to any one of (1) to (49), wherein —$R^{5C}$, if present, is —$CH_3$.

The Group —$R^{5F}$

(51) A compound according to any one of (1) to (50), wherein —$R^{5F}$, if present, is —$CF_3$.

The Group —$R^6$

(52) A compound according to any one of (1) to (51), wherein —$R^6$ is —$R^{6X}$.
(53) A compound according to any one of (1) to (51), wherein —$R^6$ is —H.

The Group —$R^{6X}$

(54) A compound according to any one of (1) to (53), wherein —$R^{6X}$ is independently —F, —$R^{6C}$ or —$R^{6F}$.
(55) A compound according to any one of (1) to (53), wherein —$R^{6X}$, if present, is —F.
(56) A compound according to any one of (1) to (53), wherein —$R^{6X}$, if present, is —$R^{6C}$.
(57) A compound according to any one of (1) to (53), wherein —$R^{6X}$, if present, is —$R^{6F}$.

The Group —$R^{6C}$

(58) A compound according to any one of (1) to (57), wherein —$R^{6C}$, if present, is —$CH_3$.

The Group —$R^{6F}$

(59) A compound according to any one of (1) to (58), wherein —$R^{6F}$, if present, is —$CF_3$.

The Groups —$R^5$ and —$R^6$ Taken Together

(60) A compound according to any one of (1) to (43), wherein —$R^5$ and —$R^6$, taken together with the carbon atom to which they are attached, form saturated C3-6cycloalkyl.
(61) A compound according to any one of (1) to (43), wherein —$R^5$ and —$R^6$, taken together with the carbon atom to which they are attached, form cyclopropyl.
(62) A compound according to any one of (1) to (43), wherein —$R^5$ and —$R^6$, taken together with the carbon atom to which they are attached, form cyclobutyl.
(63) A compound according to any one of (1) to (43), wherein —$R^5$ and —$R^6$, taken together with the carbon atom to which they are attached, form cyclopentyl.
(64) A compound according to any one of (1) to (43), wherein —$R^5$ and —$R^6$, taken together with the carbon atom to which they are attached, form cyclohexyl.

Conformation of the Cyclohexyl Ring

(65) A compound according to any one of (1) to (64), wherein the compound is a compound of the following formula, or a pharmaceutically acceptable salt or solvate thereof:

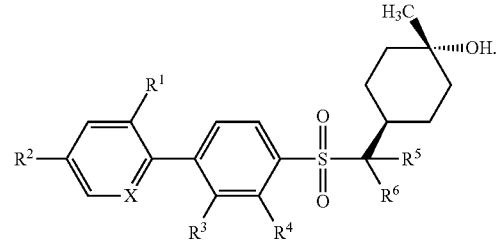

(66) A compound according to any one of (1) to (64), wherein the compound is a compound of the following formula, or a pharmaceutically acceptable salt or solvate thereof:

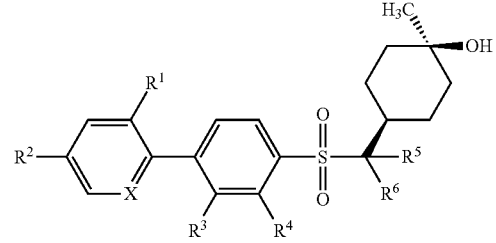

Configuration of Carbon to which —$R^5$ and —$R^6$ are Attached

(67) A compound according to any one of (1) to (66), wherein —$R^5$ and —$R^6$ are different, and the compound is a compound of the following formula, or a pharmaceutically acceptable salt or solvate thereof:

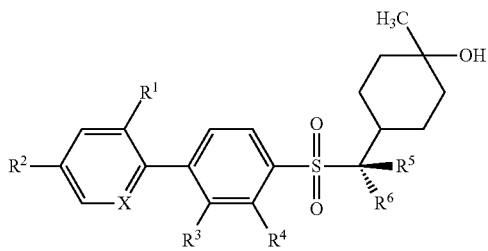

(68) A compound according to any one of (1) to (66), wherein —R⁵ and —R⁶ are different, and the compound is a compound of the following formula, or a pharmaceutically acceptable salt or solvate thereof:

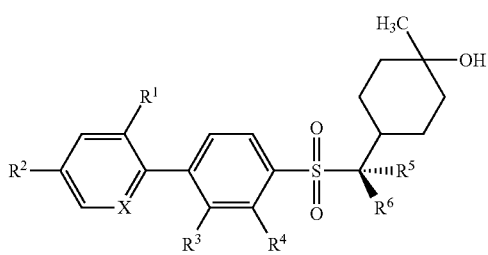

Some Preferred Compounds

(69) A compound according to (1), which is a compound of one of following formulae, or a pharmaceutically acceptable salt or solvate thereof:

| Code | Structure |
|---|---|
| CHMSA-01 | 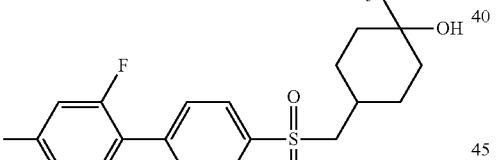 |
| CHMSA-02 | 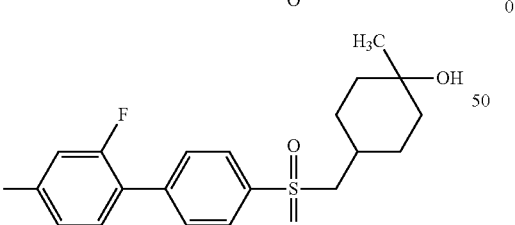 |
| CHMSA-03 | 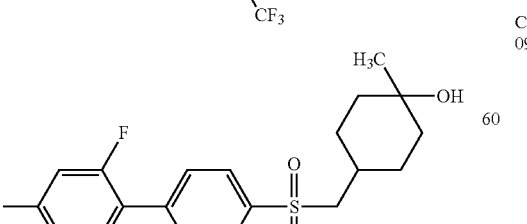 |
| CHMSA-04 | 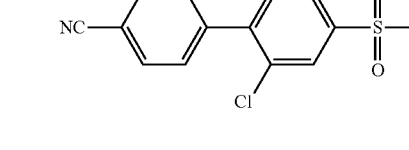 |
| CHMSA-05 | 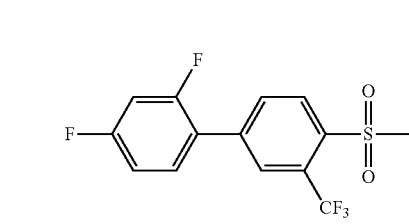 |
| CHMSA-06 | 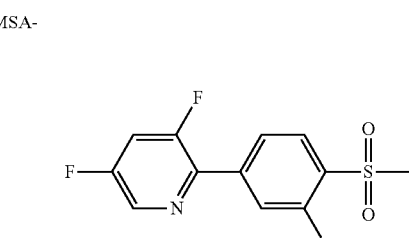 |
| CHMSA-07 | 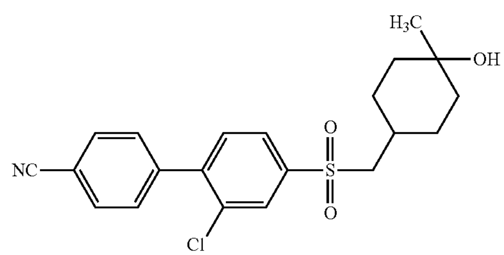 [SMILES: CC1(O)CCC(CS(=O)(=O)c2ccc(-c3ccc(C#N)cc3)c(Cl)c2)CC1] |
| CHMSA-08 | 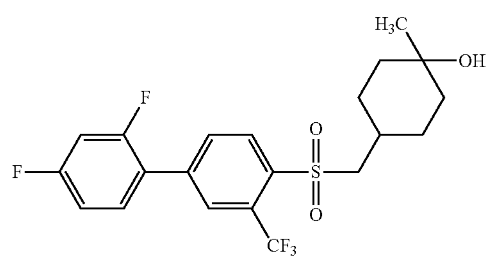 [SMILES: CC1(O)CCC(CS(=O)(=O)c2ccc(-c3ccc(F)cc3F)cc2C(F)(F)F)CC1] |
| CHMSA-09 | 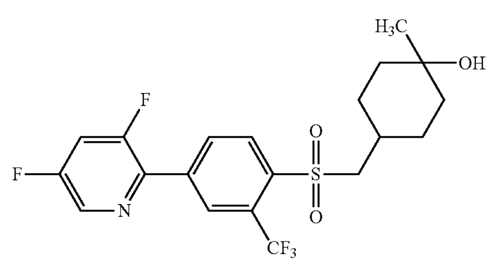 [SMILES: CC1(O)CCC(CS(=O)(=O)c2ccc(-c3ncc(F)cc3F)cc2C(F)(F)F)CC1] |

| Code | Structure |
|---|---|
| CHMSA-10 | 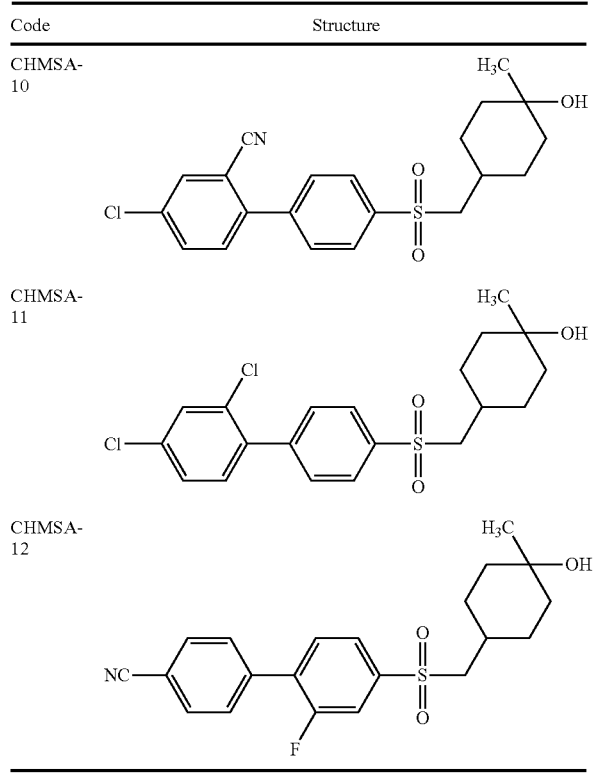 |
| CHMSA-11 | 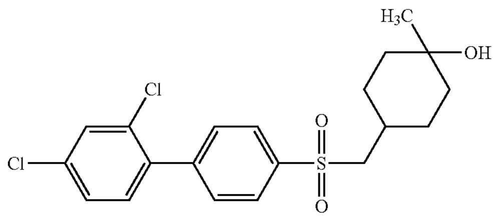 [SMILES: CC1(O)CCC(CS(=O)(=O)c2ccc(-c3ccc(Cl)cc3Cl)cc2)CC1] |
| CHMSA-12 | 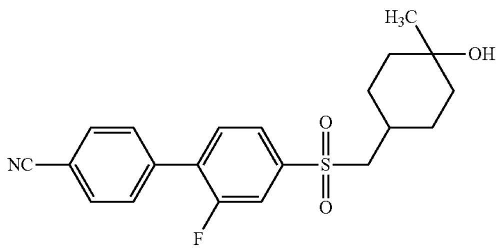 [SMILES: CC1(O)CCC(CS(=O)(=O)c2ccc(-c3ccc(C#N)cc3)c(F)c2)CC1] |
(70) A compound according to (1), which is a compound of one of following formulae, or a pharmaceutically acceptable salt or solvate thereof:
| Code | Structure |
|---|---|
| CHMSA-01-A | 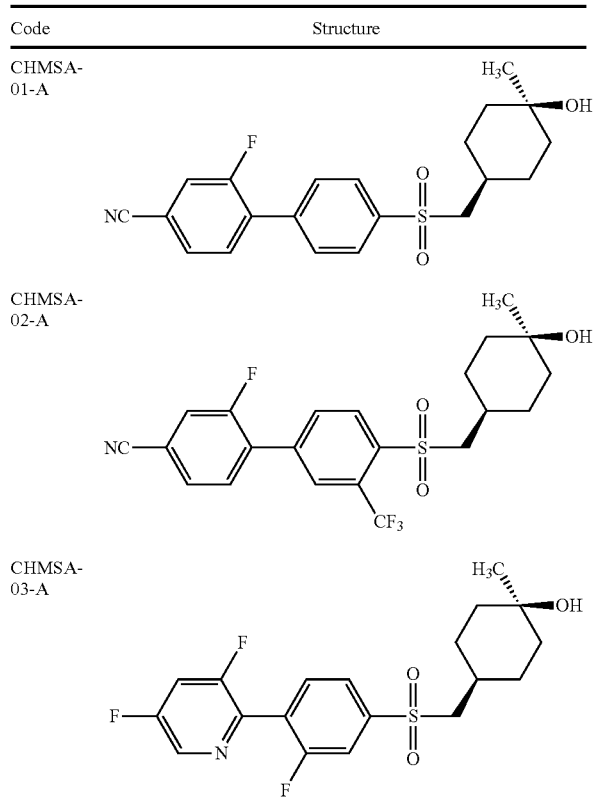 |
| CHMSA-02-A | |
| CHMSA-03-A | |
| Code | Structure |
|---|---|
| CHMSA-04-A | 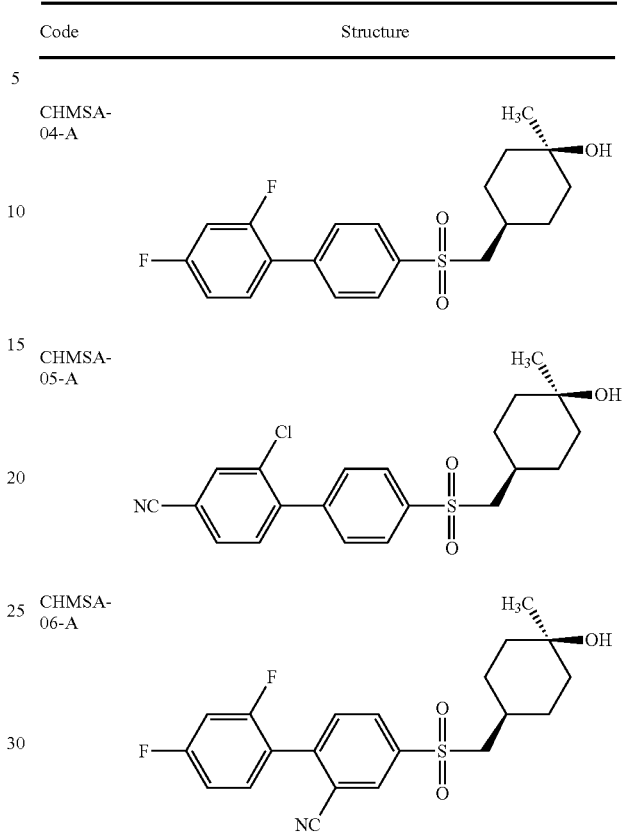 |
| CHMSA-05-A | |
| CHMSA-06-A | |
| CHMSA-07-A | |
| CHMSA-08-A | |
| CHMSA-09-A | |

| Code | Structure |
|---|---|
| CHMSA-10-A | (4-chloro-2-cyanophenyl)-biphenyl with sulfonylmethyl-(1-methyl-4-hydroxycyclohexyl) |
| CHMSA-11-A | (2,4-dichlorophenyl)-biphenyl with sulfonylmethyl-(1-methyl-4-hydroxycyclohexyl) |
| CHMSA-12-A | (4-cyanophenyl)-(2-fluorophenyl)-biphenyl with sulfonylmethyl-(1-methyl-4-hydroxycyclohexyl) |

(71) A compound according to (1), which is a compound of one of following formulae, or a pharmaceutically acceptable salt or solvate thereof:

| Code | Structure |
|---|---|
| CHMSA-01-B | (4-cyano-2-fluorophenyl)-biphenyl with sulfonylmethyl-(1-methyl-4-hydroxycyclohexyl) |
| CHMSA-02-B | (4-cyano-2-fluorophenyl)-biphenyl with CF$_3$ and sulfonylmethyl-(1-methyl-4-hydroxycyclohexyl) |
| CHMSA-03-B | (3,5-difluoropyridinyl)-(2-fluorophenyl)-biphenyl with sulfonylmethyl-(1-methyl-4-hydroxycyclohexyl) |
| CHMSA-04-B | (2,4-difluorophenyl)-biphenyl with sulfonylmethyl-(1-methyl-4-hydroxycyclohexyl) |
| CHMSA-05-B | (4-cyano-2-chlorophenyl)-biphenyl with sulfonylmethyl-(1-methyl-4-hydroxycyclohexyl) |
| CHMSA-06-B | (2,4-difluorophenyl)-(2-cyanophenyl)-biphenyl with sulfonylmethyl-(1-methyl-4-hydroxycyclohexyl) |
| CHMSA-07-B | (4-cyanophenyl)-(2-chlorophenyl)-biphenyl with sulfonylmethyl-(1-methyl-4-hydroxycyclohexyl) |
| CHMSA-08-B | (2,4-difluorophenyl)-biphenyl with CF$_3$ and sulfonylmethyl-(1-methyl-4-hydroxycyclohexyl) |

| Code | Structure |
|---|---|
| CHMSA-09-B | (3-fluoro-5-fluoropyridin-2-yl)-substituted biphenyl with CF₃ and sulfonylmethyl-trans-4-hydroxy-4-methylcyclohexane |
| CHMSA-10-B | 2,4'-dicyanobiphenyl with sulfonylmethyl-trans-4-hydroxy-4-methylcyclohexane |
| CHMSA-11-B | 2,4'-dichlorobiphenyl with sulfonylmethyl-trans-4-hydroxy-4-methylcyclohexane |
| CHMSA-12-B | 4'-cyano-2-fluorobiphenyl with sulfonylmethyl-trans-4-hydroxy-4-methylcyclohexane |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., =X—, —R$^1$, —R$^{1X}$, —R$_{1C}$, —R$^{1F}$, —R$^2$, —R$^{2X}$, —R$^{2C}$, —R$^{2F}$, —R$^3$, —R$^{3X}$, —R$^{3C}$, —R$^{3F}$, —R$^4$, —R$^{4X}$, —R$^{4C}$, —R$^{4F}$, —R$^5$, —R$^{5X}$, —R$^{5C}$, —R$^{5F}$, —R$^6$, —R$^{6X}$, —R$^{6C}$, —R$^{6F}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In this context, the skilled person will readily appreciate that certain combinations of groups (e.g., substituents) may give rise to compounds which may not be readily synthesized and/or are chemically unstable. In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to CHMSA compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless otherwise specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-3}$alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, —OCH₃, is not to be construed as a reference to its structural isomer, a hydroxymethyl group, —CH₂OH.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro. A reference herein to one tautomer is intended to encompass both tautomers.

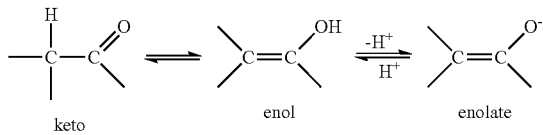

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group, which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺ as well as the ammonium ion (i.e., NH₄⁺). Examples of suitable organic cations include, but are not limited to substituted ammonium ions (e.g., NH₃R⁺, NH₂R₂⁺, NHR₃⁺, NR₄⁺), for example, where each R is independently linear or branched saturated $C_{1-18}$ alkyl, $C_{3-8}$cycloalkyl, $C_{3-8}$cycloalkyl-$C_{1-6}$alkyl, and phenyl-$C_{1-6}$alkyl, wherein the phenyl group is optionally substituted. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group, which upon protonation may become cationic (e.g., —NH₂ may become —NH₃⁺), then a salt may be formed with a suitable anion.

For example, if a parent structure contains a cationic group (e.g., —NMe₂⁺), or has a functional group, which upon protonation may become cationic (e.g., —NH₂ may become —NH₃⁺), then a salt may be formed with a suitable anion. In the case of a quaternary ammonium compound a counter-anion is generally always present in order to balance the positive charge. If, in addition to a cationic group (e.g., —NMe₂⁺, —NH₃⁺), the compound also contains a group capable of forming an anion (e.g., —COOH), then an inner salt (also referred to as a zwitterion) may be formed.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyloxybenzoic, acetic, trifluoroacetic, ascorbic, aspartic, benzoic, camphorsulfonic, cinnamic, citric, edetic, 1,2-ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Examples of suitable counter-ions which are especially suitable for quaternary ammonium compounds (e.g., those with a —NMe₂⁺ group) include 1-adamantanesulfonate, benzenesulfonate, bisulfate, bromide, chloride, iodide, methanesulfonate, methylsulfate, 1,5-napthalene-bissulfonate, 4-nitrobenzenesulfonate, formate, tartrate, tosylate, trifluoroacetate, trifluoromethylsulfonate, sulphate. Again, if the compound also contains a group capable of forming an anion (e.g., —COOH), then an inner salt may be formed.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well-known chemical methods are employed to reversibly render unreactive a functional group, which otherwise would be reactive, under specified conditions. In a chemically protected form, one or more reactive functional groups are in the form of a protected or protecting group (alternatively as a masked or masking group or a blocked or blocking group). By protecting a reactive functional group, reactions involving other unprotected reactive functional groups can be performed, without affecting the protected group; the protecting group may be removed or the masking group transformed, usually in a subsequent step, without substantially affecting the remainder of the molecule. See, for example, Protective Groups in Organic Synthesis (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

Prodrugs

It may be convenient or desirable to prepare, purify, and/or handle the compound in the form of a prodrug. The term "prodrug," as used herein, pertains to a compound, which yields the desired active compound in vivo. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound, which, upon further chemical reaction, yields the active compound (for example, as in antibody directed enzyme prodrug therapy (ADEPT), gene directed enzyme prodrug therapy (GDEPT), lipid directed enzyme prodrug therapy (LIDEPT), etc.). For example, the prodrug may be a sugar derivative or other glycoside conjugate, or may be an amino acid ester derivative.

General Chemical Synthesis

Methods for the chemical synthesis of the CHMSA compounds are described herein. These and/or other well-known methods (see, e.g., Greig et al., 2010a; Bahmanyar et al., 2010; Patel et al., 2014; Patel et al., 2016) may be modified and/or adapted in known ways in order to provide alternative or improved methods of synthesis.

In one approach, a cyclohexanone-4-ester (1) is protected with ethylene glycol (for example, in toluene with p-toluenesulfonic acid (PTSA)) (2) and reduced with lithium aluminium hydride to give the corresponding alcohol derivative (3). The alcohol (3) is converted to the bromide (4) with triphenylphosphine (PPh$_3$) and carbon tetrabromide (CBr$_4$). The bromine group of the bromide (4) is displaced by a suitable aromatic thiolate anion (for example, from 4-bromobenzenethiol, (5)) using caesium carbonate (Cs$_2$CO$_3$) as a base to give the corresponding sulphide derivative (6), which is then oxidised to give the bromophenyl sulphone (7) using m-chloroperbenzoic acid (m-CPBA). The bromophenyl sulphone (7) is coupled to an appropriate aromatic boronic ester (8) using transition metal catalysis, for example, tetrakis(triphenylphosphine)palladium(0) (Pd (PPh$_3$)$_4$), to give the corresponding biaryl sulphone (9). The ketone (10) is regenerated by deprotection using dilute aqueous hydrochloric acid (HCl) and is then reacted with methyl magnesium bromide (MeMgBr) to give a pair of isomeric tertiary alcohols (11A, 11B), which are then separated using preparative HPLC.

This approach is illustrated in the following scheme.

Scheme 1

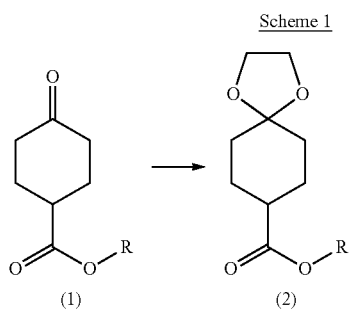

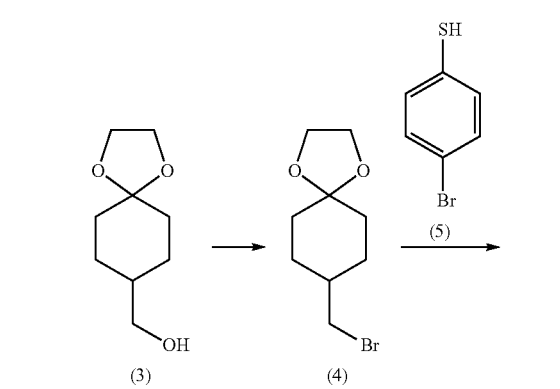

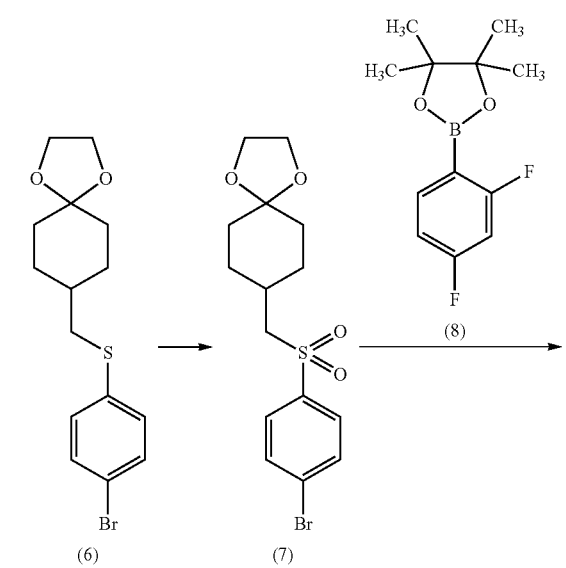

-continued

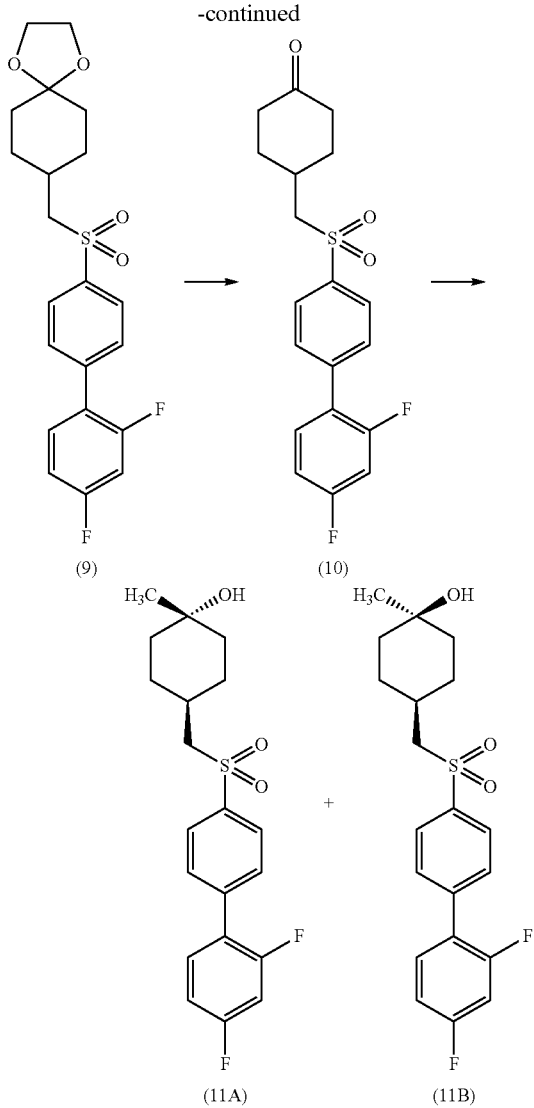

If the appropriate aromatic thiol (e.g., (5) above) is not readily commercially available, it may be prepared by reduction of the corresponding sulphonyl chloride (RSO$_2$Cl) with a reducing agent such as triphenylphosphine (PPh$_3$).

This approach is illustrated in the following scheme.

Scheme 2

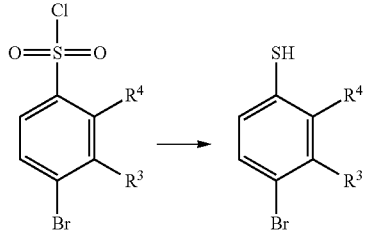

In another approach, an appropriate aniline may be diazotised, for example, with sodium nitrite (NaNO$_2$) and hydrochloric acid (HCl). The resulting diazonium salt is then reacted with potassium ethyl xanthate (CH$_3$CH$_2$OCS$_2$K) and subsequently hydrolysed with potassium hydroxide (KOH) to give the corresponding aromatic thiol (e.g., (5) above).

This approach is illustrated in the following scheme.

Scheme 3

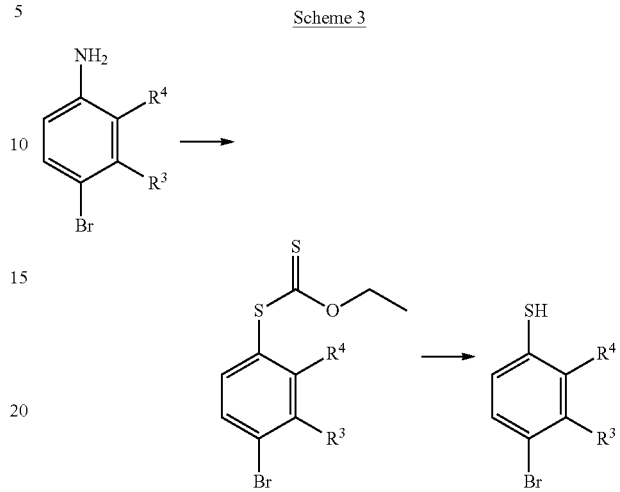

If one of the substituents (R$^3$ and R$^4$) is a nitrile group (—CN), then it is possible that the nitrile group is hydrated to the primary amide group during the potassium hydroxide hydrolysis. If that is the case, the aromatic thiol containing the primary amide group is coupled with the bromide (e.g., (4)+(5)) and then treated with a dehydrating agent, for example, trifluoroacetic anhydride (CF$_3$C(=O)OC(=O)CF$_3$), to regenerate the nitrile group from the primary amide group (e.g., (6)).

In a second approach, the bromophenyl sulphone (7) is converted into a boronic ester (13) using 4,4,5,5-tetramethyl-2-(4,4,5,5-tetramethyl-1,3,2-dioxaborolan-2-yl)-1,3,2-dioxaborolane (12) and transition metal catalysis, for example, bis(triphenylphosphine) palladium (II) dichloride. The boronic ester (13) is then coupled to an appropriate aromatic bromide (14) using transition metal catalysis, for example, tetrakis(triphenylphosphine)palladium(0) (Pd(PPh$_3$)$_4$), to give the corresponding biaryl sulphone (15). The ketone (16) is regenerated by deprotection using dilute aqueous hydrochloric acid (HCl) and is then reacted with methyl magnesium bromide (MeMgBr) to give a pair of isomeric tertiary alcohols (17A, 17B), which are then separated using preparative HPLC.

This approach is illustrated in the following scheme.

Scheme 4

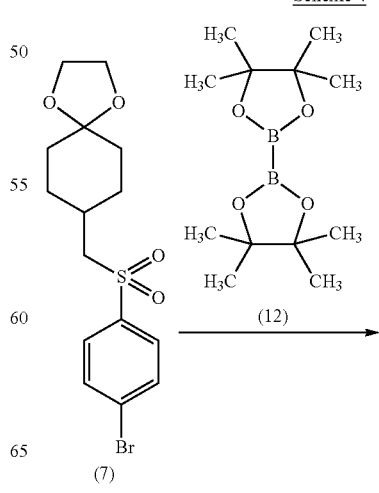

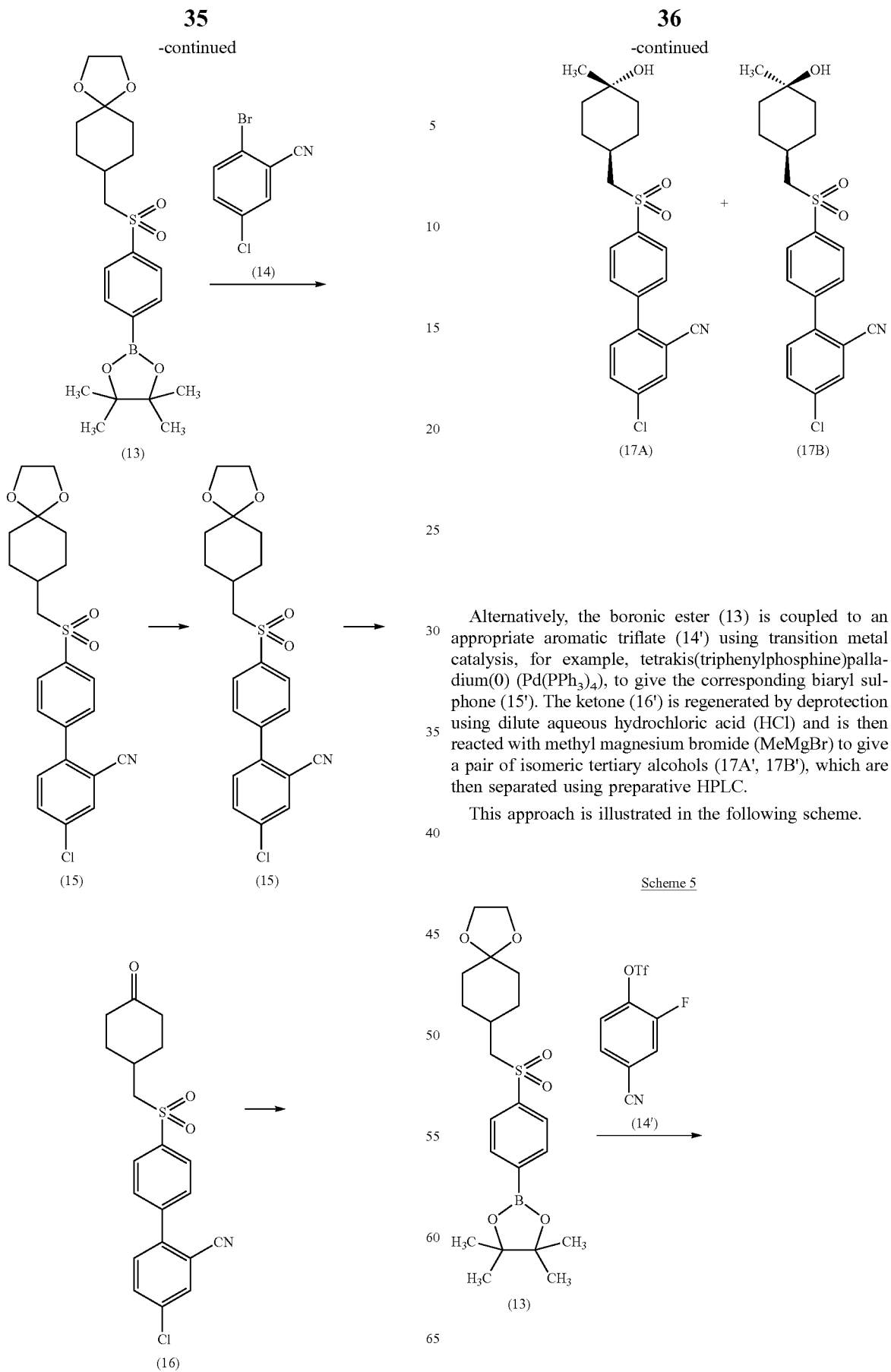

Alternatively, the boronic ester (13) is coupled to an appropriate aromatic triflate (14') using transition metal catalysis, for example, tetrakis(triphenylphosphine)palladium(0) (Pd(PPh$_3$)$_4$), to give the corresponding biaryl sulphone (15'). The ketone (16') is regenerated by deprotection using dilute aqueous hydrochloric acid (HCl) and is then reacted with methyl magnesium bromide (MeMgBr) to give a pair of isomeric tertiary alcohols (17A', 17B'), which are then separated using preparative HPLC.

This approach is illustrated in the following scheme.

Scheme 5

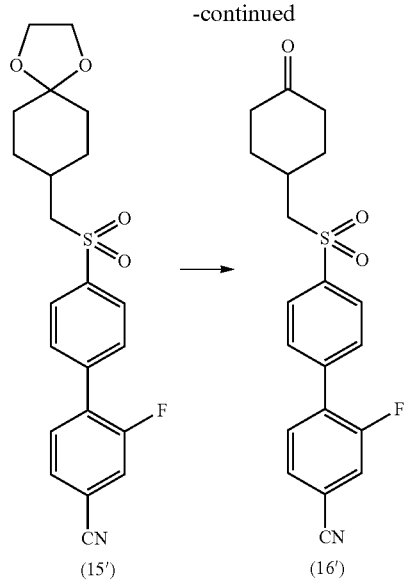

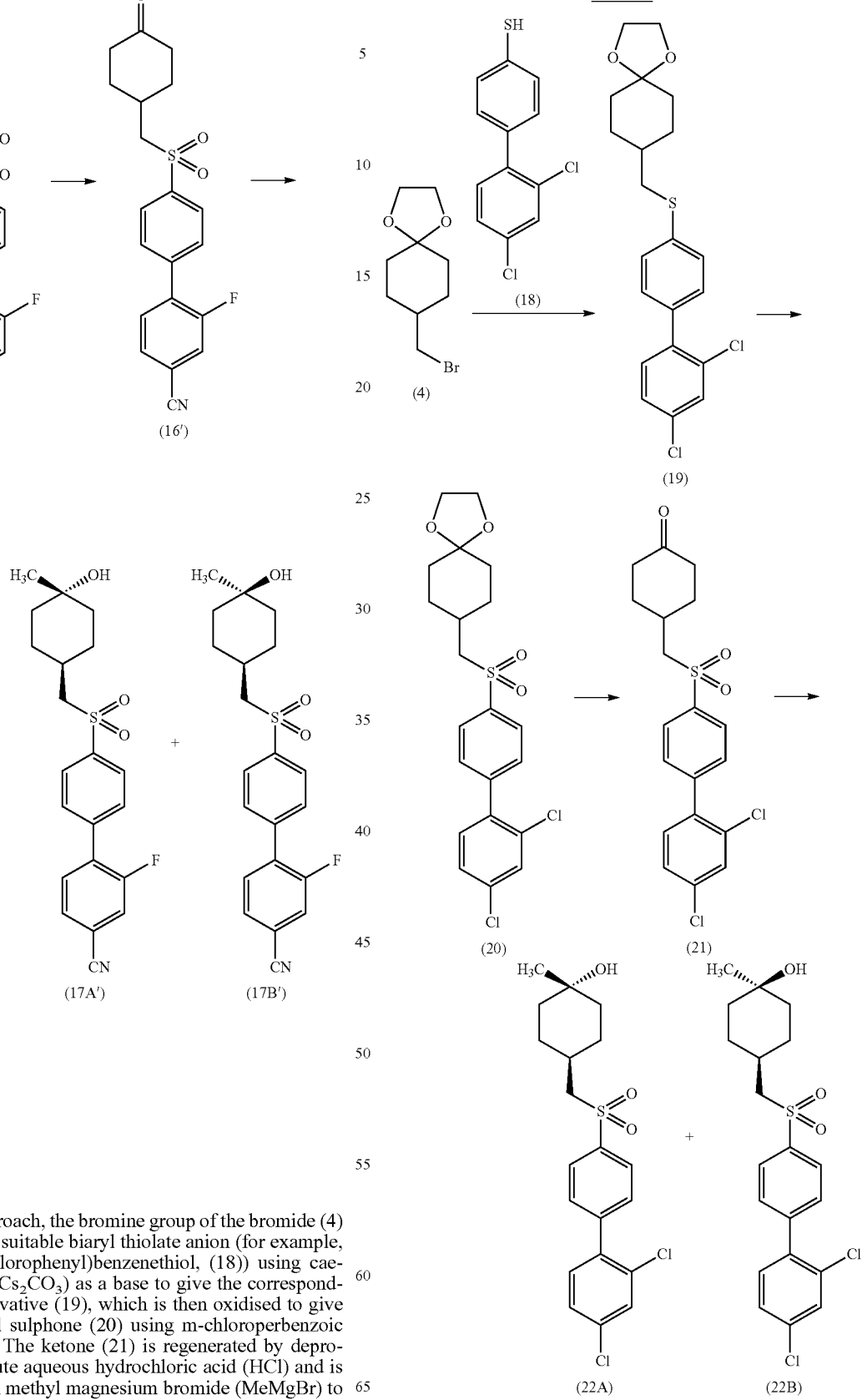

This approach is illustrated in the following scheme.

Scheme 6

In another approach, the bromine group of the bromide (4) is displaced by a suitable biaryl thiolate anion (for example, from 4-(2,4-dichlorophenyl)benzenethiol, (18)) using caesium carbonate ($Cs_2CO_3$) as a base to give the corresponding sulphide derivative (19), which is then oxidised to give the bromophenyl sulphone (20) using m-chloroperbenzoic acid (m-CPBA). The ketone (21) is regenerated by deprotection using dilute aqueous hydrochloric acid (HCl) and is then reacted with methyl magnesium bromide (MeMgBr) to give a pair of isomeric tertiary alcohols (22A, 22B), which are then separated using preparative HPLC.

If the appropriate biarylthiol (e.g., (18) above) is not readily commercially available, it may be prepared, for example, as follows. A suitable boronic acid (23) is coupled to a suitable bromobenzene (24) by Suzuki coupling. The resulting biaryl (25) is sulfonylated using chlorosulfonic acid (ClSO$_3$H) to give the corresponding sulfonic acid, which is then reacted with thionyl chloride (SOCl$_2$) to give the corresponding aryl sulfonyl chloride (26). Reduction of the sulphonyl chloride (26), for example, with triphenylphosphine (PPh$_3$), gives the biarylthiol derivative (18).

This approach is illustrated in the following scheme.

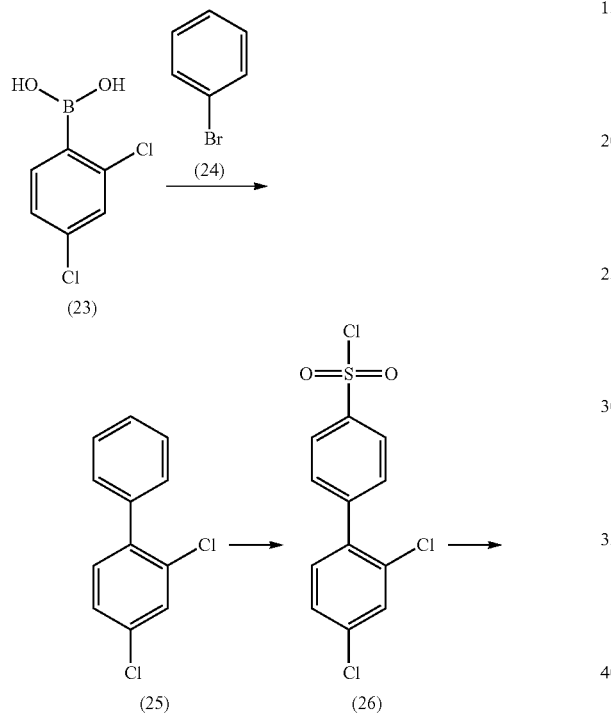

In another approach, the biaryl sulphone (9) is treated with a base, for example, lithium diisopropylamide (LDA) followed by either a fluorinating agent, for example, N-fluorobenzenesulfonimide (NFSI) or an alkylating agent, for example, methyl iodide (MeI), to give the biaryl sulphone (27) with R$^1$=fluoro or R$^1$=alkyl (e.g., methyl), respectively. The ketone (28) is regenerated by deprotection using dilute aqueous hydrochloric acid (HCl) and is then reacted with methyl magnesium bromide (MeMgBr) to give isomeric tertiary alcohols (29A, 29B), some or all of which are separated using preparative HPLC.

This approach is illustrated in the following scheme.

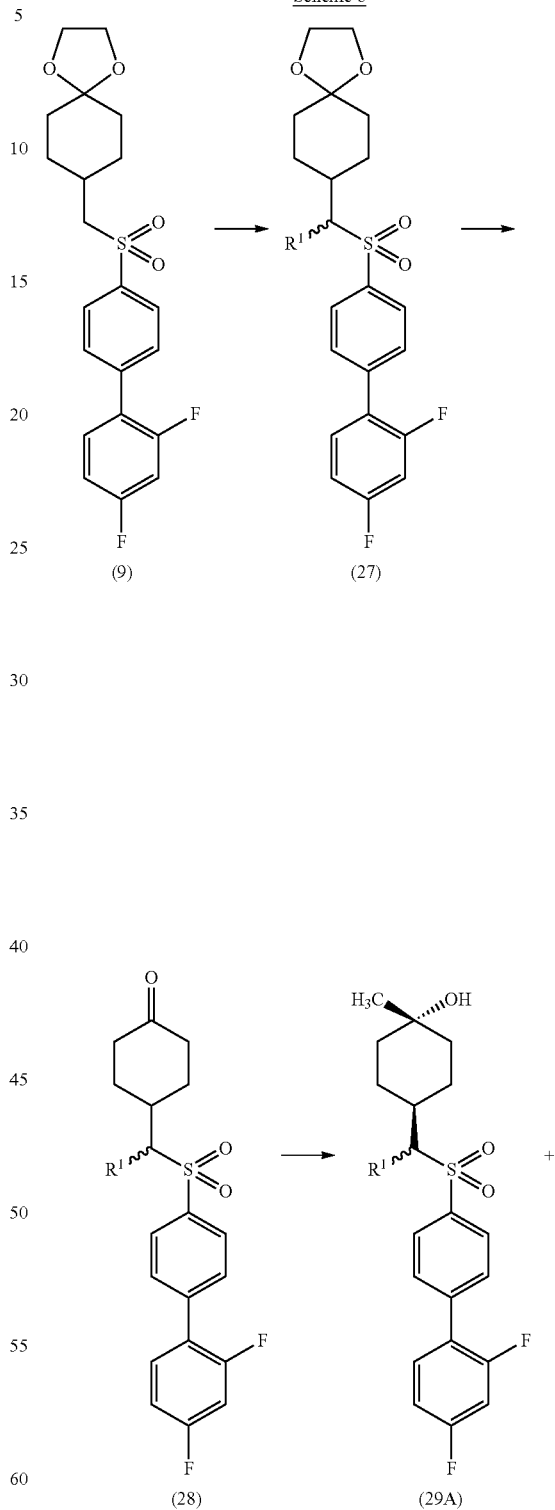

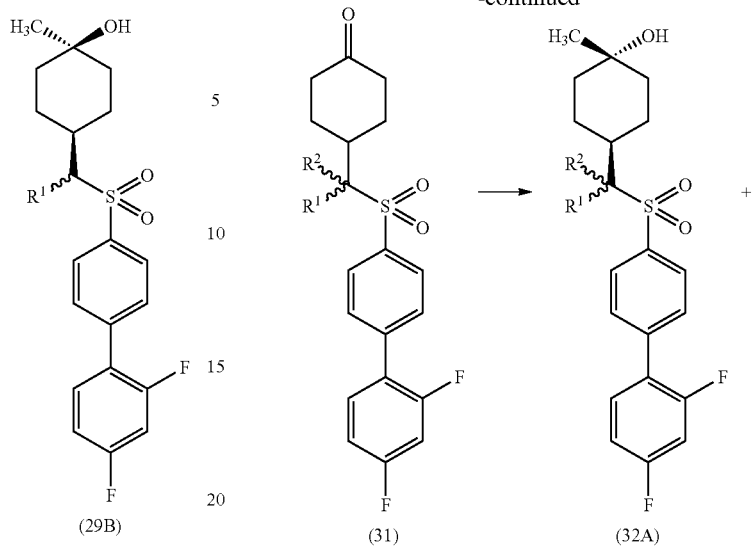

Additionally, the biaryl sulphone (27) may be treated with a base, for example, LDA, followed by either a fluorinating agent, for example, NFSI, or an alkylating agent, for example, MeI, to give the biaryl sulphone (30) with $R^2$=fluoro or $R^2$=alkyl (e.g., methyl), respectively. In this way, compounds where $R^1$ and $R^2$ are different (e.g., F and Me; Me and Et; etc.), can be prepared. The ketone (31) is regenerated by deprotection using dilute aqueous hydrochloric acid (HCl) and is then reacted with methyl magnesium bromide (MeMgBr) to give isomeric tertiary alcohols (32A, 32B). When $R^1$ and $R^2$ are the same, the pair of isomeric tertiary alcohols is separated using preparative HPLC. When $R^1$ and $R^2$ are different, some or all of the isomeric tertiary alcohols are separated using preparative HPLC.

This approach is illustrated in the following scheme.

Scheme 9

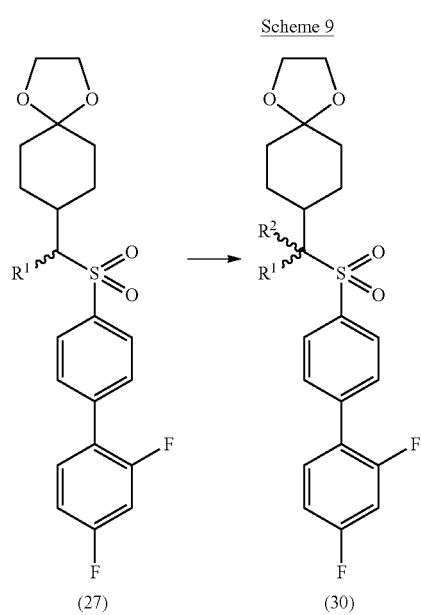

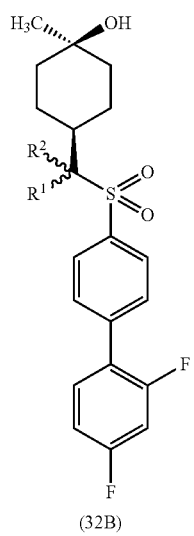

Alternatively, the biaryl sulphone (9) is treated with a base, for example, LDA, followed by a terminally dihalogenated alkane, for example, 1-bromo-2-chloroethane (32). The resulting biaryl sulphone (33) is treated with a second equivalent of a base, for example, LDA, to give the biaryl sulphone (34) in which $R^1$, $R^2$, and the carbon to which they are attached form a cycloalkyl ring, for example, a cyclopropyl ring. The ketone (35) is regenerated by deprotection using dilute aqueous hydrochloric acid (HCl) and is then reacted with methyl magnesium bromide (MeMgBr) to give a pair of isomeric tertiary alcohols (36A, 36B), which are then separated using preparative HPLC.

This approach is illustrated in the following scheme.

Scheme 10

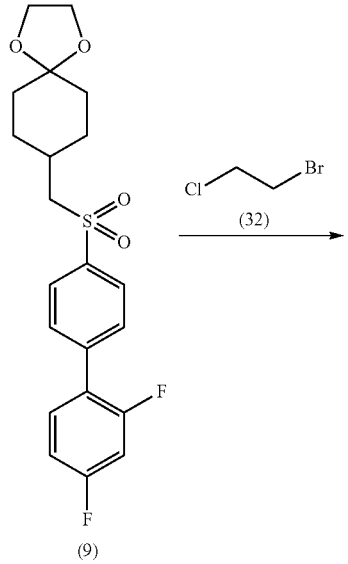

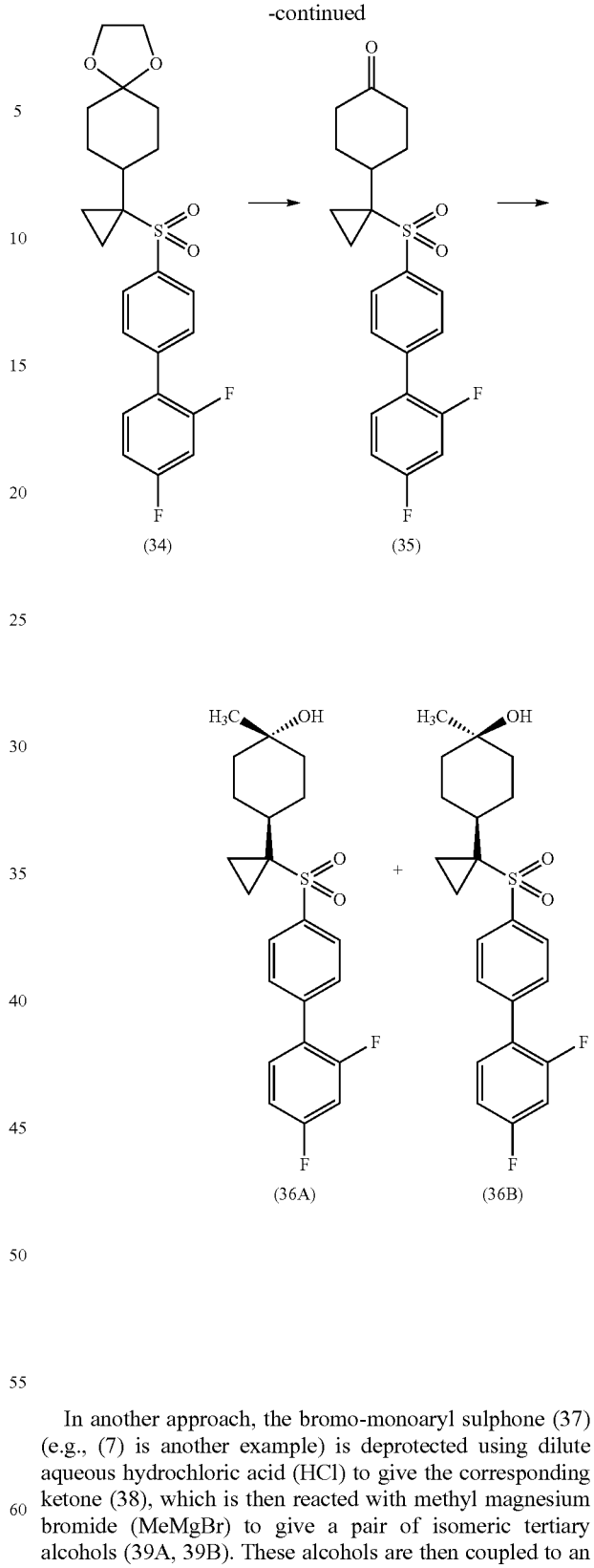

In another approach, the bromo-monoaryl sulphone (37) (e.g., (7) is another example) is deprotected using dilute aqueous hydrochloric acid (HCl) to give the corresponding ketone (38), which is then reacted with methyl magnesium bromide (MeMgBr) to give a pair of isomeric tertiary alcohols (39A, 39B). These alcohols are then coupled to an appropriate aromatic boronic ester (8) using transition metal catalysis, for example, tetrakis(triphenylphosphine)palladium(0) (Pd(PPh$_3$)$_4$), to give the corresponding pair of isomeric tertiary alcohols (40A, 40B). These isomers are then separated using preparative HPLC.

This approach is illustrated in the following scheme.

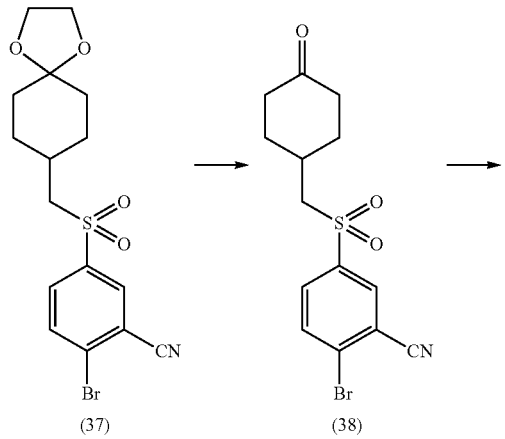

Scheme 11

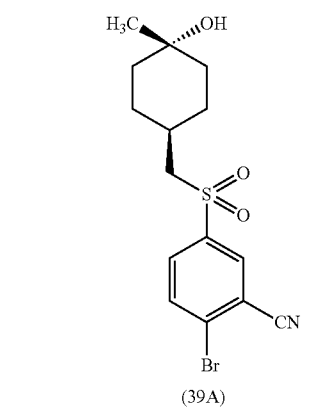

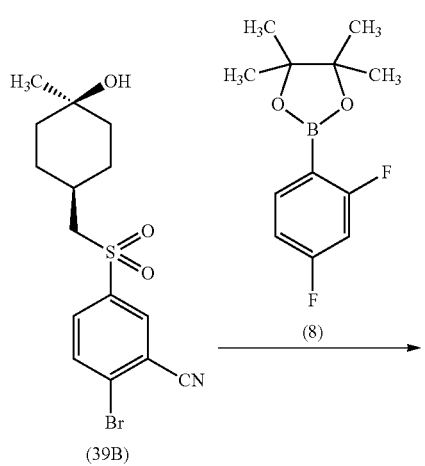

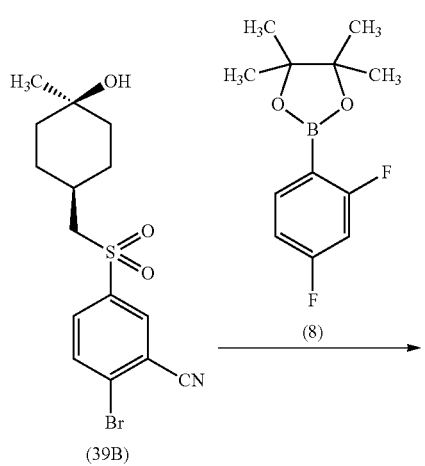

These and/or other well-known methods may be modified and/or adapted in known ways in order to facilitate the synthesis of additional compounds described herein. See, for example:

Comprehensive Organic Transformations: A Guide to Functional Group Preparations, 2$^{nd}$ Edition (Wiley) 2010. Ed. R. C. Larock. ISBN: 978-1-118-03758-4.

Comprehensive Organic Synthesis, 2nd Edition (Elsevier) 2014. Editor in Chiefs P. Knochel, G. A. Molander. eBook ISBN: 9780080977430. Hardcover ISBN: 9780080977423.

Science of Synthesis: Cross Coupling and Heck-Type Reactions, Workbench Edition (Thieme) 2013. Ed. G. Molander, J. P. Wolfe, Mats Larhed. ISBN 9783131734112.

Greene's Protective Groups in Organic Synthesis, 4$^{th}$ Edition (Wiley) 2006. P. G. M. Wuts, T. W. Greene. Print ISBN: 9780471697541. Online ISBN: 9780470053485.

e-EROS Encyclopedia of Reagents for Organic Synthesis, (Wiley). Online ISBN: 9780470842898. DOI: 10.1002/047084289X.

Organic Reactions: Electrophilic Fluorination with N-F Reagents (Wiley) 2008. J. Baudoux, D. Cahard. DOI: 10.1002/0471264180.or069.02.

Compositions

One aspect of the present invention pertains to a composition (e.g., a pharmaceutical composition) comprising a CHMSA compound, as described herein, and a carrier, diluent, or excipient (e.g., a pharmaceutically acceptable carrier, diluent, or excipient).

In one embodiment, the composition further comprises one or more (e.g., 1, 2, 3, 4) additional therapeutic agents, as described herein.

Another aspect of the present invention pertains to a method of preparing a composition (e.g., a pharmaceutical composition) comprising admixing a CHMSA compound, as described herein, and a carrier, diluent, or excipient (e.g., a pharmaceutically acceptable carrier, diluent, or excipient).

Another aspect of the present invention pertains to a method of preparing a composition (e.g., a pharmaceutical composition) comprising admixing a CHMSA compound, as described herein; one or more (e.g., 1, 2, 3, 4) additional therapeutic agents, as described herein; and a carrier, diluent, or excipient (e.g., a pharmaceutically acceptable carrier, diluent, or excipient).

Uses

The CHMSA compounds, as described herein, are useful, for example, in the treatment of disorders (e.g., diseases) including, for example, the disorders (e.g., diseases) described herein.

Use in Methods of Therapy

Another aspect of the present invention pertains to a CHMSA compound, as described herein, for use in a method of treatment of the human or animal body by therapy, for example, for use a method of treatment of a disorder (e.g., a disease) as described herein.

Another aspect of the present invention pertains to a CHMSA compound, as described herein, in combination with one or more (e.g., 1, 2, 3, 4) additional therapeutic agents, as described herein, for use in a method of treatment of the human or animal body by therapy, for example, for use in a method of treatment of a disorder (e.g., a disease) as described herein.

Use in the Manufacture of Medicaments

Another aspect of the present invention pertains to use of a CHMSA compound, as described herein, in the manufacture of a medicament for treatment, for example, treatment of a disorder (e.g., a disease) as described herein.

In one embodiment, the medicament comprises the CHMSA compound.

Another aspect of the present invention pertains to use of a CHMSA compound, as described herein, and one or more (e.g., 1, 2, 3, 4) additional therapeutic agents, as described herein, in the manufacture of a medicament for treatment, for example, treatment of a disorder (e.g., a disease) as described herein.

In one embodiment, the medicament comprises the CHMSA compound and the one or more (e.g., 1, 2, 3, 4) additional therapeutic agents.

Methods of Treatment

Another aspect of the present invention pertains to a method of treatment, for example, of a disorder (e.g., a disease) as described herein, comprising administering to a patient in need of treatment a therapeutically effective amount of a CHMSA compound, as described herein, preferably in the form of a pharmaceutical composition.

Another aspect of the present invention pertains to a method of treatment, for example, of a disorder (e.g., a disease) as described herein, comprising administering to a patient in need of treatment a therapeutically effective amount of a CHMSA compound, as described herein, preferably in the form of a pharmaceutical composition, and one or more (e.g., 1, 2, 3, 4) additional therapeutic agents, as described herein, preferably in the form of a pharmaceutical composition.

Conditions Treated—Disorders Associated with Changes in Cellular Metabolism In one embodiment, the treatment is treatment of: a disorder associated with changes in cellular metabolism.

In one embodiment, the treatment is treatment of: a disorder in which cellular metabolism is dysregulated.

Examples of such disorders include many of those described below, including, e.g., an autoimmune/inflammatory disorder; cancer; and a disorder mediated by osteoclasts.

In one embodiment, the treatment is treatment of multiple myeloma, diffuse large B-cell lymphoma, acute myeloid leukemia, eosinophilic leukemia, glioblastoma, melanoma, ovarian cancer, chemotherapy resistant cancer, radiation resistant cancer, inflammatory arthritis, rheumatoid arthritis, psoriatic arthritis, psoriasis, ulcerative colitis, Crohn's disease, systemic lupus erythematosus (SLE), lupus nephritis, asthma, chronic obstructive pulmonary disease (COPD), non-alcoholic fatty liver disease (NAFLD), non-alcoholic steatohepatitis (NASH), autoimmune hepatitis, or hidradenitis suppurativa.

Conditions Treated—Autoimmune/Inflammatory Disorders

In one embodiment, the treatment is treatment of: an autoimmune/inflammatory disorder.

In one embodiment, the treatment is treatment of: an autoimmune disorder.

In one embodiment, the treatment is treatment of: an inflammatory disorder.

In one embodiment, the treatment is treatment of: inflammatory arthritis (including, e.g., rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis); psoriasis; systemic lupus erythematosus; lupus nephritis; systemic sclerosis; scleroderma; hepatitis; endometriosis; Sjogren's syndrome; inflammatory bowel disease; ulcerative colitis; Crohn's disease; multiple sclerosis; asthma; atherosclerosis; chronic obstructive pulmonary disease (COPD); hidradenitis suppurativa; autoimmune hepatitis; uveitis; pulmonary fibrosis; non-alcoholic fatty liver disease (NAFLD); non-alcoholic steatohepatitis (NASH); allergic disease (including, e.g., atopy, allergic rhinitis, atopic dermatitis, anaphylaxis, allergic bronchopulmonary aspergillosis, allergic gastroenteritis, hypersensitivity pneumonitis); an allergy; type I diabetes; rheumatic fever; celiac disease; encephalitis; oophoritis; primary biliary cirrhosis; insulin-resistant diabetes; autoimmune adrenal insufficiency (Addison's disease); autoimmune oophoritis; autoimmune orchitis; autoimmune haemolytic anaemia; paroxysmal cold hemoglobinuria; Behçet's disease; autoimmune thrombocytopenia; autoimmune neutropenia; pernicious anaemia; pure red cell anaemia; autoimmune coagulopathy; myasthenia gravis; autoimmune polyneuritis; pemphigus; rheumatic carditis; Goodpasture's syndrome; postcardiotomy syndrome; polymyositis; dermatomyositis; irritable bowel syndrome; pancreatitis; gastritis, lichen planus; delayed type hypersensitivity; chronic pulmonary inflammation; pulmonary alveolitis; pulmonary granuloma; gingival inflammation; endodontic disease; periodontal disease; hypersensitivity pneumonitis; hay fever; anaphylaxis; skin allergy; hives; gout; polycystic kidney disease; cryopyrin-associated periodic syndrome (CAPS); Muckle-Wells Syndrome; Guillain-Barre syndrome; chronic inflammatory demyelinating polyneuropathy; organ or transplant rejection; chronic allograft rejection; acute or chronic graft versus-host disease; dermatitis; atopic dermatomyositis; Graves' disease; autoimmune (Hashimoto's) thyroiditis; blistering disorder; vasculitis syndrome; immune-complex mediated vasculitis; bronchitis; cystic fibrosis; pneumonia; pulmonary oedema; pulmonary embolism; sarcoidosis; hypertension; emphysema; respiratory failure; acute respiratory distress syndrome; BENTA disease; or polymyositis.

In one embodiment, the treatment is treatment of: inflammatory arthritis (including, e.g., rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis); psoriasis; systemic lupus erythematosus; lupus nephritis; systemic sclerosis; scleroderma; hepatitis; endometriosis; Sjogren's syndrome; inflammatory bowel disease; ulcerative colitis; Crohn's disease; multiple sclerosis; asthma, atherosclerosis; chronic obstructive pulmonary disease (COPD); hidradenitis suppurativa; autoimmune hepatitis; uveitis; pulmonary fibrosis; non-alcoholic fatty liver disease (NAFLD); or non-alcoholic steatohepatitis (NASH).

In one embodiment, the treatment is treatment of: inflammatory arthritis (including, e.g., rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis).

In one embodiment, the treatment is treatment of: psoriasis; psoriatic arthritis; systemic lupus erythematosus, lupus nephritis; systemic sclerosis; scleroderma; hepatitis; endometriosis; Sjogren's syndrome; inflammatory bowel disease; ulcerative colitis; Crohn's disease; multiple sclerosis; asthma, atherosclerosis; chronic obstructive pulmonary disease (COPD); hidradenitis suppurativa; autoimmune hepatitis; uveitis; pulmonary fibrosis; non-alcoholic fatty liver disease (NAFLD); or non-alcoholic steatohepatitis (NASH).

In one embodiment, the treatment is treatment of: inflammatory arthritis (including, e.g., rheumatoid arthritis; psoriatic arthritis; systemic lupus erythematosus; juvenile idiopathic arthritis); psoriasis; lupus nephritis; systemic sclerosis; inflammatory bowel disease; ulcerative colitis; Crohn's disease; or multiple sclerosis.

In one embodiment, the treatment is treatment of: inflammatory arthritis.

In one embodiment, the treatment is treatment of: rheumatoid arthritis.

In one embodiment, the treatment is treatment of: psoriatic arthritis.

In one embodiment, the treatment is treatment of: systemic lupus erythematosus.

In one embodiment, the treatment is treatment of: juvenile idiopathic arthritis.

In one embodiment, the treatment is treatment of: psoriasis.

In one embodiment, the treatment is treatment of: lupus nephritis.

In one embodiment, the treatment is treatment of: systemic sclerosis.

In one embodiment, the treatment is treatment of: inflammatory bowel disease.

In one embodiment, the treatment is treatment of: ulcerative colitis.

In one embodiment, the treatment is treatment of: Crohn's disease.

In one embodiment, the treatment is treatment of: multiple sclerosis.

Conditions Treated—Cancer

In one embodiment, the treatment is treatment of: cancer.

In one embodiment, the treatment is treatment of: multiple myeloma; lymphoma; leukaemia; carcinoma; or sarcoma.

Multiple Myeloma:

In one embodiment, the treatment is treatment of: multiple myeloma.

Lymphoma:

In one embodiment, the treatment is treatment of: lymphoma.

In one embodiment, the treatment is treatment of: Hodgkin's lymphoma; non-Hodgkin's lymphoma; lymphocytic lymphoma; granulocytic lymphoma; monocytic lymphoma; diffuse large B-cell lymphoma (DLBCL); mantel cell lymphoma (MCL); follicular cell lymphoma (FL); mucosa-associated lymphoid tissue (MALT) lymphoma; marginal zone lymphoma; T-cell lymphoma; marginal zone lymphoma; or Burkitt's lymphoma.

In one embodiment, the treatment is treatment of lymphocytic lymphoma; granulocytic lymphoma; monocytic lymphoma; or diffuse large B-cell lymphoma (DLBCL).

In one embodiment, the treatment is treatment of: diffuse large B-cell lymphoma (DLBCL).

Leukaemia:

In one embodiment, the treatment is treatment of: leukaemia.

In one embodiment, the treatment is treatment of: chronic lymphocytic leukemia (CLL); acute myeloid leukemia (AML); acute lymphocytic leukemia (ALL); lymphoblastic T-cell leukemia; chronic myelogenous leukemia (CML); hairy-cell leukemia; acute lymphoblastic T-cell leukemia; acute eosinophilic leukemia; immunoblastic large-cell leukemia; megakaryoblastic leukemia; acute megakaryocytic leukemia; promyelocytic leukemia; erythroleukemia; or plasmacytoma.

In one embodiment, the treatment is treatment of: chronic lymphocytic leukemia (CLL); acute myeloid leukemia (AML); acute lymphocytic leukemia (ALL); lymphoblastic T-cell leukemia; chronic myelogenous leukemia (CML); or acute eosinophilic leukemia.

In one embodiment, the treatment is treatment of: chronic lymphocytic leukemia (CLL).

In one embodiment, the treatment is treatment of: acute myeloid leukemia (AML).

In one embodiment, the treatment is treatment of: acute lymphocytic leukemia (ALL).

In one embodiment, the treatment is treatment of: lymphoblastic T-cell leukemia.

In one embodiment, the treatment is treatment of: chronic myelogenous leukemia (CML).

Carcinoma:

In one embodiment, the treatment is treatment of: carcinoma.

In one embodiment, the treatment is treatment of: colon cancer; breast cancer; ovarian cancer; lung cancer (including, e.g., small cell lung carcinoma and non-small cell lung carcinoma); prostate cancer; cancer of the oral cavity or pharynx (including, e.g., cancer of the lip, tongue, mouth, larynx, pharynx, salivary gland, buccal mucosa); esophageal cancer; stomach cancer; small intestine cancer; large intestine cancer; rectal cancer; liver passage cancer; biliary passage cancer; pancreatic cancer; bone cancer; connective tissue cancer; skin cancer; cervical cancer; uterine cancer; corpus cancer; endometrial cancer; vulval cancer; vaginal cancer; testicular cancer; bladder cancer; kidney cancer; ureter cancer; urethral cancer; urachus cancer; eye cancer; glioma; spinal cord cancer; central nervous system cancer; peripheral nervous system cancer; meningeal cancer; thyroid cancer; adrenocarcinoma; astrocytoma; acoustic neuroma; anaplastic astrocytoma; basal cell carcinoma; blastoglioma; choriocarcinoma; chordoma; craniopharyngioma; cutaneous melanoma; cystadenocarcinoma; embryonal carcinoma; ependymoma; epithelial carcinoma; gastric cancer; genitourinary tract cancer; glioblastoma multiforme; head and neck cancer; hemangioblastoma; hepatocellular carcinoma; renal cell carcinoma (RCC); hepatoma; large cell carcinoma; medullary thyroid carcinoma; medulloblastoma; meningioma mesothelioma; myeloma; neuroblastoma; oligodendroglioma; epithelial ovarian cancer; papillary carcinoma; papillary adenocarcinoma; paraganglioma; parathyroid tumour; pheochromocytoma; pinealoma; plasmacytoma; retinoblastoma; sebaceous gland carcinoma;

seminoma; melanoma; squamous cell carcinoma; sweat gland carcinoma; synovioma; thyroid cancer; uveal melanoma; or Wilm's tumor.

In one embodiment, the treatment is treatment of: colon cancer; breast cancer; ovarian cancer; lung cancer (including, e.g., small cell lung carcinoma and non-small cell lung carcinoma); prostate cancer; stomach cancer; pancreatic cancer; bone cancer; skin cancer; cervical cancer; uterine cancer; endometrial cancer; testicular cancer; bladder cancer; kidney cancer; eye cancer; liver cancer; glioma; thyroid cancer; adrenocarcinoma; astrocytoma; acoustic neuroma; anaplastic astrocytoma; cutaneous melanoma; gastric cancer; glioblastoma multiforme; head and neck cancer; hepatocellular carcinoma; renal cell carcinoma (RCC); melanoma; or squamous cell carcinoma.

In one embodiment, the treatment is treatment of: colon cancer; breast cancer; ovarian cancer; lung cancer (including, e.g., small cell lung carcinoma and non-small cell lung carcinoma); prostate cancer; pancreatic cancer; bone cancer; liver cancer; glioblastoma multiforme; head and neck cancer; or melanoma.

In one embodiment, the treatment is treatment of: melanoma.

In one embodiment, the treatment is treatment of: glioblastoma multiforme.

In one embodiment, the treatment is treatment of: breast cancer.

In one embodiment, the treatment is treatment of: prostate cancer.

In one embodiment, the treatment is treatment of: bone cancer.

In one embodiment, the treatment is treatment of: pancreatic cancer.

In one embodiment, the treatment is treatment of: head and neck cancer.

In one embodiment, the treatment is treatment of: lung cancer (including, e.g., small cell lung carcinoma and non-small cell lung carcinoma).

In one embodiment, the treatment is treatment of: ovarian cancer.

In one embodiment, the treatment is treatment of: liver cancer.

Sarcoma:

In one embodiment, the treatment is treatment of: sarcoma.

In one embodiment, the treatment is treatment of: Askin's tumour; sarcoma botryoides; chondrosarcoma; endotheliosarcoma; Ewing's sarcoma; Malignant hemagioendothelioma; malignant Schwannoma; osteosarcoma; gastrointestinal stromal tumour (GIST); myxosarcoma; alveolar soft part sarcoma; angiosarcoma; cystosarcoma phyllodes; dermatofibrosarcoma; desmoid tumour; desmoplastic small round cell tumour; extraskeletal chondrosarcoma; osteosarcoma; fibrosarcoma; hemagiopericytoma; hemangiosarcoma; Kaposi's sarcoma; leiomyosarcoma; liposarcoma; lyphangiosarcoma; lymphangioendotheliosarcoma; lymphosarcoma; malignant peripheral nerve sheath tumour; neurofibrosarcoma; plexiform fibrohistiocytic tumour; rhabdomyosarcoma; or synovial sarcoma.

Treatment Refractory Cancer:

In one embodiment, the treatment is treatment of: treatment refractory cancer (including, e.g., chemotherapy resistant cancer and radiotherapy resistant cancer); metastatic cancer; metastases; or recurrent cancer.

In one embodiment, the treatment is treatment of: chemotherapy resistant cancer (including, e.g., chemotherapy resistant multiple myeloma, lymphoma, leukaemia, carcinoma, and sarcoma).

In one embodiment, the treatment is treatment of: radiotherapy resistant cancer (including, e.g., radiotherapy resistant multiple myeloma, lymphoma, leukaemia, carcinoma, and sarcoma).

In one embodiment, the treatment is treatment of: metastatic cancer.

In one embodiment, the treatment is treatment of: metastases.

In one embodiment, the treatment is treatment of: recurrent cancer.

In one embodiment, the treatment is use in: preventing, reducing, or overcoming resistance to radiotherapy or chemotherapy (for example, due to changes in cellular metabolism); preventing or reducing tumor invasion; preventing or reducing tumor metastasis; improving the action of anti-tumour agents; and/or augmenting the action of immunomodulators.

In one embodiment, the treatment is use in: preventing, reducing, or overcoming resistance to radiotherapy.

In one embodiment, the treatment is use: in preventing, reducing, or overcoming resistance to chemotherapy.

In one embodiment, the treatment is use in: preventing or reducing tumor invasion or tumor metastasis; improving the action of anti-tumour agents; and/or augmenting the action of immunomodulators.

In one embodiment, the treatment is use in: improving the action of anti-tumour agents; and/or augmenting the action of immunomodulators.

In one embodiment, the treatment is use in: improving the action of immunomodulators.

Conditions Treated—Disorders Mediated by Osteoclasts

In one embodiment, the treatment is treatment of: a disorder mediated by osteoclasts.

In one embodiment, the treatment is treatment of: rheumatoid arthritis; osteoporosis; Paget's disease; osteopetrosis; osteoarthritis; ectopic bone formation; bone loss associated with endometriosis; neoplasia of bones (including, e.g., as a primary tumour or as metastases and including, e.g., bone cancer; osteosarcoma; or osteoma); cancer-associated bone disease (including, e.g., metastatic bone disease associated with, e.g., breast cancer, lung cancer, prostate cancer, or multiple myeloma; changes in bone mineralisation and density associated with cancer, including, e.g., hypercalcaemia associated with cancer); bone metastases (including, e.g., osteolytic bone metastases); hypercalcaemia (including, e.g., hypercalcaemia associated with cancer; hypercalcaemia caused by conditions associated with increased bone resorption (including, e.g., hypercalcaemia caused by vitamin D intoxication, primary or tertiary hyperparathyroidism, immobilisation, or sarcoidosis); or aseptic loosening of prosthetic implants (e.g., artificial joints, e.g., knees, hips, etc.).

In one embodiment, the treatment is treatment of: rheumatoid arthritis; osteoporosis; neoplasia of bones (including, e.g., as a primary tumour or as metastases and including, e.g., bone cancer; osteosarcoma; or osteoma); cancer-associated bone disease (including, e.g., metastatic bone disease associated with, e.g., breast cancer, lung cancer, prostate cancer, or multiple myeloma; changes in bone mineralisation and density associated with cancer, including, e.g., hypercalcaemia associated with cancer); or bone metastases (including, e.g., osteolytic bone metastases).

In one embodiment, the treatment is treatment of: rheumatoid arthritis.

In one embodiment, the treatment is treatment of: osteoporosis.

In one embodiment, the treatment is treatment of: neoplasia of bones (including, e.g., as a primary tumour or as metastases and including, e.g., bone cancer; osteosarcoma; or osteoma).

In one embodiment, the treatment is treatment of: bone cancer; osteosarcoma; or osteoma.

In one embodiment, the treatment is treatment of: cancer-associated bone disease (including, e.g., metastatic bone disease associated with, e.g., breast cancer, lung cancer, prostate cancer, or multiple myeloma; changes in bone mineralisation and density associated with cancer, including, e.g., hypercalcaemia associated with cancer).

In one embodiment, the treatment is treatment of: bone metastases.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment of inflammation includes the prophylaxis of inflammation, reducing the incidence of inflammation, reducing the severity of inflammation, alleviating the symptoms of inflammation, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, anti-inflammation agents, etc. Examples of treatments and therapies include chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more additional therapeutic agents.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The CHMSA compounds described herein may also be used as part of an in vitro assay, for example, in order to determine whether a candidate host is likely to benefit from treatment with the compound in question.

The CHMSA compounds described herein may also be used as a standard, for example, in an assay, in order to identify other compounds, other anti-inflammation agents, etc.

Kits

One aspect of the invention pertains to a kit comprising (a) a CHMSA compound as described herein, or a composition comprising a CHMSA compound as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

Routes of Administration

The CHMSA compound or pharmaceutical composition comprising the CHMSA compound may be administered to a subject by any convenient route of administration, whether systemically/peripherally or topically (i.e., at the site of desired action).

Routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one preferred embodiment, the route of administration is oral (e.g., by ingestion). In one preferred embodiment, the route of administration is parenteral (e.g., by injection).

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human. Furthermore, the subject/patient may be any of its forms of development, for example, a foetus.

In one preferred embodiment, the subject/patient is a human.

Formulations

While it is possible for the CHMSA compound to be administered alone, it is preferable to present it as a pharmaceutical formulation (e.g., composition, preparation, medicament) comprising at least one CHMSA compound, as described herein, together with one or more other pharmaceutically acceptable ingredients well known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined herein, and methods of making a pharmaceutical composition comprising admixing at least one CHMSA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example, from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the CHMSA compounds, and compositions comprising the CHMSA compounds, can vary from patient to patient. Determining the optimal dosage will generally involve the balancing of the level of therapeutic benefit against any risk or deleterious side effects. The selected dosage level will depend on a variety of factors including the activity of the particular CHMSA compound, the route of administration, the time of administration, the rate of excretion of the CHMSA compound, the duration of the treatment, other drugs, compounds, and/or materials used in combination, the severity of the condition, and the species, sex, age, weight, condition, general health, and prior medical history of the patient. The amount of CHMSA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the CHMSA compound is in the range of about 10 µg to about 20 mg (more typically about 100 µg to about 10 mg) per kilogram body weight of the subject per day. Where the compound is a salt, an ester, an amide, a prodrug, or the like, the amount administered is calculated on the basis of the parent compound and so the actual weight to be used is increased proportionately.

Chemical Synthesis

Acronyms and Abbreviations aq.: aqueous
$B_2pin_2$: bis(pinacolato)diborane
DCM: dichloromethane
DEA: diethylamine
DMF: dimethylformamide
DMSO: dimethyl sulfoxide
Eq: equivalent
ESI: electrospray ionization
EtOAc: ethyl acetate
FID: flame ionization detector
GC: gas chromatography
HPLC: high-performance liquid chromatography
KOAc: potassium acetate
LAH: lithium aluminium hydride
LCMS: liquid chromatography-mass spectrometry
$LiAlH_4$: lithium aluminium hydride
m-CPBA: meta-chloroperoxybenzoic acid
m/z: mass-to-charge ratio
MeOH: methanol
NaH: Sodium hydride
NMR: nuclear magnetic resonance (spectroscopy)
p-TSA: para-toluenesulfonic acid
$PdCl_2(PPh_3)_2$: bis(triphenylphosphine)palladium(II) dichloride
$Pd(dppf)Cl_2$: (1,1'-bis(diphenylphosphino)ferrocene)dichloropalladium(II)
$Pd(Ph_3)_4$: tetrakis(triphenylphosphine)palladium(0)
$PPh_3$: triphenylphosphine
rt: room temperature
SFC: supercritical fluid chromatography
TFA: trifluoroacetic acid
TFAA: trifluoroacetic anhydride
$Tf_2O$: trifluoromethanesulfonic anhydride
THF: tetrahydrofuran
TLC: thin-layer chromatography
TPP: triphenylphosphine Analytical HPLC Analytical HPLC characterisation of the final compounds was performed as follows:
Column: X-select CSH C18, 4.6 mm×150 mm, ID 3.5 μm
Injection volume: 5 μL
Flow rate: 1 mL/min
Solvents:
A: 0.1% formic acid in water:acetonitrile (95:5)
B: acetonitrile
Gradient (B % is increased linearly between 1 minute and 8 minutes):

| Gradient | | |
|---|---|---|
| Time (min) | A % | B % |
| 0 | 95 | 5 |
| 1 | 95 | 5 |
| 8 | 0 | 100 |

| Gradient | | |
|---|---|---|
| Time (min) | A % | B % |
| 12 | 0 | 100 |
| 14 | 95 | 5 |
| 18 | 95 | 5 |

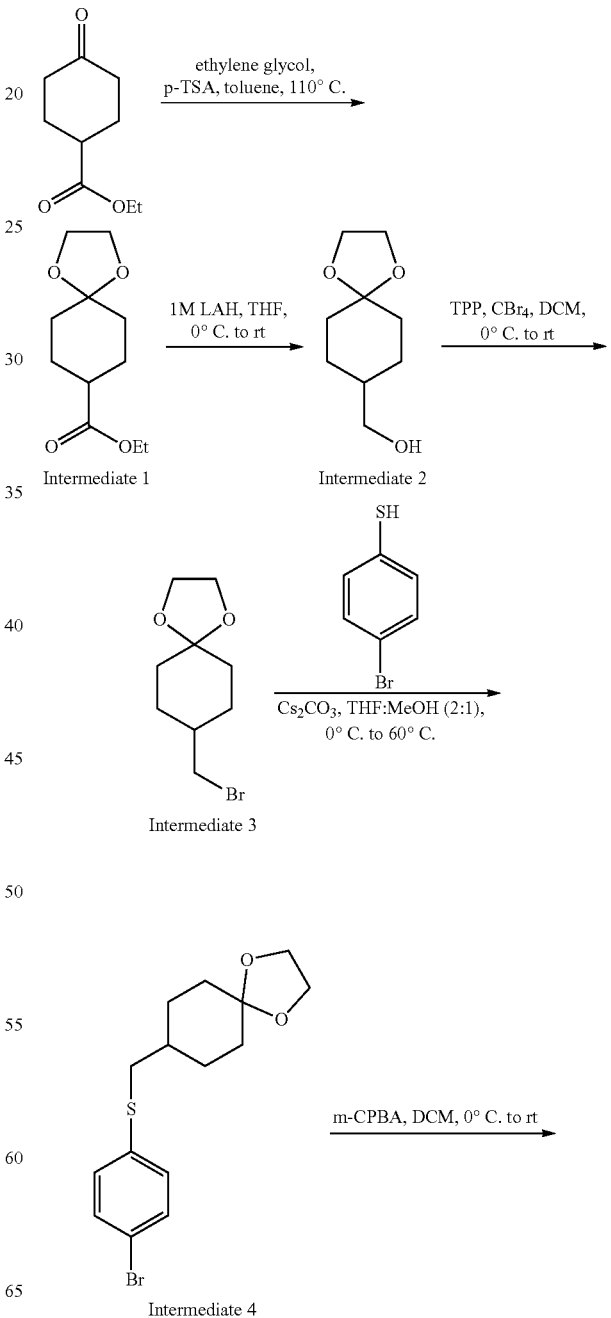

Synthetic Scheme 1

Intermediate 1

Ethyl 1,4-dioxaspiro[4.5]decane-8-carboxylate

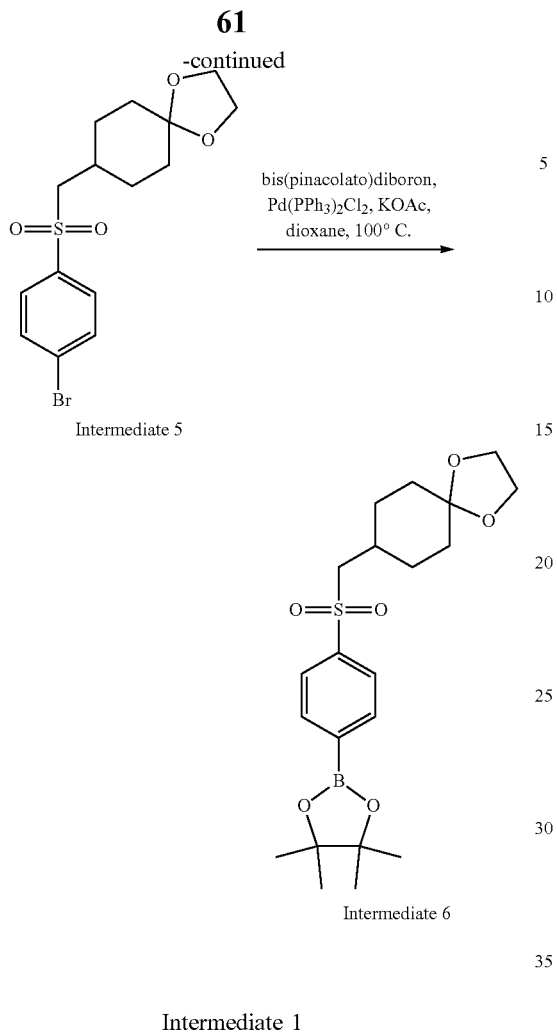

To a stirred solution of ethyl 4-oxocyclohexane-1-carboxylate (40.00 g, 235.00 mmol) in toluene (400 mL), ethylene glycol (16.05 g, 258.50 mmol) and p-toluenesulfonic acid (monohydrate) (0.45 g, 2.35 mmol) were added. The reaction mixture was heated with a Dean-Stark apparatus at 110° C. for 18 h with continuous removal of water. The progress of reaction was monitored by TLC [(TLC silica gel plate), 30% EtOAc in n-hexane]. After completion of the reaction, the reaction mixture was cooled to room temperature. It was quenched with saturated NaHCO$_3$ solution (100 mL) and extracted with EtOAc (3×200 mL). The combined organic layer was washed with brine (1×200 mL), dried over anhydrous sodium sulfate and concentrated under reduced pressure to afford the title compound Intermediate 1 (48.32 g, crude) as yellow oil which was used in the next step without further purification.

Intermediate 2

(1,4-Dioxaspiro[4.5]decan-8-yl)methanol

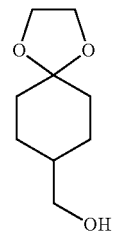

To a stirred solution of ethyl 1,4-dioxaspiro[4.5]decane-8-carboxylate Intermediate 1 (48.32 g, 225.52 mmol) in THF (300 mL), 1M LAH solution (225.52 mL, 225.52 mmol) was slowly added at 0° C. The reaction mixture was allowed to come to room temperature and stirred for 12 h. The progress of the reaction was monitored by TLC [(TLC silica gel plate), 30% EtOAc in n-hexane]. After completion of the reaction, the reaction mixture was quenched with saturated aqueous Na$_2$SO$_4$ solution (240 mL). The precipitated solid was filtered and washed with EtOAc (250 mL). From the filtrate, the organic layer was separated, and the aqueous layer was extracted with EtOAc (2×100 mL). The combined organic layer was dried over anhydrous sodium sulfate and concentrated under reduced pressure to afford the title compound Intermediate 2 (33.45 g, crude) as colorless oil which was used in the next step without further purification.

Analytical data: $^1$H NMR (400 MHz, CDCl$_3$) δ ppm: 3.95 (s, 4H), 3.49 (d, J=6.4 Hz, 2H), 1.80-1.75 (m, 4H), 1.59-1.49 (m, 3H), 1.32-1.23 (m, 2H).

Intermediate 3

8-(Bromomethyl)-1,4-dioxaspiro[4.5]decane

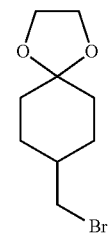

To a stirred solution of (1,4-dioxaspiro[4.5]decan-8-yl)methanol Intermediate 2 (33.45 g, 194.23 mmol) in DCM (400 mL), triphenylphosphine (50.95 g, 194.23 mmol), carbon tetrabromide (67.63 g, 203.94 mmol) were added at 0° C. The reaction mixture was allowed to come to room temperature and stirred for 12 h. The progress of the reaction was monitored by TLC [(TLC silica gel plate) 30% EtOAc in n-hexane]. After completion of the reaction, the reaction mixture was quenched with water (200 mL) and extracted with DCM (3×200 mL). The combined organic layer was washed with brine (2×150 mL), dried over anhydrous sodium sulfate and concentrated under reduced pressure to get a crude residue. The obtained residue was purified by column chromatography (230-400 mesh silica gel, gradient 1-10% EtOAc in n-hexane) to afford the title compound Intermediate 3 (35.00 g, 77%) as colorless oil.

Analytical data: LCMS (ESI) m/z=237.10 [M+1]$^+$ ($^{81}$Br).

Intermediate 4

8-(((4-Bromophenyl)thio)methyl)-1,4-dioxaspiro[4.5]decane

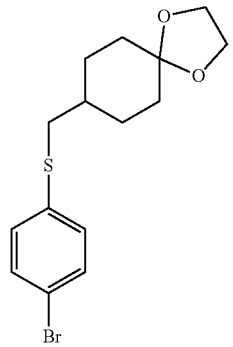 [SMILES: Brc1ccc(SCC2CCC3(CC2)OCCO3)cc1]

To a stirred solution of 4-bromobenzenethiol (11.77 g, 62.26 mmol) in THF:MeOH (2:1, 150 mL), Cs$_2$CO$_3$ (33.81 g, 103.78 mmol) was added at 0° C. and the reaction mixture was stirred for 20 min at 0° C. 8-(Bromomethyl)-1,4-dioxaspiro[4.5]decane Intermediate 3 (12.20 g, 51.89 mmol) was added to it and the reaction mixture was stirred at 60° C. for 12 h. The progress of the reaction was monitored by TLC [(TLC silica gel plate), 20% EtOAc in n-hexane]. After complete consumption of 8-(bromomethyl)-1,4-dioxaspiro[4.5]decane Intermediate 3, the reaction mixture was concentrated under reduced pressure, the obtained residue was dissolved in water (150 mL) and extracted with EtOAc (3×150 mL). The combined organic layer was dried over anhydrous sodium sulfate, filtered and concentrated under reduced pressure to get a crude residue. The residue was purified by flash column chromatography (230-400 mesh silica gel, gradient 1-10% EtOAc in n-hexane) to afford the title compound Intermediate 4 (12.00 g, 67%) as colorless oil.

Analytical data: LCMS (ESI) m/z=343.10 [M+H]$^+$.

Intermediate 5

8-(((4-Bromophenyl)sulfonyl)methyl)-1,4-dioxaspiro[4.5]decane

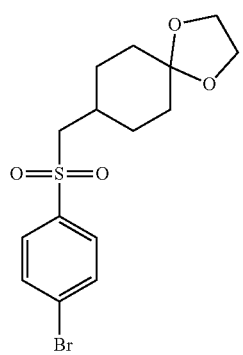 [SMILES: O=S(=O)(CC1CCC2(CC1)OCCO2)c1ccc(Br)cc1]

To a stirred solution of 8-(((4-bromophenyl)thio)methyl)-1,4-dioxaspiro[4.5]decane Intermediate 4 (12.00 g, 34.96 mmol) in DCM (150 mL), 3-chloroperoxybenzoic acid (~60% in water) (30.16 g, 104.87 mmol) was added at 0° C. portionwise over a period of 30 min. The reaction mixture was allowed to come to room temperature and stirred for 16 h. The progress of the reaction was monitored by TLC [(TLC silica gel plate) 20% EtOAc in n-hexane]. After completion of the reaction, the reaction mixture was cooled to 0° C., saturated aq. NaHCO$_3$ solution (100 mL) was added slowly and layers were separated. The separated organic layer was cooled to 0° C., saturated aq. Na$_2$S$_2$O$_3$ solution (100 mL) was slowly added. The organic layer was separated, dried over anhydrous sodium sulfate, filtered and concentrated under reduced pressure to get a crude residue. The residue obtained was purified by flash column chromatography (230-400 mesh silica gel, gradient 1-20% EtOAc in n-hexane) to afford the title compound Intermediate 5 (11.00 g, 84%) as white solid.

Analytical data: LCMS (ESI) m/z=377.10 [M+1]$^+$ ($^{81}$Br).

Intermediate 6

2-(4-(((1,4-Dioxaspiro[4.5]decan-8-yl)methyl)sulfonyl)phenyl)-4,4,5,5-tetramethyl-1,3,2-dioxaborolane

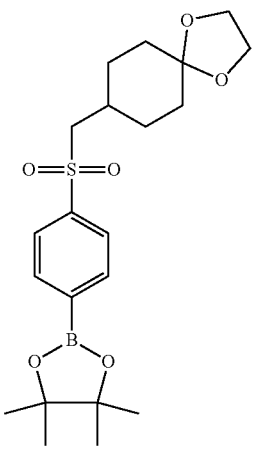 [SMILES: CC1(C)OB(c2ccc(S(=O)(=O)CC3CCC4(CC3)OCCO4)cc2)OC1(C)C]

To a stirred solution of 8-(((4-bromophenyl)sulfonyl)methyl)-1,4-dioxaspiro[4.5]decane Intermediate 5 (11.00 g, 29.31 mmol) in 1,4-dioxane (120 mL), potassium acetate (8.63 g, 87.93 mmol) and bis(pinacolato)diboron (9.68 g, 38.10 mmol) were added at room temperature and the reaction mixture was degassed using argon for 15 min. Bis(triphenylphosphine)palladium(II) dichloride (0.31 g, 0.44 mmol) was added to it and the reaction mixture was degassed for another 10 min and stirred at 100° C. for 4 h in a sealed tube. The progress of the reaction was monitored by TLC [(TLC silica gel plate), 30% EtOAc in n-hexane]. After completion of the reaction, the reaction mixture was concentrated under reduced pressure, the obtained residue was dissolved in EtOAc (250 mL) and washed with water (100 mL). The organic layer was dried over anhydrous sodium sulfate, filtered and concentrated under reduced pressure to get a crude residue. The residue obtained was purified by flash column chromatography (230-400 mesh silica gel, gradient 1-20% EtOAc in n-hexane) to afford the title compound Intermediate 6 (10.00 g, 81%) as white solid.

Analytical data: LCMS (ESI) m/z=423.30 [M+H]⁺ and 341.10 [M+H]⁺ (corresponding boronic acid).

Synthetic Scheme 2

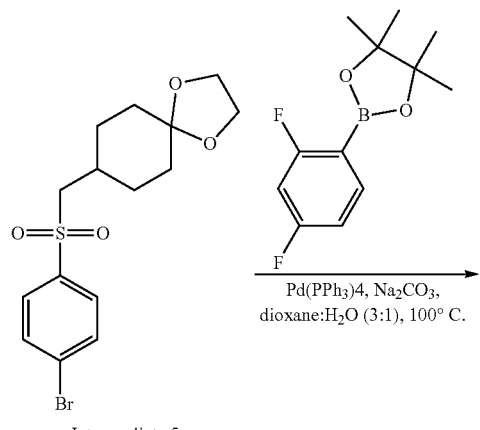

Intermediate 5

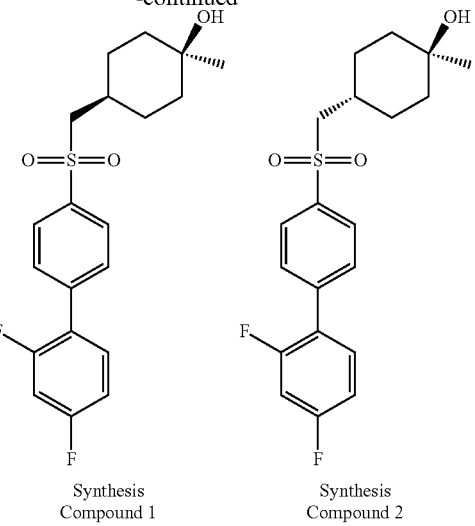

Synthesis Compound 1     Synthesis Compound 2

Intermediate 7

8-(((2',4'-Difluoro-(1,1'-biphenyl)-4-yl)sulfonyl)methyl)-1,4-dioxaspiro[4.5]decane

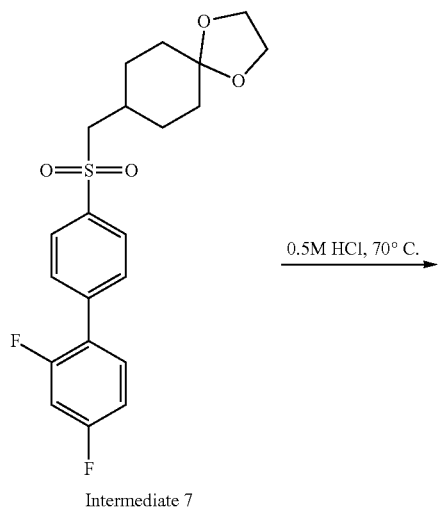

Intermediate 7

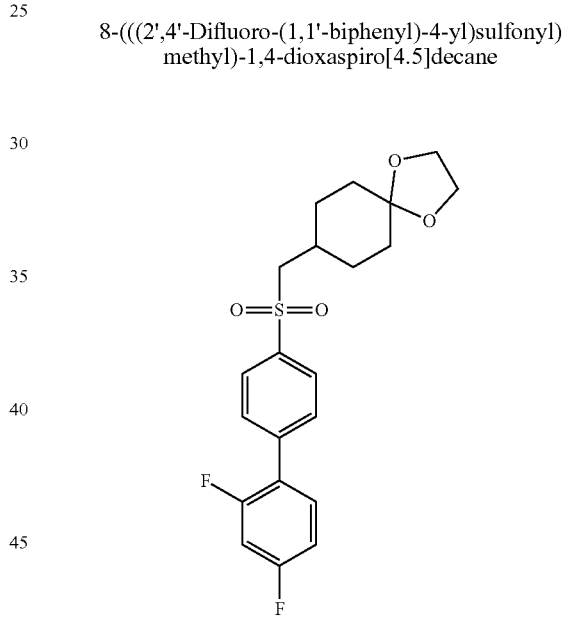

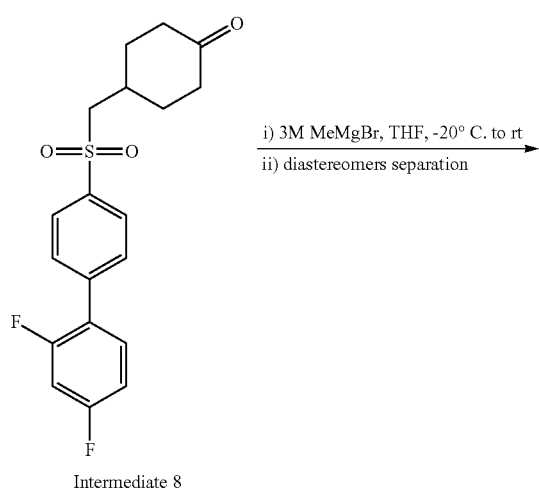

Intermediate 8

A mixture of 8-(((4-bromophenyl)sulfonyl)methyl)-1,4-dioxaspiro[4.5]decane Intermediate 5 (3.0 g, 8.0 mmol), 2-(2,4-difluorophenyl)-4,4,5,5-tetramethyl-1,3,2-dioxaborolane (2.3 g, 9.6 mmol) and sodium carbonate (2.5 g, 24 mmol) in dioxane-water (3:1, 30 mL) was degassed using argon for 30 min. Tetrakis(triphenylphosphine)palladium(0) (0.9 g, 0.78 mmol) was added to it and the reaction mixture was degassed for another 10 min and stirred at 100° C. for 12 h in a sealed tube. The progress of the reaction was monitored by TLC [(TLC silica gel plate), 60% EtOAc in n-hexane]. After completion of the reaction, the reaction mixture was concentrated under reduced pressure, the obtained residue was diluted with water and extracted with EtOAc. The organic layer was washed with brine, dried over anhydrous sodium sulfate and concentrated under reduced pressure. The residue obtained was purified by column chromatography (100-200 mesh silica gel) to afford the title compound Intermediate 7 (2.8 g, 86%) as white solid.

Analytical data: LCMS (ESI) m/z=409.20 [M+H]⁺.

Intermediate 8

4-(((2',4'-Difluoro-(1,1'-biphenyl)-4-yl)sulfonyl)methyl)cyclohexan-1-one

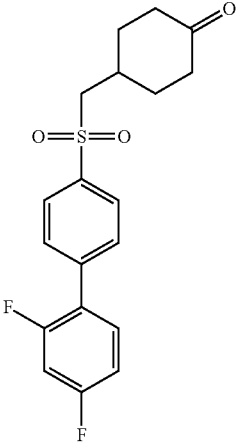 [SMILES: O=C1CCC(CS(=O)(=O)c2ccc(-c3ccc(F)cc3F)cc2)CC1]

8-(((2',4'-Difluoro-(1,1'-biphenyl)-4-yl)sulfonyl)methyl)-1,4-dioxaspiro[4.5]decane Intermediate 7 (2.8 g, 6.9 mmol) in 0.5M aq. HCl (20 mL) was stirred at 70° C. for 4 h. The progress of the reaction was monitored by TLC [(TLC silica gel plate), 1% MeOH in DCM]. After completion of the reaction, the reaction mixture was neutralized to pH 7 with 5% aq. sodium hydroxide solution, stirred for 30 min and extracted with 10% MeOH in DCM. The organic layer was washed with brine, dried over anhydrous sodium sulfate and concentrated under reduced pressure to afford the title compound Intermediate 8 (2.2 g, crude) which was used in the next step without further purification.

Analytical data: $^1$H NMR (400 MHz, DMSO-$d_6$) δ ppm, 8.04 (d, J=8.4 Hz, 2H), 7.85-7.81 (m, 2H), 7.73-7.65 (m, 1H), 7.49-7.42 (m, 1H), 7.3-7.23 (m, 1H), 3.47 (d, J=6.4 Hz, 2H), 2.42-2.3 (m, 3H), 2.25-2.16 (m, 2H), 2.15-2.05 (m, 2H), 1.63-1.51 (m, 2H).

Synthesis Compound 1 cis-4-(((2',4'-Difluoro-(1,1'-biphenyl)-4-yl)sulfonyl)methyl)-1-methylcyclohexan-1-ol

CHMSA-04-A

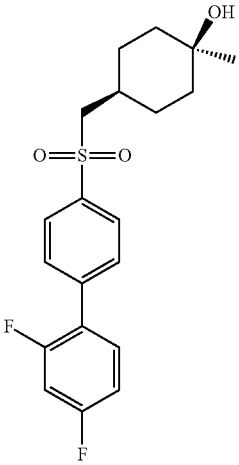 [SMILES: C[C@]1(O)CC[C@@H](CS(=O)(=O)c2ccc(-c3ccc(F)cc3F)cc2)CC1]

Synthesis Compound 2 trans-4-(((2',4'-difluoro-(1,1'-biphenyl)-4-yl)sulfonyl)methyl)-1-methylcyclohexan-1-ol

CHMSA-04-B

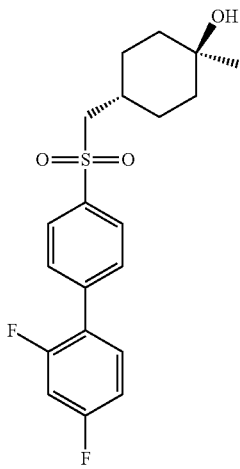 [SMILES: C[C@]1(O)CC[C@H](CS(=O)(=O)c2ccc(-c3ccc(F)cc3F)cc2)CC1]

A solution of 4-(((2',4'-difluoro-(1,1'-biphenyl)-4-yl)sulfonyl)methyl)cyclohexan-1-one) Intermediate 8 (2.70 g, crude) in THF (30 mL) under argon was cooled to −20° C. and 3M methyl magnesium bromide (2.96 mL, 8.9 mmol) was added to it, dropwise over a period of 30 min. The reaction mixture was stirred at room temperature for 12 h. The progress of the reaction was monitored by TLC [(TLC silica gel plate), 50% EtOAc in n-hexane]. After completion of the reaction, the reaction mixture was quenched with saturated ammonium chloride solution and extracted with EtOAc. The organic layer was washed with brine, dried over anhydrous sodium sulfate and concentrated under reduced pressure to give 2.5 g of material. 1 g of this crude material was purified by preparative HPLC (see below details) to afford the title compounds Synthesis Compound 1 (0.10 g) and Synthesis Compound 2 (0.10 g) as white solids.

Preparative HPLC method: Column-X-Select CSH 250 mm×30 mm, 5 µm; Flow rate: 30 mL/min; Detection wavelength: 210-400 nm; Mobile Phases: A: 0.1% formic acid in water and B: Acetonitrile.

| Gradient | |
|---|---|
| Time (min) | % B |
| 0.01 | 10 |
| 3.00 | 10 |
| 8.00 | 50 |
| 13.00 | 65 |
| 15.00 | 65 |
| 19.00 | 70 |
| 19.20 | 100 |
| 23.00 | 100 |
| 23.20 | 10 |
| 27.00 | 10 |

Analytical data (Synthesis Compound 1):
LCMS (ESI) m/z=363.05 [M−H$_2$O+1]$^+$.
HPLC (see generic method): Retention time=8.69 min. Purity=99.5%.

¹H NMR (400 MHz, DMSO-d₆) δ ppm: 8.00 (d, J=8.0 Hz, 2H), 7.83-7.78 (m, 2H), 7.72-7.65 (m, 1H), 7.48-7.41 (m, 1H), 7.29-7.23 (m, 1H), 3.94 (s, 1H), 3.26 (d, J=6.0 Hz, 2H), 1.78-1.65 (brs, 1H), 1.6-1.35 (m, 6H), 1.26-1.16 (m, 2H), 1.05 (s, 3H).

Analytical data (Synthesis Compound 2):
LCMS (ESI) m/z=363.0 [M−H₂O+1]⁺.
HPLC (see generic method): Retention time=8.43 min. Purity=98.5%.
¹H NMR (400 MHz, DMSO-d₆) δ ppm: 8.00 (d, J=8.0 Hz, 2H), 7.83-7.79 (m, 2H), 7.72-7.65 (m, 1H), 7.48-7.41 (m, 1H), 7.29-7.22 (m, 1H), 4.17 (s, 1H), 3.34-3.30 (m, 2H), 1.89-1.7 (m, 3H), 1.5-1.44 (m, 2H), 1.33-1.15 (m, 4H), 1.06 (s, 3H).

Synthetic Scheme 3

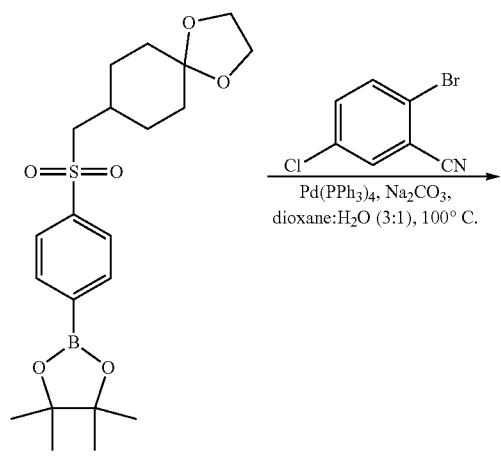

Intermediate 6

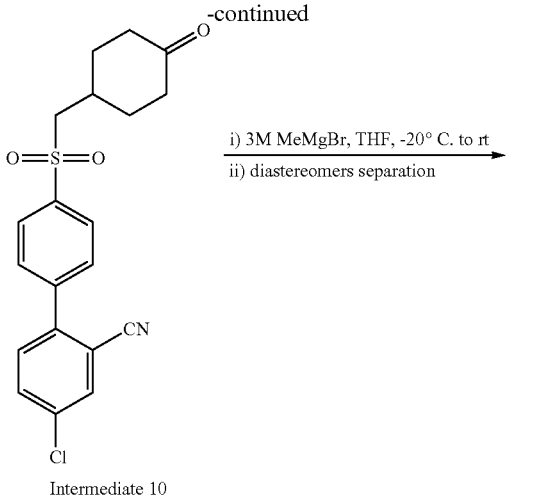

Intermediate 10

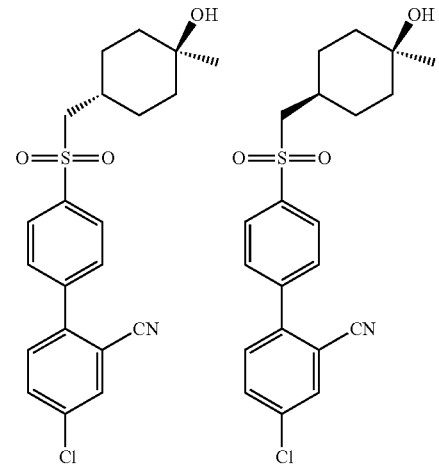

Synthesis Compound 3    Synthesis Compound 4

Intermediate 9

4-Chloro-4'-((1,4-dioxaspiro[4.5]decan-8-yl)methanesulfonyl)-(1,1'-biphenyl)-2-carbonitrile

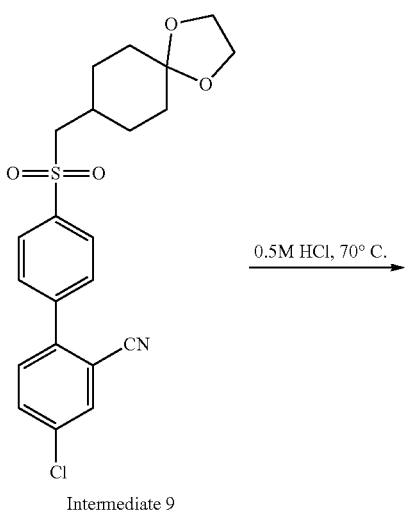

Intermediate 9

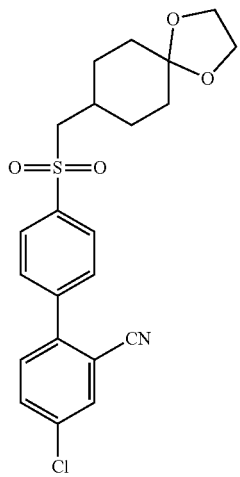 [SMILES: N#Cc1cc(Cl)ccc1-c1ccc(S(=O)(=O)CC2CCC3(CC2)OCCO3)cc1]

To a stirred solution of 2-(4-(((1,4-dioxaspiro[4.5]decan-8-yl)methyl)sulfonyl)phenyl)-4,4,5,5-tetramethyl-1,3,2-dioxaborolane Intermediate 6 (3.27 g, 7.7 mmol) in 1,4-dioxane:water (3:1) (40 mL) was added sodium carbonate (2.46 g, 23.2 mmol), followed by addition of 2-bromo-5-chlorobenzonitrile (1.67 g, 7.7 mmol). The reaction mixture was degassed for 20 min under an argon atmosphere and tetrakis(triphenylphosphine) palladium(0) (0.9 g, 0.78 mmol) was added to it and the reaction mixture was again degassed for 10 min. The reaction mixture was stirred at 100° C. for 12 h in a sealed tube. The progress of the reaction was monitored by TLC [(TLC silica gel plate), 20% EtOAc in n-hexane]. After completion of reaction, the reaction mixture was filtered through Celite® and the filtrate was evaporated under reduced pressure. The obtained residue was diluted with water and extracted with EtOAc. The organic layer was dried over anhydrous sodium sulfate and concentrated under reduced pressure. The obtained residue was purified by column chromatography (100-200 mesh silica) to afford the title compound Intermediate 9 (3.0 g) as a white solid.

Analytical data: LCMS (ESI) m/z=432.45[M+H]$^+$.

Intermediate 10

4-Chloro-4'-((4-oxocyclohexyl)methanesulfonyl)-(1,1'-biphenyl)-2-carbonitrile

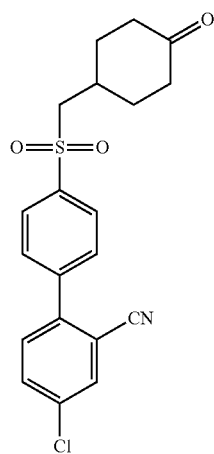

4-Chloro-4'-((1,4-dioxaspiro[4.5]decan-8-yl)methanesulfonyl)-(1,1'-biphenyl)-2-carbonitrile Intermediate 9 (3.0 g, 7.0 mmol) was stirred in 0.5M aq. HCl (30 mL) at 70° C. for 4 h. The progress of the reaction was monitored by TLC [(TLC silica gel plate), 50% EtOAc in n-hexane]. After completion of reaction, reaction mixture was neutralized to pH 7 with 5% sodium hydroxide solution and stirred for 30 min. Product was extracted with 10% MeOH in DCM. The organic layer was dried over anhydrous sodium sulfate and concentrated under reduced pressure to afford the title compound Intermediate 10 (2.3 g, crude).

Analytical data: LCMS (ESI) m/z=388.15 [M+H]$^+$.

Synthesis Compound 3

4-Chloro-4'-((trans-4-hydroxy-4-methylcyclohexyl)methanesulfonyl)-(1,1'-biphenyl)-2-carbonitrile

CHMSA-10-B

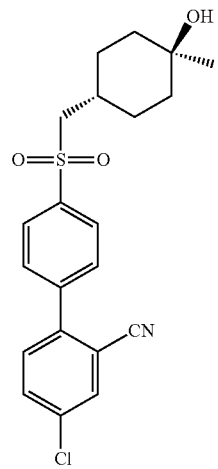 [SMILES: C[C@]1(O)CC[C@H](CS(=O)(=O)c2ccc(-c3ccc(Cl)cc3C#N)cc2)CC1]

Synthesis Compound 4

4-chloro-4'-((cis-4-hydroxy-4-methylcyclohexyl)methanesulfonyl)-(1,1'-biphenyl)-2-carbonitrile

CHMSA-10-A

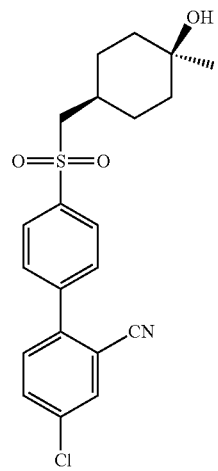 [SMILES: C[C@]1(O)CC[C@@H](CS(=O)(=O)c2ccc(-c3ccc(Cl)cc3C#N)cc2)CC1]

A stirred solution of 4-chloro-4'-((4-oxocyclohexyl)methanesulfonyl)-(1,1'-biphenyl)-2-carbonitrile Intermediate 10 (2.3 g, crude) in dry THF under an argon atmosphere was cooled to −20° C. and 3M methyl magnesium bromide (2.3 mL, 6.9 mmol) was added to it, dropwise over a period of 30 min. After the addition was completed, the reaction mixture was allowed to come to room temperature and stirred at room temperature for 12 h. The progress of the reaction was monitored by TLC [(TLC silica gel plate), 50% EtOAc in n-hexane]. After completion of the reaction, reaction mixture was quenched with saturated ammonium chloride solution and extracted with EtOAc. The organic layer was dried over anhydrous sodium sulfate and concentrated under reduced pressure to afford a residue which was purified by preparative HPLC (see below details) to get the title compounds Synthesis Compound 3 (0.110 g) and Synthesis Compound 4 (0.115 g) as white solids.

Preparative HPLC method: Column-X-Select CSH 250 mm×30 mm, 5 μm; Flow rate: 30 mL/min; Detection wavelength: 210-400 nm; Mobile Phases: A: 0.1% formic acid in water and B: Acetonitrile.

| Gradient | |
|---|---|
| Time (min) | % B |
| 0.01 | 10 |
| 3.00 | 10 |
| 8.00 | 50 |
| 13.00 | 65 |
| 15.00 | 65 |
| 19.00 | 70 |
| 19.20 | 100 |
| 23.00 | 100 |
| 23.20 | 10 |
| 27.00 | 10 |

Analytical data (Synthesis Compound 3):

LCMS (ESI) m/z=386.20 [M+1-H$_2$O]$^+$.

HPLC (see generic method): Retention time=8.37 min. Purity=99.0%.

$^1$H NMR (400 MHz, DMSO-d$_6$) δ ppm 8.22 (d, J=2.4 Hz, 1H), 8.06 (d, J=8.4 Hz, 2H), 7.93 (dd, J=8.8 Hz, J=2.4 Hz, 1H), 7.87 (d, J=8.4 Hz, 2H), 7.72 (d, J=8.8 Hz, 1H), 4.18 (s, 1H), 3.38-3.33 (m, 2H), 1.9-1.8 (m, 1H), 1.78-1.70 (m, 2H), 1.51-1.42 (m, 2H), 1.33-1.16 (m, 4H), 1.05 (s, 3H).

Analytical data (Synthesis Compound 4):

LCMS (ESI) m/z=386.05 [M+1-H$_2$O]$^+$.

HPLC (see generic method): Retention time=8.60 min. Purity=99.8%.

$^1$H NMR (400 MHz, DMSO-d$_6$) δ ppm 8.22 (d, J=2 Hz, 1H), 8.06 (d, J=8.4 Hz, 2H), 7.92 (dd, J=8.4, J=2.4 Hz, 1H), 7.86 (d, J=8.4 Hz, 2H), 7.72 (d, J=8.4 Hz, 1H), 3.94 (s, 1H), 3.32-3.27 (m, 2H), 1.79-1.67 (m, 1H), 1.57-1.36 (m, 6H), 1.26-1.17 (m, 2H), 1.05 (s, 3H).

Synthetic Scheme 4

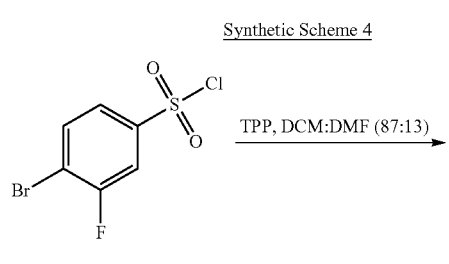

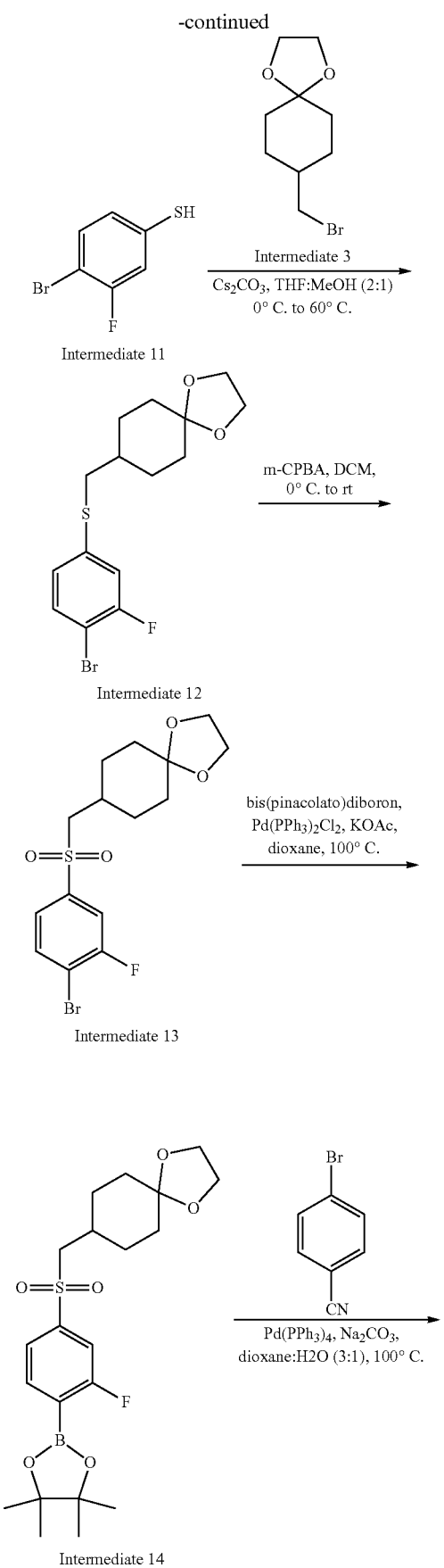

-continued

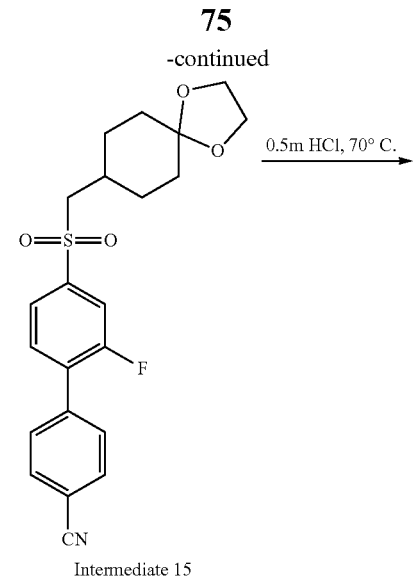

Intermediate 15

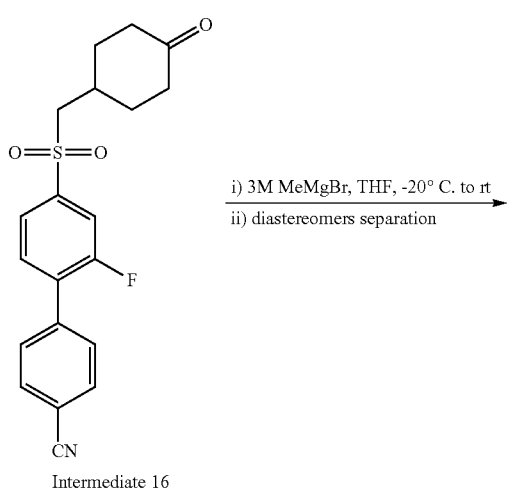

Intermediate 16

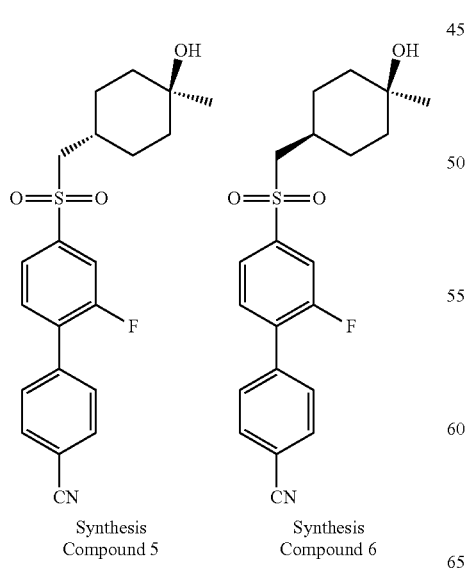

Synthesis Compound 5     Synthesis Compound 6

Intermediate 11

4-Bromo-3-fluorobenzenethiol

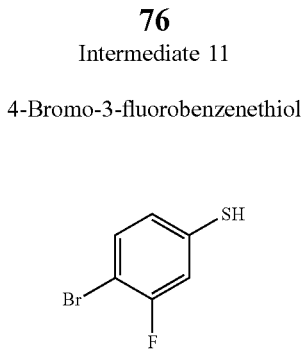

To a stirred solution of triphenylphosphine (43.16 g, 164.53 mmol) in DCM (200 mL) and DMF (30 mL), 4-bromo-3-fluorobenzenesulfonyl chloride (15.00 g, 54.84 mmol) was added dropwise at room temperature and the reaction mixture was stirred for 16 h. The progress of the reaction was monitored by TLC [(TLC silica gel plate) 5% EtOAc in n-hexane]. After completion of the reaction 1M aq. HCl (150 mL) was added, layers were separated, and organic layer was concentrated under reduced pressure to get a crude residue. The obtained residue was taken in 1M aq. NaOH solution (150 mL), the resulting suspension was filtered through Celite® and the filtrate was washed with $Et_2O$ (2×100 mL). The aqueous layer was neutralized with 1M aq. HCl (150 mL) and extracted with $Et_2O$ (3×150 mL). The combined organic layer was dried over anhydrous sodium sulfate, filtered and concentrated under reduced pressure to afford the title compound Intermediate 11 (7.00 g, crude) as colorless oil which was used as such for the next reaction without further purification.

Analytical data: $^1H$ NMR (400 MHz, $CDCl_3$) δ ppm 7.39-7.35 (m, 1H), 7.03 (dd, J=8.8, 2.4 Hz, 1H), 6.91 (dd, J=8.0, 2.0 Hz, 1H), 3.52 (s, 1H).

Intermediate 12

8-(((4-Bromo-3-fluorophenyl)thio)methyl)-1,4-dioxaspiro[4.5]decane

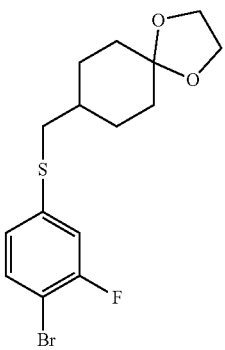 [SMILES: Fc1cc(SCC2CCC3(CC2)OCCO3)ccc1Br]

To a stirred solution of 4-bromo-3-fluorobenzenethiol Intermediate 11 (4.23 g, 20.43 mmol) in THF:MeOH (2:1, 30 mL), $Cs_2CO_3$ (16.64 g, 51.07 mmol) was added at 0° C. and the reaction mixture was stirred for 20 min. 8-(Bromomethyl)-1,4-dioxaspiro[4.5]decane Intermediate 3 (6.00 g, 25.54 mmol) dissolved in MeOH:THF (1:1, 15 mL) was added dropwise to it at the same temperature and then the reaction mixture was allowed to warm to room temperature and heated to 60° C. for 12 h. The progress of the reaction was monitored by TLC [(TLC silica gel plate), 10% EtOAc in n-hexane]. After completion of the reaction, the reaction mixture was concentrated under reduced pressure to get a crude residue. The obtained residue was dissolved in water (50 mL) and extracted with EtOAc (3×50 mL). The combined organic layer was washed with brine (2×50 mL), dried over anhydrous sodium sulfate and concentrated under reduced pressure to get a crude residue. The residue was purified by flash column chromatography (230-400 mesh silica gel, 5% EtOAc in n-hexane) to afford the title compound Intermediate 12 (6.12 g) as colorless oil.

Analytical data: LCMS (ESI) m/z=361.10 [M+1]$^+$ ($^{79}$Br).

Intermediate 13

8-(((4-Bromo-3-fluorophenyl)sulfonyl)methyl)-1,4-dioxaspiro[4.5]decane

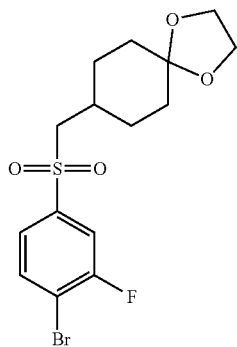 [SMILES: O=S(=O)(CC1CCC2(CC1)OCCO2)c1ccc(Br)c(F)c1]

To a stirred solution of 8-(((4-bromo-3-fluorophenyl)thio) methyl)-1,4-dioxaspiro[4.5]decane Intermediate 12 (6.10 g, 16.88 mmol) in DCM (50 mL), 3-chloroperoxybenzoic acid (~70% in water) (10.41 g, 42.21 mmol) was added at 0° C. portionwise over a period of 30 min and the reaction mixture was allowed to come to room temperature and stirred for 12 h. The progress of the reaction was monitored by TLC [(TLC silica gel plate), 20% EtOAc in n-hexane]. After completion of the reaction, the reaction mixture was quenched with saturated Na$_2$S$_2$O$_3$ solution (70 mL) and extracted with DCM (3×100 mL). The organic layer was separated, washed with brine (2×50 mL), dried over anhydrous sodium sulfate and concentrated under reduced pressure to get a crude residue. The residue obtained was purified by flash column chromatography (230-400 mesh silica gel, 10% EtOAc in n-hexane) to afford the title compound Intermediate 13 (5.80 g, 87%) as colorless solid.

Analytical data: LCMS (ESI) m/z=395.00 [M+1]$^+$ ($^{81}$Br).

Intermediate 14

2-(4-(((1,4-Dioxaspiro[4.5]decan-8-yl)methyl)sulfonyl)-2-fluorophenyl)-4,4,5,5-tetramethyl-1,3,2-dioxaborolane

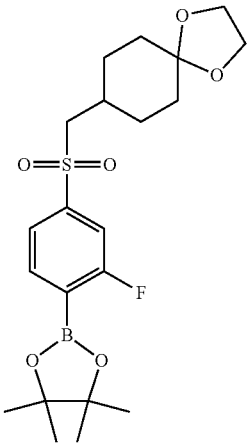 [SMILES: CC1(C)OB(c2ccc(S(=O)(=O)CC3CCC4(CC3)OCCO4)cc2F)OC1(C)C]

To a stirred solution of 8-(((4-bromo-3-fluorophenyl) sulfonyl)methyl)-1,4-dioxaspiro[4.5]decane Intermediate 13 (5.70 g, 14.49 mmol) in 1,4-dioxane (60 mL), potassium acetate (4.27 g, 43.48 mmol) and bis(pinacolato)diboron (4.78 g, 18.84 mmol) were added at room temperature and the reaction mixture was degassed using argon for 15 min. Bis(triphenylphosphine)palladium(II) dichloride (0.15 g, 0.22 mmol) was added to it and the reaction mixture was degassed for another 10 min and heated at 100° C. for 4 h in a sealed tube. The progress of the reaction was monitored by TLC [(TLC silica gel plate), 30% EtOAc in n-hexane]. After completion of the reaction, the reaction mixture was filtered, residue was washed with EtOAc (100 mL) and filtrate was concentrated under reduced pressure to afford the title compound Intermediate 14 (7.45 g, crude) as black solid which was used as such for the next reaction without further purification.

Analytical data: LCMS (ESI) m/z=359.20 [M+1]$^+$ (corresponding boronic acid).

Intermediate 15

4'-(((1,4-Dioxaspiro[4.5]decan-8-yl)methyl)sulfonyl)-2'-fluoro-[1,1'-biphenyl]-4-carbonitrile

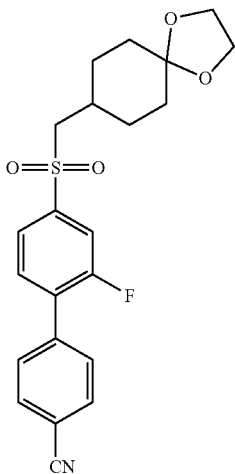

To a stirred solution of 2-(4-(((1,4-dioxaspiro[4.5]decan-8-yl)methyl)sulfonyl)-2-fluorophenyl)-4,4,5,5-tetramethyl-1,3,2-dioxaborolane Intermediate 14 (3.00 g, 6.81 mmol) in dioxane-water (3:1, 40 mL), sodium carbonate (2.17 g, 20.44 mmol), 4-bromobenzonitrile (1.24 g, 6.81 mmol) were added and the reaction mixture was degassed using argon for 20 min. Tetrakis[triphenylphosphine]palladium(0) (0.79 g, 0.68 mmol) was added to it and the reaction mixture was degassed for another 10 min and stirred at 100° C. for 12 h in a sealed tube. The progress of the reaction was monitored by TLC [(TLC silica gel plate), 40% EtOAc in n-hexane]. After completion of the reaction, the reaction mixture was cooled to room temperature, filtered through Celite® and the filtrate was concentrated under reduced pressure to get a crude residue. The obtained residue was dissolved in EtOAc (50 mL) and washed with water (50 mL). The organic layer was dried over anhydrous sodium sulfate and concentrated under reduced pressure to get a crude residue. The residue obtained was purified by flash column chromatography (230-400 mesh silica gel, 20% EtOAc in n-hexane) to afford the title compound Intermediate 15 (2.20 g) as colorless solid.

Analytical data: LCMS (ESI) m/z=416.00 [M+1]$^+$.

Intermediate 16

2'-Fluoro-4'-(((4-oxocyclohexyl)methyl)sulfonyl)-[1,1'-biphenyl]-4-carbonitrile

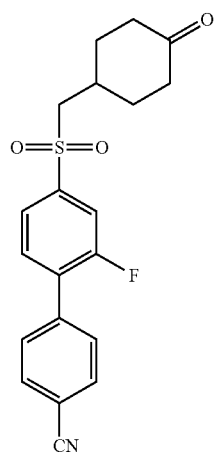 [SMILES: N#Cc1ccc(-c2ccc(S(=O)(=O)CC3CCC(=O)CC3)cc2F)cc1]

A solution of 4'-(((1,4-dioxaspiro[4.5]decan-8-yl)methyl)sulfonyl)-2'-fluoro-[1,1'-biphenyl]-4-carbonitrile Intermediate 15 (2.20 g, 5.30 mmol) in 0.5M aq. HCl (25 mL) was stirred at 70° C. for 4 h. The progress of the reaction was monitored by TLC [(TLC silica gel plate), 50% EtOAc in n-hexane]. After completion of the reaction, the reaction mixture was cooled to 0° C., neutralized to pH 7 with 5% aq. NaOH solution (~20 mL) and extracted with EtOAc (3×30 mL). The organic layer was separated, washed with brine (50 mL), dried over anhydrous sodium sulfate and concentrated under reduced pressure to get a crude residue. The residue obtained was purified by flash column chromatography (230-400 mesh silica gel, 30% EtOAc in n-hexane) to afford the title compound Intermediate 16 (1.70 g, 86%) as off-white solid.

Analytical data: LCMS (ESI) m/z=372.10 [M+1]$^+$.

Synthesis Compound 5

2'-Fluoro-4'-(((trans-4-hydroxy-4-methylcyclohexyl)methyl)sulfonyl)-[1,1'-biphenyl]-4-carbonitrile

CHMSA-12-B

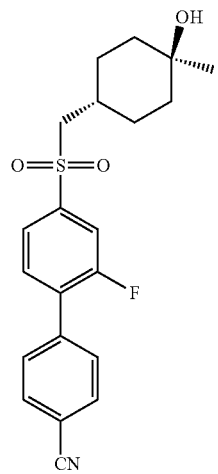 [SMILES: C[C@]1(O)CC[C@H](CS(=O)(=O)c2ccc(-c3ccc(C#N)cc3)c(F)c2)CC1]

Synthesis Compound 6

2'-fluoro-4'-(((cis-4-hydroxy-4-methylcyclohexyl)methyl)sulfonyl)-[1,1'-biphenyl]-4-carbonitrile

CHMSA-12-A

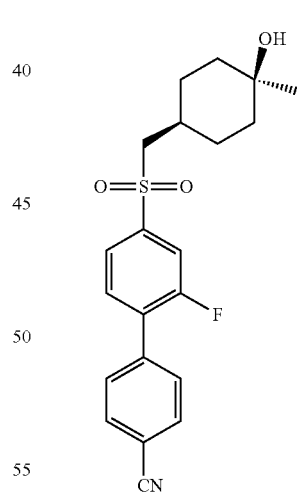

To a stirred solution of 2'-fluoro-4'-(((4-oxocyclohexyl)methyl)sulfonyl)-[1,1'-biphenyl]-4-carbonitrile Intermediate 16 (1.70 g, 4.58 mmol) in anhydrous THF (20 mL), 3M methyl magnesium bromide (1.83 mL, 5.49 mmol) was added at −20° C. and the reaction mixture was stirred at −20° C. for 1 h. The reaction mixture was allowed to come to room temperature and stirred for 4 h. The progress of the reaction was monitored by TLC [(TLC silica gel plate), 50% EtOAc in n-hexane]. After completion of the reaction, the reaction mixture was quenched with saturated aq. NH$_4$Cl solution (20 mL) and extracted with EtOAc (3×20 mL). The combined organic layer was dried over anhydrous sodium sulfate and concentrated under reduced pressure to get a crude residue. The residue obtained was purified by SFC chromatography (see below details) to afford the title compounds Synthesis Compound 5 (0.10 g, 6%) and Synthesis Compound 6 (0.18 g, 10%) as white solids.

Analytical data (Synthesis Compound 5):

LCMS (ESI) m/z=370.10 [M−H$_2$O+1]$^+$.

HPLC (see generic method): Retention time=8.07 min. Purity=98.65%.

$^1$H NMR (400 MHz, DMSO-d$_6$) δ ppm: 8.01 (d, J=8.4 Hz, 2H), 7.94-7.82 (m, 5H), 4.18 (s, 1H), 3.40 (d, J=6.0 Hz, 2H), 1.85 (br. s, 1H), 1.77-1.76 (m, 2H), 1.50-1.43 (m, 2H), 1.33-1.18 (m, 4H), 1.06 (s, 3H).

Analytical data (Synthesis Compound 6):

LCMS (ESI) m/z=370.10 [M−H$_2$O+1]$^+$.

HPLC (see generic method): Retention time=8.33 min. Purity=99.15%.

$^1$H NMR (400 MHz, DMSO-d$_6$) δ ppm: 8.01 (d, J=8.4 Hz, 2H), 7.94-7.82 (m, 5H), 3.95 (s, 1H), 1.74 (br. s, 1H), 1.57-1.39 (m, 6H), 1.26-1.20 (m, 2H), 1.05 (s, 3H). (2H's are merged in solvent peak).

SFC chromatography details:

Mobile Phases: A: CO$_2$; B: 0.1% NH$_3$ in MeOH.

Gradient: Started with 10% B, increased to 40% B over 5 min, held at 40% B for 4 min, reduced to 10% B over 1 min and held at 10% B for 2 min.

Column: Chiralpak IA (250 mm×4.6 mm, 5 μm). Wavelength: 260 nm. Flow rate: 3 mL/min.

Synthetic Scheme 5

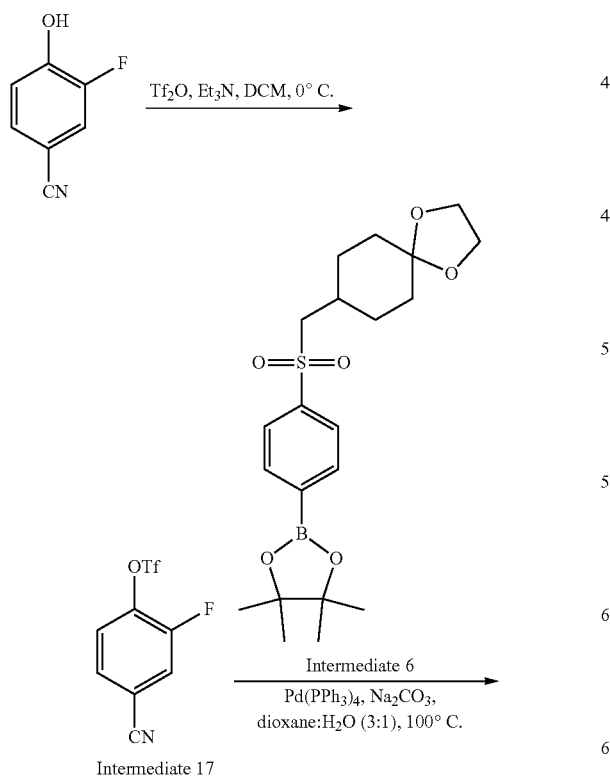

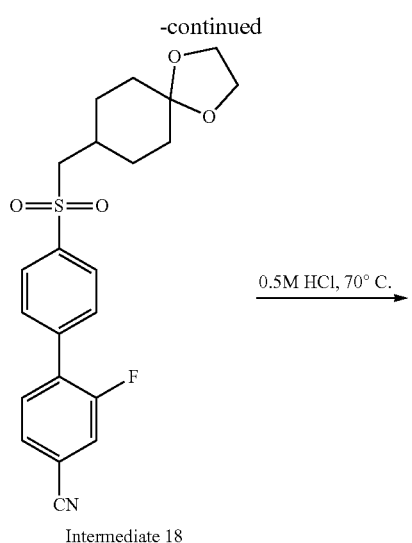

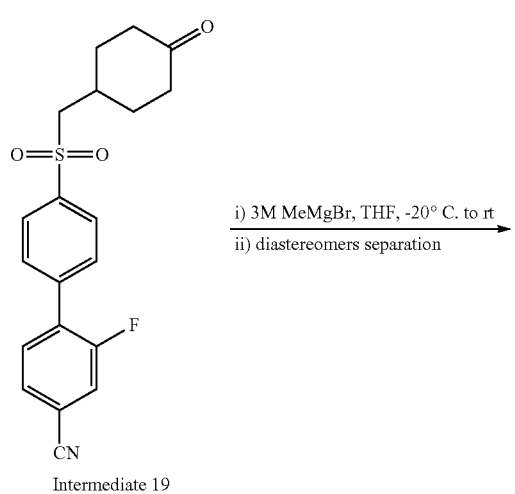

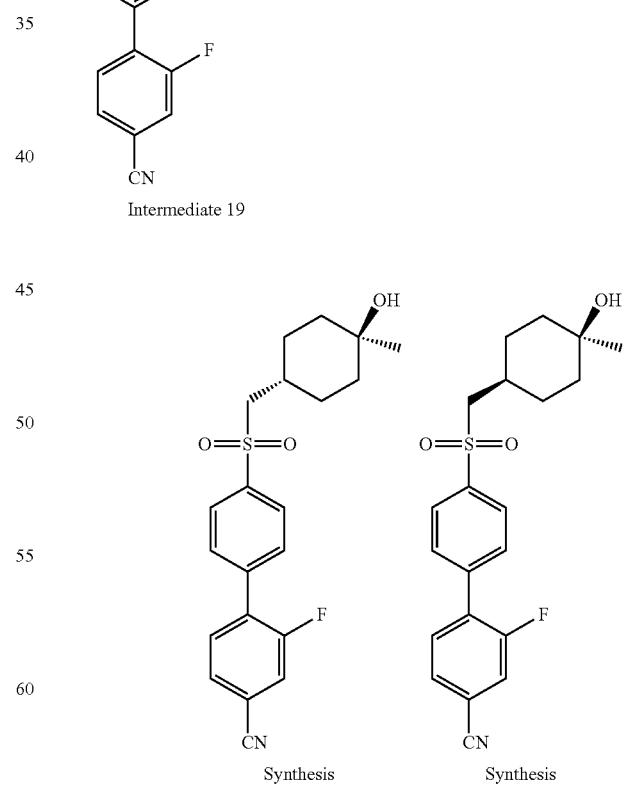

Intermediate 17

4-Cyano-2-fluorophenyl trifluoromethanesulfonate

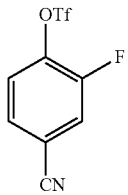

To a stirred solution of 3-fluoro-4-hydroxybenzonitrile (5.00 g, 36.47 mmol) in DCM (50 mL), triethyl amine (10.17 mL, 72.93 mmol) was added at 0° C. followed by addition of triflic anhydride (7.35 mL, 43.76 mmol) and the reaction mixture was stirred at 0° C. for 30 min. The progress of reaction was monitored by TLC [(TLC silica gel plate), 20% EtOAc in n-hexane]. After completion of the reaction, the reaction mixture was diluted with DCM (25 mL) and washed with water (50 mL). The organic layer was separated, dried over anhydrous sodium sulfate, filtered and concentrated under reduced pressure to get a crude residue. The obtained residue was purified by flash column chromatography (60-120 mesh silica gel, gradient 1-10% EtOAc in n-hexane) to afford the title compound Intermediate 17 (7.00 g, 71%) as colorless oil.

Analytical data: $^1$H NMR (400 MHz, DMSO-$d_6$) δ ppm 8.35 (dd, J=10.0, 2.0 Hz, 1H), 8.02-7.94 (m, 2H).

Intermediate 18

4'-(((1,4-Dioxaspiro[4.5]decan-8-yl)methyl)sulfonyl)-2-fluoro-[1,1'-biphenyl]-4-carbonitrile

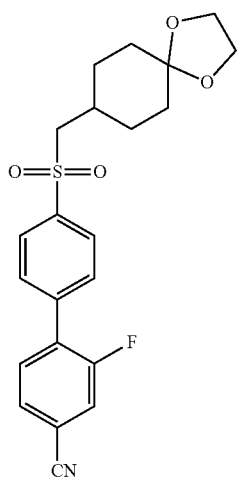 [SMILES: N#Cc1ccc(-c2ccc(S(=O)(=O)CC3CCC4(CC3)OCCO4)cc2)c(F)c1]

To a stirred solution of 2-(4-(((1,4-dioxaspiro[4.5]decan-8-yl)methyl)sulfonyl)phenyl)-4,4,5,5-tetramethyl-1,3,2-dioxaborolane Intermediate 6 (2.50 g, 5.92 mmol) in dioxane:water (3:1, 40 mL), sodium carbonate (1.88 g, 17.76 mmol), 4-cyano-2-fluorophenyl trifluoromethanesulfonate Intermediate 17 (3.20 g, 11.83 mmol) were added and the reaction mixture was degassed using argon for 20 min. Tetrakis[triphenylphosphine]palladium(0) (0.68 g, 0.59 mmol) was added to it and the reaction mixture was degassed for another 10 min and stirred at 100° C. for 12 h in a sealed tube. The progress of the reaction was monitored by TLC [(TLC silica gel plate), 30% EtOAc in n-hexane]. After completion of the reaction, the reaction mixture was filtered through Celite® and the filtrate was concentrated under reduced pressure to get a crude residue. The obtained residue was dissolved in EtOAc (50 mL) and washed with water (50 mL). The combined organic layer was dried over anhydrous sodium sulfate, filtered and concentrated under reduced pressure to get a crude residue. The residue obtained was purified by flash column chromatography (230-400 mesh silica gel, gradient 1-30% EtOAc in n-hexane) to afford the title compound Intermediate 18 (2.20 g, 89%) as an off-white solid.

Analytical data: LCMS (ESI) m/z=416.00 [M+H]$^+$.

Intermediate 19

2-Fluoro-4'-(((4-oxocyclohexyl)methyl)sulfonyl)-[1,1'-biphenyl]-4-carbonitrile

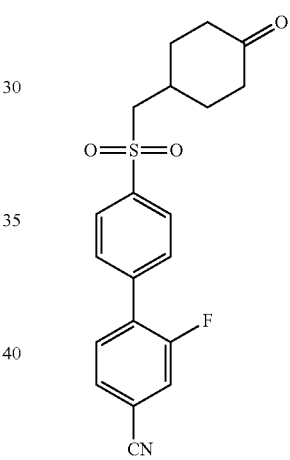

A solution of 4'-(((1,4-dioxaspiro[4.5]decan-8-yl)methyl)sulfonyl)-2-fluoro-[1,1'-biphenyl]-4-carbonitrile Intermediate 18 (2.20 g, 5.30 mmol) in 0.5M aq. HCl (40 mL) was stirred at 70° C. for 4 h. The progress of the reaction was monitored by TLC [(TLC silica gel plate), 30% EtOAc in n-hexane]. After completion of the reaction, the reaction mixture was cooled to 0° C. and neutralized to pH 7 with 5% aq. NaOH solution, extracted with EtOAc (3×50 mL). The combined organic layer was dried over anhydrous sodium sulfate, filtered and concentrated under reduced pressure to afford the title compound Intermediate 19 (1.80 g, crude) as white solid which was used in the next step without further purification.

Analytical data: LCMS (ESI) m/z=371.80 [M+H]$^+$.

Synthesis Compound 7

2-Fluoro-4'-(((trans-4-hydroxy-4-methylcyclohexyl)methyl)sulfonyl)-[1,1'-biphenyl]-4-carbonitrile

CHMSA-01-B

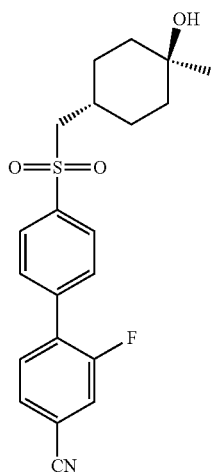 [SMILES: C[C@]1(O)CC[C@H](CS(=O)(=O)c2ccc(-c3ccc(C#N)cc3F)cc2)CC1]

Synthesis Compound 8

2-fluoro-4'-(((cis-4-hydroxy-4-methylcyclohexyl)methyl)sulfonyl)-[1,1'-biphenyl]-4-carbonitrile

CHMSA-01-A

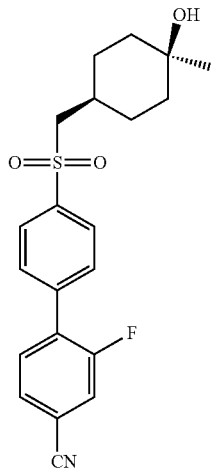 [SMILES: C[C@]1(O)CC[C@@H](CS(=O)(=O)c2ccc(-c3ccc(C#N)cc3F)cc2)CC1]

To a stirred solution of 2-fluoro-4'-(((4-oxocyclohexyl)methyl)sulfonyl)-[1,1'-biphenyl]-4-carbonitrile Intermediate 19 (1.80 g, 4.85 mmol) in anhydrous THF (25 mL), 3M methyl magnesium bromide (1.94 mL, 5.82 mmol) was added at −20° C. and the reaction mixture was allowed to warm to room temperature and stirred for 12 h. The progress of the reaction was monitored by TLC [(TLC silica gel plate), 50% EtOAc in n-hexane]. After completion of the reaction, the reaction mixture was cooled to 0° C. and quenched with saturated aq. NH$_4$Cl solution (30 mL) and extracted with EtOAc (3×50 mL). The combined organic layer was dried over anhydrous sodium sulfate, filtered and concentrated under reduced pressure to get a crude residue. The residue obtained was purified by flash column chromatography (230-400 mesh silica gel, gradient 1-30% EtOAc in n-hexane) to obtain 1.00 g mixture of diastereomers, which was purified by SFC chromatography (see below details) to afford the title compounds Synthesis Compound 7 (0.16 g, 9%) and Synthesis Compound 8 (0.20 g, 11%) as white solids.

Analytical data (Synthesis Compound 7):

LCMS (ESI) m/z=370.10 [M−H$_2$O+1]$^+$.

HPLC (see generic method): Retention time=7.94 min. Purity=98.33%.

$^1$H NMR (400 MHz, DMSO-d$_6$) δ ppm: 8.07-8.03 (m, 3H), 7.89-7.82 (m, 4H), 4.19 (s, 1H), 3.35 (s, 1H), 1.84 (br. s, 1H), 1.78-1.74 (m, 2H), 1.52-1.46 (m, 2H), 1.33-1.17 (m, 4H), 1.06 (s, 3H) (1H merged in solvent peak).

Analytical data (Synthesis Compound 8):

LCMS (ESI) m/z=370.10 [M−H$_2$O+1]$^+$.

HPLC (see generic method): Retention time=8.21 min. Purity=98.33%.

$^1$H NMR (400 MHz, DMSO-d$_6$) δ ppm: 8.07-8.03 (m, 3H), 7.90-7.82 (m, 4H), 3.95 (s, 1H), 3.28 (d, J=6.0 Hz, 2H), 1.74 (br. S, 1H), 1.57-1.54 (m, 2H), 1.49-1.37 (m, 4H), 1.25-1.17 (m, 2H), 1.05 (s, 3H).

SFC chromatography details:

Mobile Phases: A: CO$_2$; B: 0.1% NH$_3$ in MeOH.

Gradient: Started with 10% B, increased to 40% B over 5 min, held at 40% B for 4 min, reduced to 10% B over 1 min and held at 10% B for 2 min.

Column: Chiralpak IA (250 mm×4.6 mm, 5 μm). Wavelength: 260 nm. Flow rate: 3 mL/min.

Synthetic Scheme 6

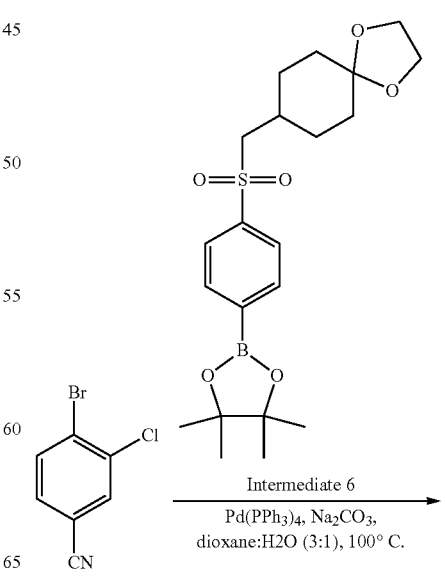

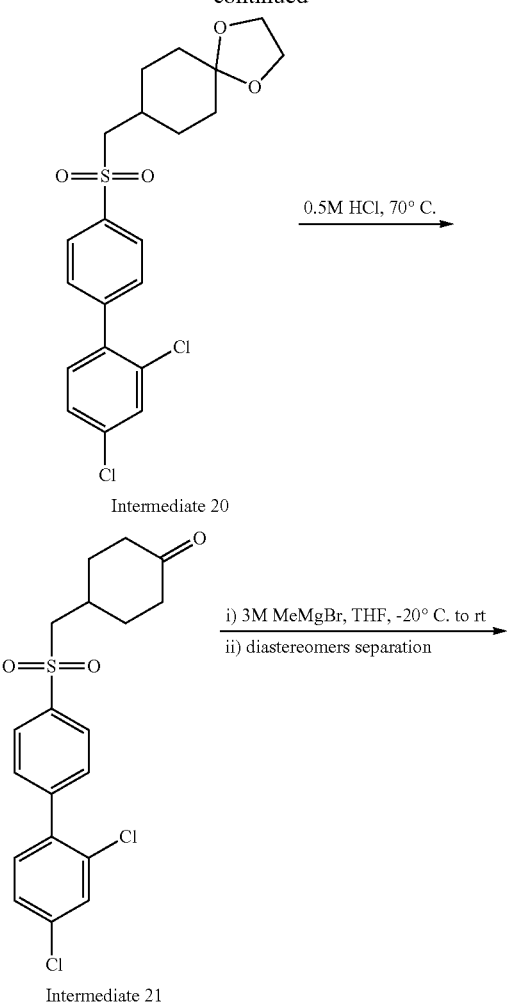

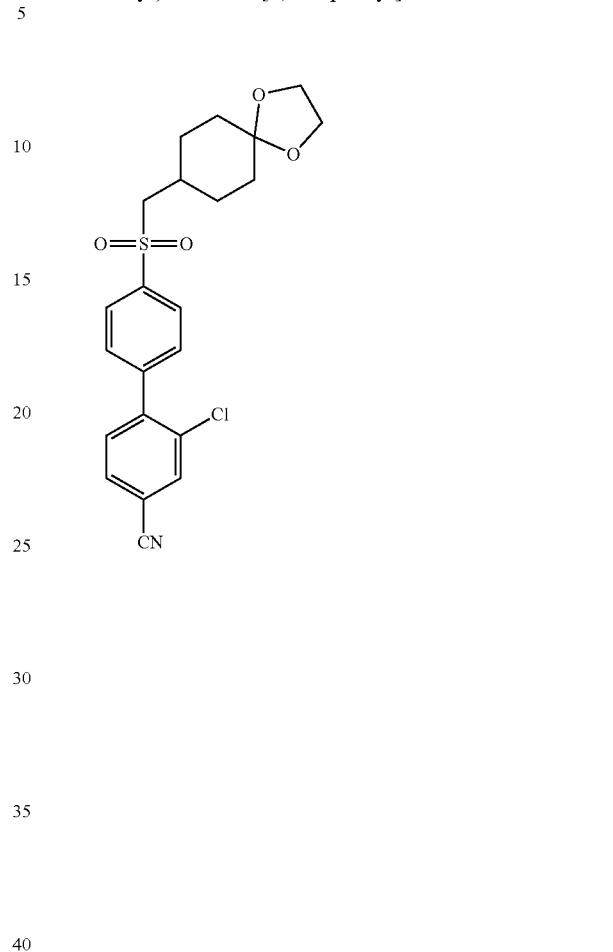

Intermediate 20

4'-(((1,4-Dioxaspiro[4.5]decan-8-yl)methyl)sulfonyl)-2-chloro-[1,1'-biphenyl]-4-carbonitrile

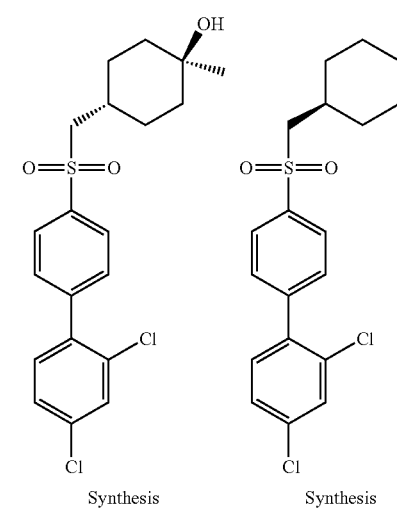

To a stirred solution of 2-(4-(((1,4-dioxaspiro[4.5]decan-8-yl)methyl)sulfonyl)phenyl)-4,4,5,5-tetramethyl-1,3,2-dioxaborolane Intermediate 6 (3.30 g, 7.81 mmol) in dioxane:water (3:1, 40 mL), sodium carbonate (2.48 g, 23.44 mmol), 4-bromo-3-chlorobenzonitrile (1.69 g 7.81 mmol) were added and the reaction mixture was degassed using argon for 20 min. Tetrakis[triphenylphosphine]palladium(0) (0.90 g, 0.78 mmol) was added to it and the reaction mixture was degassed for another 10 min and stirred at 100° C. for 12 h in a sealed tube. The progress of the reaction was monitored by TLC [(TLC silica gel plate), 30% EtOAc in n-hexane]. After completion of the reaction, the reaction mixture was filtered through Celite® and the filtrate was concentrated under reduced pressure. The obtained residue was dissolved in EtOAc (100 mL) and washed with water (50 mL). The organic layer was dried over anhydrous sodium sulfate, filtered and concentrated under reduced pressure to get a crude residue. The residue obtained was purified by flash column chromatography (230-400 mesh silica gel, gradient 1-20% EtOAc in n-hexane) to afford the title compound Intermediate 20 (3.00 g, 89%) as white solid.

Analytical data: LCMS (ESI) m/z=432.20 [M+1]$^+$.

Intermediate 21

2-Chloro-4'-(((4-oxocyclohexyl)methyl)sulfonyl)-[1,1'-biphenyl]-4-carbonitrile

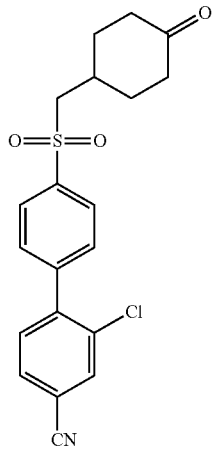 [SMILES: N#Cc1ccc(-c2ccc(S(=O)(=O)CC3CCC(=O)CC3)cc2)c(Cl)c1]

A solution of 4'-(((1,4-dioxaspiro[4.5]decan-8-yl)methyl)sulfonyl)-2-chloro-[1,1'-biphenyl]-4-carbonitrile Intermediate 20 (3.00 g, 6.95 mmol) in 0.5M aq. HCl (40 mL) was stirred at 70° C. for 4 h. The progress of the reaction was monitored by TLC [(TLC silica gel plate), 30% EtOAc in n-hexane]. After completion of the reaction, the reaction mixture was cooled to 0° C., neutralized to pH 7 with 5% aq. NaOH solution and extracted with EtOAc (3×50 mL). The combined organic layer was dried over anhydrous sodium sulfate, filtered and concentrated under reduced pressure to get a crude residue. The obtained residue was triturated with n-hexane to afford the title compound Intermediate 21 (2.50 g, 93%) as white solid.

Analytical data: LCMS (ESI) m/z=388.20 [M+1]$^+$.

Synthesis Compound 9

2-Chloro-4'-(((trans-4-hydroxy-4-methylcyclohexyl)methyl)sulfonyl)-[1,1'-biphenyl]-4-carbonitrile

CHMSA-05-B

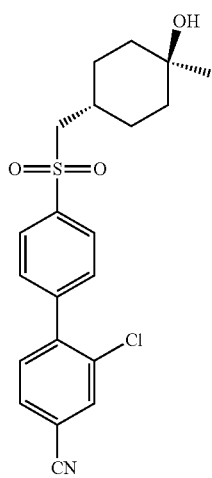 [SMILES: C[C@]1(O)CC[C@H](CS(=O)(=O)c2ccc(-c3ccc(C#N)cc3Cl)cc2)CC1]

Synthesis Compound 10

2-chloro-4'-(((cis-4-hydroxy-4-methylcyclohexyl)methyl)sulfonyl)-[1,1'-biphenyl]-4-carbonitrile

CHMSA-05-A

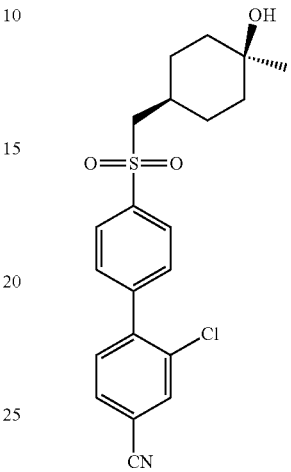

To a stirred solution of 2-chloro-4'-(((4-oxocyclohexyl)methyl)sulfonyl)-[1,1'-biphenyl]-4-carbonitrile Intermediate 21 (2.50 g, 6.45 mmol) in THF (30 mL), 3M methyl magnesium bromide (2.60 mL, 7.73 mmol) was added dropwise at −20° C. over a period of 30 min and the reaction mixture was allowed to come to room temperature and stirred for 12 h. The progress of the reaction was monitored by TLC [(TLC silica gel plate), 40% EtOAc in n-hexane]. After completion of the reaction, the reaction mixture was quenched with saturated NH$_4$Cl solution (30 mL) and extracted with EtOAc (3×50 mL). The combined organic layer was dried over anhydrous sodium sulfate and concentrated under reduced pressure to get a crude residue (2 g). The residue obtained was purified by flash column chromatography (230-400 mesh silica gel, gradient 1-30% EtOAc in n-hexane) to obtain 1.00 g mixture of diastereomers, which was purified by SFC chromatography (see below details) to afford the title compounds Synthesis Compound 9 (0.13 g, 5%) and Synthesis Compound 10 (0.20 g, 8%) as white solids.

Analytical data (Synthesis Compound 9):

LCMS (ESI) m/z=386.10 [M−H$_2$O+1]$^+$.

HPLC (see generic method): Retention time=8.12 min. Purity=99.66%.

$^1$H NMR (400 MHz, DMSO-d$_6$) δ ppm: 8.25 (d, J=1.2 Hz, 1H), 8.04-8.01 (m, 2H), 7.96 (dd, J=7.6, 1.4 Hz, 1H), 7.76-7.74 (m, 2H), 7.68 (d, J=8.0 Hz, 1H), 4.19 (s, 1H), 3.34 (d, J=6.4 Hz, 2H), 1.85 (br. s, 1H), 1.77-1.73 (m, 2H), 1.50-1.44 (m, 2H), 1.32-1.17 (m, 4H), 1.05 (s, 3H).

Analytical data (Synthesis Compound 9):

LCMS (ESI) m/z=386.15 [M−H$_2$O+1]$^+$.

HPLC (see generic method): Retention time=8.38 min. Purity=98.48%.

$^1$H NMR (400 MHz, DMSO-d$_6$) δ ppm: 8.24 (br. s, 1H), 8.03 (d, J=8.0 Hz, 2H), 7.96 (d, J=8.0 Hz, 1H), 7.75 (d, J=8.4 Hz, 2H), 7.68 (d, J=7.6 Hz, 1H), 3.95 (s, 1H), 3.28 (d, J=6.4 Hz, 2H), 1.75 (br. s, 1H), 1.56-1.39 (m, 6H), 1.25-1.19 (m, 2H), 1.05 (s, 3H).

SFC chromatography details:

Mobile Phases: A: $CO_2$; B: 0.1% $NH_3$ in MeOH.

Gradient: Isocratic: 30% B.

Column: Chiralpak IA (250 mm×4.6 mm, 5 μm). Wavelength: 256 nm. Flow rate: 3 mL/min.

Synthetic Scheme 7

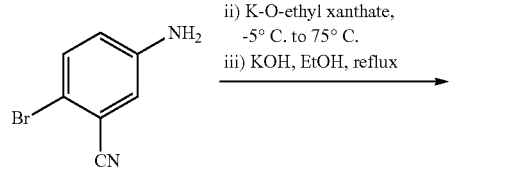

i) HCl, $NaNO_2$, $H_2O$, -5° C.
ii) K-O-ethyl xanthate, -5° C. to 75° C.
iii) KOH, EtOH, reflux

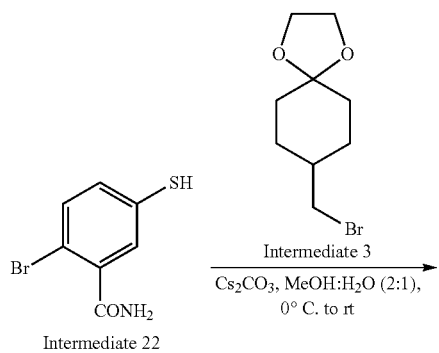

Intermediate 22

Intermediate 3

$Cs_2CO_3$, MeOH:$H_2O$ (2:1), 0° C. to rt

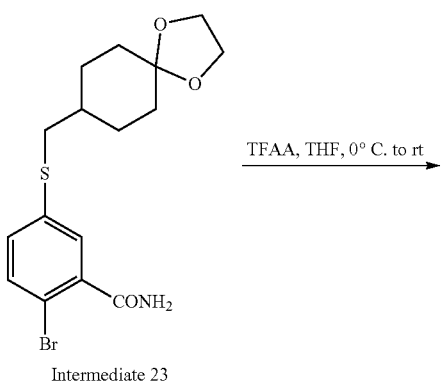

Intermediate 23

TFAA, THF, 0° C. to rt

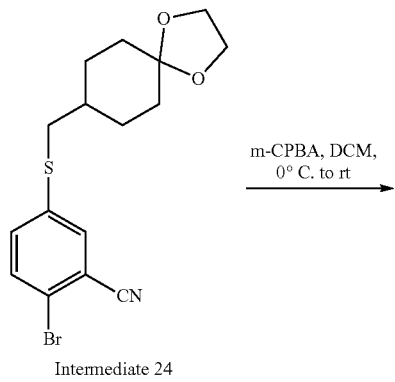

Intermediate 24 m-CPBA, DCM, 0° C. to rt

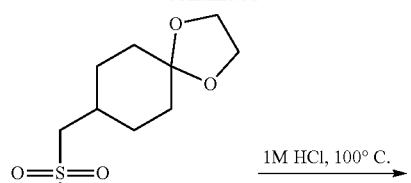

1M HCl, 100° C.

Intermediate 25

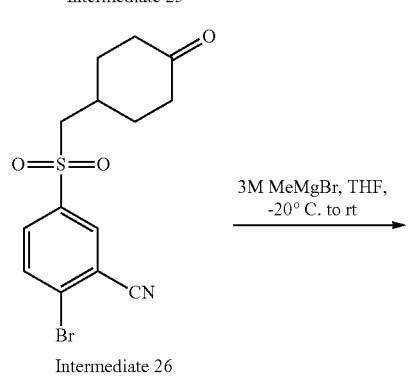

3M MeMgBr, THF, -20° C. to rt

Intermediate 26

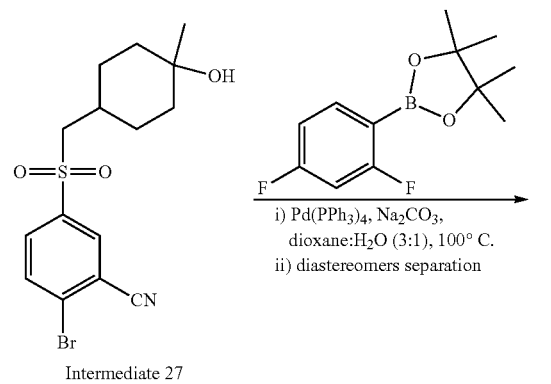

Intermediate 27 i) Pd(PPh$_3$)$_4$, $Na_2CO_3$, dioxane:$H_2O$ (3:1), 100° C.
ii) diastereomers separation

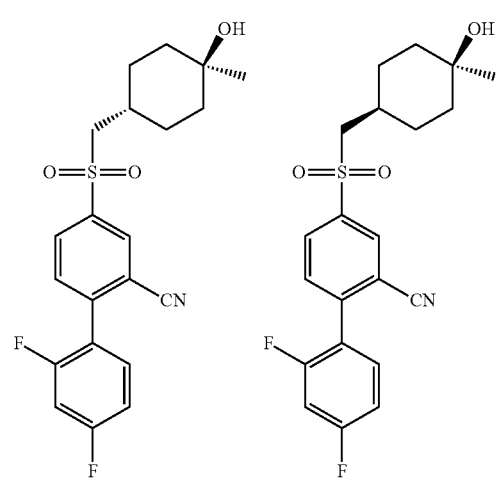

Synthesis Compound 11     Synthesis Compound 12

Intermediate 22

2-Bromo-5-mercaptobenzamide

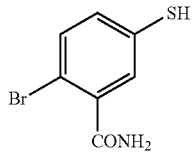

To a slurry of 5-amino-2-bromobenzonitrile (4.00 g, 20.30 mmol) in concentrated HCl (5.50 mL) and ice (10 g), NaNO$_2$ (1.46 g, 21.11 mmol) and H$_2$O (10 mL) were added at −5° C. and the resulting reaction mixture was added to a solution of potassium O-ethyl xanthate (6.51 g, 40.60 mmol) in H$_2$O (10 mL). The resulting mixture was stirred at 75° C. stirred for 1.5 h. The reaction mixture was cooled to room temperature, pH was adjusted to 8 with 5% NaHCO$_3$ solution (50 mL) and extracted with Et$_2$O (3×200 mL). The organic layer was separated, washed with water (200 mL) and concentrated under reduced pressure to get a crude residue. The obtained residue was dissolved in EtOH (35 mL), KOH (4.56 g, 81.20 mmol) was added and the resulting reaction mixture was refluxed for 17 h. The progress of the reaction was monitored by TLC [(TLC silica gel plate), 30% EtOAc in n-hexane]. After completion of the reaction, the reaction mixture was concentrated under reduced pressure to get a crude residue. Water (70 mL) was added to the crude residue and extracted with Et$_2$O (2×50 mL). The aqueous layer was acidified to pH 1-2 with 3N H$_2$SO$_4$ (60 mL) and extracted with DCM (3×100 mL). The combined organic layer was separated, washed with water (200 mL), dried over anhydrous sodium sulfate and concentrated under reduced pressure to afford the title compound Intermediate 22 (1.63 g, crude) as pale brown oil which was used as such for the next reaction without further purification.

Analytical data: LCMS (ESI) m/z=233.90 [M+1]+(81Br).

Intermediate 23

5-(((1,4-Dioxaspiro[4.5]decan-8-yl)methyl)thio)-2-bromobenzamide

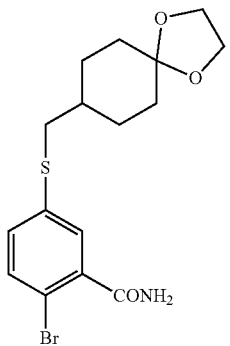 [SMILES: NC(=O)c1cc(SCC2CCC3(CC2)OCCO3)ccc1Br]

To a stirred solution of 2-bromo-5-mercaptobenzamide Intermediate 22 (1.63 g, 7.03 mmol) in MeOH:H$_2$O (2:1, 30 mL), Cs$_2$CO$_3$ (4.58 g, 14.06 mmol) was added at 0° C. and the reaction mixture was stirred for 15 min. 8-(Bromomethyl)-1,4-dioxaspiro[4.5]decane Intermediate 3 (1.65 g, 7.03 mmol) was added dropwise to it and the reaction mixture was allowed to come to room temperature and stirred for 12 h. The progress of the reaction was monitored by TLC [(TLC silica gel plate), 40% EtOAc in n-hexane]. After completion of the reaction, the reaction mixture was concentrated under reduced pressure to get a crude residue. Water (10 mL) was added to the residue and extracted with EtOAc (3×20 mL). The combined organic layer was washed with brine (2×20 mL), dried over anhydrous sodium sulfate and concentrated under reduced pressure to get a crude residue. The residue was purified by flash column chromatography (230-400 mesh silica gel, 40% EtOAc in n-hexane) to afford the title compound Intermediate 23 (0.80 g) as off-white solid.

Analytical data: LCMS (ESI) m/z=385.93 [M+1]+.

Intermediate 24

5-(((1,4-Dioxaspiro[4.5]decan-8-yl)methyl)thio)-2-bromobenzonitrile

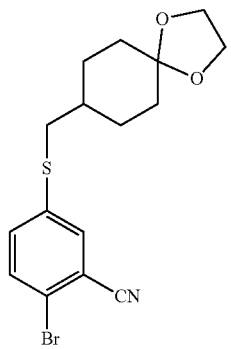 [SMILES: N#Cc1cc(SCC2CCC3(CC2)OCCO3)ccc1Br]

To a stirred solution of 5-(((1,4-dioxaspiro[4.5]decan-8-yl)methyl)thio)-2-bromobenzamide Intermediate 23 (0.80 g, 2.07 mmol) in anhydrous THF (10 mL), TFAA (0.87 g, 4.14 mmol) was added dropwise at 0° C. and the reaction mixture was allowed to come to room temperature and stirred for 1 h. The progress of the reaction was monitored by TLC [(TLC silica gel plate), 50% EtOAc in n-hexane]. After completion of the reaction, the reaction mixture was quenched with saturated NaHCO$_3$ solution (10 mL) and extracted with EtOAc (3×15 mL). The organic layer was separated, washed with brine (2×15 mL), dried over anhydrous sodium sulfate and concentrated under reduced pressure to get a crude residue. The residue obtained was purified by flash column chromatography (230-400 mesh silica gel, 20% EtOAc in n-hexane) to afford the title compound Intermediate 24 (0.70 g, 92%) as pale yellow solid.

Analytical data: LCMS (ESI) m/z=369.90 [M+1]+ (81Br).

Intermediate 25

5-(((1,4-Dioxaspiro[4.5]decan-8-yl)methyl)sulfonyl)-2-bromobenzonitrile

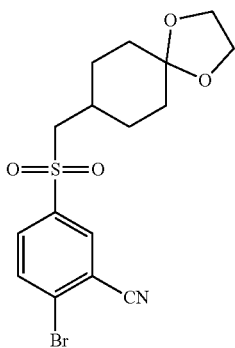

To a stirred solution of 5-(((1,4-dioxaspiro[4.5]decan-8-yl)methyl)thio)-2-bromobenzonitrile Intermediate 24 (0.70 g, 1.90 mmol) in DCM (20 mL), 3-chloroperoxybenzoic acid (~70% in water) (0.94 g, 3.80 mmol) was added at 0° C. portionwise over a period of 15 min and the reaction mixture was allowed to come to room temperature and stirred for 12 h. The progress of the reaction was monitored by TLC [(TLC silica gel plate), 50% EtOAc in n-hexane]. After completion of the reaction, the reaction mixture was quenched with saturated NaHCO$_3$ solution (10 mL). The organic layer was separated, and the aqueous layer was extracted with DCM (3×15 mL). The combined organic layer was washed with brine (2×15 mL), dried over anhydrous sodium sulfate and concentrated under reduced pressure to get a crude residue. The residue obtained was purified by flash column chromatography (230-400 mesh silica gel, 40% EtOAc in n-hexane) to afford the title compound Intermediate 25 (0.30 g, 39%) as off-white solid.

Analytical data: LCMS (ESI) m/z=400.05 [M+1]$^+$.

Intermediate 26

2-Bromo-5-(((4-oxocyclohexyl)methyl)sulfonyl)benzonitrile

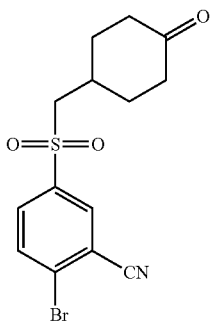 [SMILES: N#Cc1cc(S(=O)(=O)CC2CCC(=O)CC2)ccc1Br]

A solution of 5-(((1,4-dioxaspiro[4.5]decan-8-yl)methyl)sulfonyl)-2-bromobenzonitrile Intermediate 25 (0.20 g, 0.50 mmol) in 1M HCl (20 mL) was heated at 100° C. for 12 h. The progress of the reaction was monitored by TLC [(TLC silica gel plate), 50% EtOAc in n-hexane]. After completion of the reaction, the reaction mixture was cooled to room temperature, pH was adjusted to 8 with saturated NaHCO$_3$ solution (30 mL) and extracted with DCM (3×20 mL). The organic layer was separated, washed with brine (2×15 mL), dried over anhydrous sodium sulfate and concentrated under reduced pressure to afford the title compound Intermediate 26 (0.12 g, crude) as yellow solid which was used as such for the next reaction without further purification.

Analytical data: LCMS (ESI) m/z=399.05 [M+CH$_3$CN+1]+($^{81}$Br).

Intermediate 27

2-Bromo-5-(((4-oxocyclohexyl)methyl)sulfonyl)benzonitrile

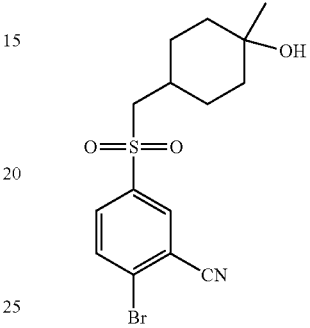

To a stirred solution of 2-bromo-5-(((4-oxocyclohexyl)methyl)sulfonyl)benzonitrile Intermediate 26 (0.12 g, 0.34 mmol) in THF (15 mL), 3M methyl magnesium bromide (0.13 mL, 0.40 mmol) was added at −20° C. and the reaction mixture was allowed to come to room temperature and stirred for 4 h. The progress of the reaction was monitored by TLC [(TLC silica gel plate), 50% EtOAc in n-hexane]. After completion of the reaction, the reaction mixture was quenched with saturated NH$_4$Cl solution (20 mL) and extracted with EtOAc (3×20 mL). The combined organic layer was dried over anhydrous sodium sulfate and concentrated under reduced pressure to afford the title compound Intermediate 27 (0.10 g, crude) as pale yellow solid which was used as such for the next reaction without further purification.

Synthesis Compound 11

2',4'-Difluoro-4-(((trans-4-hydroxy-4-methylcyclohexyl)methyl)sulfonyl)-[1,1'-biphenyl]-2-carbonitrile

CHMSA-06-B

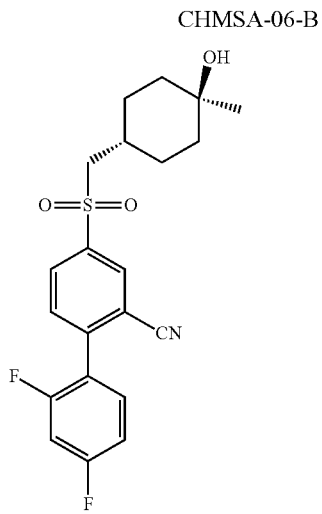

Synthesis Compound 12

2',4'-difluoro-4-(((cis-4-hydroxy-4-methylcyclohexyl)methyl)sulfonyl)-[1,1'-biphenyl]-2-carbonitrile

CHMSA-06-A

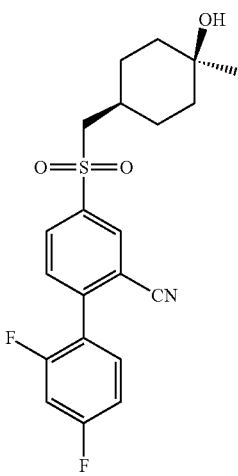 [SMILES: C[C@]1(O)CC[C@@H](CS(=O)(=O)c2ccc(-c3ccc(F)cc3F)c(C#N)c2)CC1]

To a stirred solution of 2-bromo-5-(((4-hydroxy-4-methylcyclohexyl)methyl)sulfonyl)benzonitrile Intermediate 27 (0.10 g, 0.27 mmol) and 2-(2,4-difluorophenyl)-4,4,5,5-tetramethyl-1,3,2-dioxaborolane (0.065 g, 0.27 mmol) in dioxane:water (3:1, 8 mL), sodium carbonate (0.085 g, 0.81 mmol) was added and the reaction mixture was degassed using argon for 20 min. Tetrakis[triphenylphosphine]palladium(0) (0.031 g, 0.027 mmol) was added to it and the reaction mixture was degassed for another 20 min and stirred at 100° C. for 12 h in a sealed tube. The progress of the reaction was monitored by TLC [(TLC silica gel plate), 60% EtOAc in n-hexane] and LCMS. After completion of the reaction, the reaction mixture was cooled to room temperature, filtered over Celite®, washed with EtOAc (30 mL) and the filtrate was concentrated under reduced pressure. The obtained residue was dissolved in water (20 mL), extracted with EtOAc (3×20 mL). The organic layer was separated, washed with brine (2×15 mL), dried over anhydrous sodium sulfate and concentrated under reduced pressure to get a crude residue. The residue obtained was purified by flash column chromatography (230-400 mesh silica gel, 40% EtOAc in n-hexane) to obtain mixture of diastereomers. This batch crude material was mixed with another batch prepared similarly (50 mg scale reaction). The combined crude material from both batches was purified by SFC chromatography (see below details) to afford the title compounds Synthesis Compound 11 (0.007 g, 4%) and Synthesis Compound 12 (0.02 g, 12%) as off-white solids.

Analytical data (Synthesis Compound 11):

LCMS (ESI) m/z=388.15 [M–H$_2$O+1]$^+$.

HPLC (see generic method): Retention time=8.23 min. Purity=96.29%.

$^1$H NMR (400 MHz, DMSO-d$_6$) δ ppm: 8.53 (d, J=2.0 Hz, 1H), 8.29 (dd, J=8.0, 1.6 Hz, 1H), 7.91 (d, J=8.0 Hz, 1H), 7.72-7.66 (m, 1H), 7.58-7.53 (m, 1H), 7.36-7.32 (m, 1H), 4.19 (s, 1H), 3.46 (d, J=6.4 Hz, 2H), 1.91 (br. s, 1H), 1.78 (br. s, 2H), 1.51-1.47 (m, 2H), 1.36-1.20 (m, 4H), 1.07 (s, 3H).

Analytical data (Synthesis Compound 12):

LCMS (ESI) m/z=388.10 [M–H$_2$O+1]$^+$.

HPLC (see generic method): Retention time=8.48 min. Purity=98.05%.

$^1$H NMR (400 MHz, DMSO-d6) δ ppm: 8.54 (d, J=2.0 Hz, 1H), 8.29 (dd, J=8.0, 1.6 Hz, 1H), 7.90 (d, J=8.4 Hz, 1H), 7.72-7.66 (m, 1H), 7.58-7.53 (m, 1H), 7.36-7.32 (m, 1H), 3.96 (s, 1H), 3.40 (d, J=5.6 Hz, 2H), 1.80 (br. s, 1H), 1.58-1.56 (m, 2H), 1.51-1.40 (m, 4H), 1.29-1.23 (m, 2H), 1.06 (s, 3H).

SFC chromatography details:

Mobile Phases: A: CO$_2$; B: 0.1% NH$_3$ in MeOH.

Gradient: Started with 25% B, increased to 50% B over 5 min, held at 50% B for 4 min, reduced to 25% B over 1 min, held at 25% B for 2 min.

Column: Chiralpak IG (250 mmx 4.6 mm, 5 μm). Wavelength: 258 nm. Flow rate: 3 mL/min.

Synthetic Scheme 8

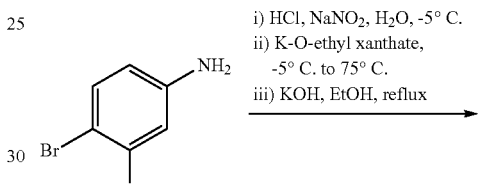

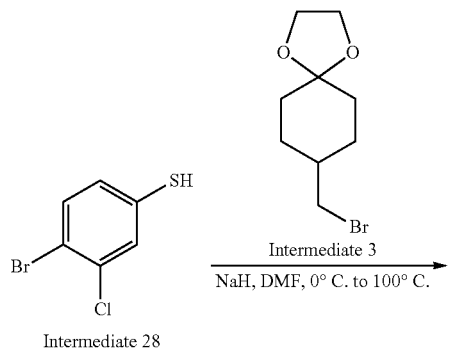

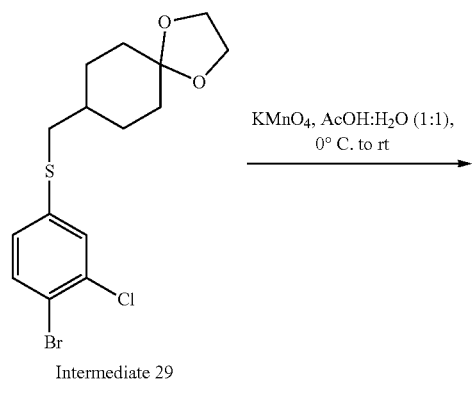

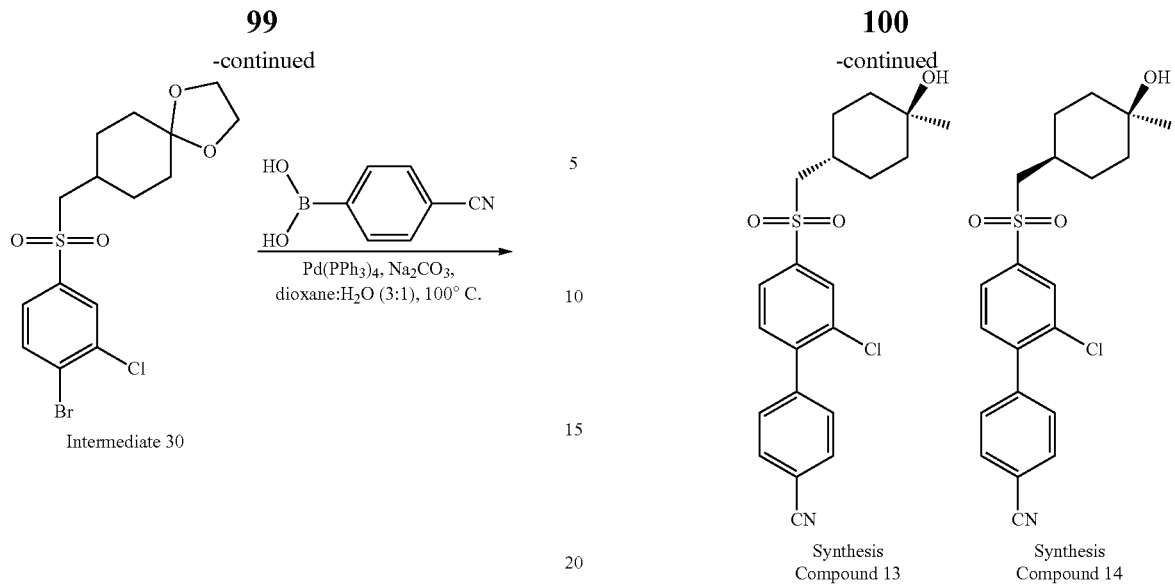

Intermediate 30

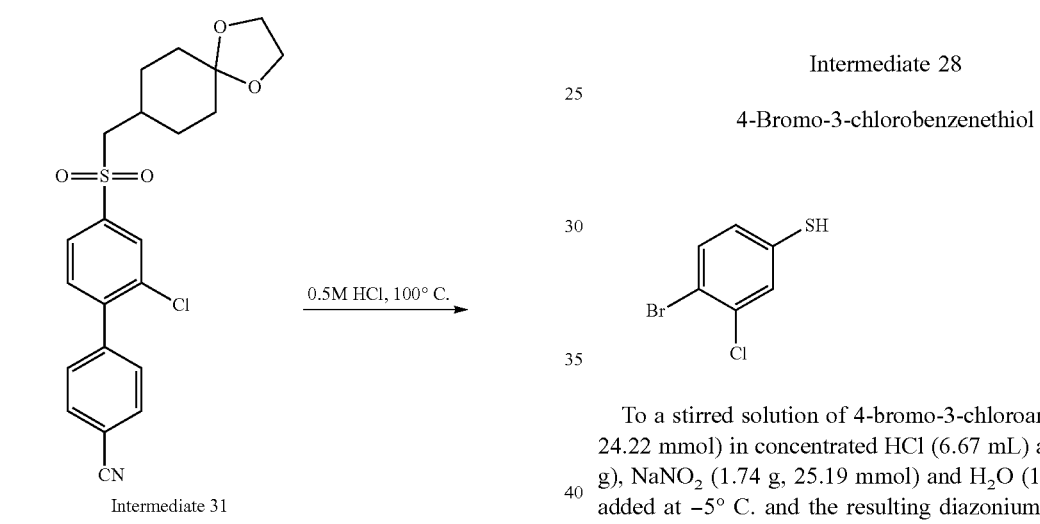

Intermediate 31

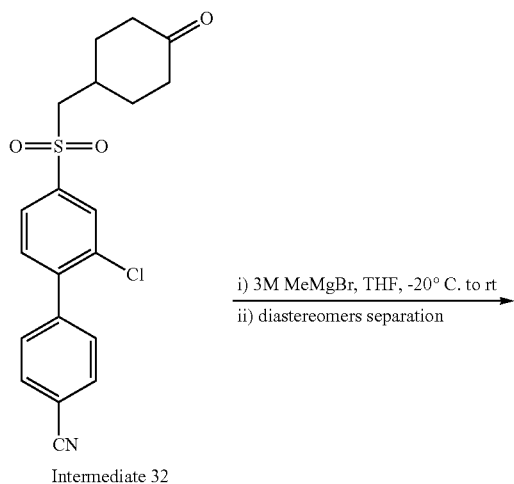

Intermediate 32

Synthesis Compound 13    Synthesis Compound 14

Intermediate 28

4-Bromo-3-chlorobenzenethiol

To a stirred solution of 4-bromo-3-chloroaniline (5.00 g, 24.22 mmol) in concentrated HCl (6.67 mL) and ice (11.67 g), NaNO$_2$ (1.74 g, 25.19 mmol) and H$_2$O (11.7 mL) were added at −5° C. and the resulting diazonium solution was added to s solution of potassium O-ethyl xanthate (7.76 g, 48.43 mmol) in H$_2$O (11.7 mL). The resulting mixture was stirred at 75° C. and stirred for 1.5 h. The reaction mixture was cooled to room temperature, pH was adjusted to 8 with saturated NaHCO$_3$ solution (50 mL) and extracted with Et$_2$O (4×100 mL). The organic layer was separated, washed with water (200 mL), dried over anhydrous sodium sulfate and concentrated under reduced pressure to get a crude residue. The obtained residue was added to a solution of KOH (6.21 g, 110.67 mmol) in EtOH (41.67 mL) and the resulting reaction mixture was refluxed for 17 h. The progress of the reaction was monitored by TLC [(TLC silica gel plate), 10% EtOAc in n-hexane]. After completion of the reaction, the reaction mixture was concentrated under reduced pressure to get a crude residue. The obtained residue was diluted with water (50 mL) and washed with Et$_2$O (50 mL). The aqueous layer was acidified to pH 1-2 with 3N H$_2$SO$_4$ (80 mL) and extracted with DCM (3×150 mL). The combined organic layer was separated, washed with water (200 mL), dried over anhydrous sodium sulfate and concentrated under reduced pressure to afford the title compound Intermediate 28 (2.20 g, crude) as pale brown oil which was used as such for the next reaction without further purification.

Intermediate 29

8-(((4-Bromo-3-chlorophenyl)thio)methyl)-1,4-dioxaspiro[4.5]decane

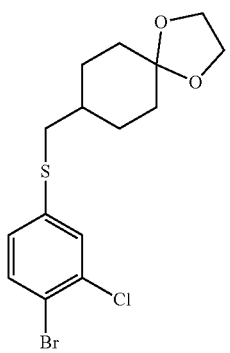 [SMILES: Clc1cc(SCC2CCC3(CC2)OCCO3)ccc1Br]

To a stirred solution of 4-bromo-3-chlorobenzenethiol Intermediate 28 (3.42 g, 15.31 mmol) in DMF (20 mL), NaH (60% dispersion in mineral oil, 1.02 g, 25.52 mmol) was added at 0° C. and the reaction mixture was stirred for 30 min. 8-(Bromomethyl)-1,4-dioxaspiro[4.5]decane Intermediate 3 (3.00 g, 12.76 mmol) dissolved in DMF (10 mL) was added dropwise to it and the reaction mixture was allowed to come to room temperature, stirred for 30 min and further heated to 100° C. for 12 h. The progress of the reaction was monitored by TLC [(TLC silica gel plate), 20% EtOAc in n-hexane] and LCMS. After completion of the reaction, the reaction mixture was cooled to room temperature, quenched with water (30 mL) and extracted with EtOAc (3×30 mL). The combined organic layer was washed with brine (2×30 mL), dried over anhydrous sodium sulfate and concentrated under reduced pressure to get a crude residue. The residue was purified by flash column chromatography (230-400 mesh silica gel, 10% EtOAc in n-hexane) to afford the title compound Intermediate 29 (2.50 g) as pale yellow solid.

Analytical data: LCMS (ESI) m/z=379.05 [M+1]$^+$ ($^{81}$Br).

Intermediate 30

8-(((4-Bromo-3-chlorophenyl)sulfonyl)methyl)-1,4-dioxaspiro[4.5]decane

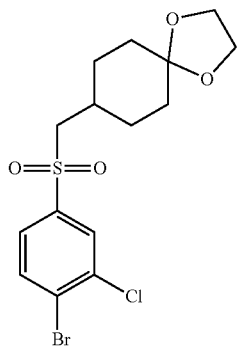

To a stirred solution of 8-(((4-bromo-3-chlorophenyl)thio)methyl)-1,4-dioxaspiro[4.5]decane Intermediate 29 (2.00 g, 5.29 mmol) in AcOH (20 mL) and H$_2$O (20 mL), potassium permanganate (2.51 g, 15.88 mmol) was added portionwise at 0° C. and the reaction mixture was allowed to come to room temperature and stirred for 8 h. The progress of the reaction was monitored by TLC [(TLC silica gel plate) 20% EtOAc in n-hexane]. After completion of the reaction, the reaction mixture was basified to pH 8 with saturated NaHCO$_3$ solution (20 mL) and extracted with EtOAc (3×30 mL). The organic layer was separated, washed with brine (50 mL), dried over anhydrous sodium sulfate and concentrated under reduced pressure to get a crude residue. The residue obtained was purified by flash column chromatography (230-400 mesh silica gel, 20% EtOAc in n-hexane) to afford the title compound Intermediate 30 (1.20 g, 55%) as colorless solid.

Analytical data: LCMS (ESI) m/z=411.05 [M+1]$^+$ ($^{81}$Br).

Intermediate 31

4'-(((1,4-Dioxaspiro[4.5]decan-8-yl)methyl)sulfonyl)-2'-chloro-[1,1'-biphenyl]-4-carbonitrile

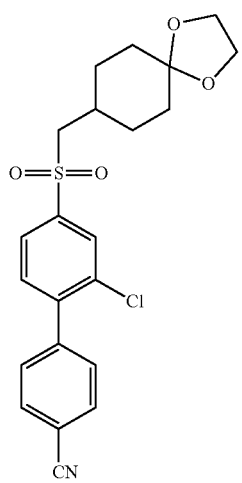 [SMILES: N#Cc1ccc(-c2ccc(S(=O)(=O)CC3CCC4(CC3)OCCO4)cc2Cl)cc1]

To a stirred solution of 8-(((4-bromo-3-chlorophenyl)sulfonyl)methyl)-1,4-dioxaspiro[4.5]decane Intermediate 30 (1.20 g, 2.93 mmol) in dioxane:water (3:1, 20 mL), sodium carbonate (0.93 g, 8.79 mmol), (4-cyanophenyl)boronic acid (0.43 g, 2.93 mmol) were added and the reaction mixture was degassed with argon for 30 min. Tetrakis[triphenylphosphine]palladium(0) (0.34 g, 0.29 mmol) was added to it and the reaction mixture was degassed for another 15 min and stirred at 100° C. for 12 h in a sealed tube. The progress of the reaction was monitored by TLC [(TLC silica gel plate), 50% EtOAc in n-hexane]. After completion of the reaction, the reaction mixture was cooled to room temperature, filtered through Celite® and the filtrate was concentrated under reduced pressure to get a crude residue. Water (10 mL) was added to the crude residue, extracted with EtOAc (3×20 mL). The organic layer was separated, washed with brine (15 mL), dried over anhydrous sodium sulfate and concentrated under reduced pressure to get a crude residue. The residue obtained was purified by flash column chromatography (230-400 mesh silica gel, 10% EtOAc in n-hexane) to afford the title compound Intermediate 31 (0.50 g, 39%) as pale yellow solid.

Analytical data: LCMS (ESI) m/z=432.10 [M+1]$^+$.

Intermediate 32

2'-Chloro-4'-(((4-oxocyclohexyl)methyl)sulfonyl)-[1,1'-biphenyl]-4-carbonitrile

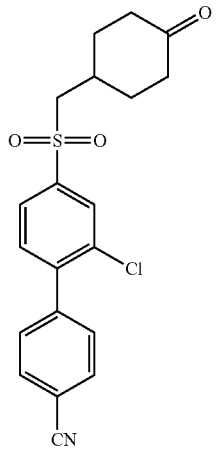

A solution of 4'-(((1,4-dioxaspiro[4.5]decan-8-yl)methyl)sulfonyl)-2'-chloro-[1,1'-biphenyl]-4-carbonitrile Intermediate 31 (0.50 g, 1.16 mmol) in 0.5M aq. HCl (15 mL) was heated at 100° C. for 12 h. The progress of the reaction was monitored by TLC [(TLC silica gel plate), 50% EtOAc in n-hexane]. After completion of the reaction, the reaction mixture was cooled to 0° C., pH was adjusted to 7 with 10% NaOH solution (10 mL) and extracted with EtOAc (3×15 mL). The organic layer was separated, washed with brine (20 mL), dried over anhydrous sodium sulfate and concentrated under reduced pressure to get a crude residue. The residue obtained was purified by flash column chromatography (230-400 mesh silica gel, 20% EtOAc in n-hexane) to afford the title compound Intermediate 32 (0.43 g, 96%) as off-white solid.

Analytical data: LCMS (ESI) m/z=429.25 [M+CH$_3$CN+1]+.

Synthesis Compound 13

2'-Chloro-4'-(((trans-4-hydroxy-4-methylcyclohexyl)methyl)sulfonyl)-[1,1'-biphenyl]-4-carbonitrile

CHMSA-07-B

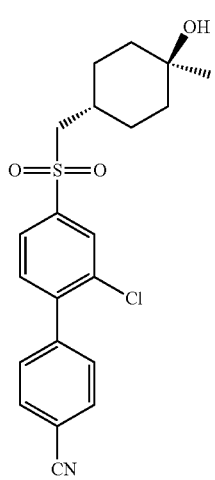 [SMILES: C[C@]1(O)CC[C@H](CS(=O)(=O)c2ccc(-c3ccc(C#N)cc3)c(Cl)c2)CC1]

Synthesis Compound 14

2'-chloro-4'-(((cis-4-hydroxy-4-methylcyclohexyl)methyl)sulfonyl)-[1,1'-biphenyl]-4-carbonitrile

CHMSA-07-A

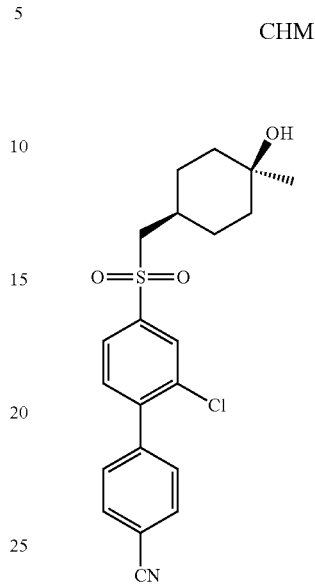

To a stirred solution of 2'-chloro-4'-(((4-oxocyclohexyl)methyl)sulfonyl)-[1,1'-biphenyl]-4-carbonitrile Intermediate 32 (0.43 g, 1.11 mmol) in anhydrous THF (10 mL), 3M methyl magnesium bromide (0.44 mL, 1.33 mmol) was added at −20° C. and the reaction mixture was allowed to come to room temperature and stirred for 12 h. The progress of the reaction was monitored by TLC [(TLC silica gel plate), 50% EtOAc in n-hexane]. After completion of the reaction, the reaction mixture was quenched with saturated NH$_4$Cl solution (10 mL) and extracted with EtOAc (3×15 mL). The combined organic layer was dried over anhydrous sodium sulfate and concentrated under reduced pressure to get a crude residue. This batch crude material was mixed with another batch prepared similarly (0.45 g scale reaction). The combined crude material from both batches was purified by SFC chromatography (see below details) to afford the title compounds Synthesis Compound 13 (0.09 g, 10%) and Synthesis Compound 14 (0.15 g, 16%) as off-white solids.

Analytical data (Synthesis Compound 13):
LCMS (ESI) m/z=386.10 [M−H$_2$O+1]$^+$.
HPLC (see generic method): Retention time=8.31 min. Purity=99.52%.
$^1$H NMR (400 MHz, DMSO-d$_6$) δ ppm: 8.12 (br. s, 1H), 8.01-7.96 (m, 3H), 7.75-7.71 (m, 3H), 4.19 (s, 1H), 3.43 (d, J=6.4 Hz, 2H), 1.89 (br. s, 1H), 1.83-1.75 (m, 2H), 1.51-1.48 (m, 2H), 1.35-1.23 (m, 4H), 1.07 (s, 3H).

Analytical data (Synthesis Compound 14):
LCMS (ESI) m/z=386.15 [M−H$_2$O+1]$^+$.
HPLC (see generic method): Retention time=8.57 min. Purity=97.31%.
$^1$H NMR (400 MHz, DMSO-d$_6$) δ ppm: 8.12 (d, J=2.0 Hz, 1H), 8.01-7.96 (m, 3H), 7.75-7.70 (m, 3H), 3.96 (s, 1H), 3.36 (d, J=6.4 Hz, 2H), 1.78 (br. s, 1H), 1.59-1.57 (m, 2H), 1.51-1.40 (m, 4H), 1.28-1.22 (m, 2H), 1.06 (s, 3H).

SFC chromatography details:
Mobile Phases: A: CO$_2$; B: 0.1% NH$_3$ in MeOH.
Gradient: Started with 25% B, increased to 50% B over 5 min, held at 50% B for 4 min, reduced to 25% B over 1 min and held at 25% B for 2 min.

Column: Chiralpak IG (250 mm×4.6 mm, 5 μm). Wavelength: 256 nm. Flow rate: 3 mL/min.
Synthetic Scheme 9
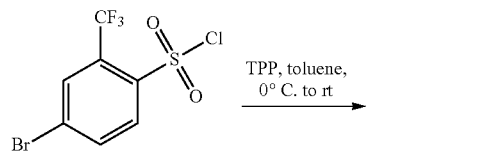
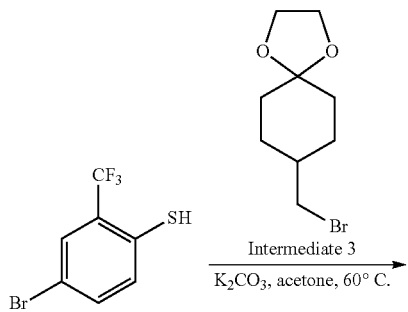
Intermediate 33
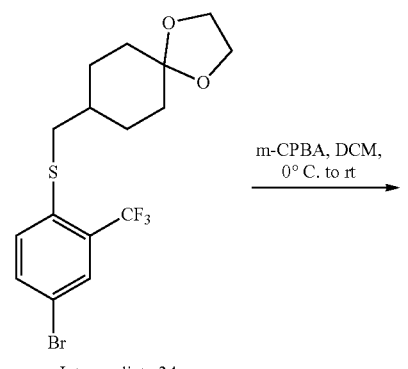
Intermediate 34
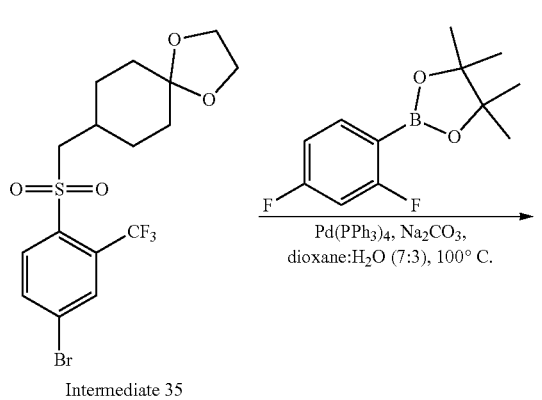
Intermediate 35
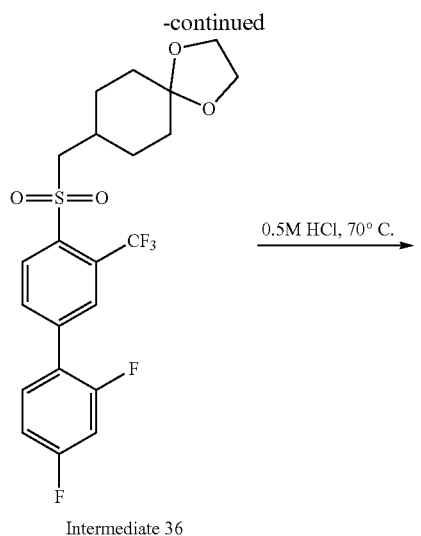
Intermediate 36
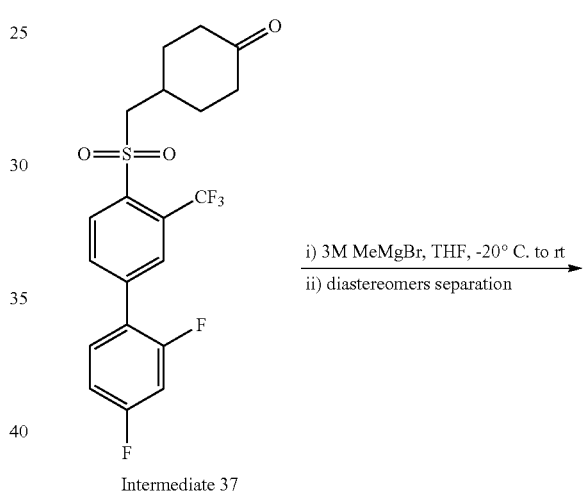
Intermediate 37
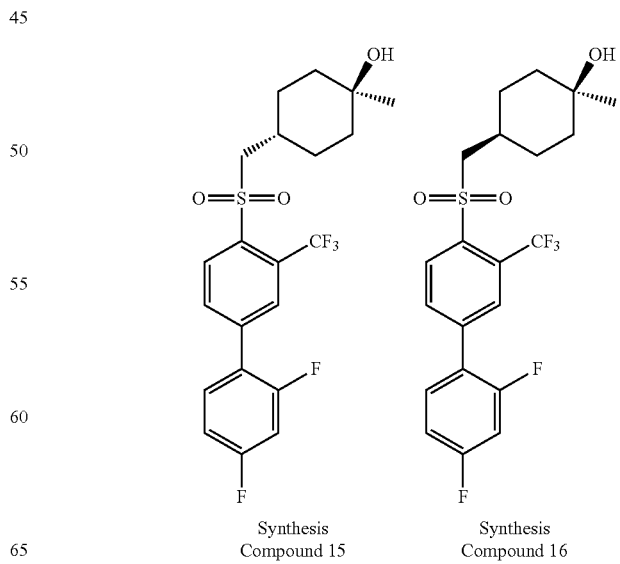
Synthesis Compound 15     Synthesis Compound 16

Intermediate 33

4-Bromo-2-(trifluoromethyl)benzenethiol

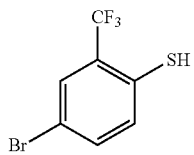

To a stirred solution of 4-bromo-2-(trifluoromethyl)benzenesulfonyl chloride (2.00 g, 6.18 mmol) in toluene (20 mL), triphenylphosphine (4.86 g, 18.55 mmol) was added slowly at 0° C. and the reaction mixture was allowed to come to room temperature and stirred for 16 h. The progress of the reaction was monitored by TLC [(TLC silica gel plate) 20% EtOAc in n-hexane]. After completion of the reaction, the reaction mixture was quenched with 1N HCl (5 mL) and concentrated under reduced pressure to get a crude residue. The obtained residue was basified to pH~10 with 10% KOH solution (~10 mL), the obtained solid was filtered, washed with water (10 mL) and filtrate was extracted with $Et_2O$ (2×25 mL). The aqueous layer was neutralized to pH 7 with 2N HCl (~20 mL) and extracted with EtOAc (3×50 mL). The combined organic layer was dried over anhydrous sodium sulfate, filtered and concentrated under reduced pressure to afford the title compound Intermediate 33 (1.00 g, crude) as brown liquid.

Analytical data: $^1$H NMR (400 MHz, $CDCl_3$) δ ppm 7.73 (s, 1H), 7.46 (dd, J=8.4, 2.0 Hz, 1H), 7.24 (d, J=2.8 Hz, 1H), 3.75-3.73 (m, 1H).

Intermediate 34

8-(((4-Bromo-2-(trifluoromethyl)phenyl)thio)methyl)-1,4-dioxaspiro[4.5]decane

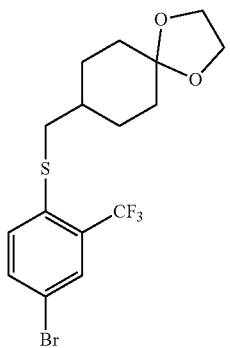 [SMILES: FC(F)(F)c1cc(Br)ccc1SCC1CCC2(CC1)OCCO2]

To a stirred solution of 8-(bromomethyl)-1,4-dioxaspiro[4.5]decane Intermediate 3 (7.00 g, 29.77 mmol) and 4-bromo-2-(trifluoromethyl)benzenethiol Intermediate 33 (9.18 g, 35.73 mmol) in acetone (100 mL), $K_2CO_3$ (8.23 g, 59.54 mmol) was added and the reaction mixture was heated to 60° C. for 18 h. The progress of the reaction was monitored by TLC [(TLC silica gel plate), 30% EtOAc in n-hexane]. After completion of the reaction, the reaction mixture was concentrated under reduced pressure to obtain a crude residue. The residue was purified by flash column chromatography (230-400 mesh silica gel, gradient 1-20% EtOAc in n-hexane) to afford the title compound Intermediate 34 (6.00 g, 49%) as brown oil.

Analytical data: $^1$H NMR (400 MHz, $CDCl_3$) δ ppm 7.77 (br s, 1H), 7.60-7.58 (m, 1H), 7.32 (d, J=8.4 Hz, 1H), 3.96 (s, 4H), 2.89 (d, J=6.8 Hz, 2H), 1.94-1.92 (m, 2H), 1.79-1.76 (m, 2H), 1.55-1.51 (m, 1H), 1.45-1.32 (m, 2H), 1.30-1.26 (m, 2H).

Intermediate 35

8-(((4-Bromo-2-(trifluoromethyl)phenyl)sulfonyl)methyl)-1,4-dioxaspiro[4.5]decane

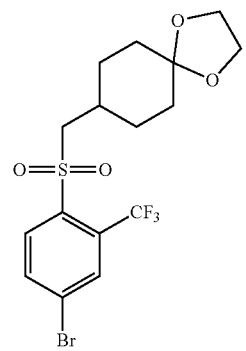 [SMILES: O=S(=O)(CC1CCC2(CC1)OCCO2)c1ccc(Br)cc1C(F)(F)F]

To a stirred solution of 8-(((4-bromo-2-(trifluoromethyl)phenyl)thio)methyl)-1,4-dioxaspiro[4.5]decane Intermediate 34 (6.00 g, 14.59 mmol) in DCM (70 mL), 3-chloroperoxybenzoic acid (~60% in water) (12.58 g, 43.77 mmol) was added slowly at 0° C. and the reaction mixture was allowed to come to room temperature and stirred for 12 h. The progress of the reaction was monitored by TLC [(TLC silica gel plate) 30% EtOAc in n-hexane]. After completion of the reaction, the reaction mixture was cooled to 0° C., saturated $NaHCO_3$ solution (50 mL) was added slowly and layers were separated. The organic layer was washed with saturated $Na_2S_2O_3$ solution (50 mL), dried over anhydrous sodium sulfate and concentrated under reduced pressure to obtain a crude residue. The residue obtained was purified by flash column chromatography (230-400 mesh silica gel, gradient 1-40% EtOAc in n-hexane) to afford the title compound Intermediate 35 (2.00 g, 31%) as white solid.

Analytical data: LCMS (ESI) m/z=445.05 $[M+1]^+$ ($^{81}Br$).

Intermediate 36

8-(((2',4'-Difluoro-3-(trifluoromethyl)-[1,1'-biphenyl]-4-yl)sulfonyl)methyl)-1,4-dioxaspiro[4.5]decane

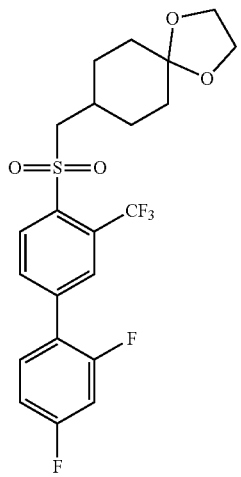

To a stirred solution of 8-(((4-bromo-2-(trifluoromethyl)phenyl)sulfonyl)methyl)-1,4-dioxaspiro[4.5]decane Intermediate 35 (1.00 g, 2.26 mmol) in dioxane:water (7:3, 10 mL), sodium carbonate (0.72 g, 6.77 mmol), 2-(2,4-difluorophenyl)-4,4,5,5-tetramethyl-1,3,2-dioxaborolane (0.54 g, 2.26 mmol) were added and the reaction mixture was degassed using argon for 10 min. Tetrakis[triphenylphosphine]palladium(0) (0.26 g, 0.23 mmol) was added to it and the reaction mixture was degassed for another 10 min and stirred at 100° C. for 12 h in a sealed tube. The progress of the reaction was monitored by TLC [(TLC silica gel plate), 30% EtOAc in n-hexane]. After completion of the reaction, the reaction mixture was filtered through Celite® and the filtrate was concentrated under reduced pressure to get a crude residue. The obtained residue was dissolved in EtOAc (30 mL) and washed with water (25 mL). The organic layer was dried over anhydrous sodium sulfate, filtered and concentrated under reduced pressure to get a crude residue. The residue obtained was purified by flash column chromatography (230-400 mesh silica gel, gradient 1-20% EtOAc in n-hexane) to afford the title compound Intermediate 36 (1.00 g, 93%) as white solid.

Analytical data: LCMS (ESI) m/z=477.10 [M+1]$^+$.

Intermediate 37

4-(((2',4'-Difluoro-3-(trifluoromethyl)-[1,1'-biphenyl]-4-yl)sulfonyl)methyl)cyclohexan-1-one

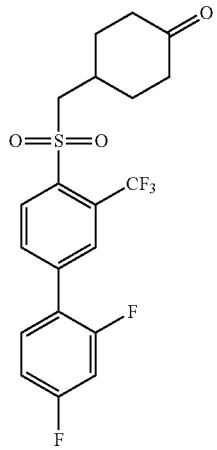 [SMILES: O=C1CCC(CS(=O)(=O)c2ccc(-c3ccc(F)cc3F)cc2C(F)(F)F)CC1]

A solution of 8-(((2',4'-difluoro-3-(trifluoromethyl)-[1,1'-biphenyl]-4-yl)sulfonyl)methyl)-1,4-dioxaspiro[4.5]decane Intermediate 36 (1.00 g, 2.10 mmol) in 0.5M aq. HCl (30 mL) was stirred at 70° C. for 4 h. The progress of the reaction was monitored by TLC [(TLC silica gel plate), 40% EtOAc in n-hexane]. After completion of the reaction, the reaction mixture was cooled to 0° C., neutralized to pH 7 with 5% NaOH solution (~10 mL), stirred for 30 min and extracted with EtOAc (3×50 mL). The combined organic layer was dried over anhydrous sodium sulfate, filtered and concentrated under reduced pressure to afford the title compound Intermediate 37 (0.90 g, crude) as white solid which was used in the next step without further purification.

Analytical data: LCMS (ESI) m/z=433.10 [M+1]$^+$.

Synthesis Compound 15 trans-4-(((2',4'-Difluoro-3-(trifluoromethyl)-[1,1'-biphenyl]-4-yl)sulfonyl)methyl)-1-methylcyclohexan-1-ol

CH MSA-08-B

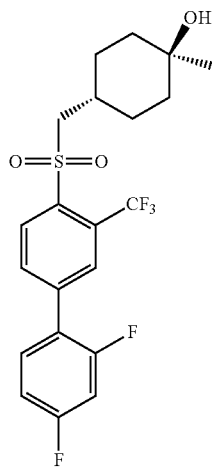 [SMILES: C[C@]1(O)CC[C@H](CS(=O)(=O)c2ccc(-c3ccc(F)cc3F)cc2C(F)(F)F)CC1]

Synthesis Compound 16 cis-4-(((2',4'-difluoro-3-(trifluoromethyl)-[1,1'-bi-phenyl]-4-yl)sulfonyl)methyl)-1-methylcyclohexan-1-ol

CHMSA-08-A

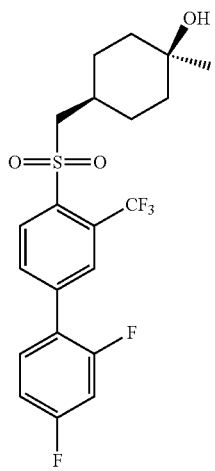 [SMILES: C[C@]1(O)CC[C@@H](CS(=O)(=O)c2ccc(-c3ccc(F)cc3F)cc2C(F)(F)F)CC1]

To a stirred solution of 4-(((2',4'-difluoro-3-(trifluoromethyl)-[1,1'-biphenyl]-4-yl)sulfonyl)methyl)cyclohexan-1-one Intermediate 37 (0.90 g, 2.08 mmol) in anhydrous THF (15 mL), 3M methyl magnesium bromide (0.83 mL, 2.50 mmol) was added dropwise at −20° C. and the reaction mixture was allowed to come to room temperature and stirred for 12 h. The progress of the reaction was monitored by TLC [(TLC silica gel plate), 50% EtOAc in n-hexane]. After completion of the reaction, the reaction mixture was quenched with saturated aq. NH$_4$Cl solution (20 mL) and extracted with EtOAc (3×50 mL). The combined organic layer was dried over anhydrous sodium sulfate, filtered and concentrated under reduced pressure to get a crude residue. The residue obtained was purified by column chromatography (230-400 mesh silica gel, gradient 1-40% EtOAc in n-hexane) to obtain 0.60 g mixture of diastereomers, which was purified by chiral preparative HPLC (see below details) to afford the title compounds Synthesis Compound 15 (0.18 g, 19%) and Synthesis Compound 16 (0.06 g, 6%) as white solids.

Analytical data (Synthesis Compound 15):
LCMS (ESI) m/z=431.15 [M−H$_2$O+1]$^+$.
HPLC (see generic method): Retention time=9.05 min. Purity=98.26%.
$^1$H NMR (400 MHz, DMSO-d$_6$) δ ppm: 8.31 (d, J=8.8 Hz, 1H), 8.15-8.14 (m, 2H), 7.83-7.77 (m, 1H), 7.52-7.46 (m, 1H), 7.32-7.28 (m, 1H), 4.21 (s, 1H), 3.37 (d, J=6.4 Hz, 2H), 1.99 (br. s, 1H), 1.79-1.76 (m, 2H), 1.50-1.47 (m, 2H), 1.36-1.20 (m, 4H), 1.07 (s, 3H).

Analytical data (Synthesis Compound 16):
LCMS (ESI) m/z=431.10 [M−H$_2$O+1]$^+$.
HPLC (see generic method): Retention time=9.27 min. Purity=98.20%.
$^1$H NMR (400 MHz, DMSO-d$_6$) δ ppm: 8.31 (d, J=8.4 Hz, 1H), 8.13 (br. s, 2H), 7.82-7.76 (m, 1H), 7.51-7.46 (m, 1H), 7.31-7.27 (m, 1H), 3.97 (s, 1H), 3.29 (d, J=6.4 Hz, 2H), 1.89 (br. s, 1H), 1.59-1.42 (m, 6H), 1.30-1.23 (m, 2H), 1.07 (s, 3H).

Chiral preparative HPLC method:
Column: YMC CHIRAL AMYLOSE-SA, 250 mm×4.6 mm, 5 μm; Mobile Phases: A: n-hexane+0.1% DEA and B: DCM:MeOH (1:1); Flow rate: 1.0 mL/min; Isocratic: 15% B.

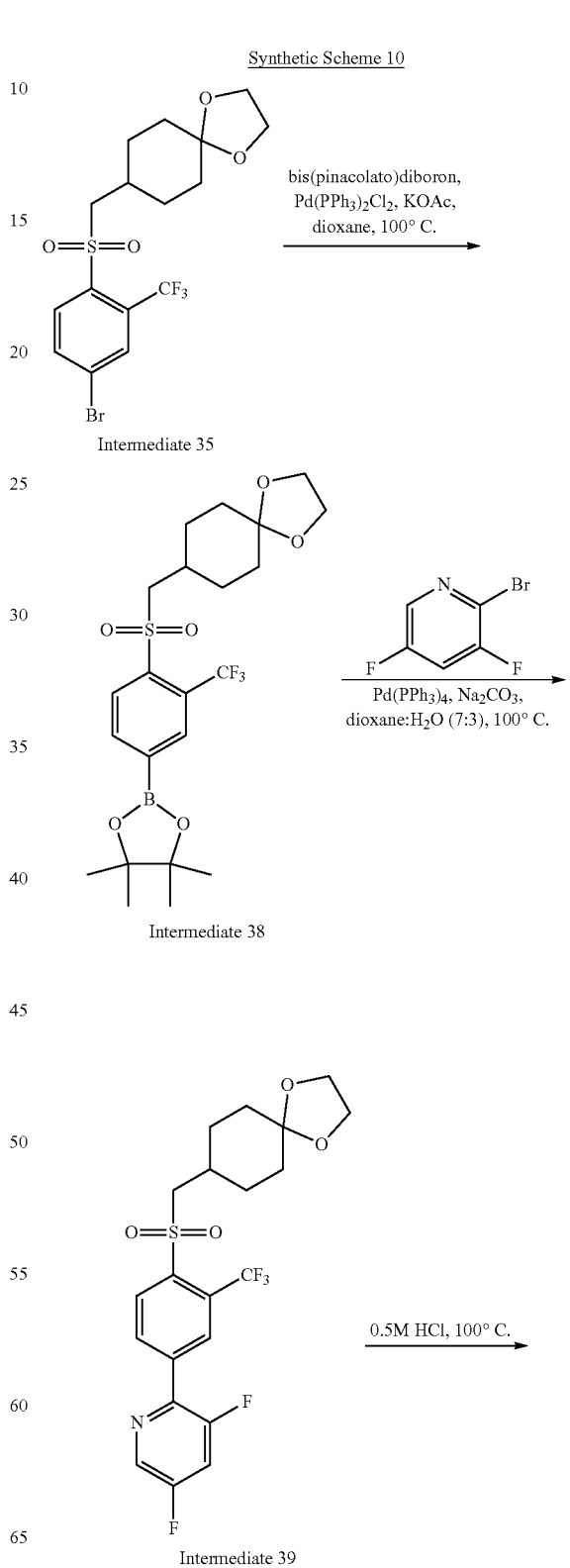

Synthetic Scheme 10

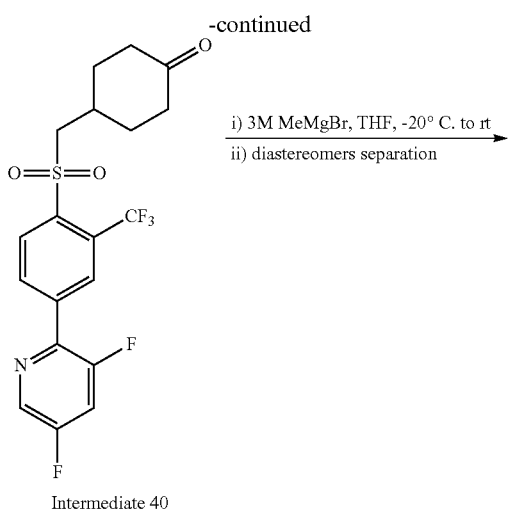

Intermediate 40

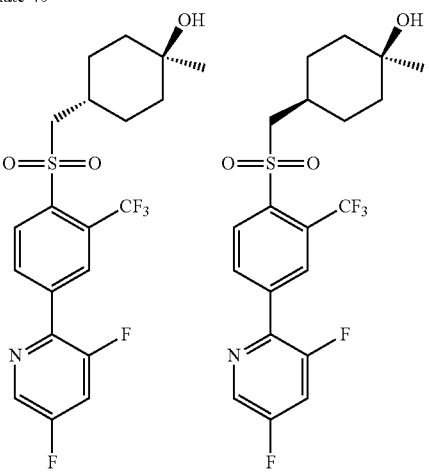

Synthesis Compound 17    Synthesis Compound 18

Intermediate 38

2-(4-(((1,4-Dioxaspiro[4.5]decan-8-yl)methyl)sulfonyl)-3-(trifluoromethyl)phenyl)-4,4,5,5-tetramethyl-1,3,2-dioxaborolane

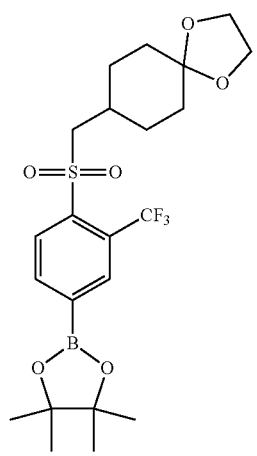 [SMILES: CC1(C)OB(c2ccc(S(=O)(=O)CC3CCC4(CC3)OCCO4)c(C(F)(F)F)c2)OC1(C)C]

To a stirred solution of 8-(((4-bromo-2-(trifluoromethyl)phenyl)sulfonyl)methyl)-1,4-dioxaspiro[4.5]decane Intermediate 35 (4.00 g, 9.02 mmol) in 1,4-dioxane (40 mL), potassium acetate (2.66 g, 27.07 mmol) and bis(pinacolato)diboron (2.98 g, 11.73 mmol) were added at room temperature and the reaction mixture was degassed using argon for 20 min. Bis(triphenylphosphine)palladium(II) dichloride (0.14 g, 0.198 mmol) was added to it and the reaction mixture was degassed for another 20 min and stirred at 100° C. for 4 h in a sealed tube. The progress of the reaction was monitored by TLC [(TLC silica gel plate), 50% EtOAc in n-hexane]. After completion of the reaction, the reaction mixture was concentrated under reduced pressure, the obtained residue was dissolved in EtOAc (150 mL) and washed with water (100 mL). The organic layer was dried over anhydrous sodium sulfate, filtered and concentrated under reduced pressure to get a crude residue. The residue obtained was purified by flash column chromatography (230-400 mesh silica gel, gradient 1-30% EtOAc in n-hexane) to afford the title compound Intermediate 38 (3.80 g, 86%) as white solid.

Analytical data: LCMS (ESI) m/z=409.10 [M+1]+(corresponding boronic acid).

Intermediate 39

2-(4-(((1,4-Dioxaspiro[4.5]decan-8-yl)methyl)sulfonyl)-3-(trifluoromethyl)phenyl)-3,5-difluoropyridine

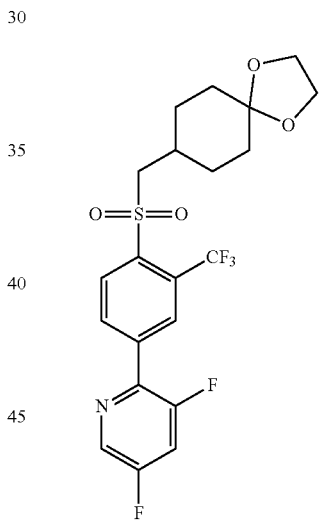

To a stirred solution of 2-(4-(((1,4-dioxaspiro[4.5]decan-8-yl)methyl)sulfonyl)-3-(trifluoromethyl)phenyl)-4,4,5,5-tetramethyl-1,3,2-dioxaborolane Intermediate 38 (1.00 g, 2.04 mmol) and 2-bromo-3,5-difluoropyridine (0.40 g, 2.04 mmol) in dioxane:water (7:3, 10 mL), sodium carbonate (0.65 g, 6.12 mmol) was added and the reaction mixture was degassed using argon for 15 min. Tetrakis[triphenylphosphine]palladium(0) (0.24 g, 0.20 mmol) was added to it and the reaction mixture was degassed for another 10 min and stirred at 100° C. for 12 h in a sealed tube. The progress of the reaction was monitored by TLC [(TLC silica gel plate), 50% EtOAc in n-hexane]. After completion of the reaction, the reaction mixture was filtered through Celite® and the filtrate was concentrated under reduced pressure to get a crude residue. The obtained residue was dissolved in EtOAc (100 mL) and washed with water (75 mL). The organic layer was dried over anhydrous sodium sulfate, filtered and concentrated under reduced pressure to get a crude residue. The residue obtained was purified by flash column chromatography (230-400 mesh silica gel, gradient 1-50% EtOAc in n-hexane) to afford the title compound Intermediate 39 (0.80 g, 82%) as white solid.

Analytical data: LCMS (ESI) m/z=478.10 [M+1]+.

Intermediate 40

4-(((4-(3,5-Difluoropyridin-2-yl)-2-(trifluoromethyl)phenyl)sulfonyl)methyl)cyclohexan-1-one

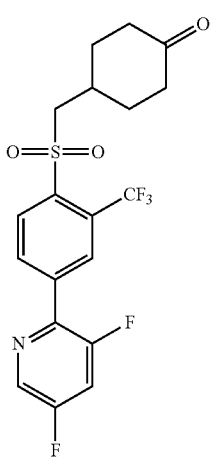 [SMILES: O=C1CCC(CS(=O)(=O)c2ccc(-c3ncc(F)cc3F)cc2C(F)(F)F)CC1]

A solution of 2-(4-(((1,4-dioxaspiro[4.5]decan-8-yl)methyl)sulfonyl)-3-(trifluoromethyl)phenyl)-3,5-difluoropyridine Intermediate 39 (0.80 g, 1.68 mmol) in 0.5M aq. HCl (50 mL) was stirred at 100° C. for 12 h. The progress of the reaction was monitored by TLC [(TLC silica gel plate), 50% EtOAc in n-hexane]. After completion of the reaction, the reaction mixture was cooled to 0° C., neutralized to pH 7 with 5% aq. NaOH solution (~20 mL) and extracted with EtOAc (3×70 mL). The combined organic layer was dried over anhydrous sodium sulfate, filtered and concentrated under reduced pressure to get a white solid. The obtained white solid was triturated with n-hexane (25 mL) to afford the title compound Intermediate 40 (0.70 g, 96%) as white solid.

Analytical data: LCMS (ESI) m/z=474.10 [M+CH₃CN]+.

Synthesis Compound 17 trans-4-(((4-(3,5-Difluoropyridin-2-yl)-2-(trifluoromethyl)phenyl)sulfonyl)methyl)-1-methylcyclohexan-1-ol

CHMSA-09-B

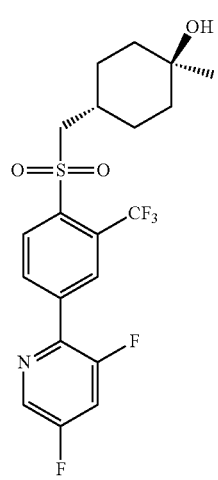 [SMILES: C[C@]1(O)CC[C@H](CS(=O)(=O)c2ccc(-c3ncc(F)cc3F)cc2C(F)(F)F)CC1]

Synthesis Compound 18 cis-4-(((4-(3,5-difluoropyridin-2-yl)-2-(trifluoromethyl)phenyl)sulfonyl)methyl)-1-methylcyclohexan-1-ol

CHMSA-09-A

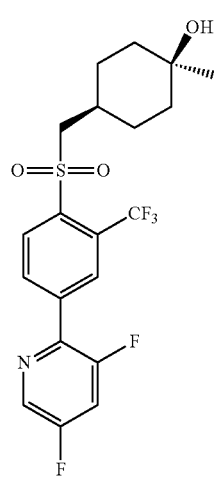 [SMILES: C[C@]1(O)CC[C@@H](CS(=O)(=O)c2ccc(-c3ncc(F)cc3F)cc2C(F)(F)F)CC1]

To a stirred solution of 4-(((4-(3,5-difluoropyridin-2-yl)-2-(trifluoromethyl)phenyl)sulfonyl)methyl)cyclohexan-1-one Intermediate 40 (0.70 g, 1.62 mmol) in THF (20 mL), 3M methyl magnesium bromide (0.65 mL, 1.95 mmol) was added at −20° C. and the reaction mixture was allowed to come to room temperature and stirred for 4 h. The progress of the reaction was monitored by TLC [(TLC silica gel plate), 50% EtOAc in n-hexane]. After completion of the reaction, the reaction mixture was cooled to 0° C., quenched with saturated aq. NH₄Cl solution (30 mL) and extracted with EtOAc (3×100 mL). The combined organic layer was dried over anhydrous sodium sulfate, filtered and concentrated under reduced pressure to get a crude residue. The residue obtained was purified by column chromatography (230-400 mesh silica gel, gradient 1-50% EtOAc in n-hexane) to obtain 0.50 g mixture of diastereomers, which was purified by SFC chromatography (see below details) to afford the title compounds Synthesis Compound 17 (0.14 g, 19%) and Synthesis Compound 18 (0.15 g, 21%) as white solids.

Analytical data (Synthesis Compound 17):

LCMS (ESI) m/z=432.10 [M–H$_2$O+1]$^+$.

HPLC (see generic method): Retention time=8.66 min. Purity=98.63%.

$^1$H NMR (400 MHz, DMSO-d$_6$) δ ppm: 8.76-8.75 (m, 1H), 8.48-8.44 (m, 2H), 8.37 (d, J=8.4 Hz, 1H), 8.24-8.19 (m, 1H), 4.21 (s, 1H), 3.38 (d, J=6.4 Hz, 2H), 1.98 (br. s, 1H), 1.79-1.75 (m, 2H), 1.50-1.46 (m, 2H), 1.37-1.20 (m, 4H), 1.07 (s, 3H).

Analytical data (Synthesis Compound 18):

LCMS (ESI) m/z=432.10 [M–H$_2$O+1]$^+$.

HPLC (see generic method): Retention time=8.91 min. Purity=99.21%.

$^1$H NMR (400 MHz, DMSO-d$_6$) δ ppm: 8.76 (br. s, 1H), 8.48-8.44 (m, 2H), 8.38 (d, J=8.4 Hz, 1H), 8.24-8.20 (m, 1H), 3.97 (s, 1H), 3.30 (s, 1H), 1.88 (br. s, 1H), 1.59-1.56 (m, 2H), 1.51-1.42 (m, 4H), 1.30-1.24 (m, 2H), 1.07 (s, 3H). (1H merged in solvent peak).

SFC chromatography details:

Mobile Phases: A: CO$_2$; B: 0.1% NH$_3$ in MeOH.

Gradient: Started with 10% B, increased to 40% B over 5 min, held at 40% B for 4 min, reduced to 10% B over 1 min and held at 10% B for 2 min.

Column: Chiralpak IG (250 mm×4.6 mm, 5 μm). Wavelength: 250 nm. Flow rate: 3 mL/min.

Synthetic Scheme 11

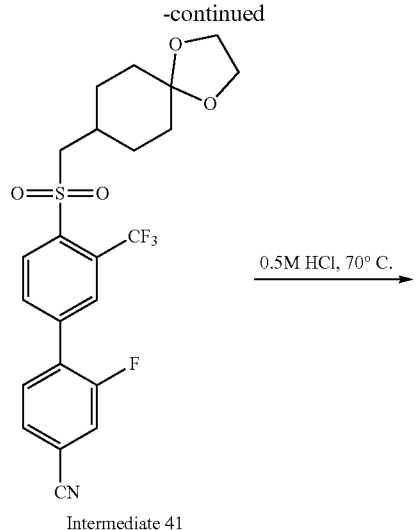

Intermediate 41

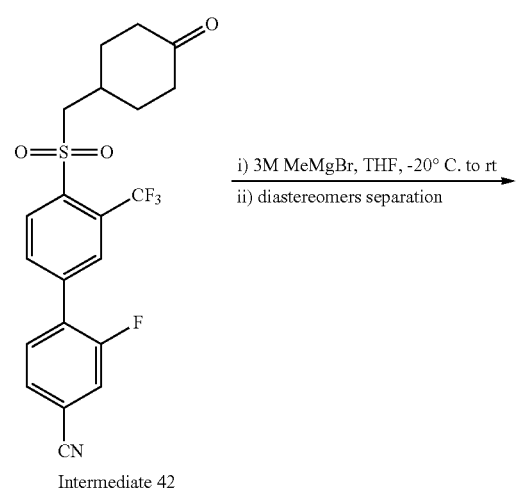

Intermediate 42

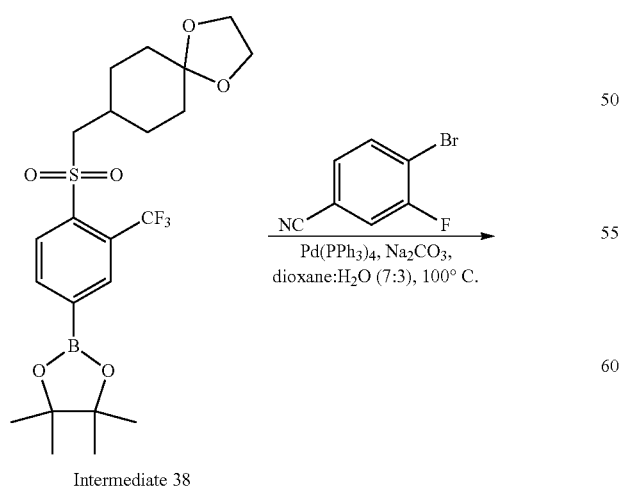

Intermediate 38

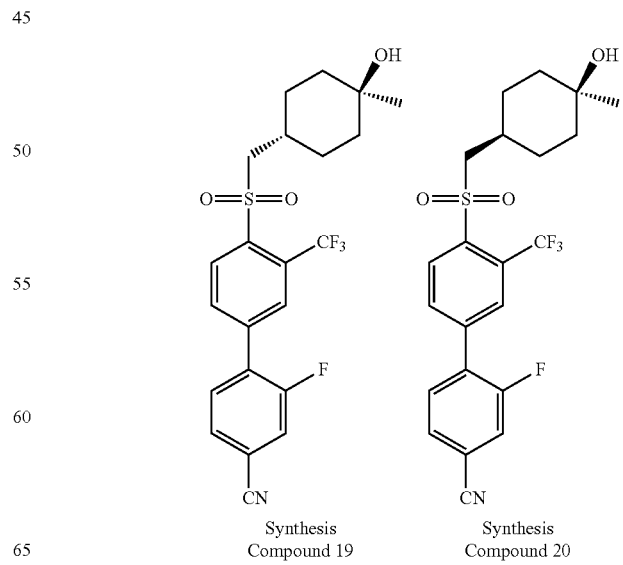

Synthesis Compound 19        Synthesis Compound 20

Intermediate 41

4'-(((1,4-Dioxaspiro[4.5]decan-8-yl)methyl)sulfonyl)-2-fluoro-3-(trifluoromethyl)-[1,1'-biphenyl]-4-carbonitrile

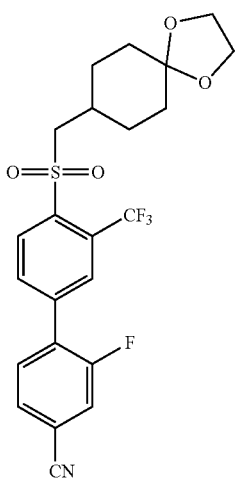

To a stirred solution of 2-(4-(((1,4-dioxaspiro[4.5]decan-8-yl)methyl)sulfonyl)-3-(trifluoromethyl)phenyl)-4,4,5,5-tetramethyl-1,3,2-dioxaborolane Intermediate 38 (1.00 g, 2.04 mmol) and 4-bromo-3-fluorobenzonitrile (0.49 g, 2.45 mmol) in dioxane:water (7:3, 10 mL), sodium carbonate (0.65 g, 6.12 mmol) was added and the reaction mixture was degassed using argon for 15 min. Tetrakis[triphenylphosphine]palladium(0) (0.24 g, 0.20 mmol) was added to it and the reaction mixture was degassed for another 10 min and stirred at 100° C. for 12 h in a sealed tube. The progress of the reaction was monitored by TLC [(TLC silica gel plate), 50% EtOAc in n-hexane]. After completion of the reaction, the reaction mixture was filtered through Celite® and the filtrate was concentrated under reduced pressure to get a crude residue. The obtained residue was dissolved in EtOAc (50 mL) and washed with water (50 mL). The organic layer was dried over anhydrous sodium sulfate, filtered and concentrated under reduced pressure to get a crude residue. The residue obtained was purified by flash column chromatography (230-400 mesh silica gel, gradient 1-35% EtOAc in n-hexane) to afford the title compound Intermediate 41 (0.90 g, 91%) as white solid.

Analytical data: LCMS (ESI) m/z=484.15 [M+1]⁺.

Intermediate 42

2-Fluoro-4'-(((4-oxocyclohexyl)methyl)sulfonyl)-3-(trifluoromethyl)-[1,1'-biphenyl]-4-carbonitrile

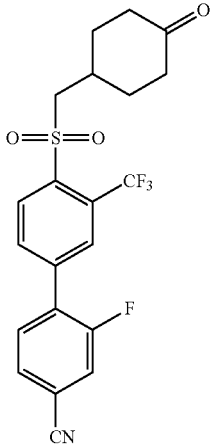 [SMILES: N#Cc1ccc(-c2ccc(S(=O)(=O)CC3CCC(=O)CC3)c(C(F)(F)F)c2)c(F)c1]

A solution of 4'-(((1,4-dioxaspiro[4.5]decan-8-yl)methyl)sulfonyl)-2-fluoro-3'-(trifluoromethyl)-[1,1'-biphenyl]-4-carbonitrile Intermediate 41 (0.90 g, 1.86 mmol) in 0.5M aq. HCl (30 mL) was stirred at 70° C. for 12 h. The progress of the reaction was monitored by TLC [(TLC silica gel plate), 50% EtOAc in n-hexane]. After completion of the reaction, the reaction mixture was cooled to 0° C., neutralized to pH 7 with 5% aq. NaOH solution (~20 mL) and extracted with EtOAc (3×50 mL). The combined organic layer was dried over anhydrous sodium sulfate, filtered and concentrated under reduced pressure to afford the title compound Intermediate 42 (0.85 g, crude) as white solid which was used in the next step without further purification.

Synthesis Compound 19

2-Fluoro-4'-(((trans-4-hydroxy-4-methylcyclohexyl)methyl)sulfonyl)-3-(trifluoromethyl)-[1,1'-biphenyl]-4-carbonitrile

CHMSA-02-B

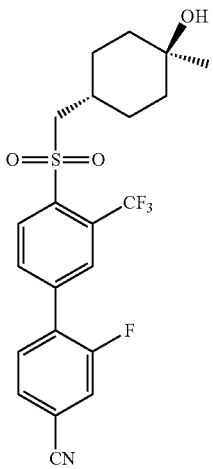 [SMILES: C[C@]1(O)CC[C@H](CS(=O)(=O)c2ccc(-c3ccc(C#N)cc3F)cc2C(F)(F)F)CC1]

Synthesis Compound 20

2-fluoro-4'-(((cis-4-hydroxy-4-methylcyclohexyl)methyl)sulfonyl)-3'-(trifluoromethyl)-[1,1'-biphenyl]-4-carbonitrile

CHMSA-02-A

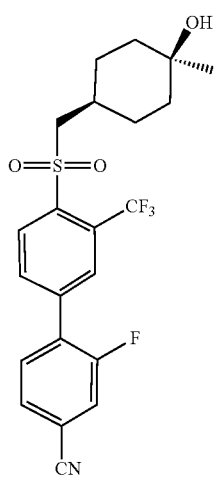 [SMILES: C[C@]1(O)CC[C@@H](CS(=O)(=O)c2ccc(-c3ccc(C#N)cc3F)cc2C(F)(F)F)CC1]

To a stirred solution of 2-fluoro-4'-(((4-oxocyclohexyl)methyl)sulfonyl)-3'-(trifluoromethyl)-[1,1'-biphenyl]-4-carbonitrile Intermediate 42 (0.85 g, 1.93 mmol) in anhydrous THF (10 mL), 3M methyl magnesium bromide (0.80 mL, 2.32 mmol) was added at −20° C. and the reaction mixture was allowed to come to room temperature and stirred for 4 h. The progress of the reaction was monitored by TLC [(TLC silica gel plate), 50% EtOAc in n-hexane]. After completion of the reaction, the reaction mixture was cooled to 0° C. and quenched with saturated aq. NH$_4$Cl solution (~30 mL) and extracted with EtOAc (3×50 mL). The combined organic layer was dried over anhydrous sodium sulfate, filtered and concentrated under reduced pressure to get a crude residue. The residue obtained was purified by flash column chromatography (230-400 mesh silica gel, gradient 1-50% EtOAc in n-hexane) to obtain 0.60 g mixture of diastereomers, which was purified by SFC chromatography (see below details) to afford the title compounds Synthesis Compound 19 (0.09 g, 10%) and Synthesis Compound 20 (0.09 g, 10%) as white solids.

Analytical data (Synthesis Compound 19):

LCMS (ESI) m/z=438.10 [M−H$_2$O+1]$^+$.

HPLC (see generic method): Retention time=8.77 min. Purity=99.07%.

$^1$H NMR (400 MHz, DMSO-d$_6$) δ ppm: 8.34 (d, J=8.4 Hz, 1H), 8.22-8.20 (m, 2H), 8.09 (d, J=10.4 Hz, 1H), 7.96-7.88 (m, 2H), 4.21 (s, 1H), 3.38 (d, J=6.4 Hz, 2H), 1.99 (br. s, 1H), 1.82-1.73 (m, 2H), 1.50-1.47 (m, 2H), 1.37-1.20 (m, 4H), 1.07 (s, 3H).

Analytical data (Synthesis Compound 20):

LCMS (ESI) m/z=438.15 [M−H$_2$O+1]$^+$.

HPLC (see generic method): Retention time=8.83 min. Purity=99.33%.

$^1$H NMR (400 MHz, DMSO-d$_6$) δ ppm: 8.35 (d, J=8.4 Hz, 1H), 8.22-8.19 (m, 2H), 8.09 (d, J=10.0 Hz, 1H), 7.96-7.88 (m, 2H), 3.97 (s, 1H), 3.31 (d, J=6.4 Hz, 2H), 1.89 (br. s, 1H), 1.59-1.57 (m, 2H), 1.51-1.42 (m, 4H), 1.30-1.23 (m, 2H), 1.07 (s, 3H).

SFC chromatography details:

Mobile Phases: A: CO$_2$; B: 0.1% NH$_3$ in MeOH.

Gradient: Started with 10% B, increased to 40% B over 5 min, held at 40% B for 4 min, reduced to 10% B over 1 min and held at 10% B for 2 min.

Column: Chiralpak IG (250 mm×4.6 mm, 5 μm). Wavelength: 262 nm. Flow rate: 3 mL/min.

Synthetic Scheme 12

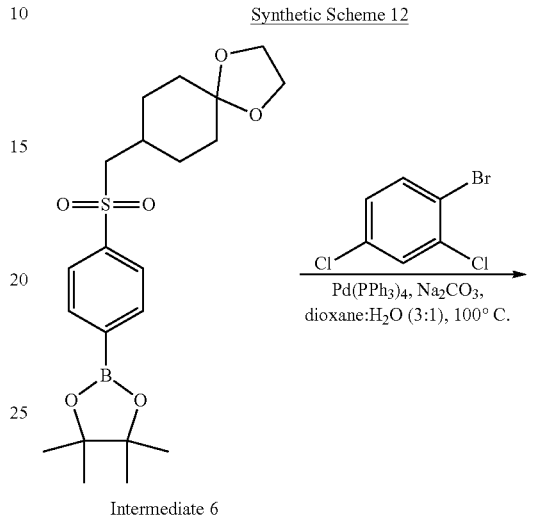

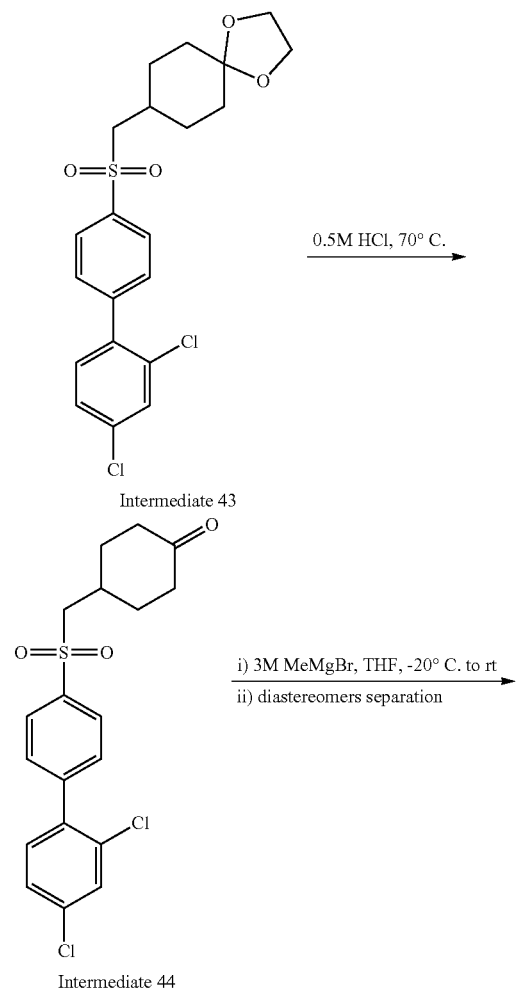

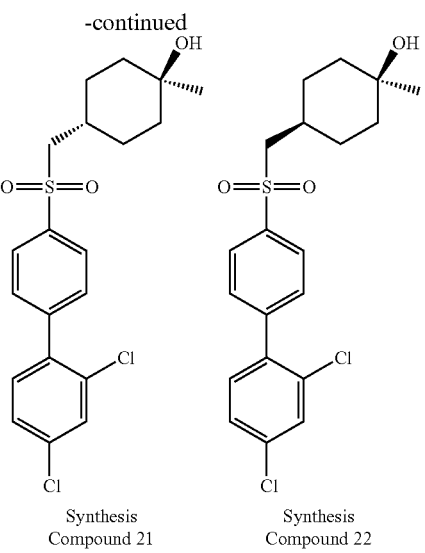

Synthesis Compound 21

Synthesis Compound 22

Intermediate 43

8-(((2',4'-Dichloro-[1,1'-biphenyl]-4-yl)sulfonyl)methyl)-1,4-dioxaspiro[4.5]decane

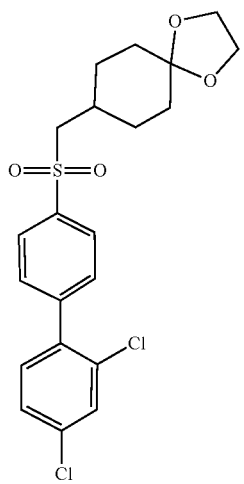 [SMILES: O=S(=O)(CC1CCC2(CC1)OCCO2)c1ccc(-c2ccc(Cl)cc2Cl)cc1]

To a stirred solution of 2-(4-(((1,4-dioxaspiro[4.5]decan-8-yl)methyl)sulfonyl)phenyl)-4,4,5,5-tetramethyl-1,3,2-dioxaborolane Intermediate 6 (3.27 g, 7.74 mmol) in dioxane: water (3:1, 40 mL), sodium carbonate (2.46 g, 23.23 mmol), 1-bromo-2,4-dichlorobenzene (1.75 g 7.74 mmol) were added and the reaction mixture was degassed using argon for 20 min. Tetrakis[triphenylphosphine]palladium(0) (0.89 g, 0.77 mmol) was added to it and the reaction mixture was degassed for another 10 min and stirred at 100° C. for 12 h in a sealed tube. The progress of the reaction was monitored by TLC [(TLC silica gel plate), 30% EtOAc in n-hexane]. After completion of the reaction, the reaction mixture was filtered through Celite® and the filtrate was concentrated under reduced pressure to get a crude residue. The obtained residue was dissolved in EtOAc (150 mL) and washed with water (100 mL). The organic layer was dried over anhydrous sodium sulfate, filtered and concentrated under reduced pressure to get a crude residue. The residue obtained was purified by flash column chromatography (230-400 mesh silica gel, gradient 1-20% EtOAc in n-hexane) to afford the title compound Intermediate 43 (3.00 g, 88%) as white solid.

Analytical data: LCMS (ESI) m/z=441.10 [M+1]$^+$.

Intermediate 44

4-(((2',4'-Dichloro-[1,1'-biphenyl]-4-yl)sulfonyl)methyl)cyclohexan-1-one

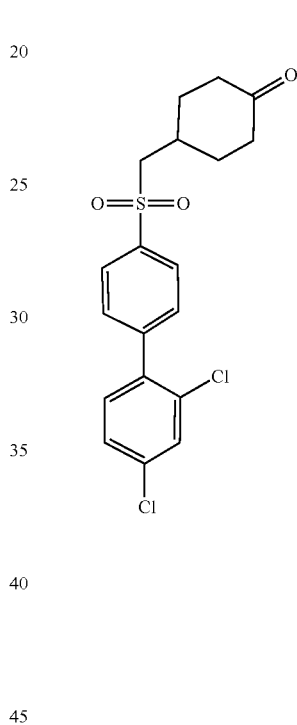

A solution of 8-(((2',4'-dichloro-[1,1'-biphenyl]-4-yl)sulfonyl)methyl)-1,4-dioxaspiro[4.5]decane Intermediate 43 (3.00 g, 6.80 mmol) in 0.5M aq. HCl (40 mL) was stirred at 70° C. for 4 h. The progress of the reaction was monitored by TLC [(TLC silica gel plate), 30% EtOAc in n-hexane]. After completion of the reaction, the reaction mixture was cooled to 0° C., neutralized to pH 7 with 5% aq. NaOH solution, stirred for 30 min and extracted with EtOAc (3×50 mL). The combined organic layer was dried over anhydrous sodium sulfate, filtered and concentrated under reduced pressure to get a crude residue. The obtained residue was dissolved in DCM (10 mL), stirred at room temperature and n-hexane (50 mL) was slowly added to it. The precipitate obtained was filtered, washed with n-hexane (25 mL) and dried to afford the title compound Intermediate 44 (2.50 g, 93%) as white solid.

Analytical data: LCMS (ESI) m/z=397.10 [M+1]$^+$.

Synthesis Compound 21 trans-4-(((2',4'-Dichloro-[1,1'-biphenyl]-4-yl)sulfonyl)methyl)-1-methylcyclohexan-1-ol

CHMSA-11-B

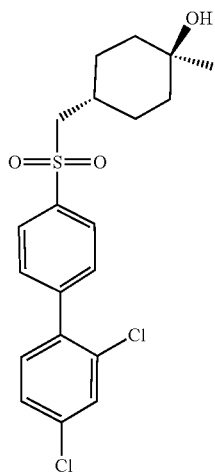 [SMILES: C[C@]1(O)CC[C@H](CS(=O)(=O)c2ccc(-c3ccc(Cl)cc3Cl)cc2)CC1]

Synthesis Compound 22 cis-4-(((2',4'-dichloro-[1,1'-biphenyl]-4-yl)sulfonyl)methyl)-1-methylcyclohexan-1-ol

CHMSA-11-A

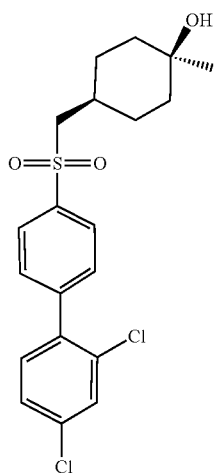 [SMILES: C[C@]1(O)CC[C@@H](CS(=O)(=O)c2ccc(-c3ccc(Cl)cc3Cl)cc2)CC1]

To a stirred solution of 4-(((2',4'-dichloro-[1,1'-biphenyl]-4-yl)sulfonyl)methyl)cyclohexan-1-one Intermediate 44 (2.50 g, 6.29 mmol) in anhydrous THF (30 mL), 3M methyl magnesium bromide (2.52 mL, 7.55 mmol) was added dropwise at −20° C. over a period of 30 min and the reaction mixture was allowed to come to room temperature and stirred for 12 h. The progress of the reaction was monitored by TLC [(TLC silica gel plate), 40% EtOAc in n-hexane].

After completion of the reaction, the reaction mixture was quenched with saturated aq. NH$_4$Cl solution (30 mL) and extracted with EtOAc (3×50 mL). The combined organic layer was dried over anhydrous sodium sulfate and concentrated under reduced pressure to get a crude residue. The residue obtained was purified by column chromatography (230-400 mesh silica gel, gradient 1-40% EtOAc in n-hexane) to obtain 1.00 g of a mixture of diastereomers, which was purified by SFC chromatography (see below details) to afford the title compounds Synthesis Compound 21 (0.20 g, 8%) and Synthesis Compound 22 (0.20 g, 8%) as white solids.

Analytical data (Synthesis Compound 21):

LCMS (ESI) m/z=395.10 [M−H$_2$O+1]$^+$.

HPLC (see generic method): Retention time=9.23 min. Purity=98.26%.

$^1$H NMR (400 MHz, DMSO-d$_6$) δ ppm: 8.00 (d, J=8.4 Hz, 2H), 7.81-7.80 (m, 1H), 7.71 (d, J=8.4 Hz, 2H), 7.57 (dd, J=8.4, 2.0 Hz, 1H), 7.51 (d, J=8.4 Hz, 1H), 4.18 (s, 1H), 1.85 (br. s, 1H), 1.77-1.73 (m, 2H), 1.49-1.46 (m, 2H), 1.33-1.15 (m, 4H), 1.06 (s, 3H) (2H's are merged in solvent peak).

Analytical data (Synthesis Compound 22):

LCMS (ESI) m/z=435.00 [M+Na]+.

HPLC (see generic method): Retention time=9.51 min. Purity=98.80%.

$^1$H NMR (400 MHz, DMSO-d$_6$) δ ppm: 8.00 (d, J=8.4 Hz, 2H), 7.80 (d, J=2.0 Hz, 1H), 7.71 (d, J=8.4 Hz, 2H), 7.57 (dd, J=8.4, 2.0 Hz, 1H), 7.51 (d, J=8.4 Hz, 1H), 3.94 (s, 1H), 3.27 (d, J=6.0 Hz, 2H), 1.76 (br. s, 1H), 1.56-1.39 (m, 6H), 1.26-1.18 (m, 2H), 1.06 (s, 3H).

SFC chromatography details:

Mobile Phases: A: CO$_2$; B: 0.1% NH$_3$ in MeOH.

Gradient: Started with 10% B, increased to 40% B over 5 min, held at 40% B for 4 min, reduced to 10% B over 1 min and held at 10% B for 2 min.

Column: Chiralpak IA (250 mm×4.6 mm, 5 μm). Wavelength: 253 nm. Flow rate: 3 mL/min.

Synthetic Scheme 13

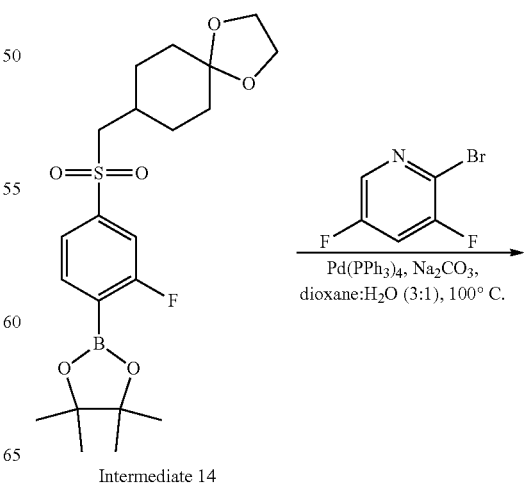

Intermediate 14

Intermediate 45

2-(4-(((1,4-Dioxaspiro[4.5]decan-8-yl)methyl)sulfonyl)-2-fluorophenyl)-3,5-difluoropyridine

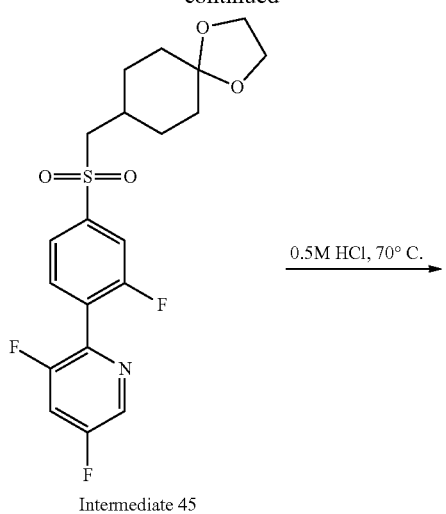

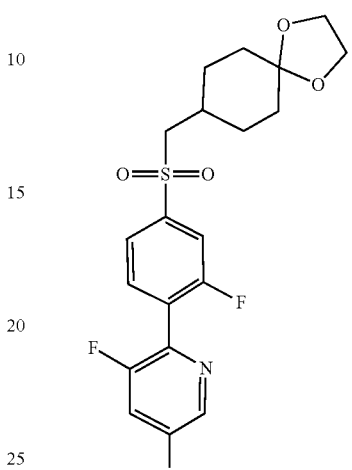

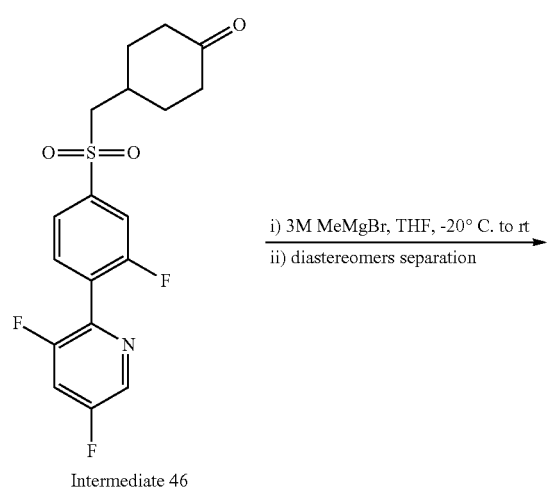

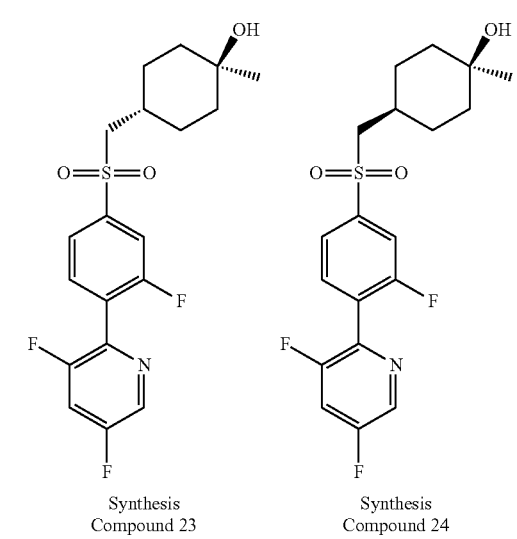 [SMILES: C[C@]1(O)CC[C@H](CS(=O)(=O)c2ccc(-c3ncc(F)cc3F)c(F)c2)CC1 ; C[C@]1(O)CC[C@@H](CS(=O)(=O)c2ccc(-c3ncc(F)cc3F)c(F)c2)CC1]

To a stirred solution of 2-(4-(((1,4-dioxaspiro[4.5]decan-8-yl)methyl)sulfonyl)-2-fluorophenyl)-4,4,5,5-tetramethyl-1,3,2-dioxaborolane Intermediate 14 (3.00 g, 6.81 mmol) in dioxane:water (3:1, 40 mL), sodium carbonate (2.17 g, 20.44 mmol), 2-bromo-3,5-difluoropyridine (1.32 g, 6.81 mmol) were added and the reaction mixture was degassed using argon for 20 min. Tetrakis[triphenylphosphine]palladium(0) (0.79 g, 0.68 mmol) was added to it and the reaction mixture was degassed for another 10 min and heated at 100° C. for 12 h in a sealed tube. The progress of the reaction was monitored by TLC [(TLC silica gel plate), 50% EtOAc in n-hexane]. After completion of the reaction, the reaction mixture was cooled to room temperature, filtered over Celite® and the filtrate was concentrated under reduced pressure to get a crude residue. The obtained residue was dissolved in EtOAc (50 mL) and washed with water (50 mL). The organic layer was dried over anhydrous sodium sulfate and concentrated under reduced pressure to get a crude residue. The residue obtained was purified by flash column chromatography (230-400 mesh silica gel, 30% EtOAc in n-hexane) to afford the title compound Intermediate 45 (2.50 g) as colorless solid.

Analytical data: LCMS (ESI) m/z=428.15 [M+1]$^+$.

Intermediate 46

4-(((4-(3,5-Difluoropyridin-2-yl)-3-fluorophenyl)sulfonyl)methyl)cyclohexan-1-one

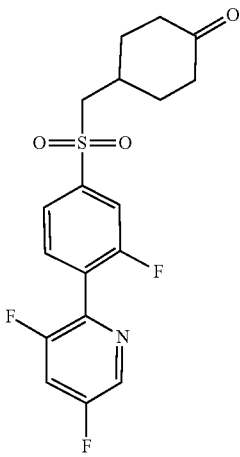 [SMILES: O=C1CCC(CS(=O)(=O)c2ccc(-c3ncc(F)cc3F)c(F)c2)CC1]

A solution of 2-(4-(((1,4-dioxaspiro[4.5]decan-8-yl)methyl)sulfonyl)-2-fluorophenyl)-3,5-difluoropyridine Intermediate 45 (2.50 g, 5.85 mmol) in 0.5M aq. HCl (30 mL) was stirred at 70° C. for 4 h. The progress of the reaction was monitored by TLC [(TLC silica gel plate), 50% EtOAc in n-hexane]. After completion of the reaction, the reaction mixture was brought to 0° C., neutralized to pH 7 with 5% NaOH solution (20 mL) and extracted with EtOAc (3×30 mL). The organic layer was separated, washed with brine (50 mL), dried over anhydrous sodium sulfate and concentrated under reduced pressure to get a crude residue. The residue obtained was purified by flash column chromatography (230-400 mesh silica gel, 30% EtOAc in n-hexane) to afford the title compound Intermediate 46 (2.10 g, 94%) as colorless oil.

Analytical data: LCMS (ESI) m/z=384.10 [M+1]$^+$.

Synthesis Compound 23 trans-4-(((4-(3,5-Difluoropyridin-2-yl)-3-fluorophenyl)sulfonyl)methyl)-1-methylcyclohexan-1-ol

CHMSA-03-B

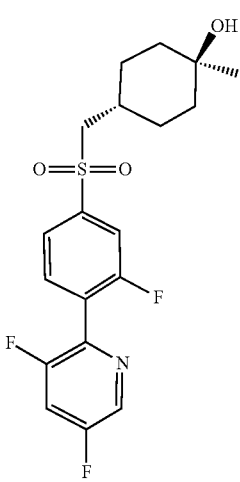 [SMILES: C[C@]1(O)CC[C@H](CS(=O)(=O)c2ccc(-c3ncc(F)cc3F)c(F)c2)CC1]

Synthesis Compound 24 cis-4-(((4-(3,5-difluoropyridin-2-yl)-3-fluorophenyl)sulfonyl)methyl)-1-methylcyclohexan-1-ol

CHMSA-03-A

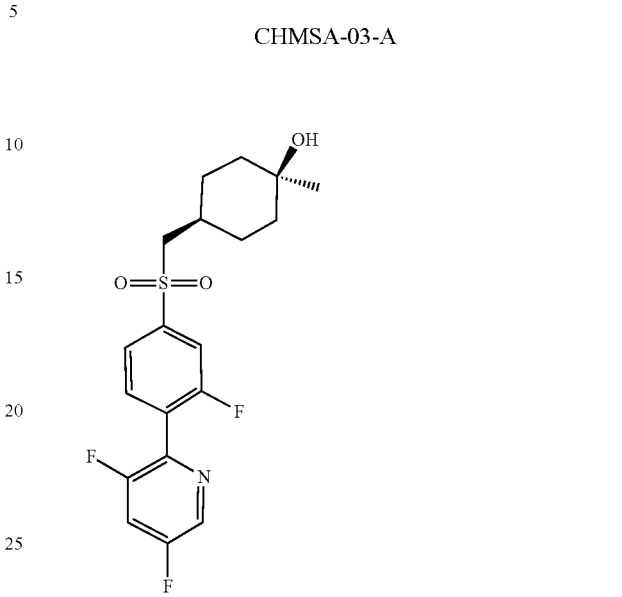

To a stirred solution of 4-(((4-(3,5-difluoropyridin-2-yl)-3-fluorophenyl)sulfonyl)methyl)cyclohexan-1-one Intermediate 46 (2.10 g, 5.48 mmol) in anhydrous THF (20 mL), 3M methyl magnesium bromide (2.19 mL, 6.57 mmol) was added at −20° C. and the reaction mixture was allowed to come to room temperature and stirred for 4 h. The progress of the reaction was monitored by TLC [(TLC silica gel plate), 50% EtOAc in n-hexane]. After completion of the reaction, the reaction mixture was quenched with saturated NH$_4$Cl solution (20 mL) and extracted with EtOAc (3×20 mL). The combined organic layer was dried over anhydrous sodium sulfate and concentrated under reduced pressure to get a crude residue. The residue obtained was purified by SFC chromatography (see below details) to afford the title compounds Synthesis Compound 23 (0.10 g, 5%) and Synthesis Compound 24 (0.10 g, 5%) as white solids.

Analytical data (Synthesis Compound 23): LCMS (ESI) m/z=382.10 [M−H$_2$O+1]$^+$.

HPLC (see generic method): Retention time=7.91 min. Purity=99.42%.

$^1$H NMR (400 MHz, DMSO-d$_6$) δ ppm: 8.74-8.73 (m, 1H), 8.22-8.17 (m, 1H), 7.96-7.87 (m, 3H), 4.18 (s, 1H), 3.42 (d, J=6.4 Hz, 2H), 1.86 (br. s, 1H), 1.77-1.76 (m, 2H), 1.49-1.46 (m, 2H), 1.33-1.20 (m, 4H), 1.06 (s, 3H).

Analytical data (Synthesis Compound 24):

LCMS (ESI) m/z=382.15 [M−H$_2$O+1]$^+$.

HPLC (see generic method): Retention time=8.19 min. Purity=99.83%.

$^1$H NMR (400 MHz, DMSO-d$_6$) δ ppm: 8.70 (d, J=2.0 Hz, 1H), 8.19-8.14 (m, 1H), 7.94-7.84 (m, 3H), 3.92 (s, 1H), 3.33 (d, J=6.0 Hz, 2H), 1.72 (br. s, 1H), 1.53-1.36 (m, 6H), 1.24-1.17 (m, 2H), 1.02 (s, 3H).

SFC chromatography details:

Mobile Phases: A: CO$_2$; B: 0.1% NH$_3$ in MeOH.

Gradient: Started with 10% B, increased to 40% B over 5 min, held at 40% B for 4 min, reduced to 10% B over 1 min, held at 10% B for 2 min.

Column: Chiralpak IA (250 mm×4.6 mm, 5 μm). Wavelength: 277 nm. Flow: 3 mL/min.

X-Ray Analysis

Confirmation of Structure for CHMSA-04-B

A crystal of appropriate size was selected from the bulk sample of CHMSA-04-B and subjected to single crystal x-ray analysis at 100° K. The analysis confirmed the structure and indicated a trans configuration of the hydroxyl group to the carbon substituent at the 4-position on the cyclohexane ring.

Single crystal data were collected on a Rigaku Oxford Diffraction Supernova Dual Source, Cu at Zero, Atlas CCD diffractometer equipped with an Oxford Cryosystems Cobra cooling device. The data were collected using Cu Kα radiation as stated in the experimental table. Structures were solved and refined using the Bruker AXS SHELXTL suite or the OLEX² crystallographic software. A reference diffractogram for the crystal structure was generated using C. F. a. Macrae, "Mercury: visualization and analysis of crystal structures," J. Appl. Cryst., vol. 39, pp. 453-457, 2006.

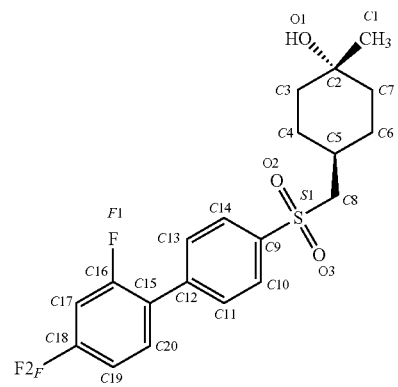

TABLE 1

X-Ray Analysis: Sample and Crystal Data

| | |
|---|---|
| Empirical formula | $C_{20}H_{22}F_2O_3S$ |
| Formula weight | 380.43 |
| Temperature | 100(2)° K |
| Wavelength | 1.54184 Å |
| Crystal size | 0.200 × 0.050 × 0.030 mm |
| Crystal habit | Colourless Column |
| Crystal system | Monoclinic |
| Space group | $P2_1/c$ |
| Unit cell dimensions | a = 15.9704(3) Å; α = 90° |
| | b = 11.9467(2) Å; β = 107.047(2)° |
| | c = 9.9018(2) Å; γ = 90° |
| Volume | 1806.19(7) Å³ |
| Z | 4 |
| Density (calculated) | 1.399 Mg/m³ |
| Absorption coefficient | 1.925 mm⁻¹ |
| F(000) | 800 |
| Diffractometer | SuperNova, Dual, Cu at zero, Atlas |
| Radiation source | SuperNova (Cu) X-ray Source, CuKα |
| Data collection method | omega scans |
| Theta range for data collection | 4.700 to 74.582° |
| Index ranges | −19 ≤ h ≤ 19; −14 ≤ k ≤ 13; −12 ≤ l ≤ 12 |
| Reflections collected | 33265 |
| Independent reflections | 3655 [R(int) = 0.0428] |
| Coverage of independent reflections | 99.9% |
| Absorption correction | Semi-empirical from equivalents |
| Max. and min. transmission | 1.00000 and 0.83197 |
| Structure solution technique | Direct Methods |
| Structure solution program | SHELXTL-2013 |
| Refinement technique | Full-matrix least-squares on F² |
| Refinement program | SHELXL-2013 |
| Function minimized | $\Sigma w(F_o^2 - F_c^2)^2$ |
| Data/restraints/parameters | 3655/0/250 |
| Goodness-of-fit on F² | 1.035 |
| $\Delta/\sigma_{max}$ | 0.000 |
| Final R indices (3246 data; I > 2σ(I)) | R1 = 0.0323, wR2 = 0.0817 |
| Final R indices (all data) | R1 = 0.0376, wR2 = 0.0855 |
| Weighting scheme | $w = 1/[\sigma^2(F_o^2) + (0.0451P)^2 + 0.8328P]$ where $P = (F_o^2 + 2F_c^2)/3$ |
| Largest diff. peak and hole | 0.391 and −0.396 eÅ⁻³ |

Atomic coordinates and equivalent isotropic atomic displacement parameters (Å²) (U(eq) is defined as one third of the trace of the orthogonalized Uij tensor) are summarised in the following table. F1 is 97% orientated in one rotamer about the central aryl-aryl bond and 3% in a rotamer that is at 180 degrees to the major rotamer.

TABLE 2

Atomic Coordinates and Equivalent Isotropic Atomic Displacement Parameters

| Atom | x/a | y/b | z/c | U(eq) |
|---|---|---|---|---|
| S1 | 0.21867(2) | 0.34174(3) | 0.51209(3) | 0.01580(10) |
| F1A | 0.55064(6) | 0.39175(7) | 0.25634(10) | 0.0244(3) |
| F1B | 0.5486(19) | 0.034(2) | 0.447(3) | 0.032(9) |
| F2 | 0.73785(6) | 0.11438(8) | 0.18146(10) | 0.0263(2) |
| O1 | −0.22081(6) | 0.45131(8) | 0.16221(11) | 0.0176(2) |
| O2 | 0.23618(7) | 0.44273(9) | 0.59611(11) | 0.0245(2) |
| O3 | 0.18156(7) | 0.24742(9) | 0.56496(11) | 0.0236(2) |
| C1 | −0.14088(10) | 0.35565(13) | 0.03519(16) | 0.0237(3) |
| C2 | −0.13297(9) | 0.41757(11) | 0.17243(15) | 0.0149(3) |
| C3 | −0.07428(9) | 0.52098(11) | 0.18838(16) | 0.0184(3) |
| C4 | 0.02201(9) | 0.49109(12) | 0.21008(16) | 0.0185(3) |
| C5 | 0.05785(8) | 0.41229(11) | 0.33642(15) | 0.0146(3) |
| C6 | −0.00145(9) | 0.30983(11) | 0.32544(16) | 0.0178(3) |
| C7 | −0.09762(9) | 0.34201(11) | 0.30111(15) | 0.0170(3) |
| C8 | 0.15142(8) | 0.37854(11) | 0.34119(14) | 0.0156(3) |
| C9 | 0.31699(9) | 0.30016(12) | 0.47931(14) | 0.0153(3) |
| C10 | 0.32171(9) | 0.19404(12) | 0.42490(15) | 0.0181(3) |
| C11 | 0.39486(9) | 0.16573(11) | 0.38329(15) | 0.0173(3) |
| C12 | 0.46348(9) | 0.24207(11) | 0.39704(15) | 0.0153(3) |
| C13 | 0.45830(9) | 0.34672(11) | 0.45782(16) | 0.0173(3) |
| C14 | 0.38509(9) | 0.37671(11) | 0.49785(15) | 0.0171(3) |
| C15 | 0.53888(8) | 0.21021(11) | 0.34603(15) | 0.0156(3) |
| C16 | 0.57905(9) | 0.28478(11) | 0.27645(15) | 0.0177(3) |
| C17 | 0.64610(9) | 0.25582(12) | 0.22086(16) | 0.0189(3) |
| C18 | 0.67301(9) | 0.14591(12) | 0.23661(16) | 0.0192(3) |
| C19 | 0.63799(9) | 0.06714(12) | 0.30630(16) | 0.0208(3) |
| C20 | 0.57108(9) | 0.10062(12) | 0.36038(15) | 0.0180(3) |

An XRPD pattern was calculated from the crystal structure (100° K) and compared to the experimental diffractogram for the bulk crystals (collected at room temperature). The diffractograms match well and demonstrate that the single crystal structure obtained is representative of the bulk supplied material.

X-ray Powder Diffraction (XRPD) diffractograms were collected on a Bruker D8 diffractometer using Cu Kα radiation (40 kV, 40 mA) and a θ-2θ goniometer fitted with a Ge monochromator. The incident beam passed through a 2.0 mm divergence slit followed by a 0.2 mm antiscatter slit and knife edge. The diffracted beam passed through an 8.0 mm receiving slit with 2.5° Soller slits followed by the Lynxeye Detector. The software used for data collection and analysis was Diffrac Plus XRD Commander and Diffrac Plus EVA respectively.

XRPD samples were run under ambient conditions as flat plate specimens using the compound in powder form. The sample was prepared on a polished, zero-background (510)

silicon wafer by gently pressing onto the flat surface or packed into a cut cavity. The sample was rotated in its own plane.

The XRPD data collection parameters included:
Angular range: 2 to 42° 2θ;
Step size: 0.05° 2θ; and
Collection time: 0.5 s/step (total collection time: 6.40 min).

Additional "Scaled-Up" Synthesis Methods

Analytical Gas Chromatography (GC)
The analyses were carried out on the following system:
System: Agilent 7890 series gas chromatograph or equivalent.
Column: HP-5, 30 m×0.32 mm, 0.25 μm film thickness (Ex: J&W, Part number: 19091J-413).
Oven programme: 40° C. (hold for 1 minute), ramp 10° C. per minute up to 260° C. (hold for 5 minutes).
Injector: 250° C.
Detector: 350° C. FID.
Head pressure: 10 psi, constant pressure.
Carrier gas: Nitrogen.
Split ratio: 10:1 (Split).
Injection volume: 1 μL.
Liner: SGE focusliner with glass wool insert.
Diluent: Dichloromethane.

Analytical High-Performance Liquid Chromatography (HPLC)
The analyses were carried out on the following system:
System: Agilent 1100 series liquid chromatograph or equivalent.
Column: Acquity BEH Phenyl 4.6×30 mm; 1.7 μm particle size (ex: Waters #186004644).
Injection volume: 5 μL.
Flow rate: 2.0 mL/min.
Detection: 210 nm ultraviolet detection.
Column temperature: 40° C.
Post run: 2.3 min.
Solvents: A: water:TFA (100:0.03); B: acetonitrile:TFA (100:0.03)
Gradient:

| Time (min) | A % | B % |
|---|---|---|
| 0 | 95 | 5 |
| 5.2 | 5 | 95 |
| 5.7 | 5 | 95 |
| 5.8 | 95 | 5 |
| 6.2 | 95 | 5 |

Mass Spectrometry Conditions
The analyses were carried out on the following system:
System: Bruker Esquire 3000 Plus Ion Trap MS.
Ion polarity: Positive.
Ion source type: ESI.
Nebuliser: 50 psi.
Dry gas: 10 L/min.
Dry temperature: 350° C.
Target mass: 400 m/z.
Scan range: 50 m/z-1000 m/z.

Synthetic Scheme 14

Intermediate 47

1-Methyl-2-oxabicyclo[2.2.2]octan-3-one

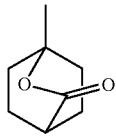

To a 10 L flange flask under N₂ was charged ethyl 4-oxocyclohexane-1-carboxylate (550 g, 3.23 mol) and THF (5060 mL). The reaction mixture was cooled to 0° C. and 3M MeMgCl in THF (1078 mL, 3.23 mol) was charged dropwise at 0-5° C. over 30 minutes. The reaction mixture was warmed to room temperature and stirred for 2 h. TLC (1% EtOAc/DCM) indicated no starting material remained. The reaction mixture was quenched into a mixture of saturated NH₄Cl solution (2.75 L) and water (5.5 L) at <15° C. The product was extracted with EtOAc (5.5 L) and the aqueous layer separated before being back extracted with EtOAc (5.5 L). The organics were combined, dried over MgSO₄ and concentrated in vacuo. This provided 470.9 g of crude product, which was purified on silica (10 kg) eluting with 1% EtOAc/DCM. The clean fractions were concentrated in vacuo to provide the title compound Intermediate 47 (104.0 g, 23%) in a purity of >95% by NMR.

Analytical Data:
$^1$H NMR (400 MHz, CDCl₃) δ (ppm): 2.62-2.58 (m, 1H), 1.95-1.86 (m, 2H), 1.82-1.69 (m, 6H), 1.36 (s, 3H).

Intermediate 48 cis-4-(Hydroxymethyl)-1-methylcyclohexan-1-ol

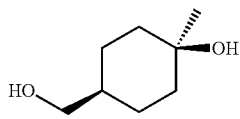

To a 5 L flange flask under N₂ was charged 1-methyl-2-oxabicyclo[2.2.2]octan-3-one Intermediate 47 (104.0 g, 0.742 mol) and THF (1.5 L). The reaction mixture was cooled to 0° C. and 3M LiAlH₄ solution (739.8 mL, 2.219 mol) was charged dropwise at 0-5° C. over 30 minutes. The reaction mixture was warmed to room temperature and stirred for 1 h. TLC (1% EtOAc/DCM) indicated no 1-methyl-2-oxabicyclo[2.2.2]octan-3-one Intermediate 47 remained. The reaction mixture was quenched with saturated Rochelle salts aqueous solution (0.75 L) to give a thick suspension. The suspension was partitioned between EtOAc (0.75 L) and water (1.5 L). The layers were separated, and the aqueous layer back extracted with EtOAc (0.75 L). The organics were combined, dried over MgSO₄ and concentrated in vacuo. This provided the title compound Intermediate 48 (86.2 g, crude) in a purity of >95% by NMR and 98.0% by GC.

Analytical Data:
GC: Retention time: 10.0 min.; Purity: 98.0%.
$^1$H NMR (400 MHz, CDCl₃) δ (ppm): 3.48 (d, J=6.1 Hz, 2H), 1.75-1.57 (m, 4H), 1.47-1.24 (m, 5H), 1.22 (s, 3H). The two exchangeable protons of this molecule do not appear in this NMR spectrum.

Intermediate 49 cis-4-(Bromomethyl)-1-methylcyclohexan-1-ol

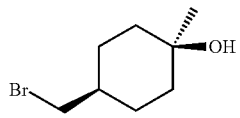

To a 2 L flange flask under N₂ was charged triphenylphosphine (334.7 g, 1.276 mol) and DCM (1 L). The reaction mixture was cooled to 0° C. and CBr4 (22.2 g, 0.670 mol) was charged in portions at 0-5° C. over 20 minutes. cis-4-(Hydroxymethyl)-1-methylcyclohexan-1-ol Intermediate 48 (92.0 g, 0.638 mol) was charged in portions over 30 minutes at 0-5° C. The reaction mixture was warmed to room temperature and stirred for 3 h where NMR analysis showed ~13% starting material remained. Triphenylphosphine (33.5 g, 0.128 mol) was charged and the reaction mixture was stirred for 1 h at room temperature. NMR analysis showed <1% starting material remained. The solids were removed by filtration and the filtrate washed with water (1 L). The layers were separated, and the aqueous layer back extracted with DCM (1 L). The organics were combined, dried over MgSO₄ and concentrated in vacuo. The crude was purified on silica (2 kg) loaded in 20% EtOAc/heptane and eluted with 25% EtOAc/heptane. The clean fractions were concentrated in vacuo to provide the title compound Intermediate 49 (96.1 g, 73%) in a purity of >95% by NMR and 98.3% by GC.

Analytical Data:
GC: Retention time: 11.0 min.; Purity: 98.3%.
$^1$H NMR (400 MHz, CDCl₃) δ (ppm): 3.29 (d, J=6.7 Hz, 2H), 1.73-1.63 (m, 4H), 1.62-1.53 (m, 1H), 1.45-1.30 (m, 4H), 1.21 (s, 3H), 1.17 (s, 1H).

Intermediate 50 cis-4-{[(4-Bromophenyl)sulfanyl]methyl}-1-methyl-cyclohexan-1-ol

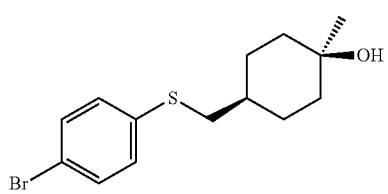 [SMILES: C[C@]1(O)CC[C@@H](CSc2ccc(Br)cc2)CC1]

To a 1 L 3-neck flask under N₂ was charged cis-4-(bromomethyl)-1-methylcyclohexan-1-ol Intermediate 49 (42.3 g, 0.204 mol), 4-bromothiophenol (38.6 g, 0.204 mol), cesium carbonate (133.1 g, 0.408 mol), MeOH (210 mL) and THF (420 mL). The reaction mixture was heated to 60° C. for 2 h where HPLC indicated 2.2% 4-bromothiophenol remained. To the reaction mixture was charged cis-4-(bromomethyl)-1-methylcyclohexan-1-ol Intermediate 49 (0.86 g, 4.15 mmol) and the reaction was stirred for a further 30 minutes at 60° C. HPLC indicated 0.3% 4-bromothiophenol remained. The reaction mixture was cooled to room temperature, filtered and the filtrate concentrated in vacuo. The residue was partitioned between EtOAc (390 mL) and water (390 mL), the layers were separated, and the aqueous layer back extracted with EtOAc (195 mL). The organics were combined, dried over MgSO₄ and concentrated in vacuo. This provided the title compound Intermediate 50 (57.3 g, crude) in a purity of 99.4% by HPLC and >95% by NMR.

Analytical Data:

HPLC: Retention time: 3.5 min.; Purity: 99.4%.

$^1$H NMR (400 MHz, CDCl$_3$) δ (ppm): 7.39-7.35 (m, 2H), 7.17-7.13 (m, 2H), 2.81 (d, J=6.1 Hz, 2H), 1.75-1.70 (m, 2H), 1.67-1.62 (m, 2H), 1.49-1.40 (m, 1H), 1.39-1.33 (m, 4H), 1.20 (s, 3H), 1.13 (s, 1H).

Intermediate 51 cis-4-[(4-Bromobenzenesulfonyl)methyl]-1-methyl-cyclohexan-1-ol

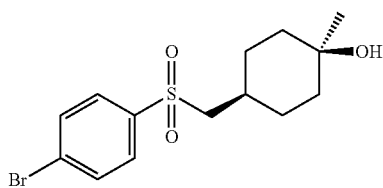 [SMILES: C[C@]1(O)CC[C@@H](CS(=O)(=O)c2ccc(Br)cc2)CC1]

To a 2 L flange flask under N₂ was charged cis-4-{[(4-bromophenyl)sulfanyl]methyl}-1-methylcyclohexan-1-ol Intermediate 50 (56.0 g, 0.178 mol) and DCM (560 mL). The reaction mixture was cooled to 0° C. and meta-chloroperbenzoic acid (77%) (79.6 g, 0.355 mol) was charged in portions at 0-5° C. over 15 minutes. The reaction mixture was warmed to room temperature and stirred for 8 h. HPLC analysis indicated 0.2% cis-4-{[(4-bromophenyl)sulfanyl]methyl}-1-methylcyclohexan-1-ol Intermediate 50 remained. The reaction mixture was filtered, and the filtrate was washed with saturated NaHCO₃ solution (560 mL+280 mL) and saturated Na₂S₂O₃ (560 mL+280 mL). The organics were separated, dried over MgSO₄ and concentrated in vacuo. This provided the title compound Intermediate 51 (52.4 g, crude) in a purity of 97.0% by HPLC and >95% by NMR.

Analytical Data:

HPLC: Retention time: 2.9 min.; Purity: 97.0%.

$^1$H NMR (400 MHz, CDCl$_3$) δ (ppm): 7.78-7.74 (m, 2H), 7.71-7.67 (m, 2H), 2.99 (d, J=6.1 Hz, 2H), 1.98-1.85 (m, 1H), 1.76-1.68 (m, 2H), 1.64-1.58 (m, 2H), 1.52-1.33 (m, 4H), 1.19 (s, 3H), 1.10 (br s, 1H).

Intermediate 52

1-Methyl-cis-4-{[4-(4,4,5,5-tetramethyl-1,3,2-dioxaborolan-2-yl)benzenesulfonyl]methyl}cyclohexan-1-ol

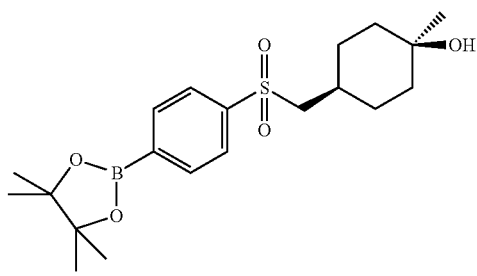 [SMILES: CC1(C)OB(c2ccc(S(=O)(=O)C[C@H]3CC[C@@](C)(O)CC3)cc2)OC1(C)C]

To a 1 L 3-neck flask under N₂ was charged cis-4-[(4-bromobenzenesulfonyl)methyl]-1-methylcyclohexan-1-ol Intermediate 51 (46.5 g, 0.134 mol), potassium acetate (39.4 g, 0.402 mol), bis(pinacolato)diborane (44.2 g, 0.174 mol) and dioxane (460 mL). The flask was sealed and degassed by purging with nitrogen. To the reaction mixture was charged bis(triphenylphosphine)palladium(II) dichloride (1.42 g, 2.02 mmol). The flask was sealed and degassed by purging with nitrogen. The reaction mixture was heated to reflux (100° C.) for 2 h where HPLC indicated 2.2% cis-4-[(4-bromobenzenesulfonyl)methyl]-1-methylcyclohexan-1-ol Intermediate 51 remained. The reaction mixture was cooled to room temperature and filtered over celite. The filtrate was concentrated in vacuo to provide the title compound Intermediate 52 (98.2 g, 51.0 g active, crude) in a purity of 73.3% by HPLC and 52% by NMR assay.

Analytical Data:

HPLC: Retention time: 1.9 min.; Purity: 73.3%.

Synthesis Compound 25

2-Fluoro-4'-{[cis-4-hydroxy-4-methylcyclohexyl]methanesulfonyl}-[1,1'-biphenyl]-4-carbonitrile

CHMSA-01-A

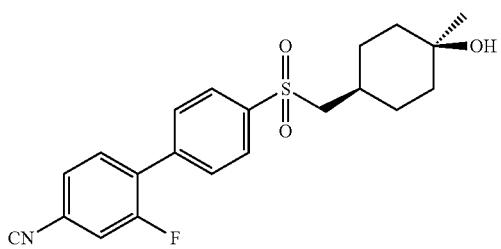

To a 1 L 3-neck flask under N₂ was charged 1-methyl-cis-4-{[4-(4,4,5,5-tetramethyl-1,3,2-dioxaborolan-2-yl)benzenesulfonyl]methyl}cyclohexan-1-ol Intermediate 52 (51.0 g, 0.129 mol), sodium carbonate (41.1 g, 0.388 mol), 4-bromo-3-fluorobenzonitrile (28.8 g, 0.144 mol), dioxane (500 mL) and water (153 mL). The flask was sealed and degassed by purging with nitrogen. Tetrakis(triphenylphosphine)palladium(0) (14.95 g, 0.013 mol) was charged to the reaction mixture. The flask was sealed and degassed by purging with nitrogen. The reaction mixture was heated to reflux (~90° C.) for 11 h where HPLC indicated 0.9% 1-methyl-cis-4-{[4-(4,4,5,5-tetramethyl-1,3,2-dioxaborolan-2-yl)benzenesulfonyl]methyl}cyclohexan-1-ol Intermediate 52 remained. The reaction mixture was cooled to room temperature, filtered and concentrated in vacuo. The residue was taken up in EtOAc (510 mL) before being washed with water (510 mL×2). The aqueous layer was separated and back extracted with EtOAc (510 mL). The organics were combined, dried over MgSO$_4$ and concentrated in vacuo. This provided 75.5 g of crude material which was purified on silica (2.55 kg) eluting with 40-60% EtOAc/heptane. The clean fractions containing product were concentrated in vacuo to provide the title compound Synthesis Compound 25 (26.1 g, 52%) in a purity of 97.9% by HPLC and >95% by NMR.

Analytical Data:
HPLC: Retention time: 3.1 min.; Purity: 97.9%.
LCMS (ESI): m/z=370.10 [M−H$_2$O+1]$^+$.
$^1$H NMR (400 MHz, DMSO-d$_6$) δ (ppm): 8.05-7.99 (m, 3H), 7.87-7.77 (m, 4H), 3.93 (s, 1H), 3.25 (d, J=6.1 Hz, 2H), 1.77-1.63 (m, 1H), 1.56-1.48 (m, 2H), 1.48-1.33 (m, 4H), 1.23-1.12 (m, 2H), 1.01 (s, 3H).

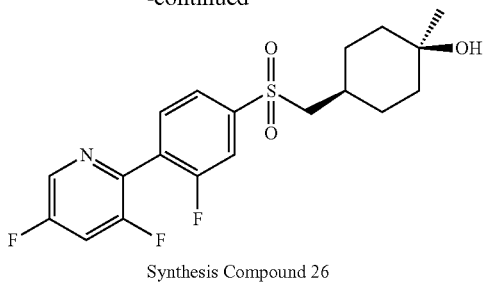

Synthesis Compound 26

Intermediate 53 cis-4-{[(4-Bromo-3-fluorophenyl)sulfanyl]methyl}-1-methylcyclohexan-1-ol

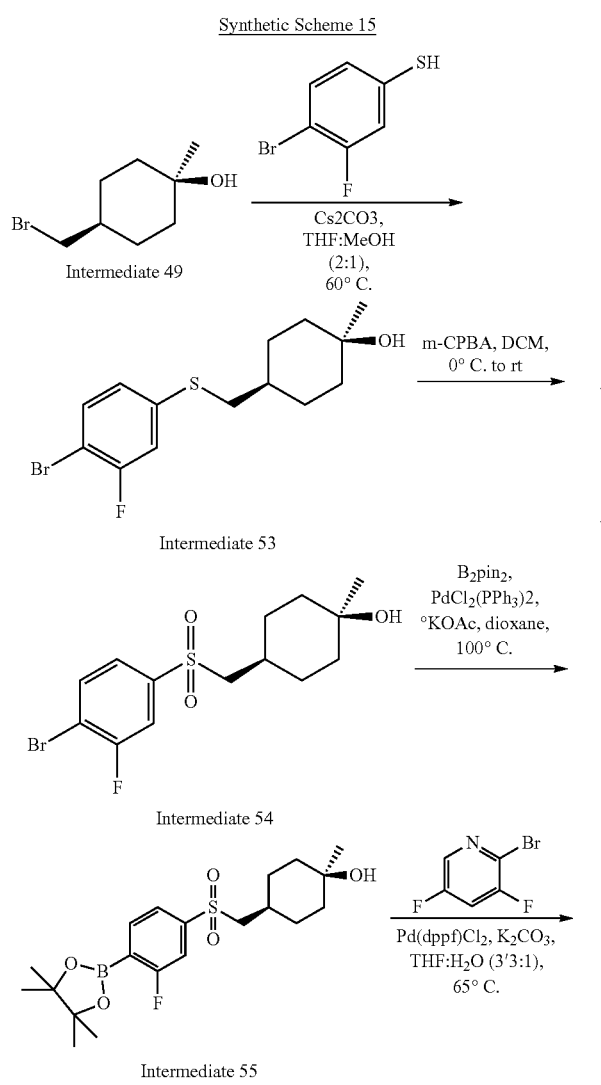

To a 1 L 3-neck flask under N$_2$ was charged cis-4-(bromomethyl)-1-methylcyclohexan-1-ol Intermediate 49 (35.5 g, 0.171 mol), 4-bromo-3-fluoro-benzenethiol (35.5 g, 0.171 mol), cesium carbonate (111.7 g, 0.343 mol), MeOH (142 mL) and THF (284 mL). The reaction mixture was heated to 60° C. for 2 h where HPLC indicated 3.5% 4-bromo-3-fluoro-benzenethiol remained. To the reaction mixture was charged cis-4-(bromomethyl)-1-methylcyclohexan-1-ol Intermediate 49 (2.23 g, 10.77 mmol) and the reaction was stirred for a further 30 minutes at 60° C. HPLC indicated 0.3% 4-bromo-3-fluoro-benzenethiol remained. The reaction mixture was cooled to room temperature, filtered and the filtrate concentrated in vacuo. The residue was partitioned between EtOAc (360 mL) and water (360 mL), the layers were separated, and the aqueous layer back extracted with EtOAc (180 mL). The organics were combined, dried over MgSO$_4$ and concentrated in vacuo. This provided the title compound Intermediate 53 (54.9 g, crude) in a purity of 97.6% by HPLC and >95% by NMR.

Analytical Data:
HPLC: Retention time: 3.6 min.; Purity: 97.6%.
$^1$H NMR (400 MHz, CDCl$_3$) δ (ppm): 7.41-7.36 (m, 1H), 7.02 (dd, J=2.1, 9.5 Hz, 1H), 6.94-6.90 (m, 1H), 2.82 (d, J=6.7 Hz, 2H), 1.74-1.69 (m, 2H), 1.68-1.62 (m, 2H), 1.50-1.42 (m, 1H), 1.41-1.33 (m, 4H), 1.20 (s, 3H). The exchangeable proton of this molecule does not appear in this NMR spectrum.

Intermediate 54 cis-4-[(4-Bromo-3-fluorobenzenesulfonyl)methyl]-1-methylcyclohexan-1-ol

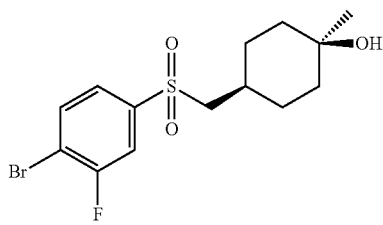 [SMILES: C[C@]1(O)CC[C@@H](CS(=O)(=O)c2ccc(Br)c(F)c2)CC1]

To a 2 L flange flask under $N_2$ was charged cis-4-{[(4-bromo-3-fluorophenyl)sulfanyl]methyl}-1-methylcyclohexan-1-ol Intermediate 53 (54.0 g, 0.162 mol) and DCM (540 mL). The reaction mixture was cooled to 0° C. and meta-chloroperbenzoic acid (77%) (79.9 g, 0.356 mol) was charged in portions at 0-5° C. over 15 minutes. The reaction mixture was warmed to room temperature and stirred for 8 h. HPLC analysis indicated 0.9% cis-4-{[(4-bromo-3-fluorophenyl)sulfanyl]methyl}-1-methylcyclohexan-1-ol Intermediate 53 remained. The reaction mixture was filtered, and the filtrate was washed with saturated $NaHCO_3$ solution (540 mL+270 mL) and saturated $Na_2S_2O_3$ solution (540 mL+270 mL). The organics were separated, dried over $MgSO_4$ and concentrated in vacuo. This provided the title compound Intermediate 54 (50.1 g, crude) in a purity of 98.2% by HPLC and >95% by NMR.

Analytical Data:

HPLC: Retention time: 3.0 min.; Purity: 98.2%.

$^1$H NMR (400 MHz, $CDCl_3$) δ (ppm): 7.77-7.72 (m, 1H), 7.64-7.60 (m, 1H), 7.57-7.53 (m, 1H), 2.99 (d, J=6.7 Hz, 2H), 1.94-1.83 (m, 1H), 1.72-1.65 (m, 2H), 1.63-1.56 (m, 2H), 1.50-1.30 (m, 5H), 1.16 (s, 3H).

Intermediate 55 cis-4-{[3-Fluoro-4-(4,4,5,5-tetramethyl-1,3,2-dioxaborolan-2-yl)benzenesulfonyl]methyl}-1-methylcyclohexan-1-ol

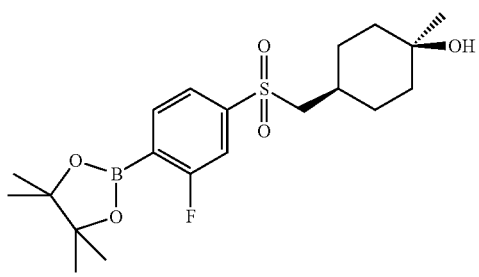 [SMILES: CC1(C)OB(c2ccc(S(=O)(=O)C[C@H]3CC[C@@](C)(O)CC3)cc2F)OC1(C)C]

To a 1 L 3-neck flask under $N_2$ was charged cis-4-[(4-bromo-3-fluorobenzenesulfonyl)methyl]-1-methylcyclohexan-1-ol Intermediate 54 (45.0 g, 0.123 mol), potassium acetate (36.3 g, 0.370 mol), bis(pinacolato)diborane (40.7 g, 0.160 mol) and dioxane (450 mL). The flask was sealed and degassed by purging with nitrogen. To the reaction mixture was charged bis(triphenylphosphine)palladium(II) dichloride (1.3 g, 1.85 mmol). The flask was sealed and degassed by purging with nitrogen. The reaction mixture was heated to reflux (100 QC) for 2 h where HPLC indicated 3.3% cis-4-[(4-bromo-3-fluorobenzenesulfonyl)methyl]-1-methylcyclohexan-1-ol Intermediate 54 remained. To the reaction mixture was charged bis(triphenylphosphine)palladium(II) dichloride (0.4 g, 0.57 mmol) before stirring at reflux (100° C.) for 45 minutes where there was no significant change in HPLC profile. The reaction mixture was cooled to room temperature and filtered over celite. The filtrate was concentrated in vacuo to provide the title compound Intermediate 55 (94.5 g, 35.9 g active, crude) in a purity of 90.0% by HPLC and 38% by NMR assay.

Analytical Data: HPLC: Retention time: 1.9 min.; Purity: 90.0%.

Synthesis Compound 26 cis-4-{[4-(3,5-Difluoropyridin-2-yl)-3-fluorobenzenesulfonyl]methyl}-1-methylcyclohexan-1-ol

CHMSA-03-A

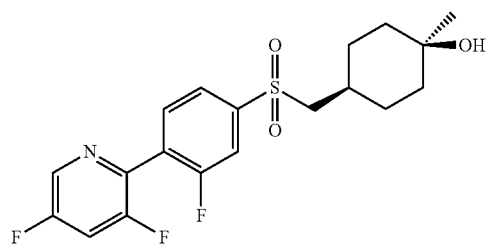 [SMILES: C[C@]1(O)CC[C@@H](CS(=O)(=O)c2ccc(-c3ncc(F)cc3F)c(F)c2)CC1]

To a 500 mL 3-neck flask under $N_2$ was charged cis-4-{[3-fluoro-4-(4,4,5,5-tetramethyl-1,3,2-dioxaborolan-2-yl)benzenesulfonyl]methyl}-1-methylcyclohexan-1-ol Intermediate 55 (25.9 g, 0.063 mol), 2-bromo-3,5-difluoropyridine (12.8 g, 0.066 mol), potassium carbonate (26.1 g, 0.189 mol), THF (260 mL) and water (78 mL). The flask was sealed and degassed by purging with nitrogen. To the reaction mixture was charged (1,1'-bis(diphenylphosphino)ferrocene)dichloropalladium(II) (4.6 g, 6.3 mmol). The flask was sealed and degassed by purging with nitrogen. The reaction mixture was heated to reflux (65° C.) for 1 h where HPLC indicated 0.9% cis-4-{[3-fluoro-4-(4,4,5,5-tetramethyl-1,3,2-dioxaborolan-2-yl)benzenesulfonyl]methyl}-1-methylcyclohexan-1-ol Intermediate 55 remained and no 2-bromo-3,5-difluoropyridine was observed. The reaction mixture was cooled to room temperature and filtered through celite. The filtrate was concentrated in vacuo to provide 70.3 g of crude material. This crude material was combined with the crude material from another similar reaction using 2 g of cis-4-{[3-fluoro-4-(4,4,5,5-tetramethyl-1,3,2-dioxaborolan-2-yl)benzenesulfonyl]methyl}-1-methylcyclohexan-1-ol Intermediate 55. The combined crude materials were purified on silica (50 eq) eluting with 1% MeOH/DCM to provide 20.1 g of the title compound Synthesis Compound 26 in a purity of 97.0% by HPLC but NMR of the isolated material showed some cyclohexane related impurity and cis-4-{[3-fluoro-4-(4,4,5,5-tetramethyl-1,3,2-dioxaborolan-2-yl)benzenesulfonyl]methyl}-1-methylcyclohexan-1-ol Intermediate 55 remained. The material was combined with 6 g of crude material isolated from the mixed fractions and purified a second time on silica (50 eq) eluting with 40-50% EtOAc/Heptane. The clean fractions were concentrated in vacuo to provide the title compound Synthesis Compound 26 (10.3 g, 38%) in a purity of 98.9% by HPLC and >95% by NMR.

Analytical Data:
HPLC: Retention time: 2.9 min.; Purity: 98.9%.
LCMS (ESI): m/z=382.2 [M–H$_2$O+1]$^+$.
$^1$H NMR (400 MHz, DMSO-d$_6$) δ (ppm): 8.70 (d, J=2.4 Hz, 1H), 8.19-8.12 (m, 1H), 7.95-7.91 (m, 1H), 7.90-7.83 (m, 2H), 3.94 (s, 1H), 3.34 (d, J=6.7 Hz, 2H), 1.78-1.65 (m, 1H), 1.56-1.49 (m, 2H), 1.48-1.34 (m, 4H), 1.24-1.14 (m, 2H), 1.02 (s, 3H).

Biological Studies

Biological Study 1

Monocyte ATP Production Assay

In vitro potency of test compounds was determined by incubation with Thp1 human monocytic cells and subsequent determination of Adenosine TriPhosphate (ATP) levels using firefly luciferase.

ATP is present in all metabolically active cells. When cells lose integrity, their ability to synthesise ATP is rapidly lost. ATP concentration is hence reduced when cells undergo necrosis or apoptosis and its concentrations are commonly used as a marker of cell viability or of cellular proliferation. See, e.g., Kang et al., 2015; Jiang et al., 2013. Levels of ATP can be monitored using a system based on firefly (Photinus pyralis) luciferase (see, e.g., Auld et al., 2009) using commercially available kits. A system known as ATPlite™ was using to measure effects of the test compounds on cellular viability in vitro. This one-step assay system is an adenosine triphosphate (ATP) monitoring system based on the production of light caused by the reaction of ATP from the cells with added luciferase and D-luciferin, as illustrated in the reaction scheme below:

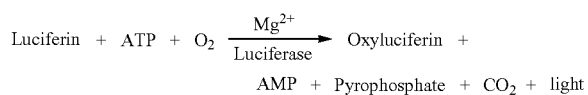

Luciferin + ATP + O$_2$ $\xrightarrow[\text{Luciferase}]{\text{Mg}^{2+}}$ Oxyluciferin + AMP + Pyrophosphate + CO$_2$ + light The emitted light is proportional to the ATP concentration.

Thp1 cells were plated at 112500 cells per well in 125 μL RPMI-1640 (no glucose) with 1% FBS in 96-well plates. Test compounds were prepared as 100 mM solutions in DMSO. These stock solutions were diluted in DMSO and then diluted 1000× in culture medium (RPMI) before being added directly to the wells so as to give the desired final compound concentration. After a 24 hour incubation at 37° C./5% CO$_2$, ATPLite™ (Perkin Elmer) was added to each well (1:10 v/v, 10 μL). The plate was then incubated at room temperature for 5 minutes and the emitted light was quantified on Viewlux with a measurement time of 0.3 seconds and binning 4×4.

The average results for each test compound were expressed as a percent (%) of the average control value reflecting cell viability. The average values across the concentrations tested were then plotted and the IC$_{50}$ for was calculated by fitting the data to a 4-parameter IC$_{50}$ equation using software from Graf it (Erithacus Software). Each experiment was repeated twice and the data are presented as the mean IC$_{50}$ from both experiments.

The results are summarised in the following table.

TABLE 3

| Thp1 Monocyte ATP Assay | |
|---|---|
| Compound | IC$_{50}$ (μM) [1] |
| HMC-C-01-A | 0.63 |
| ABD899 | 0.2 |
| ABD900 | 1.1 |
| CHMSA-01-A | 0.7 |
| CHMSA-01-B | 4.4 |
| CHMSA-02-A | 0.1 |
| CHMSA-02-B | 0.3 |
| CHMSA-03-A | 0.7 |
| CHMSA-03-B | 5.4 |
| CHMSA-04-A | 0.98 |
| CHMSA-04-B | 2.4 |
| CHMSA-05-A | 0.8 |
| CHMSA-05-B | 2.7 |
| CHMSA-06-A | 1.8 |
| CHMSA-06-B | 4.5 |
| CHMSA-07-A | 1.3 |
| CHMSA-07-B | 2.5 |
| CHMSA-08-A | 0.2 |
| CHMSA-08-B | 0.4 |
| CHMSA-09-A | 0.3 |
| CHMSA-09-B | 0.5 |
| CHMSA-10-A | 1.63 |
| CHMSA-10-B | 1.96 |
| CHMSA-11-A | 0.5 |
| CHMSA-11-B | 0.8 |
| CHMSA-12-A | 1.8 |
| CHMSA-12-B | 3.2 |

[1] Obtained using a 9-point concentration range from 10 μM to 10 nM with n = 2 replicates per concentration. Data are the mean from 2 independent experiments.

The data demonstrate that many of the CHMSA compounds described herein, and particularly compounds CHMSA-02-A, CHMSA-02-B, CHMSA-08-A, and CHMSA-09-A show excellent potency in the Thp1 monocytic ATP assay, as well as no loss of potency, as compared to the reference compounds.

Biological Study 2

Human and Rat Hepatocyte Study

Metabolic stability of test compounds was measured by determination of the rate of disappearance of the compound when incubated in the presence of rat or human hepatocytes, a primary source of the most important enzymes (cytochrome P450s) involved in drug metabolism. Study of drug stability in the presence of primary hepatocytes is accepted as a valuable model permitting rapid prediction of in vivo drug stability.

Rat or human hepatocytes were obtained from a commercial source and viability was assessed using a trypan blue solution prior to use. Test compounds (final concentration 1 μM, 0.1% DMSO, 0.9% acetonitrile) or a marker (diclofenac or diltiazem, final assay concentration 1 μM, 0.1% DMSO, 0.9% acetonitrile) were incubated with pooled hepatocytes for a 60 minute period and samples removed at up to 6 time points and analysed by LC-MS/MS for the presence/amount of test compounds.

Each compound was incubated for 0, 5, 15, 30, 45, or 60 minutes. The reactions were stopped by the addition of methanol containing an internal standard (1 μM Tolbutamide) at the appropriate time points, mixed and placed at –20° C. for ≥1 hour to quench and allow protein to precipitate. All samples were centrifuged (2500×g, 20 minutes, 4° C.). The aliquots were analysed using LC-MS/MS. Reactions were performed in duplicate at 37° C.

Data were processed, and the results plotted as ln(concentration) vs. time. The elimination rate constant (slope of the regression line, k) was calculated using the following formula, where C(t) is the concentration at time t and C(0) is the starting concentration:

$$k = \frac{\ln C(0) - \ln C(t)}{t}$$

The half-life ($t_{1/2}$) was calculated using the following formula:

$$t_{1/2} = \frac{\ln 2}{k}$$

The intrinsic clearance ($CI_{int}$) was calculated using the following formula, where [cell] is the hepatocyte concentration in the assay:

$$CI_{int} = \frac{k}{[cell]}$$

The data are summarised in the following table.

TABLE 4

Hepatocyte Stability

| Compound | Rat $t_{1/2}$ (min) | Rat $CI_{int}$ (μL/min/ million cells) | Human $t_{1/2}$ (min) | Human $CI_{int}$ (uL/min/ million cells) |
|---|---|---|---|---|
| HMC-C-01-A | 7 | 188 | 154 | 7.6 |
| ABD599 | | 112 | 22 | |
| ABD899 | 24 | 57 | 149 | 9 |
| ABD900 | 17.9 | 79 | 220 | 6.3 |
| CHMSA-01-A | 106 | 12.4 | 354.9 | 3.7 |
| CHMSA-01-B | | | 297.1 | 4.5 |
| CHMSA-02-A | 13 | 102.3 | >412.2 | <3.3 |
| CHMSA-02-B | | | 122.1 | 10.8 |
| CHMSA-03-A | 91.2 | 14.4 | >460.0 | <3.0 |
| CHMSA-03-B | | | >460.0 | <3.0 |
| CHMSA-04-A | 47.1 | 37.4 | 27.5 | 40.6 |
| CHMSA-04-B | 31.4 | 51.3 | >460 | <3.0 |
| CHMSA-05-A | | | 396.8 | 3.3 |
| CHMSA-05-B | | | 227.4 | 6.5 |
| CHMSA-08-A | | | 73.2 | 18.0 |
| CHMSA-08-B | | | 138.0 | 9.8 |
| CHMSA-09-A | | | 112.3 | 12.1 |
| CHMSA-09-B | | | 25.0 | 52.9 |
| CHMSA-10-A | 10.7 | 149.2 | 37 | 30.8 |
| CHMSA-10-B | 4.8 | 336.2 | 195.1 | 5.8 |
| CHMSA-11-A | | | 172.3 | 7.8 |
| CHMSA-11-B | | | 99.8 | 13.3 |
| CHMSA-12-A | | | >436.5 | <3.1 |
| CHMSA-12-B | | | >441.5 | <3.1 |

The data demonstrate that many of the CHMSA compounds described herein show metabolic stability greater than that of the reference compounds, with CHMSA-02-A, CHMSA-03-A, CHMSA-03-B, CHMSA-12-A, and CHMSA-12-B showing exceptionally good stability.

Biological Study 3

Aqueous Solubility

Aqueous solubility was measured by equilibration of compounds with fasted state simulated intestinal fluid (FaSSIF) and quantified spectrophotometrically.

FaSSIF was prepared as described below:

Preparation of blank FaSSIF: 0.21 g of sodium hydroxide (NaOH) pellets, 1.97 g of dihydrogen sodium phosphate ($NaH_2PO_4 \cdot 2H_2O$) and 3.09 g of sodium chloride (NaCl) were dissolved in 400 mL of deionised water. The pH was adjusted to 6.5 using 1 M hydrochloric acid and further deionised water added to a final volume of 500 mL.

Preparation of FaSSIF: 0.056 g of SIF Powder (containing sodium taurocholate and lecithin) (Phares AG) was dissolved in 25 mL of blank FaSSIF and stirred until the powder was completely dissolved. The solution was allowed to stand for 2 hours during which it became opalescent; it was used within 24 hours. The final solution composition was characterised as follows:

Sodium taurocholate: 3 mM
Lecithin: 0.75 mM
Osmolarity: 270±10 mOsmol
pH: 6.5

Aqueous solubility was determined by spiking a known concentration of test compound (dissolved in DMSO) into FaSSIF followed by incubation for 16 hours. The optical density was measured at the end of the incubation period for test compounds and a reference used to determine solubility. In brief, two samples were prepared for each determination: a reference sample consisting of a stock solution of test compound in DMSO diluted in system solution (a phosphate free, low absorption buffer) and propanol; and a test sample (prepared in triplicate) consisting of 0.5 mL FaSSIF spiked with test compound at 0.2 mM. Each sample was incubated at room temperature for 16 hours with constant shaking at 250 rpm. At the end of the incubation period, 0.3 mL of each sample was filtered through a pION filter plate (PION, Woburn MA), diluted 1:1 with propanol and scanned using UV spectrophotometry at $\lambda_{max}$ (190-400 nM) using a Spectra Max Plus—Version 2.1000 (Molecular Devices, Sunnyvale, CA), with pSOL Explorer solubility determination software (pION, Woburn, MA).

FaSSIF solubility was calculated using the following formula:

$$FaSSIF\ \text{Solubility} \frac{mg}{mL} = \frac{\left[\frac{150}{75}\right] * \left[\frac{OD\ of\ sample}{OD\ of\ reference}\right] * Cr * \text{molecular weight}}{10^6}$$

wherein:
"OD" is the optical density;
"Cr" is the concentration of the reference (33.4 μM); and
"molecular weight" is for the test compound (e.g., 381.44 for ABD735).

The data are summarised in the following table.

TABLE 5

FaSSIF Solubility

| Compound | Solubility (mg/mL) [1] | Solubility (mg/mL) [2] |
|---|---|---|
| HMC-C-01-A | 0.06 | |
| ABD599 | 0.03 | |
| ABD735 | 0.02 | |
| ABD836 | 0.03 | |
| ABD899 | 0.06 | 0.13 |
| ABD900 | | 0.12 |
| REF001 | 0.05 | |
| CHMSA-01-A | 0.01 | |
| CHMSA-02-A | 0.02 | |

TABLE 5-continued

FaSSIF Solubility

| Compound | Solubility (mg/mL) [1] | Solubility (mg/mL) [2] |
|---|---|---|
| CHMSA-03-A | 0.07 | |
| CHMSA-04-A | >0.07 | |
| CHMSA-04-B | 0.04 | |

[1] Three replicates were run per study at pH 6.5.
[2] Two replicates were run per study at pH 6.8.

The data demonstrate that the CHMSA compounds described herein show solubility equivalent to that of the reference compounds.

Biological Study 4

Metabolite Identification

The formation of metabolites in rats was assessed to determine the propensity of the compounds to form a biaryl metabolite.

The corresponding sulfonamide compounds (for example, reference compound HMC-C-01-A) give rise to a sulphonamide metabolite which is persistent and has a long half-life. In addition, the biaryl sulphonamide metabolite acts as an inducer of metabolism in rats, which may complicate the assessment of toxicity in rodents. Therefore, the lower the propensity to form a biaryl sulphonamide metabolite, the greater the potential suitability of the compound for development for human use.

Plasma samples from Han Wistar rats, aged 8-12 weeks, were collected from animals dosed with test compound. Test compounds at a dose of 1 mg/kg were administered intravenously as a solution in 5% NMP, 5% Solutol HS, and 90% normal saline. Animals were given free access to food throughout the study. Blood samples were taken under light isoflurane anaesthesia at 12 time points following an intravenous dose (0.033, 0.1, 0.167, 0.25, 0.5, 1, 2, 4, 6, 8, 12, and 24 hours). The blood samples were collected from a set of three rats at each time point in labelled micro centrifuge tube containing $K_2$EDTA as anticoagulant. Plasma samples were separated by centrifugation of whole blood.

All samples were processed for analysis by protein precipitation using acetonitrile and analysed with a fit-for-purpose LC-MS/MS method.

At the completion of the study, the results were expressed as detection of the metabolite and time course of formation.

FIG. 1 is a graph of plasma concentration (ng/mL) versus time post-dose (hours) for reference compound HMC-C-01-A (filled circles) and the corresponding biaryl sulfonamide metabolite (MET-001) (open circles), as obtained using the methods described herein. The metabolite was formed in large quantities and accumulated over time.

TABLE 6

Reference Compound HMC-C-01-A and Biaryl Sulfonamide Metabolite (MET-001)

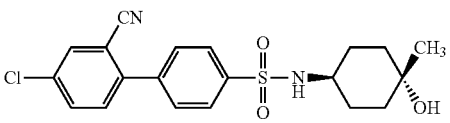 [SMILES: C[C@]1(O)CC[C@H](NS(=O)(=O)c2ccc(-c3ccc(Cl)cc3C#N)cc2)CC1]

TABLE 6-continued

Reference Compound HMC-C-01-A and Biaryl Sulfonamide Metabolite (MET-001)

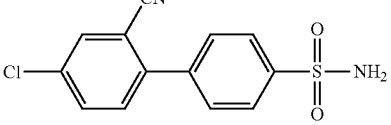

Figure 2:
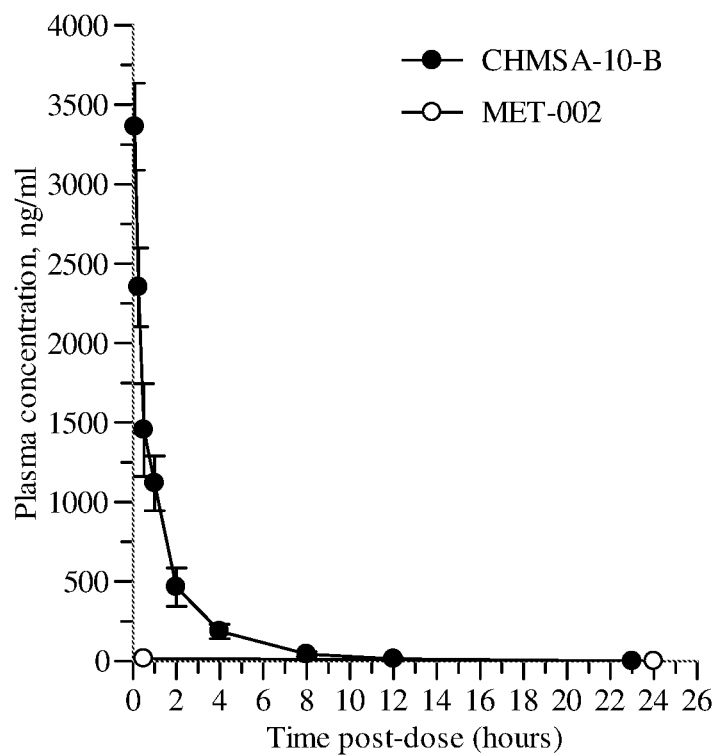
FIG. 2 is a graph of plasma concentration (ng/mL) versus time post-dose (hours) for compound CHMSA-10-B (filled circles) and the corresponding biaryl sulfonic acid metabolite (MET-002) (open circles), as obtained using the methods described herein. The metabolite was detected only transiently, 0.5 hours after administration.

FIG. 2 is a graph of plasma concentration (ng/mL) versus time post-dose (hours) for compound CHMSA-10-B (filled circles) and the corresponding biaryl sulfonic acid metabolite (MET-002) (open circles), as obtained using the methods described herein. The metabolite was detected only transiently, 0.5 hours after administration.

TABLE 7

CHMSA-10-B and Biaryl Sulfonic Acid Metabolite (MET-002)

CHMSA-10-B
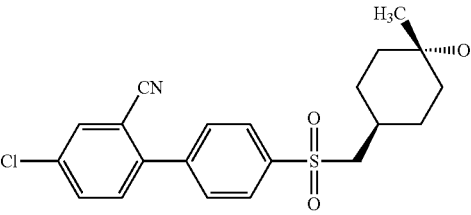

MET-002
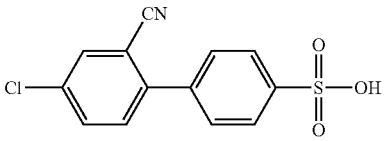 [SMILES: N#Cc1cc(Cl)ccc1-c1ccc(S(=O)(=O)O)cc1]

Whereas the reference compound HMC-C-01-A gave rise to the biaryl sulphonamide metabolite (MET-001) in large quantities (which accumulated over time), compound CHMSA-10-B did not produce any biaryl sulphonamide metabolite (MET-001), and the biaryl sulphonic acid metabolite (MET-002) was only transiently detected.

The data therefore demonstrate that the CHMSA compounds described herein show greatly increased potential suitability for development for human use, as compared to the reference compound (HMC-C-01-A).

Biological Study 5 hERG Ion Channel Assay

Inhibition of the human Ether-á-go-go-Related Gene (hERG) ion channel mediates the repolarizing IKr current in the cardiac action potential, thereby indicating that it contributes to the electrical activity that coordinates the beating of the heart. When the ability of hERG to conduct electrical current across the cell membrane is inhibited or compromised, it can result in a potentially fatal disorder called long QT syndrome. This association between hERG and long QT syndrome has made hERG inhibition an important anti-target that must be avoided during drug development.

The activity of the compounds against the hERG ion channel was tested using two approaches: a binding assay and an automated patch-clamp, Q-patch method using stably transfected Chinese Hamster Ovary cells (hERG-CHO). hERG-CHO cells were cultured in F-12 Kaighn's Nutrient Mixture medium (Invitrogen)+10% FBS at 37° C. for 1-3 days. Cells were kept at 30° C. for 24 to 48 hours prior to patch clamping in order to increase the hERG current amplitude. Subsequently, the cells were harvested by trypsinisation, and kept in Serum Free Medium (SFM) in the Q-patch cell preparation state for up to 6 hours at room temperature before being washed and re-suspended in extracellular solution and applied to the patch clamp sites for data recording.

Patch-clamp voltage protocol: After whole cell configuration was achieved, the cell was held at −80 mV. A 50 millisecond pulse to −40 mV was delivered to measure the leaking current, which was subtracted from the tail current on-line. Then the cell was depolarized to +20 mV for 2 seconds, followed by a one second pulse to −40 mV to reveal hERG tail current. This paradigm was delivered once every 5 seconds to monitor the current amplitude.

Extracellular solution: 137 mM NaCl, 4 mM KCl, 1.8 mM $CaCl_2$), 1 mM $MgCl_2$, 10 mM D(+)-glucose, 10 mM HEPES buffer (pH adjusted to 7.4 with NaOH).

After the whole cell configuration was achieved, the extracellular solution (control) was applied first and the cell was stabilized for 2 minutes in extracellular solution. The test compound was then applied from low concentrations to high concentrations cumulatively. The cell was incubated with each test concentration for 5 minutes. During each incubation, the cell was repetitively stimulated using the voltage protocol described above, and the tail current amplitude was continuously monitored.

Acceptance Criteria:
(1) Peak tail current >100 pA in control.
(2) Initial run-down <30% and the run-down stops before first application of the test compound.
(3) Leak currents <50% of the control peak tail currents at any time.
(4) rs<20 MΩ throughout the experiment.

The degree of inhibition (%) was obtained by measuring the tail current amplitude, induced by a one second test pulse to −40 mV after a two second pulse to +20 mV, before and after incubation with the test compound. The difference in current was normalized to control and multiplied by 100 in order to obtain the percent inhibition.

Concentration (log) response curves were fitted to a logistic equation (three parameters assuming complete block of the current at very high test compound concentrations) to generate estimates of the 50% inhibitory concentration ($IC_{50}$). The concentration-response relationship of each compound was constructed from the percentage reductions of current amplitude by sequential concentrations.

The results are summarised in the following table.

TABLE 8 hERG Ion Channel Activity

| Compound | $IC_{50}$ (µM) [1] |
|---|---|
| ABD599 | 4.9 |
| ABD899 | 2.9 |
| HMC-C-01-A | 19.3 |
| CHMSA-01-A | 24 |
| CHMSA-02-A | >100 |
| CHMSA-03-A | >100 |

[1] $IC_{50}$'s were calculated using a four parameter logistic equation calculated automatically in Grafit version 6.0.12 (Erithacus Software Ltd., by Dr Robin Leatherbarrow).

The data demonstrate that the CHMSA compounds described herein have cardiac safety properties required for an orally active drug, and have safety advantages as compared to the reference compounds, such as ABD599 and ABD899, with CHMSA-02-A and CHMSA-03-A showing a particularly positive profile.

Biological Study 6

Human Cytochrome P450 Inhibition Assay

Inhibition of cytochrome P450 (CYP450) enzymes is one of the major reasons for drug-drug interactions in clinical use, and can complicate, or stop the development of a new drug.

The ability of test compounds to inhibit five of the most relevant cytochrome P450 enzymes was measured by determination of the activity of cytochrome P450 enzymes in recombinant cytochrome preparations, called Bactosomes (Cypex Ltd, Dundee, Scotland UK DD2 1NH), in the presence of a specific probe substrate. Bactosomes are a highly efficient and cost-effective source of recombinant CYP450s which have a higher specific activity of enzyme compared to other sources, such as liver microsomes. If a compound inhibits enzyme activity, the rate of disappearance of the probe substrate is reduced. The following CYP450 isoforms were assayed: CYP1A2, CYP2C9, CYP2C19, CYP2D6, and CYP3A4. The study of CYP450 inhibition potential in Bactosomes is accepted as a valuable model permitting rapid prediction of potential drug-drug interactions in vivo (see, e.g., Weaver et al., 2003).

Bactosomes were obtained from a commercial source (Cypex, Scotland, UK). Test compounds were incubated with Bactosomes at 6 concentrations. Samples were incubated for 10 minutes, after which the reaction was stopped and the samples analysed by LC-MS/MS Multiple Reaction Monitoring (MRM) for the presence/amount of substrate probe.

CYP450 enzymes (final protein 75 pmol/mL for CYP1A2; 12.5 pmol/mL for CYP2C19; and 25 pmol/mL for CYP2C9, 2D6, and 3A4), 0.1 M phosphate buffer pH 7.4, probe and test compound (final concentration 50, 15.8, 5, 1.58, 0.5, and 0.158 µM; diluted from 10 mM stock solution to give a final DMSO concentration of 1%) were pre-incubated at 37° C. for 5 minutes. The reaction was initiated by the addition of 20 µL of 10 mM NADPH in phosphate buffer. The final incubation volume was 200 µL. The following control inhibitors were used for each CYP450 inhibition assay: CYP1A2: α-naphthoflavone; CYP2C9: sulfaphenazole; CYP2C19: tranylcypromine; CYP2D6: quinidine; CYP3A4: ketoconazole.

Each compound was incubated for 10 minutes at 37° C. The reactions were stopped by the addition of methanol (final composition 1:1, aqueous: methanol). The incubation plates were shaken, chilled at 20° C. for 2 hours, and centrifuged at 3500 rpm for 15 minutes at 4° C. to precipitate the protein. The supernatant was then transferred to vials for analysis using MS/MRM, with the conditions shown in the following table.

TABLE 9

MS Conditions

| | |
|---|---|
| HPLC: | Waters Alliance 2790 |
| MS/MS: | Triple Quadrupole Quattro Ultima (Micromass, Manchester) |
| Software: | Analyst 1.5 |
| Ionisation mode: | ESI+ |
| Scan mode: | Multiple reaction monitoring (MRM) |
| Column: | Devosil C30 |

TABLE 9-continued

| MS Conditions | |
| --- | --- |
| Column Temperature (° C.): | 40 |
| Phase A: | 0.1% formic acid in water |
| Phase B: | 0.1% formic acid in methanol |
| Gradient | 97% A (0-0.3 min), 5% A (0.55-1.55 min), 97% A (1.6 min) |
| Stop time | 2.5 min |
| Injection volume (µL): | 30 |
| Flow Rate (mL/min): | 1.2 |

$IC_{50}$ values were determined by linear transformation within Microsoft Excel.

The data are summarised in the following table.

TABLE 10

Human CYP450 inhibition

| | $IC_{50}$ (µM) | | | | |
| --- | --- | --- | --- | --- | --- |
| Compound | CYP1A2 | CYP2C9 | CYP2C19 | CYP2D6 | CYP3A4 |
| ABD899 | >25 | 3.9 | 7.3 | 45.3 | 21.6 |
| HMC-C-01-A | 25 | 21 | >25 | 16.6 | >25 |
| HMC-C-08-A | 27 | 6.7 | 30 | 19 | 29 |
| HMC-C-09-A | 23 | 34 | >50 | >50 | 33 |
| HMC-C-10-B | >16 | 2.4 | 8.5 | >16 | 9.2 |
| HMC-C-11-A | 11 | 2.7 | 5.1 | 9.3 | 12 |
| HMC-N-05-A | 36 | 27 | >50 | >50 | >50 |
| CHMSA-01-A | >50 | 39.4 | >50 | >50 | >50 |
| CHMSA-02-A | >50 | >50 | >50 | >50 | >50 |
| CHMSA-02-B | >10 | >10 | >10 | >10 | >10 |
| CHMSA-03-A | >50 | 14.7 | >50 | >50 | >50 |
| CHMSA-05-A | >50 | 7 | 36.6 | >50 | 26.3 |
| CHMSA-08-B | >10 | >25 | >25 | >10 | ND |
| CHMSA-09-A | >25 | >25 | 25 | >25 | >25 |
| CHMSA-11-A | >10 | >10 | 25 | >10 | ND |

ND: Not determined

The data demonstrate that the CHMSA compounds described herein show reduced drug-drug interaction liability as compared with the reference compounds, with compounds CHMSA-01-A, CHMSA-02-A and CHMSA-03-A showing a particularly good profile.

Biological Study 7

Mouse Collagen-Induced Arthritis

Seven- to eight-week-old male DBA/1j mice were used for all procedures. Animals were housed in groups of 10, and were maintained at 21° C.±2° C. on a 12-hour light/dark cycle with food and water ad libitum. Complete Freund's adjuvant (CFA) was prepared by emulsifying bovine type II collagen at 4 mg/mL with a 4 mg/mL suspension of *Mycobacterium tuberculosis* H37Ra in Incomplete Freund's Adjuvant (IFA) (0.85 mL paraffin oil and 0.15 mL mannide monooleate) in a 1:1 (v/v) ratio. All mice were immunised subcutaneously with 200 µg of bovine type II collagen in CFA. 21 days later, all mice were immunised subcutaneously with 100 µg of bovine type II collagen in IFA. The mice started to develop signs and symptoms of arthritis following the 'booster' immunisation.

For macroscopic assessment of arthritis, the following signs were monitored in each paw of each mouse three times per week and summed to generate the Arthritic Index (AI) (the maximum AI for one animal is 16):
0=no visible effects of arthritis.
1=oedema and/or erythema of 1 digit.
2=oedema and/or erythema of 2 digits.
3=oedema and/or erythema of more than 2 digits.
4=severe arthritis of entire paw and digits.

Animals were sorted into treatment groups with a mean arthritic index of 2.5 and then dosed once daily for 14 days with compound: by oral gavage for test compounds, or by subcutaneous injection at a dose of 10 mg/kg for the positive control, etanercept. After completion of the experiment, the mice were sacrificed.

The data were analysed by generating an average of the arthritic index across each treatment group. The mean arthritic index was then compared to the arthritic index of control (untreated) animals using the following formula to generate a percentage inhibition of disease.

$$\% \text{ inhibition of disease} = 100 - \left[ \frac{\text{average arthritic index: treated animals}}{\text{average arthritic index: untreated animals}} \star 100 \right]$$

The data are summarised in the following table.

TABLE 11

| Inhibition of Arthritis | | |
| --- | --- | --- |
| Compound | Dose (mg/kg/day) | % inhibition of disease |
| ABD899 | 10 | 77 |
| HMC-C-01-A | 10 | 40 |
| HMC-N-01-A | 10 | 45 |
| HMC-C-02-A | 10 | 61 |
| HMC-N-02-A | 10 | 36 |
| HMC-C-01-B | 10 | 26 |
| HMC-N-01-B | 10→1 (*) | 38 |
| CHMSA-01-A | 10 | 63 |
| CHMSA-03-A | 10 | 62 |

(*) Reduced from 10 to 1 mg/kg/day due to mortality.

Figure 3:
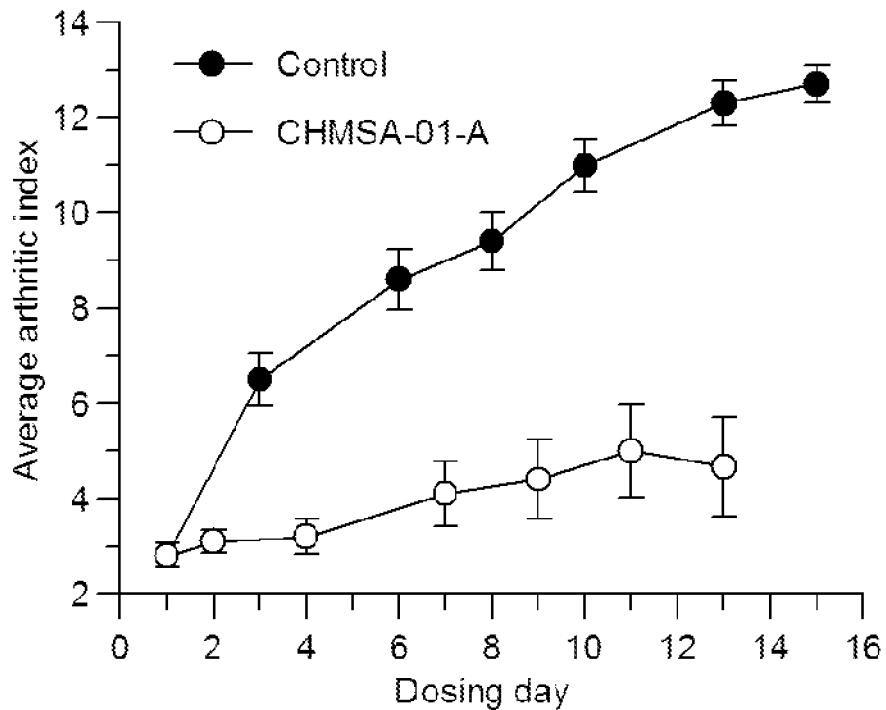
FIG. 3 is a graph of average arthritic index as a function of time (dosing day) for test compound CHMSA-01-A dosed at 10 mg/kg/day by oral gavage (open circles) and control (solid circles), as obtained using the methods described herein.

FIG. 3 is a graph of average arthritic index as a function of time (dosing day) for test compound CHMSA-01-A dosed at 10 mg/kg/day by oral gavage (open circles) and control (solid circles).

Figure 4:
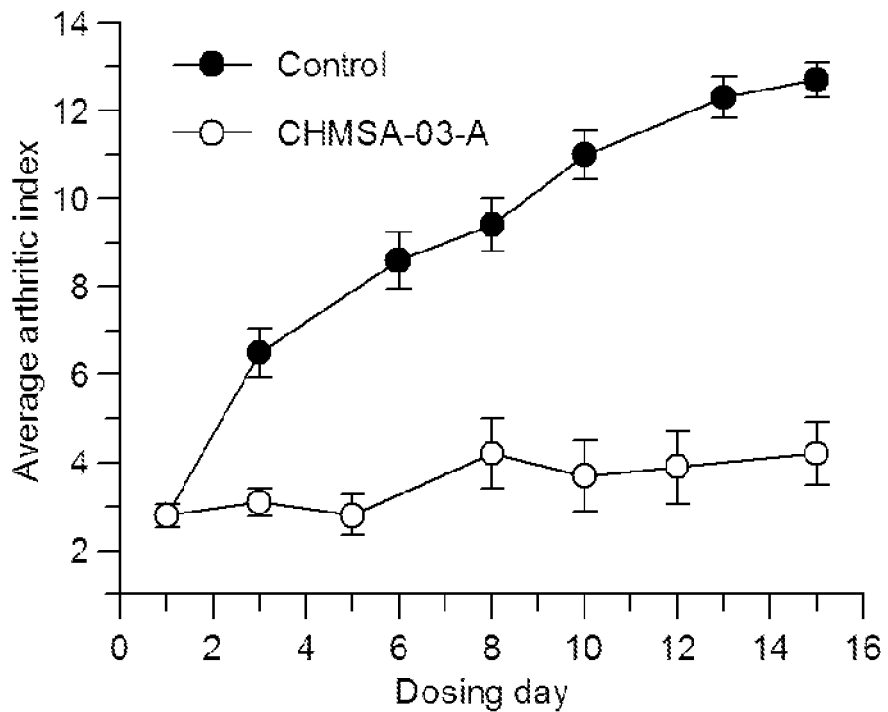
FIG. 4 is a graph of average arthritic index as a function of time (dosing day) for test compound CHMSA-03-A dosed at 10 mg/kg/day by oral gavage (open circles) and control (solid circles), as obtained using the methods described herein.

FIG. 4 is a graph of average arthritic index as a function of time (dosing day) for test compound CHMSA-03-A dosed at 10 mg/kg/day by oral gavage (open circles) and control (solid circles).

Figure 5:
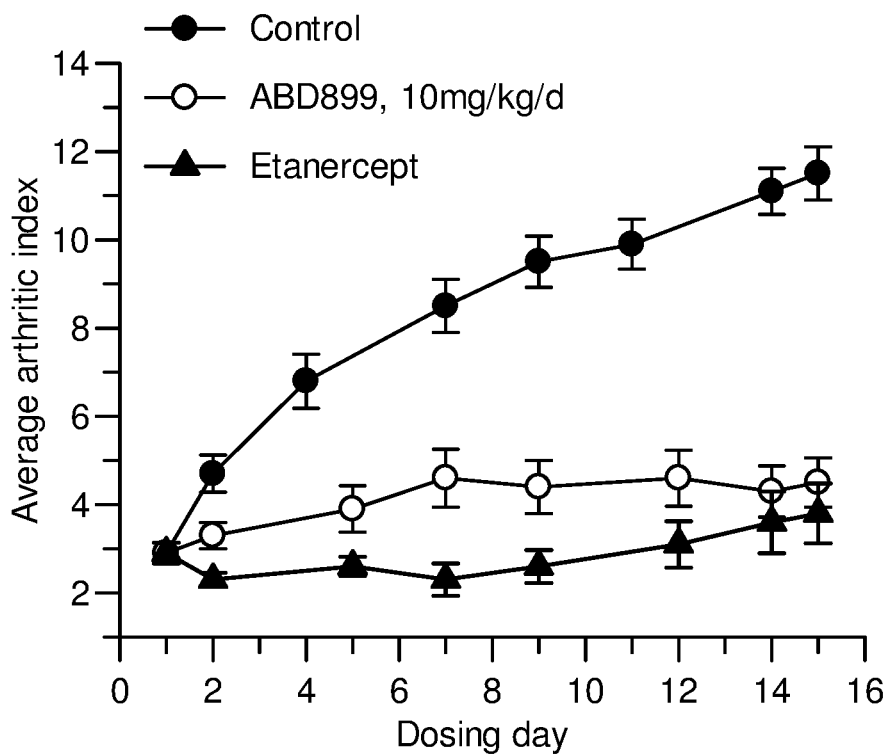
FIG. 5 is a graph of arthritic index as a function of time (dosing day) for reference compound ABD899 dosed at 10 mg/kg/day (open circles, open squares), control (solid circles), and positive control, the marketed drug etanercept (triangles), as obtained using the methods described herein.

FIG. 5 is a graph of arthritic index as a function of time (dosing day) for reference compound ABD899 dosed at 10 mg/kg/day (open circles, open squares), control (solid circles), and positive control, the marketed drug etanercept (triangles).

Figure 6:
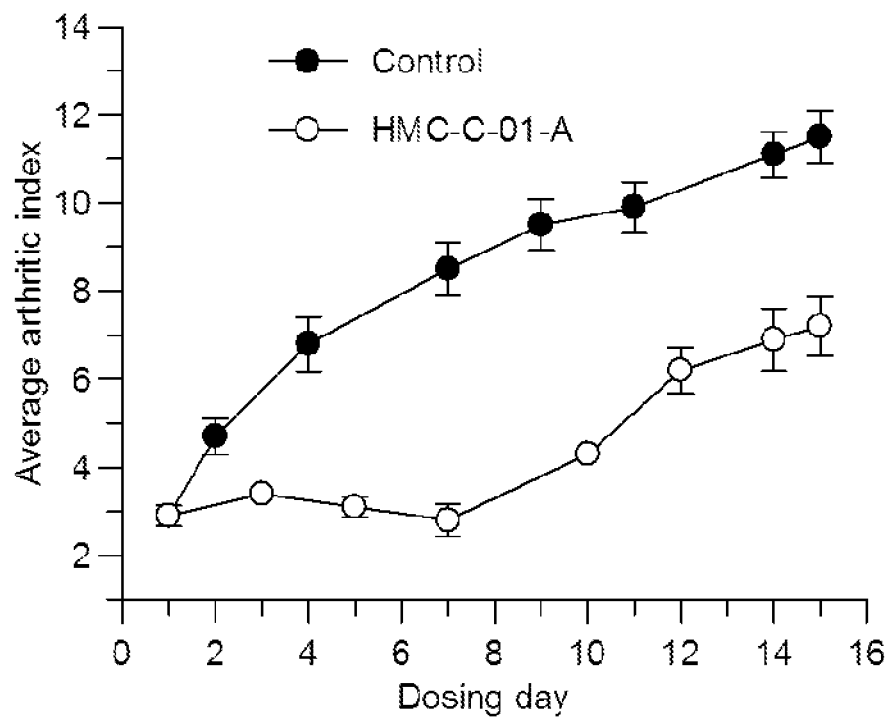
FIG. 6 is a graph of arthritic index as a function of time (dosing day) for reference compound HMC-C-01-A dosed at 10 mg/kg/day (open circles) and control (solid circles), as obtained using the methods described herein.

FIG. 6 is a graph of arthritic index as a function of time (dosing day) for reference compound HMC-C-01-A dosed at 10 mg/kg/day (open circles), and control (solid circles).

These data indicate that the CHMSA compounds described herein show excellent oral in vivo activity in preventing the progression of established, severe arthritis.

Reference Compounds

The following reference compounds are mentioned hereinabove.

TABLE 12

Reference Compounds

| Compound | Structure |
|---|---|
| HMC-C-01-A | [structure] |
| ABD599 | [structure] |
| ABD735 | [structure] |
| ABD836 | [structure] |
| ABD899 | [structure] |
| ABD900 | [structure] |
| REF001 | [structure] |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these publications are provided below.

Each of these publications is incorporated herein by reference in its entirety into the present disclosure, to the same extent as if each individual publication was specifically and individually indicated to be incorporated by reference.

Astry et al., 2011, "A cytokine-centric view of the pathogenesis and treatment of autoimmune arthritis", *J Interferon Cytokine Res.*, Vol. 31, pp. 927-940.

Auld et al., 2009, "A basis for reduced chemical library inhibition of firefly luciferase obtained from directed evolution", J. Med. Chem., Vol. 52, No. 5, pp. 1450-1458.

Bahmanyar et al., 2010, "Aminotriazolopyridines and their use as kinase inhibitors", international patent publication number WO 2010/027500 A1 published 11 Mar. 2010.

Baud et al., 2009, "Is NFκB a good target for cancer therapy? Hopes and pitfalls", *Nat. Rev. Drug Disc.*, Vol. 8, pp. 33-40.

Billiau, 2010, "Etanercept improves linear growth and bone mass acquisition in MTX-resistant polyarticular-course juvenile idiopathic arthritis", *Rheumatology* (Oxford), Vol. 49, pp. 1550-1558.

Brennan et al., 1992, "Enhanced expression of tumor necrosis factor receptor mRNA and protein in mononuclear cells isolated from rheumatoid arthritis synovial joints", *Eur. J. Immunol.*, Vol. 22, pp. 1907-1912.

Brennan et al., 1996, "Cytokines in autoimmunity", *Curr. Opin. Immunol.*, Vol. 8, pp. 872-877.

Bridges et al., 2014, "Effects of metformin and other biguanides on oxidative phosphorylation in mitochondria", *Biochem. J.*, Vol. 462, No. 3, pp. 475-487.

Bursulaya et al., 2018, "Aza-indazole compounds for use in tendon and/or ligament injuries", international patent publication number WO 2018/055551 A1 published 29 Mar. 2018.

Chimenti et al., 2015, "The interplay between inflammation and metabolism in rheumatoid arthritis", *Cell Death and Disease*, Vol. 17, No. 6, e1887.

Dallas et al., 2011, "Osteoimmunology at the *nexus* of arthritis, osteoporosis, cancer, and infection", *J. Clin. Invest.*, Vol. 121, pp. 2534-2542.

Ellinghaus et al., 2013, "BAY 87-2243, a highly potent and selective inhibitor of hypoxia-induced gene activation has antitumor activities by inhibition of mitochondrial complex I", *Cancer Med.*, Vol. 2, No. 5, pp. 611-624.

Evans et al., 2005, "Metformin and reduced risk of cancer in diabetic patients", *BMJ*, Vol. 330, pp. 1304-1305.

Fearon et al., 2016 "Hypoxia, mitochondrial dysfunction and synovial invasiveness in rheumatoid arthritis", *Nat. Rev. Rheumatol.*, Vol. 12, pp. 385-397.

Fiorillo et al., 2016, "Repurposing atovaquone: targeting mitochondrial complex III and OXPHOS to eradicate cancer stem cells", *Oncotarget*, Vol. 7, pp. 34084-34099.

Firestein, 2005 "Immunologic mechanisms in the pathogenesis of rheumatoid arthritis", *J. Clin. Rheumatol.*, Vol. 11. pp. S39-S44.

Ganeshan et al., 2014, "Metabolic Regulation of Immune Responses", *Ann. Rev. Immunol.*, Vol. 32, pp. 609-634.

Garcia-Carbonnel et al., 2016, "Critical Role of Glucose Metabolism in Rheumatoid Arthritis Fibroblast-like Synoviocytes", *Arthritis Rheumatol.*, Vol. 68, No. 7, pp. 1614-1626.

Greig et al., 2010a, "Aryl-phenyl-sulfonamido-cycloalkyl compounds and their use", international patent publication number WO 2010/032009 A1 published 25 Mar. 2010.

Greig et al., 2010b, "Aryl-phenyl-sulfonamido-phenylene compounds and their use", international patent publication number WO 2010/032010 A1 published 25 Mar. 2010.

Jiang et al., 2013, "Letml, the mitochondrial Ca2+/H+ antiporter, is essential for normal glucose metabolism and alters brain function in Wolf-Hirschhorn syndrome", PNAS, E2249-E2254.

Jung et al., 2014, "Cytokine-mediated bone destruction in rheumatoid arthritis", *J. Immunol. Res.*, Vol. 2014, p. 263625.

Kang et al., 2015, "Combinations of kinase inhibitors protecting myoblasts against hypoxia", PLOS, PLoS ONE 10(6): e0126718.

Karsenty et al., 2002, "Reaching a genetic and molecular understanding of skeletal development", *Dev. Cell.*, Vol. 2, pp. 389-406.

Klareskog et al., 2006, "Mechanisms of disease: Genetic susceptibility and environmental triggers in the development of rheumatoid arthritis," *Nat. Clin. Pract. Rheumatol.*, Vol. 2, pp. 425-433.

Kleyer et al., 2014, "Arthritis and bone loss: a hen and egg story", *Curr. Opin. Rheumatol.*, Vol. 26, No. 1, pp. 80-84.

Koppenol et al., 2011, "Otto Warburg's contributions to current concepts of cancer metabolism", *Nat. Rev. Cancer*, Vol. 11, No. 5, pp. 325-337.

LeBleu et al., 2014, "PGC-la mediates mitochondrial biogenesis and oxidative phosphorylation in cancer cells to promote metastasis", *Nat. Cell Biol.*, Vol. 16, pp. 992-1003.

Long, 2012, "Osteoimmunology: the expanding role of immunoreceptors in osteoclasts and bone remodeling", *Bone Key Rep.*, Vol. 1, p. 59.

Malemud et al., 2010, "Myeloid-related protein activity in Rheumatoid Arthritis", *International Journal of Interferon, Cytokine and Mediator Research*, Vol. 2, pp. 97-111.

Mantovani, 2009, "Inflaming metastasis", *Nature*, Vol. 457, pp. 36-37.

McInnes et al., 2011, "The pathogenesis of rheumatoid arthritis", *N. Engl. J. Med.*, Vol. 365, No. 23, 2205-2219.

Nutsch et al. 2011, "When T cells run out of breath: the HIF-la story", *Cell*, Vol. 146, No. 5 pp. 673-674.

Ogata et al., 2012, "Safety and Efficacy of Tocilizumab for the Treatment of Rheumatoid Arthritis", *Clin Med Insights Arthritis Musculoskelet Disord.*, Vol. 5, pp. 27-42.

Oslob et al., 2016, "4-Methylsulfonyl-substituted piperidine urea compounds for the treatment of dilated cardiomyopathy (DCM)", international patent publication number WO 2016/118774 A1 published 28 Jul. 2016.

Patel et al., 2014, "N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds and their therapeutic use", international patent publication number WO 2014/207445 A1 published 31 Dec. 2014.

Patel et al., 2016, "N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds and their therapeutic use", international patent publication number WO 2016/097001 A1 published 23 Jun. 2016.

Perl, 2017, "Metabolic Control of Immune System Activation in Rheumatic Diseases", *Arthritis & Rheumatology*, Vol. 69, No. 12, pp. 2259-2270.

Philchenkov et al., 2004, "Caspases and cancer: mechanisms of inactivation and new treatment modalities", *Exp. Oncol.*, Vol 26, pp 82-97.

Pollak, 2014, "Overcoming drug development bottlenecks with repurposing: repurposing biguanides to target energy metabolism for cancer treatment", *Nat. Med.*, Vol. 20, No. 6, pp. 591-593.

Procaccini et al., 2012, "Intracellular metabolic pathways control immune tolerance", *Trends Immunol.*, Vol. 33, No. 1, pp. 1-7.

Roodman, 2006, "Regulation of osteoclast differentiation", *Ann. N. Y. Acad. Sci*; Vol. 1068, pp. 100-109.

Scott et al., 2010, "Rheumatoid Arthritis", *Lancet*, Vol. 376, pp. 1094-1108.

Smolen et al., 2015, "Rheumatoid arthritis therapy reappraisal: strategies, opportunities and challenges", *Nat. Rev. Rheumatol.*, Vol. 11, pp. 276-289.

Spies et al., 2012, "Energy metabolism and rheumatic diseases: from cell to organism", *Arthritis Research & Therapy*, Vol. 14, p. 216.

Steger et al., 2011, "Denosumab for the treatment of bone metastases in breast cancer: evidence and opinion", *Ther. Adv. Med. Oncol.*, Vol. 3, pp. 233-243.

Straub et al., 2010, "Energy regulation and neuroendocrine-immune control in chronic inflammatory diseases", *J. Intern. Med.*, Vol. 267, No. 6, pp. 543-560.

Sun, 2010, "Mechanical loading, cartilage degradation and arthritis", *Annals of the New York Academy of Sciences*, Vol. 1211, pp. 37-50.

Takayanagi, 2009, "Osteoimmunology and the effects of the immune system on bone", *Nature Reviews Rheumatology*, Vol. 5, pp. 667-676.

Tanaka et al., 2003, "Signal transduction pathways regulating osteoclast differentiation and function", *J. Bone Miner. Metab.*, Vol. 21, pp. 123-133.

Weinberg et al., 2010, "Mitochondrial metabolism and ROS generation are essential for Kras-mediated tumorigenicity", *Proc. Natl. Acad. Sci. USA*, Vol. 107, No. 19, pp. 8788-8793.

Weaver, et al., 2003, "Cytochrome p450 inhibition using recombinant proteins and mass spectrometry/multiple reaction monitoring technology in a cassette incubation", *Drug Metabolism and Disposition*, Vol. 31, No. 7, pp. 955-966.

Weyand et al., 2017a, "Immunometabolism in early and late stages of rheumatoid arthritis", *Nature Reviews Rheumatology*, Vol. 13, pp. 291-301.

Weyand et al., 2017b, "Metabolic Signatures of T-cells and Macrophages in Rheumatoid Arthritis", *Curr. Opin. Immunol.*, Vol. 46, pp. 112-120.

Wheaton et al., 2014, "Metformin inhibits mitochondrial complex I of cancer cells to reduce tumorigenesis", *eLife*, Vol. 3, e02242.

Yang et al., 2013, "Phosphofructokinase deficiency impairs ATP generation, autophagy, and redox balance in rheumatoid arthritis T cells", *J. Exp. Med.*, Vol. 210, pp. 2119-2134.

The invention claimed is:
1. A compound of the following formula:

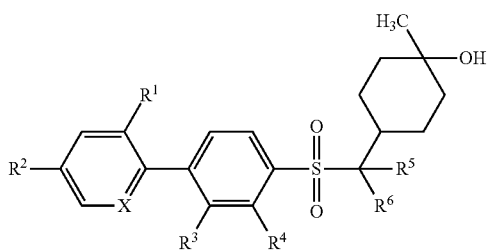

or a pharmaceutically acceptable salt thereof;
wherein:
=X— is independently —CH= or —N=;
—R¹ is independently —H or —R¹ˣ;
—R¹ˣ is independently —F, —Cl, —R¹ᶜ, —R¹ᶠ For —CN;
—R¹ᶜ is independently saturated linear or branched C₁₋₃alkyl;
—R¹ᶠ is independently saturated linear or branched C₁₋₃fluoroalkyl;
—R² is independently —H or —R³ˣ;
—R²ˣ is independently —F, —Cl, —R²ᶜ, —R²ᶠ, or —CN;
—R²ᶜ is independently saturated linear or branched C₁₋₃alkyl;
—R²ᶠ is independently saturated linear or branched C₁₋₃fluoroalkyl;
—R³ is independently —H or —R³ˣ;
—R³ˣ is independently —F, —Cl, —R³ᶜ, —R³ᶠ, or —CN;
—R³ᶜ is independently saturated linear or branched C₁₋₃alkyl;
—R³ᶠ is independently saturated linear or branched C₁₋₃fluoroalkyl;
—R⁴ is independently —H or —R⁴ˣ;
—R⁴ˣ is independently —F, —Cl, —R⁴ᶜ, —R⁴ᶠ, or —CN;
—R⁴ᶜ is independently saturated linear or branched C₁₋₃alkyl;
—R⁴ᶠ is independently saturated linear or branched C₁₋₃fluoroalkyl;
—R⁵ is independently —H or —R⁵ˣ;
—R⁵ˣ is independently —F, —R⁵ᶜ, or —R⁵ᶠ;
—R⁵ᶜ is independently saturated linear or branched C₁₋₃alkyl;
—R⁵ᶠ is independently saturated linear or branched C₁₋₃fluoroalkyl;
—R⁶ is independently —H or —R⁶ˣ;
—R⁶ˣ is independently —F, —R⁶ᶜ, or —R⁶ᶠ;
—R⁶ᶜ is independently saturated linear or branched C₁₋₃alkyl; and
—R⁶ᶠ is independently saturated linear or branched C₁₋₃fluoroalkyl;
or —R⁵ and —R⁶, taken together with the carbon atom to which they are attached, form saturated C₃₋₆cycloalkyl.

2. A compound according to claim 1, wherein —R⁵ is —H and —R⁶ is —H.

3. A compound according to claim 2, wherein =X— is —CH=.

4. A compound according to claim 2, wherein =X— is —N=.

5. A compound according to claim 3, wherein:
—R¹ is independently —H, —F, —Cl, or —CN; and
—R² is independently —H, —F, —Cl, or —CN.

6. A compound according to claim 4, wherein:
—R¹ is independently —H, —F, —Cl, or —CN; and
—R² is independently —H, —F, —Cl, or —CN.

7. A compound according to claim 3, wherein:
—R³ is independently —H, —F, —Cl, or —CN; and
—R⁴ is independently —H or —CF₃.

8. A compound according to claim 4, wherein:
—R³ is independently —H, —F, —Cl, or —CN; and
—R⁴ is independently —H or —CF₃.

9. A compound according to claim 5, wherein:
—R³ is independently —H, —F, —Cl, or —CN; and
—R⁴ is independently —H or —CF₃.

10. A compound according to claim 6, wherein:
—R³ is independently —H, —F, —Cl, or —CN; and
—R⁴ is independently —H or —CF₃.

11. A compound according to claim 3, wherein the compound is a compound of the following formula, or a pharmaceutically acceptable salt thereof:

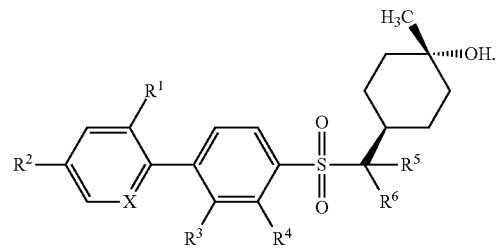

12. A compound according to claim 5, wherein the compound is a compound of the following formula, or a pharmaceutically acceptable salt thereof:

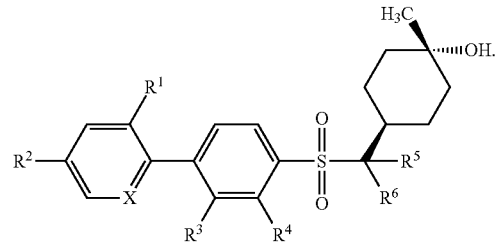

13. A compound according to claim 7, wherein the compound is a compound of the following formula, or a pharmaceutically acceptable salt thereof:

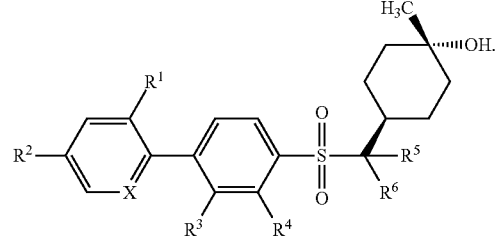

14. A compound according to claim 9, wherein the compound is a compound of the following formula, or a pharmaceutically acceptable salt thereof:

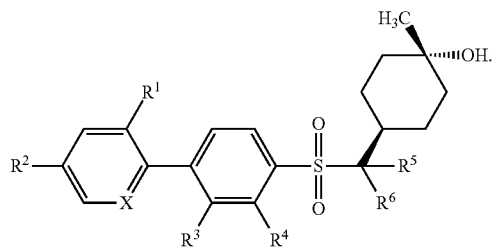

15. A compound according to claim 3, wherein the compound is a compound of the following formula, or a pharmaceutically acceptable salt thereof:

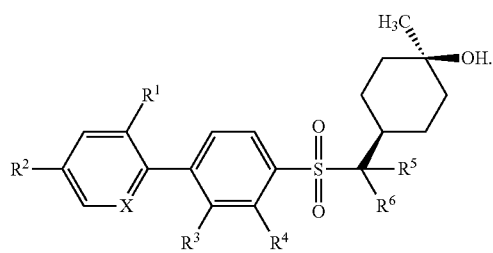

16. A compound according to claim 5, wherein the compound is a compound of the following formula, or a pharmaceutically acceptable salt thereof:

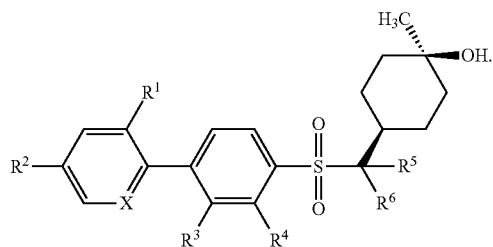

17. A compound according to claim 7, wherein the compound is a compound of the following formula, or a pharmaceutically acceptable salt thereof:

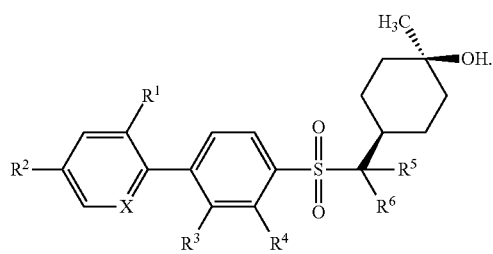

18. A compound according to claim 9, wherein the compound is a compound of the following formula, or a pharmaceutically acceptable salt thereof:

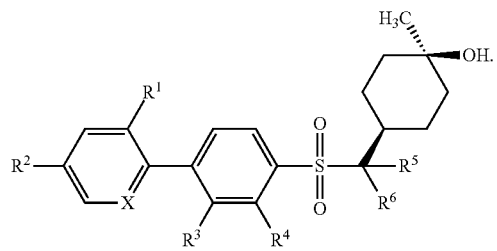

19. A compound according to claim 1, which is a compound of one of following formulae, or a pharmaceutically acceptable salt thereof:

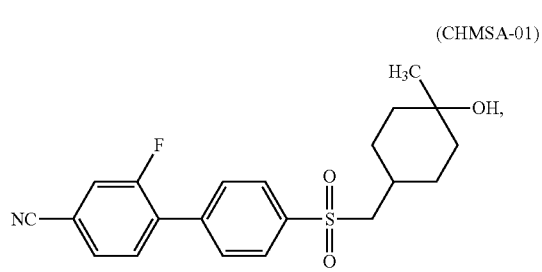

(CHMSA-01)

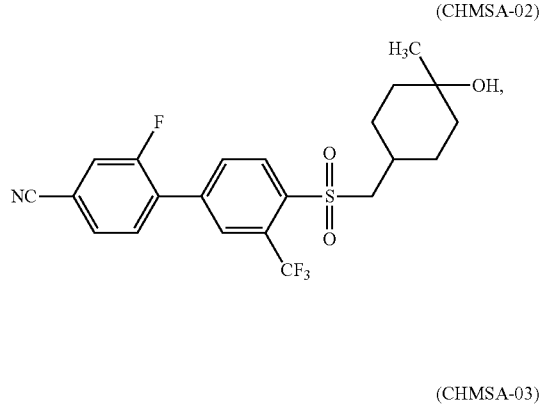

(CHMSA-02)

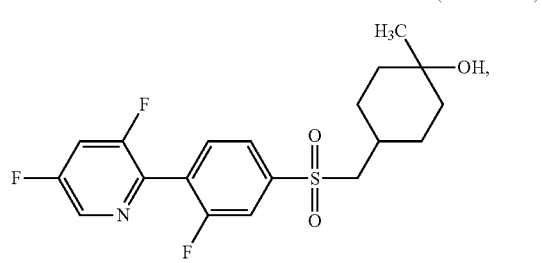

(CHMSA-03)

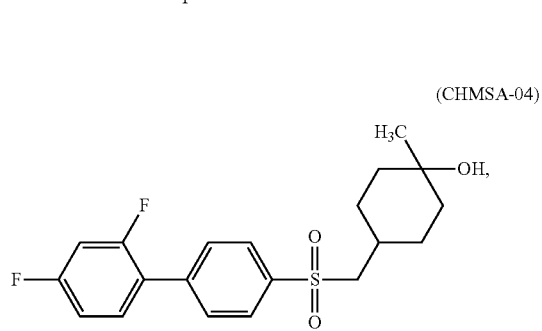

(CHMSA-04)

(CHMSA-05)
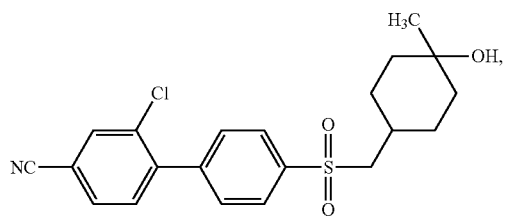
(CHMSA-06)
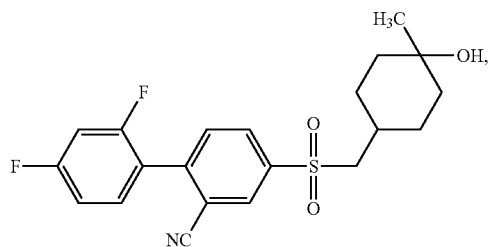
(CHMSA-07)
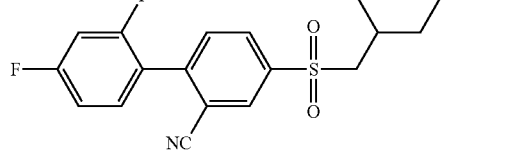
(CHMSA-08)
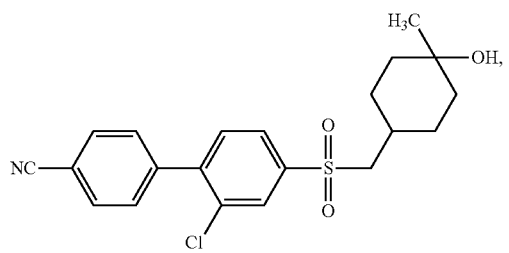
(CHMSA-09)
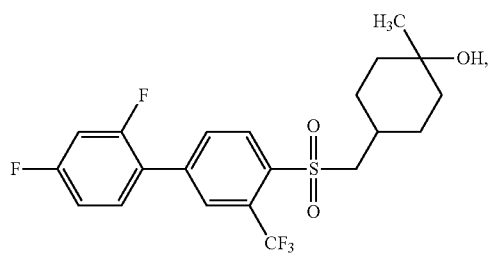
(CHMSA-10)
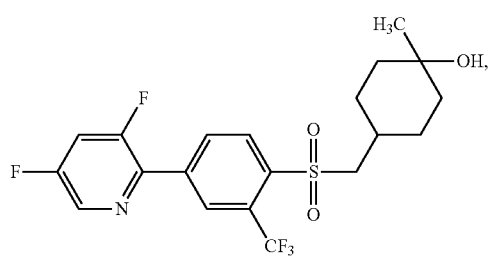
(CHMSA-11)
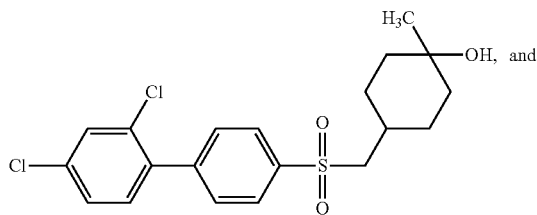
(CHMSA-12)
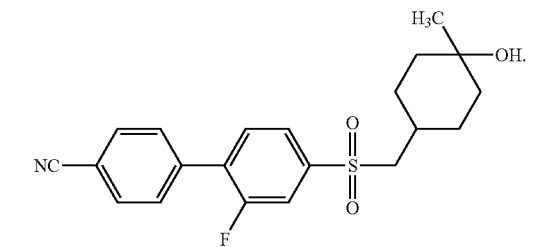
20. A compound according to claim 1, which is a compound of one of following formulae, or a pharmaceutically acceptable salt thereof:
(CHMSA-01-A)
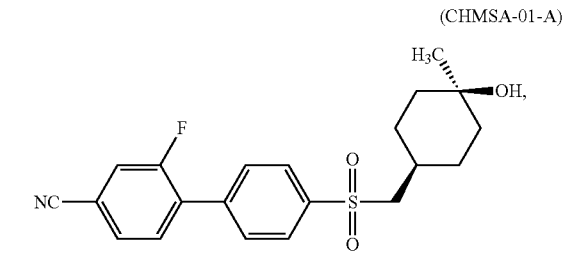
(CHMSA-02-A)
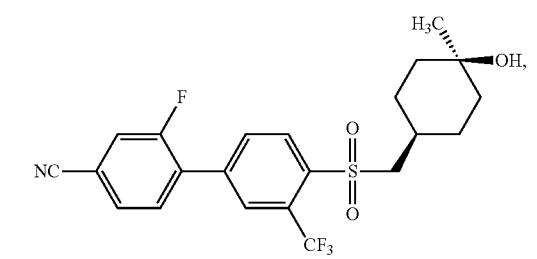
(CHMSA-03-A)
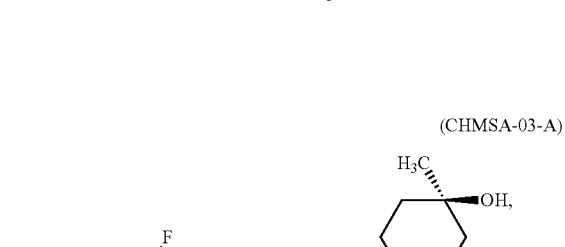

(CHMSA-04-A)
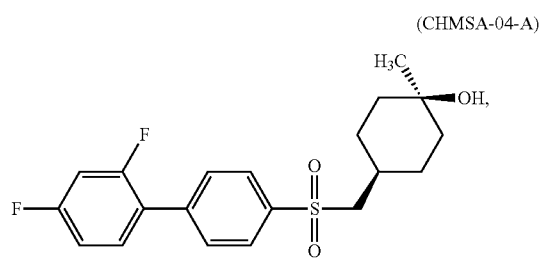
(CHMSA-05-A)
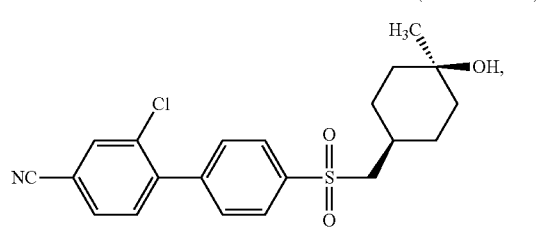
(CHMSA-06-A)
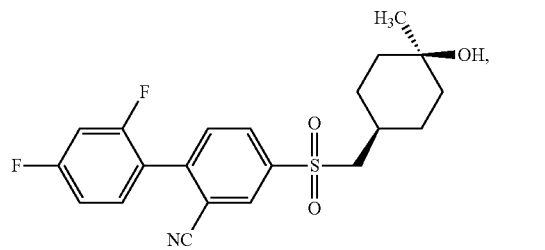
(CHMSA-07-A)
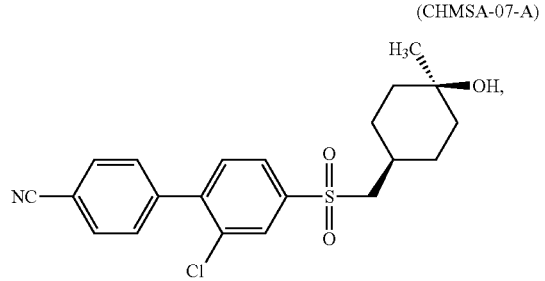
(CHMSA-08-A)
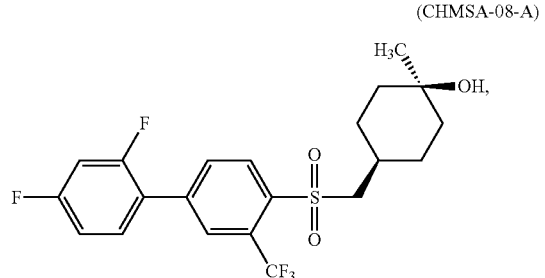
(CHMSA-09-A)
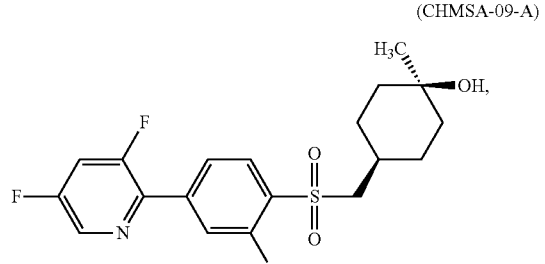
(CHMSA-10-A)
(CHMSA-11-A)
(CHMSA-12-A)
21. A compound according to claim 1, which is a compound of one of following formulae, or a pharmaceutically acceptable salt thereof:
(CHMSA-01-B)
(CHMSA-02-B)
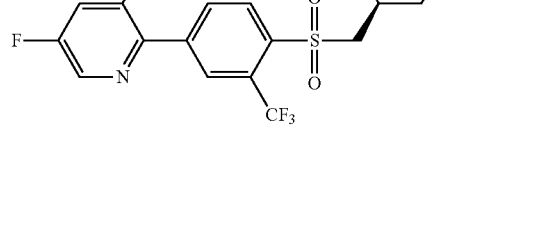

22. A composition comprising a compound according to claim 1, and a carrier, diluent, or excipient.

* * * * *

UNITED STATES PATENT AND TRADEMARK OFFICE
CERTIFICATE OF CORRECTION

PATENT NO. : 11,834,414 B2
APPLICATION NO. : 17/265929
DATED : December 5, 2023
INVENTOR(S) : Lisa Patel et al.

Page 1 of 1

It is certified that error appears in the above-identified patent and that said Letters Patent is hereby corrected as shown below:

In the Claims

In Claim 1, at Column 157, Line 20, "For" should read --, or--; and

In Claim 1, at Column 157, Line 26, "$R^{3x}$" should read --$R^{2x}$--.

Signed and Sealed this
Twenty-third Day of April, 2024

Katherine Kelly Vidal
*Director of the United States Patent and Trademark Office*